US011492647B2

(12) United States Patent
Tsakraklides et al.

(10) Patent No.: US 11,492,647 B2
(45) Date of Patent: *Nov. 8, 2022

(54) INCREASING LIPID PRODUCTION IN OLEAGINOUS YEAST

(71) Applicant: Ginkgo Bioworks, Inc., Boston, MA (US)

(72) Inventors: Vasiliki Tsakraklides, Lexington, MA (US); Elena E. Brevnova, Belmont, MA (US)

(73) Assignee: Ginkgo Bioworks, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/376,886

(22) Filed: Apr. 5, 2019

(65) Prior Publication Data

US 2019/0225996 A1 Jul. 25, 2019

Related U.S. Application Data

(62) Division of application No. 15/312,852, filed as application No. PCT/US2015/033251 on May 29, 2015, now Pat. No. 10,260,077.

(60) Provisional application No. 62/090,169, filed on Dec. 10, 2014, provisional application No. 62/033,853, filed on Aug. 6, 2014, provisional application No. 62/004,502, filed on May 29, 2014.

(51) Int. Cl.
*C12P 7/6463* (2022.01)
*C12N 9/20* (2006.01)
*C12N 9/10* (2006.01)

(52) U.S. Cl.
CPC .......... *C12P 7/6463* (2013.01); *C12N 9/1025* (2013.01); *C12N 9/1029* (2013.01); *C12N 9/20* (2013.01); *C12Y 203/0102* (2013.01); *C12Y 301/01003* (2013.01)

(58) Field of Classification Search
CPC ...... C12N 9/1029; C12N 9/1025; C12N 9/20; C12Y 301/01003; C12Y 203/0102; C12P 7/6463
See application file for complete search history.

(56) References Cited

U.S. PATENT DOCUMENTS

| | | | |
|---|---|---|---|
| 7,198,937 | B2 | 4/2007 | Xue et al. |
| 8,502,026 | B2 | 8/2013 | Daley et al. |
| 8,691,555 | B2 | 4/2014 | Bailey et al. |
| 10,260,052 | B2 | 4/2019 | Brevnova et al. |
| 10,260,077 | B2 | 4/2019 | Tsakraklides et al. |
| 2003/0233675 | A1 | 12/2003 | Cao et al. |
| 2006/0094091 | A1 | 5/2006 | Macool et al. |
| 2008/0295204 | A1 | 11/2008 | Meyer et al. |
| 2009/0291479 | A1 | 11/2009 | Hong et al. |
| 2010/0062502 | A1 | 3/2010 | Hong et al. |
| 2010/0305341 | A1 | 12/2010 | Bailey et al. |
| 2011/0047659 | A1 | 2/2011 | Daley et al. |
| 2012/0096588 | A1 | 4/2012 | Meyer et al. |
| 2013/0123361 | A1 | 5/2013 | Damude et al. |
| 2013/0143282 | A1 | 6/2013 | Stephanopoulos et al. |
| 2013/0149754 | A1 | 6/2013 | Dulermo et al. |
| 2014/0106417 | A1 | 4/2014 | Schneider et al. |
| 2016/0145599 | A1 | 5/2016 | Nicaud et al. |
| 2017/0107500 | A1 | 4/2017 | Tsakraklides et al. |
| 2017/0191073 | A1 | 7/2017 | Brevnova et al. |
| 2017/0191093 | A1 | 7/2017 | Tsakraklides et al. |
| 2017/0369910 | A1 | 12/2017 | Tsakraklides et al. |
| 2017/0369912 | A1 | 12/2017 | Shaw et al. |

FOREIGN PATENT DOCUMENTS

| | | | |
|---|---|---|---|
| CN | 1816632 | A | 8/2006 |
| CN | 101437953 | A | 5/2009 |
| CN | 102812124 | A | 12/2012 |
| WO | WO-03053363 | A2 | 7/2003 |
| WO | WO-2009/129582 | A1 | 10/2009 |
| WO | WO-2010/025374 | A2 | 3/2010 |
| WO | WO-2012/001144 | A1 | 1/2012 |
| WO | WO-2013/059649 | A1 | 4/2013 |

OTHER PUBLICATIONS

Beopoulos et al., Metabolic engineering for ricinoleic acid production in the oleaginous yeast *Yarrowia lipolytica*. Appl Microbiol. Biotechnol., 2014, vol. 98: 251-262. (Year: 2014).*

Dulermo et al., Characterization of the two intracellular lipases of Y. lipolytica encoded by TGL3 and TGL4 gene: New insights into the role intracellular lipases and lipid body organisation. Bicochim. Biophys. Acta., 2013, vol. 1831: 1486-1495. (Year: 2013).*

Chawla et al., Identification and functional characterization of two acyl CoA:diacylglycerol acyltransferase 1 (DGAT1) genes from forage sorghum (*Sorghum bicolor*). Phytochemistry, 2020, vol. 176, 112405: pp. 1-12. (Year: 2020).*

Zheng et al., Discovery of a new mechanism for regulation of plant triacylglycerol metabolism: The peanut diacylglycerol acyltransferase-1 gene family transcriptome is highly enriched in alternative splicing variants. J. Plant Physiol., 2017, vol. 219: 62-70. (Year: 2017).*

Beopoulos et al., "Identification and characterization of DGA2, an acyltransferase of the DGAT1 acyl-CoA: diacylglycerol acyltransferase family in the oleaginous yeast *Yarrowia lipolytica*" *Appl. Microbiol. Biotechnol.*, 2012, 93:1523-1537.

(Continued)

*Primary Examiner* — Ganapathirama Raghu
(74) *Attorney, Agent, or Firm* — Foley Hoag LLP; Janine S. Ladislaw; Mohanad Mossalam

(57) ABSTRACT

Disclosed are methods and compositions for increasing the triacylglycerol content of a cell by increasing the activity of a type 1 diacylglycerol acyltransferase (i.e., DGA2) and increasing the activity of a type 2 diacylglycerol acyltransferase (i.e., DGA1). In some embodiments, the triacylglycerol content of a cell is also modified my decreasing the activity of a triacylglycerol lipase in the same cell. Also disclosed are methods and compositions for increasing the triacylglycerol content of a cell by increasing the activity of a type 1 diacylglycerol acyltransferase (i.e., DGA2), or by increasing the activity of a type 3 diacylglycerol acyltransferase (i.e., DGA3).

7 Claims, 10 Drawing Sheets

Specification includes a Sequence Listing.

(56) References Cited

OTHER PUBLICATIONS

Broun et al., "Catalytic plasticity of fatty acid modification enzymes underlying chemical diversity of plant lipids" *Science*, 1998, 282:1315-1317.

Chica et al., "Semi-rational approaches to engineering enzyme activity: combining the benefits of directed evolution and rational design" *Curr. Opi. Biotechnol*., 2005, 16:378-384.

Devos et al., "Practical limits of function prediction" *Proteins: Structure, Function, and Genetics*, 2000, 41:98-107.

EEF43203.1 GenBank Accession No. EEF43203.1, soluble diacylglycerol acyltransferase [Ricinus communis], Jul. 14, 2012 [online].

International Search Report issued in International Application No. PCT/US2015/033251, dated Sep. 15, 2015.

Kisselev, L., "Polypeptide release factors in prokaryotes and eukaryotes: same function, different structure." *Structure*, 2002, 10:8-9.

Mavraganis et al., "Type II diacylglycerol acyltransferase from Claviceps purpurea with ricinoleic acid, a hydroxyl fatty acid of industrial importance, as preferred substrate" *Appl. Environ. Microbiol*., 2010, 76(4): 1135-1142.

Seffemick et al., "Melamine deaminase and Atrazine chlorhohydrolase: 98 percent identical but functionally different," *J. Bacteriol*., 2001, 183(8):2405-2410.

Sen et al., "Developments in directed evolution for improving enzyme functions" *Appl. Biochem. Biotechnol*., 2007, 143:212-223.

Thevenieau et al., "Microorganizms as sources of oils" *OCL*., 2013, 20(6):1-8.

Whisstock et al., "Prediction of protein function from protein sequence" *Q. Rev. Biophysics*., 2003, 36(3):307.

Wishart et al., "A single mutation converts a novel phophotyrosine binding domain into a dual-specificity phosphatase" *J. Biol. Chem*., 1995, 270(45):26782-26785.

Witkowski et al., "Conversion of b-ketoacyl synthase to a malonyl Decarboxylase by replacement of the active cysteine with glutamine" *Biochemistry*, 1999, 38:11643-11650.

Boer et al., "An Extracellular Lipase From the Dimorphic Yeast *Arxula adeninivorans*: Molecular Cloning of the ALIPI Gene and Characterization of the Purified Recombinant Enzyme," Yeast, 22: 523-535 (2005).

Dulermo et al., "Characterization of the two intracellular lipases of Y. lipolytica encoded by TGL3 and TGL4 genes: new insights into the role of intracellular lipases and lipid body organization," Biochim Biophys Acta, 1831:1486-1495 (Jul. 2013).

Dulermo et al., "Involvement of the G3P shuttle and Beta-oxidation pathway in the control of TAG synthesis and lipid accumulation in Yarrowia lipolytica," Metab Eng, 13: 482-491 (May 2011).

GenBank Accession No. CDR46911.1, Rhodosporidium toruloides, Jun. 5, 2014.

International Search Report and Written Opinion for International Application No. PCT/US15/64710 dated Apr. 19, 2016.

International Search Report for International Application No. PCT/US2015/033211, dated Nov. 6, 2015.

International Search Report for International Application No. PCT/US2015/033251, dated Sep. 15, 2015.

Jankowska et al., "Arxula adeninivorans xanthine oxidoreductase and its application in the production of food with low purine content," J Appl Microbiol, 115: 796-807 (2013).

Kunze et al., "The complete genome of Blastobotrys (Arxula) adeninivorans LS3—a yeast of biotechnological interest," Biotechnology for Biofuels, 7(66): 1-15 (2014).

Kurat et al., "Obese Yeast. Triglyceride Lipolysis is Functionally Conserved from Mammals to Yeast," The Journal of Biological Chemistry, 281(1): 491-500 (2006).

Maskow et al., "On-line Monitoring of Lipid Storage in Yeasts Using Impedance Spectroscopy," Journal of Biotechnology, 135: 64-70 (2008).

Tai et al., "Engineering the push and pull of lipid biosynthesis in oleaginous yeast *Yarrowia lipolytica* for biofuel production," Metab Eng, 15: 1-9 (Sep. 2012).

* cited by examiner

INCREASING LIPID PRODUCTION IN OLEAGINOUS YEAST

RELATED APPLICATIONS

This application is a divisional of U.S. patent application Ser. No. 15/312,852 (now U.S. Pat. No. 10,260,077), filed Nov. 21, 2016; which is a U.S. National Stage Application of PCT/US2015/033251, filed May 29, 2015; which claims the benefit of priority to U.S. Provisional Patent Application No. 62/004,502, filed May 29, 2014; U.S. Provisional Patent Application No. 62/033,853, filed Aug. 6, 2014; and U.S. Provisional Patent Application No. 62/090,169, filed Dec. 10, 2014.

SEQUENCE LISTING

The instant application contains a Sequence Listing which has been submitted electronically in ASCII format and is hereby incorporated by reference in its entirety. Said ASCII copy, created on May 29, 2015, is named NGX-03225_SL.txt and is 259,379 bytes in size.

BACKGROUND

Lipids are indispensable ingredients in the food and cosmetics industries, and they are important precursors in the biodiesel and biochemical industries. Many oleaginous microorganisms produce lipids, including the well-characterized yeast *Yarrowia lipolytica.*

The lipid yield of oleaginous organisms can be increased by the up-regulation, down-regulation, or deletion of genes implicated in a lipid pathway. Recent data suggests that the activity of the diacylglycerol acyltransferase protein DGA1 may be a significant factor for accumulating high levels of lipids in oleaginous organisms. For example, it was reported that the up-regulation of the native *Y. lipolytica* diacylglycerol acyltransferase protein DGA1 in *Y. lipolytica* significantly increases its lipid yield and productivity (METABOLIC ENGINEERING 15:1-9 (2013)).

The *Y. lipolytica* DGA1 protein is a type 2 diacylglycerol acyltransferase encoded by the *Y. lipolytica* diacylglycerol acyltransferase gene DGAT2. DGA1 is one of the key enzymes in the lipid pathway, involved in the final step of triacylglycerol ("TAG") synthesis. Triacylglycerols are the major form of storage lipids in *Y. lipolytica*. Yeast also contain a type 1 diacylglycerol acyltransferase gene DGAT1, which encodes the DGA2 protein.

Diacylglycerol acyltransferase genes can be introduced into a host genome to affect lipid production and composition, including the DGA1 and DGA2 genes from other organisms. For example, other oleaginous yeasts, such as *Rhodosporidium toruloides* and *Lipomyces starkeyi*, are able to accumulate significantly more lipids than wild type *Y. lipolytica* strains, and the expression of DGA1 proteins from organisms with higher native lipid production levels has a greater effect on *Y. lipolytica* lipid production than the overexpression of native *Y. lipolytica* DGA1 (U.S. Ser. No. 61/943,664 and PCT Patent Application No. PCT/US15/017227; hereby incorporated by reference).

Additionally, genes involved in the breakdown of lipids or in pathways that draw flux away from lipid biosynthesis have been deleted to increase a cell's lipid content. For example, Dulermo et al. demonstrated that the deletion of the triacylglycerol lipase gene TGL3 nearly doubled the total lipid content accumulated by *Y. lipolytica* (BIOCHIMICA BIOPHYSICA ACTA 1831:1486-95 (2013)).

The successful upregulation of functional enzymes, however, is unpredictable at best. For example, other experiments have shown that expressing DGA1 from *Mortierella alpine* has no significant effect on *Y. lipolytica* lipid content (U.S. Pat. No. 7,198,937; hereby incorporated by reference). Similarly, expressing DGA2 has been shown to have no significant effect on the lipid content of yeast in the absence of other genetic modifications.

SUMMARY

In some embodiments, the invention relates to a transformed cell, comprising a first genetic modification and second genetic modification, wherein said first genetic modification increases the activity of a native type 1 diacylglycerol acyltransferase or encodes at least one copy of a type 1 diacylglycerol acyltransferase gene native to the cell or from a different species, and said second genetic modification increases the activity of a native type 2 diacylglycerol acyltransferase or encodes at least one copy of a type 2 diacylglycerol acyltransferase gene native to the cell or from a different species. In some embodiments, the transformed cell comprises a third genetic modification, wherein said third genetic modification decreases the activity of a triacylglycerol lipase in the cell.

In some embodiments, the invention relates to a transformed cell, comprising a genetic modification, wherein said genetic modification increases the activity of a native type 1 diacylglycerol acyltransferase or encodes at least one copy of a type 1 diacylglycerol acyltransferase gene native to the cell or from a different species.

In some embodiments, the invention relates to a transformed cell, comprising a genetic modification, wherein said genetic modification increases the activity of a native type 3 diacylglycerol acyltransferase or encodes at least one copy of a type 3 diacylglycerol acyltransferase gene native to the cell or from a different species.

In some aspects, the invention provides a method of increasing the lipid content of a cell, comprising transforming a parent cell with a first nucleotide sequence and a second nucleotide sequence, wherein said first nucleotide sequence increases the activity of a native type 1 diacylglycerol acyltransferase or encodes at least one copy of a type 1 diacylglycerol acyltransferase gene, and said second nucleotide sequence increases the activity of a native type 2 diacylglycerol acyltransferase or encodes at least one copy of a type 2 diacylglycerol acyltransferase gene. In some embodiments, the method comprises transforming the parent cell with a third nucleotide sequence, wherein said third nucleotide sequence decreases the activity of a triacylglycerol lipase. The aforementioned method may also be used to modify the lipid composition of a cell.

In some aspects, the invention provides a method of increasing the lipid content of a cell, comprising transforming a parent cell with a nucleotide sequence, wherein said nucleotide sequence increase the activity of a native type 1 diacylglycerol acyltransferase or encodes at least one copy of a type 1 diacylglycerol acyltransferase gene. The aforementioned method may also be used to modify the lipid composition of a cell.

In some aspects, the invention provides a method of increasing the lipid content of a cell, comprising transforming a parent cell with a nucleotide sequence, wherein said nucleotide sequence increase the activity of a native type 3 diacylglycerol acyltransferase or encodes at least one copy of a type 3 diacylglycerol acyltransferase gene. The aforementioned method may also be used to modify the lipid composition of a cell.

In some aspects, the invention provides a method of increasing the triacylglycerol content of a cell, comprising: (a) providing a cell, comprising (i) a first genetic modification, wherein said first genetic modification increases the activity of a native type 1 diacylglycerol acyltransferase or encodes at least one copy of a type 1 diacylglycerol acyltransferase gene native to the cell or from a different species; and (ii) a second genetic modification, wherein said second genetic modification increases the activity of a native type 2 diacylglycerol acyltransferase or encodes at least one copy of a type 2 diacylglycerol acyltransferase gene native to the cell or from a different species; (b) growing said cell under conditions whereby the first and second genetic modifications are expressed, thereby producing a triacylglycerol; and (c) optionally recovering the triacylglycerol. In some embodiments, the cell comprises a third genetic modification, wherein said third genetic modification decreases the activity of a triacylglycerol lipase in the cell. The aforementioned method may also be used to modify the lipid composition of a cell.

In some aspects, the invention provides a method of increasing the triacylglycerol content of a cell, comprising: (a) providing a cell comprising a genetic modification, wherein said genetic modification increases the activity of a native type 1 diacylglycerol acyltransferase or encodes at least one copy of a type 1 diacylglycerol acyltransferase gene native to the cell or from a different species; (b) growing said cell under conditions whereby the genetic modification is expressed, thereby producing a triacylglycerol; and (c) optionally recovering the triacylglycerol.

In some aspects, the invention provides a method of increasing the triacylglycerol content of a cell, comprising: (a) providing a cell comprising a genetic modification, wherein said genetic modification increases the activity of a native type 3 diacylglycerol acyltransferase or encodes at least one copy of a type 3 diacylglycerol acyltransferase gene native to the cell or from a different species; (b) growing said cell under conditions whereby the genetic modification is expressed, thereby producing a triacylglycerol; and (c) optionally recovering the triacylglycerol.

DETAILED DESCRIPTION

Overview

Figure 1:
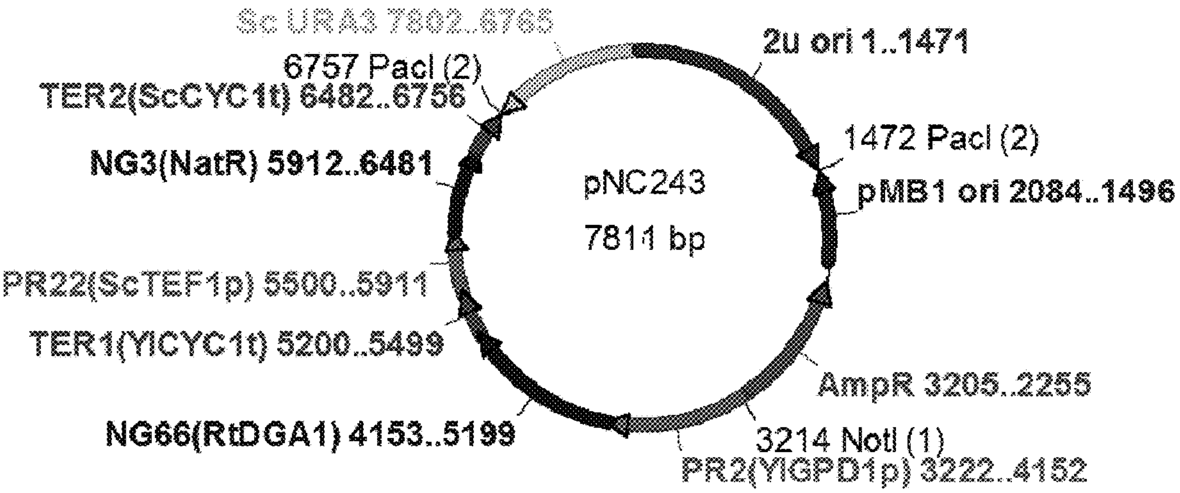
FIG. 1 depicts a map of the pNC243 construct used to express the diacylglycerol acyltransferase DGA1 gene NG66 in *Y. lipolytica* strain NS18 (obtained from ARS Culture Collection, NRRL #YB 392). Vector pNC243 was linearized by a PacI/NotI restriction digest before transformation. "2u ori" denotes the *S. cerevisiae* origin of replication from the 2 μm circle plasmid; "pMB1 ori" denotes the *E. coli* pMB1 origin of replication from the pBR322 plasmid; "AmpR" denotes the bla gene used as a marker for selection with ampicillin; "PR2" denotes the *Y. lipolytica* GPD1 promoter −931 to −1; "NG66" denotes the native *Rhodosporidium toruloides* DGA1 cDNA synthesized by GenScript; "TER1" denotes the *Y. lipolytica* CYC1 terminator 300 base pairs after stop; "PR22" denotes the *S. cerevisiae* TEF1 promoter −412 to −1; "NG3" denotes the *Streptomyces noursei* Nat1 gene used as a marker for selection with nourseothricin; "TER2" denotes the *S. cerevisiae* CYC1 terminator 275 base pairs after stop; and "Sc URA3" denotes the *S. cerevisiae* URA3 auxotrophic marker for selection in yeast.

Disclosed are methods and compositions for creating transformed cells with increased triacylglycerol content. Expressing the type 2 diacylglycerol acyltransferase DGA1 increases the amount of protein that can synthesize triacylglycerol, and expressing the DGA1 protein from *Rhodosporidium toruloides* in a *Yarrowia lipolytica* cell is effective at increasing the triacylglycerol content of the cell (U.S. Ser. No. 61/943,664 and PCT Patent Application No. PCT/US15/017227; hereby incorporated by reference). The type 1 diacylglycerol acyltransferase DGA2 can also catalyze the synthesis of triacylglycerol, and the expression of carefully selected DGA1 and DGA2 transgenes may further increase the lipid content of an oleaginous cell relative to DGA1 alone. Specifically, *Yarrowia lipolytica* that expresses DGA1 from *Rhodosporidium toruloides* and DGA2 from *Claviceps purpurea* produces high triacylglycerol yields. Finally, triacylglycerol lipases catalyze the degradation of triacylglycerols, and thus, the down-regulation of triacylglycerol lipases can increase the triacylglycerol content of a cell. Specifically, *Yarrowia lipolytica* cells that contain a TGL3 knockout and express DGA1 from *Rhodosporidium toruloides* produce higher triacylglycerol yields than DGA1-expressing controls (U.S. Ser. No. 61/987,098 and PCT Patent Application No. PCT/US15/28760; hereby incorporated by reference). The combination of DGA1 and DGA2 expression with TGL3 down-regulation may further increase triacylglycerol yields.

The simultaneous expression of DGA1 and DGA2 and concomitant down-regulation of TGL3 could be an attractive approach to increase the triacylglycerol content of a cell; however, the manipulation of proteins that affect a metabolic pathway is unpredictable at best. For example, the overexpression of native DGA2 alone in *Y. lipolytica* does not increase the cell's lipid production efficiency, whereas DGA1 increases lipid production. DGA2 localizes to the ER and synthesizes triacylglycerol in newly formed lipid bodies. In contrast, DGA1 localizes to lipid body membranes and synthesizes triacylglycerols within these lipid bodies. Whether this distinction or some other difference affects the cell's ability to suppress the effects of a genetic modification is not well understood. Thus, the combination of DGA1 and DGA2 expression with a TGL3 knockout would not be expected to produce cells with a higher lipid content than those cells containing one or two of the genetic modifications.

Disclosed is the successful combination of DGA1 and DGA2 expression and TGL3 down-regulation to increase the triacylglycerol content of a cell. For example, a *Yarrowia lipolytica* strain that contains a TGL3 knockout and expresses DGA1 from *Rhodosporidium toruloides* and DGA2 from *Claviceps purpurea* produced high triacylglycerol yields.

Definitions

The articles "a" and "an" are used herein to refer to one or to more than one (i.e., to at least one) of the grammatical object of the article. By way of example, "an element" means one element or more than one element.

The term "activity" refers to the total capacity of a cell to perform a function. For example, a genetic modification that decreases the activity of a triacylglycerol lipase in a cell may reduce the amount of triacylglycerol lipase in a cell or reduce the efficiency of triacylglycerol lipase. A triacylglycerol lipase knockout reduces the amount of triacylglycerol lipase in the cell. Alternatively, a mutation to a triacylglycerol lipase gene may reduce the efficiency of its triacylglycerol lipase protein product with little effect on the amount of cellular triacylglycerol lipase. Mutations that reduce the efficiency of triacylglycerol lipase may affect the active site, for example, by changing one or more active site residues; they may impair the enzyme's kinetics, for example, by sterically blocking substrates or products; they may affect protein folding or dynamics, for example, by reducing the proportion of properly-folded enzymes; they may affect protein localization, for example, by preventing the lipase from localizing to lipid particles; or they may affect protein degradation, for example, by adding one or more protein cleavage sites or by adding one or more residues or amino acid sequences that target the protein for proteolysis. These mutations affect coding regions. Mutations that decrease triacylglycerol lipase activity may instead affect the transcription or translation of the gene. For example, mutation to a triacylglycerol lipase enhancer or promoter can reduce triacylglycerol lipase activity by reducing its expression. Mutating or deleting the non-coding portions of a triacylglycerol lipase gene, such as its introns, may also reduce transcription or translation. Additionally, mutations to the upstream regulators of a triacylglycerol lipase may affect triacylglycerol lipase activity; for example, the over-expression of one or more repressors may decrease triacylglycerol lipase activity, and a knockout or mutation of one or more activators may similarly decrease triacylglycerol lipase activity.

A genetic modification that increases the activity of a diacylglycerol acyltransferase in a cell may increase the amount of triacylglycerol acyltransferase in a cell or increase the efficiency of diacylglycerol acyltransferase. For example, the genetic modification may simply insert an additional copy of diacylglycerol acyltransferase into the cell such that the additional copy is transcribed and translated into additional functional diacylglycerol acyltransferase. The added diacylglycerol acyltransferase gene can be native to the host organism or from a different organism. Alternatively, mutating or deleting the non-coding portions of a native diacylglycerol acyltransferase gene, such as its introns, may also increase translation. A native diacylglycerol acyltransferase gene can be altered by adding a new promoter that causes more transcription. Similarly, enhancers may be added to the diacylglycerol acyltransferase gene that increase transcription, or silencers may be mutated or deleted from the diacylglycerol acyltransferase gene to increase transcription. Mutations to a native gene's coding region might also increase diacylglycerol acyltransferase activity, for example, by producing a protein variant that does not interact with inhibitory proteins or molecules. The over-expression of one or more activators may increase diacylglycerol acyltransferase activity by increasing the expression of a diacylglycerol acyltransferase protein, and a knockout or mutation of one or more repressors may similarly increase diacylglycerol acyltransferase activity.

The term "biologically-active portion" refers to an amino acid sequence that is less than a full-length amino acid sequence, but exhibits at least one activity of the full length sequence. For example, a biologically-active portion of a diacylglycerol acyltransferase may refer to one or more domains of DGA1 or DGA2 having biological activity for converting acyl-CoA and diacylglycerol to triacylglycerol. Biologically-active portions of a DGA1 protein include peptides or polypeptides comprising amino acid sequences sufficiently similar to or derived from the amino acid sequence of the DGA1 protein, e.g., the amino acid sequence as set forth in SEQ ID NOs: 15, 17, 19, 21, 23, 25, 27, 29, 31, 33, 51, 53, 55, 57, 59, 61, 63, 65, 67, and 69, which include fewer amino acids than the full length DGA1, and exhibit at least one activity of a DGA1 protein. Similarly, biologically-active portions of a DGA2 protein include peptides or polypeptides comprising amino acid sequences sufficiently similar to or derived from the amino acid sequence of the DGA2 protein, e.g., the amino acid sequence as set forth in SEQ ID NOs: 1, 3, 5, 7, 9, 11, 13, 71, 73, 75, 77, 79, 81, and 83, which include fewer amino acids than the full length DGA2, and exhibit at least one activity of a DGA2 protein. Similarly, biologically-active portions of a DGA3 protein include peptides or polypeptides comprising amino acid sequences sufficiently similar to or derived from the amino acid sequence of the DGA3 protein, e.g., the amino acid sequence as set forth in SEQ ID NOs: 87 and 89, which include fewer amino acids than the full length DGA3, and exhibit at least one activity of a DGA3 protein. A biologically-active portion of a diacylglycerol acyltransferase may comprise, for example, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, or 696 amino acids. Typically, biologically active portions comprise a domain or motif having the catalytic activity of converting acyl-CoA and diacylglycerol to triacylglycerol. A biologically active portion of a DGA1 protein can be a polypeptide which is, for example, 262 amino acids in length.

The term "DGAT1" refers to a gene that encodes a type 1 diacylglycerol acyltransferase protein, such as a gene that encodes a DGA2 protein.

The term "DGAT2" refers to a gene that encodes a type 2 diacylglycerol acyltransferase protein, such as a gene that encodes a DGA1 protein.

The term "DGAT2" refers to a gene that encodes a type 3 diacylglycerol acyltransferase protein, such as a gene that encodes a DGA3 protein.

"Diacylglyceride," "diacylglycerol," and "diglyceride," are esters comprised of glycerol and two fatty acids.

The terms "diacylglycerol acyltransferase" and "DGA" refer to any protein that catalyzes the formation of triacylglycerides from diacylglycerol. Diacylglycerol acyltransferases include type 1 diacylglycerol acyltransferases (DGA2), type 2 diacylglycerol acyltransferases (DGA1), and type 3 diacylglycerol acyltransferases (DGA3) and all homologs that catalyze the above-mentioned reaction.

The terms "diacylglycerol acyltransferase, type 1" and "type 1 diacylglycerol acyltransferases" refer to DGA2 and DGA2 orthologs.

The terms "diacylglycerol acyltransferase, type 2" and "type 2 diacylglycerol acyltransferases" refer to DGA1 and DGA1 orthologs.

The terms "diacylglycerol acyltransferase, type 3" and "type 3 diacylglycerol acyltransferases" refer to DGA1 and DGA1 orthologs.

The term "domain" refers to a part of the amino acid sequence of a protein that is able to fold into a stable three-dimensional structure independent of the rest of the protein.

The term "drug" refers to any molecule that inhibits cell growth or proliferation, thereby providing a selective advantage to cells that contain a gene that confers resistance to the drug. Drugs include antibiotics, antimicrobials, toxins, and pesticides.

"Dry weight" and "dry cell weight" mean weight determined in the relative absence of water. For example, reference to oleaginous cells as comprising a specified percentage of a particular component by dry weight means that the percentage is calculated based on the weight of the cell after substantially all water has been removed.

The term "encode" refers to nucleic acids that comprise a coding region, portion of a coding region, or compliments thereof. Both DNA and RNA may encode a gene. Both DNA and RNA may encode a protein.

The term "exogenous" refers to anything that is introduced into a cell. An "exogenous nucleic acid" is a nucleic acid that entered a cell through the cell membrane. An exogenous nucleic acid may contain a nucleotide sequence that exists in the native genome of a cell and/or nucleotide sequences that did not previously exist in the cell's genome. Exogenous nucleic acids include exogenous genes. An "exogenous gene" is a nucleic acid that codes for the expression of an RNA and/or protein that has been introduced into a cell (e.g., by transformation/transfection), and is also referred to as a "transgene." A cell comprising an exogenous gene may be referred to as a recombinant cell, into which additional exogenous gene(s) may be introduced. The exogenous gene may be from the same or different species relative to the cell being transformed. Thus, an exogenous gene can include a native gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

The term "expression" refers to the amount of a nucleic acid or amino acid sequence (e.g., peptide, polypeptide, or protein) in a cell. The increased expression of a gene refers to the increased transcription of that gene. The increased expression of an amino acid sequence, peptide, polypeptide, or protein refers to the increased translation of a nucleic acid encoding the amino acid sequence, peptide, polypeptide, or protein.

The term "gene," as used herein, may encompass genomic sequences that contain exons, particularly polynucleotide sequences encoding polypeptide sequences involved in a specific activity. The term further encompasses synthetic nucleic acids that did not derive from genomic sequence. In certain embodiments, the genes lack introns, as they are synthesized based on the known DNA sequence of cDNA and protein sequence. In other embodiments, the genes are synthesized, non-native cDNA wherein the codons have been optimized for expression in *Y. lipolytica* based on codon usage. The term can further include nucleic acid molecules comprising upstream, downstream, and/or intron nucleotide sequences.

The term "genetic modification" refers to the result of a transformation. Every transformation causes a genetic modification by definition.

The term "homolog", as used herein, refers to (a) peptides, oligopeptides, polypeptides, proteins, and enzymes having amino acid substitutions, deletions and/or insertions relative to the unmodified protein in question and having similar biological and functional activity as the unmodified protein from which they are derived, and (b) nucleic acids which encode peptides, oligopeptides, polypeptides, proteins, and enzymes with the same characteristics described in (a).

"Inducible promoter" is a promoter that mediates the transcription of an operably linked gene in response to a particular stimulus.

The term "integrated" refers to a nucleic acid that is maintained in a cell as an insertion into the cell's genome, such as insertion into a chromosome, including insertions into a plastid genome.

"In operable linkage" refers to a functional linkage between two nucleic acid sequences, such a control sequence (typically a promoter) and the linked sequence (typically a sequence that encodes a protein, also called a coding sequence). A promoter is in operable linkage with a gene if it can mediate transcription of the gene.

The term "knockout mutation" or "knockout" refers to a genetic modification that prevents a native gene from being transcribed and translated into a functional protein.

The term "native" refers to the composition of a cell or parent cell prior to a transformation event. A "native gene" refers to a nucleotide sequence that encodes a protein that has not been introduced into a cell by a transformation event. A "native protein" refers to an amino acid sequence that is encoded by a native gene.

The terms "nucleic acid" refers to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The term "parent cell" refers to every cell from which a cell descended. The genome of a cell is comprised of the parent cell's genome and any subsequent genetic modifications to the parent cell's genome.

As used herein, the term "plasmid" refers to a circular DNA molecule that is physically separate from an organism's genomic DNA. Plasmids may be linearized before being introduced into a host cell (referred to herein as a linearized plasmid). Linearized plasmids may not be self-replicating, but may integrate into and be replicated with the genomic DNA of an organism.

The term "portion" refers to peptides, oligopeptides, polypeptides, protein domains, and proteins. A nucleotide sequence encoding a "portion of a protein" includes both nucleotide sequences that can be transcribed and/or translated and nucleotide sequences that must undergo one or more recombination events to be transcribed and/or translated. For example, a nucleic acid may comprise a nucleotide sequence encoding one or more amino acids of a selectable marker protein. This nucleic acid can be engineered to recombine with one or more different nucleotide sequences that encode the remaining portion of the protein. Such nucleic acids are useful for generating knockout mutations because only recombination with the target sequence is likely to reconstitute the full-length selectable marker gene whereas random-integration events are unlikely to result in a nucleotide sequence that can produce a functional marker protein. A "biologically-active portion" of a polypeptide is any amino acid sequence found in the polypeptide's amino acid sequence that is less than the full amino acid sequence but can perform the same function as the full-length polypeptide. A biologically-active portion of a diacylglycerol acyltransferase includes any amino acid sequence found in a full-length diacylglycerol acyltransferase that can catalyze the formation of triacylglycerol from diacylglycerol and acyl-CoA. A biologically-active portion of a polypeptide includes portions of the polypeptide that have the same activity as the full-length peptide and every portion that has more activity than background. For example, a biologically-active portion of a diacylglycerol acyltransferase may have 0.1, 0.5, 1, 2, 3, 4, 5, 10, 25, 30, 35, 40, 45, 50, 55, 60, 65, 70, 75, 80, 85, 86, 87, 88, 89, 90, 91, 92, 93, 94, 95, 96, 97, 98, 99, 99.5, 99.6, 99.7, 99.8, 99.9, 100, 100.1, 100.2, 100.3, 100.4, 100.5, 100.6, 100.7, 100.8, 100.9, 101, 105, 110, 115, 120, 125, 130, 135, 140, 145, 150, 160, 170, 180, 190, 200, 220, 240, 260, 280, 300, 320, 340, 360, 380, 400 percent activity relative to the full-length polypeptide or higher. A biologically-active portion of a polypeptide may include portions of a peptide that lack a domain that targets the polypeptide to a cellular compartment.

A "promoter" is a nucleic acid control sequence that directs the transcription of a nucleic acid. As used herein, a promoter includes the necessary nucleic acid sequences near the start site of transcription. A promoter also optionally includes distal enhancer or repressor elements, which can be located as much as several thousand base pairs from the start site of transcription.

"Recombinant" refers to a cell, nucleic acid, protein, or vector, which has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi), or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

The term "regulatory region" refers to nucleotide sequences that affect the transcription or translation of a gene but do not encode an amino acid sequence. Regulatory regions include promoters, operators, enhancers, and silencers.

"Transformation" refers to the transfer of a nucleic acid into a host organism or the genome of a host organism, resulting in genetically stable inheritance. Host organisms containing the transformed nucleic acid fragments are referred to as "recombinant", "transgenic" or "transformed" organisms. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region (e.g., a regulatory region controlling inducible or constitutive, environmentally- or developmentally-regulated, or location-specific expression), a transcription initiation start site, a ribosome binding site, a transcription termination site, and/or a polyadenylation signal.

The term "transformed cell" refers to a cell that has undergone a transformation. Thus, a transformed cell comprises the parent's genome and an inheritable genetic modification.

The terms "triacylglyceride," "triacylglycerol," "triglyceride," and "TAG" are esters comprised of glycerol and three fatty acids.

The term "triacylglycerol lipase" refers to any protein that can catalyze the removal of a fatty acid chain from a triacylglycerol. Triacylglycerol lipases include TGL3, TGL4, and TGL3/4.

The term "vector" refers to the means by which a nucleic acid can be propagated and/or transferred between organisms, cells, or cellular components. Vectors include plasmids, linear DNA fragments, viruses, bacteriophage, proviruses, phagemids, transposons, and artificial chromosomes, and the like, that may or may not be able to replicate autonomously or integrate into a chromosome of a host cell.

Microbe Engineering

A. Overview

In certain embodiments, the invention relates to a microorganism genetically modified to increase its triacylglycerol content or modify its lipid profile.

Genes and gene products may be introduced into microbial host cells. Suitable host cells for expression of the genes and nucleic acid molecules are microbial hosts that can be found broadly within the fungal or bacterial families. Examples of suitable host strains include but are not limited to fungal or yeast species, such as *Arxula, Aspergillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces, Yarrowia*, or bacterial species, such as members of proteobacteria and actinomycetes, as well as the genera *Acinetobacter, Arthrobacter, Brevibacterium, Acidovorax, Bacillus, Clostridia, Streptomyces, Escherichia, Salmonella, Pseudomonas*, and *Cornyebacterium. Yarrowia lipolytica* and *Arxula adeninivorans* are well-suited for use as the host microorganism because they can accumulate a large percentage of their weight as triacylglycerols.

Microbial expression systems and expression vectors containing regulatory sequences that direct high level expression of foreign proteins are known to those skilled in the art. Any of these could be used to construct chimeric genes to produce any one of the gene products of the instant sequences. These chimeric genes could then be introduced into appropriate microorganisms via transformation techniques to provide high-level expression of the enzymes.

For example, a gene encoding an enzyme can be cloned in a suitable plasmid, and an aforementioned starting parent strain as a host can be transformed with the resulting plasmid. This approach can increase the copy number of each of the genes encoding the enzymes and, as a result, the activities of the enzymes can be increased. The plasmid is not particularly limited so long as it renders a desired genetic modification inheritable to the microorganism's progeny.

Vectors or cassettes useful for the transformation of suitable host cells are well known in the art. Typically the vector or cassette contains sequences that direct the transcription and translation of the relevant gene, a selectable marker, and sequences that allow autonomous replication or chromosomal integration. Suitable vectors comprise a region 5' of the gene harboring transcriptional initiation controls and a region 3' of the DNA fragment which controls transcriptional termination. Both control regions may be derived from genes homologous to the transformed host cell, although it is to be understood that such control regions need not be derived from the genes native to the specific species chosen as a production host.

Promoters, cDNAs, and 3'UTRs, as well as other elements of the vectors, can be generated through cloning techniques using fragments isolated from native sources (Green & Sambrook, *Molecular Cloning: A Laboratory Manual*, (4th ed., 2012); U.S. Pat. No. 4,683,202; hereby incorporated by reference). Alternatively, elements can be generated synthetically using known methods (Gene 164:49-53 (1995)).

B. Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding homologous genomic sequences.

The ability to carry out homologous recombination in a host organism has many practical implications for what can be carried out at the molecular genetic level and is useful in the generation of a microbe that can produce a desired product. By its very nature homologous recombination is a precise gene targeting event, and hence, most transgenic lines generated with the same targeting sequence will be essentially identical in terms of phenotype, necessitating the screening of far fewer transformation events. Homologous recombination also targets gene insertion events into the host chromosome, potentially resulting in excellent genetic stability, even in the absence of genetic selection. Because different chromosomal loci will likely impact gene expression, even from exogenous promoters/UTRs, homologous recombination can be a method of querying loci in an unfamiliar genome environment and to assess the impact of these environments on gene expression.

A particularly useful genetic engineering approach using homologous recombination is to co-opt specific host regulatory elements such as promoters/UTRs to drive heterologous gene expression in a highly specific fashion.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, thereby affecting a desired change in the metabolism of the host cell. Homologous recombination provides a powerful means to manipulate the host genome resulting in gene targeting, gene conversion, gene deletion, gene duplication, gene inversion, and exchanging gene expression regulatory elements such as promoters, enhancers and 3'UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) by cutting the transgenic DNA with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

C. Vectors and Vector Components

Vectors for transforming microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell.

1. Control Sequences

Control sequences are nucleic acids that regulate the expression of a coding sequence or direct a gene product to a particular location inside or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location inside or outside the cell.

Thus, an exemplary vector design for expression of a gene in a microbe contains a coding sequence for a desired gene product (for example, a selectable marker, or an enzyme) in operable linkage with a promoter active in yeast. Alternatively, if the vector does not contain a promoter in operable linkage with the coding sequence of interest, the coding sequence can be transformed into the cells such that it becomes operably linked to an endogenous promoter at the point of vector integration.

The promoter used to express a gene can be the promoter naturally linked to that gene or a different promoter.

A promoter can generally be characterized as constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule, temperature (heat or cold), lack of nitrogen in culture media, etc. Suitable promoters can activate transcription of an essentially silent gene or upregulate, preferably substantially, transcription of an operably linked gene that is transcribed at a low level.

Inclusion of termination region control sequence is optional, and if employed, then the choice is primarily one of convenience, as the termination region is relatively interchangeable. The termination region may be native to the transcriptional initiation region (the promoter), may be native to the DNA sequence of interest, or may be obtainable from another source (See, e.g., Chen & Orozco, Nucleic Acids Research 16:8411 (1988)).

2. Genes and Codon Optimization

Typically, a gene includes a promoter, coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., an episome), in which case, the vector typically includes an origin of replication, which is capable of providing for replication of the vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. Any of a wide variety of selectable markers can be employed in a transgene construct useful for transforming the organisms of the invention.

For optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the transgenic mRNA resulting in ribosomal stalling and termination and possible instability of the transgenic mRNA.

C. Transformation

Cells can be transformed by any suitable technique including, e.g., biolistics, electroporation, glass bead transformation, and silicon carbide whisker transformation. Any convenient technique for introducing a transgene into a microorganism can be employed in the present invention. Transformation can be achieved by, for example, the method of D. M. Morrison (Methods in Enzymology 68:326 (1979)), the method by increasing permeability of recipient cells for DNA with calcium chloride (Mandel & Higa, J. Molecular Biology, 53:159 (1970)), or the like.

Examples of expression of transgenes in oleaginous yeast (e.g., *Yarrowia lipolytica*) can be found in the literature (Bordes et al., J. Microbiological Methods, 70:493 (2007); Chen et al., Applied Microbiology & Biotechnology 48:232 (1997)). Examples of expression of exogenous genes in bacteria such as *E. coli* are well known (Green & Sambrook, *Molecular Cloning: A Laboratory Manual*, (4th ed., 2012)).

Vectors for transformation of microorganisms in accordance with the present invention can be prepared by known techniques familiar to those skilled in the art. In one embodiment, an exemplary vector design for expression of a gene in a microorganism contains a gene encoding an enzyme in operable linkage with a promoter active in the microorganism. Alternatively, if the vector does not contain a promoter in operable linkage with the gene of interest, the gene can be transformed into the cells such that it becomes operably linked to a native promoter at the point of vector integration. The vector can also contain a second gene that encodes a protein. Optionally, one or both gene(s) is/are followed by a 3' untranslated sequence containing a polyadenylation signal. Expression cassettes encoding the two genes can be physically linked in the vector or on separate vectors. Co-transformation of microbes can also be used, in which distinct vector molecules are simultaneously used to transform cells (Protist 155:381-93 (2004)). The transformed cells can be optionally selected based upon the ability to grow in the presence of the antibiotic or other selectable marker under conditions in which cells lacking the resistance cassette would not grow.

Exemplary Nucleic Acids, Cells, and Methods

A. Diacylglycerol Acyltransferase Nucleic Acid Molecules and Vectors

In some embodiments, the type 2 diacylglycerol acyltransferase is DGA1. For example, the diacylglycerol acyltransferase may be a DGA1 protein encoded by a DGAT2 gene selected from the group consisting of *Arxula adeninivorans, Aspergillus terreus, Aurantiochytrium limacinum, Claviceps purpurea, Gloeophyllum trabeum, Lipomyces starkeyi, Microbotryum violaceum, Pichia guilliermondii, Phaeodactylum tricornutum, Puccinia graminis, Rhodosporidium diobovatum, Rhodosporidium toruloides, Rhodotorula graminis*, and *Yarrowia lipolytica*.

The DGAT2 gene may have a nucleotide sequence set forth in SEQ ID NO: 16, 18, 20, 22, 24, 26, 28, 30, 32, 34, 52, 54, 56, 58, 60, 62, 64, 66, 68, or 70. In other embodiments, the DGAT2 gene is substantially identical to SEQ ID NO: 16, 18, 20, 22, 24, 26, 28, 30, 32, 34, 52, 54, 56, 58, 60, 62, 64, 66, 68, or 70, and the nucleotide sequence encodes a protein that retains the functional activity of a protein encoded by SEQ ID NO: 16, 18, 20, 22, 24, 26, 28, 30, 32, 34, 52, 54, 56, 58, 60, 62, 64, 66, 68, or 70, yet differs in nucleotide sequence due to natural allelic variation or mutagenesis. In another embodiment, the DGAT2 gene comprises a nucleotide sequence at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO: 16, 18, 20, 22, 24, 26, 28, 30, 32, 34, 52, 54, 56, 58, 60, 62, 64, 66, 68, or 70.

The DGA1 protein may have an amino acid sequence set forth in SEQ ID NO: 15, 17, 19, 21, 23, 25, 27, 29, 31, 33, 51, 53, 55, 57, 59, 61, 63, 65, 67, or 69. In other embodiments, the DGA1 protein is substantially identical to SEQ ID NO: 15, 17, 19, 21, 23, 25, 27, 29, 31, 33, 51, 53, 55, 57, 59, 61, 63, 65, 67, or 69, and retains the functional activity of the protein of SEQ ID NO: 15, 17, 19, 21, 23, 25, 27, 29, 31, 33, 51, 53, 55, 57, 59, 61, 63, 65, 67, or 69, yet differs in amino acid sequence due to natural allelic variation or mutagenesis. In another embodiment, the DGA1 protein comprises an amino acid sequence at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO: 15, 17, 19, 21, 23, 25, 27, 29, 31, 33, 51, 53, 55, 57, 59, 61, 63, 65, 67, or 69.

In some embodiments, the type 1 diacylglycerol acyltransferase is DGA2. For example, the diacylglycerol acyltransferase may be a DGA2 protein encoded by a DGAT1 gene found in an organism selected from the group consisting of *Arxula adeninivorans, Aspergillus terreus, Chaetomium globosum, Claviceps purpurea, Lipomyces starkeyi, Metarhizium acridum, Ophiocordyceps sinensis, Phaeodactylum tricornutum, Pichia guilliermondii, Rhodosporidium toruloides, Rhodotorula graminis, Trichoderma vixens*, and *Yarrowia lipolytica*.

The DGAT1 gene may have a nucleotide sequence set forth in SEQ ID NO: 2, 4, 6, 8, 10, 12, 14, 72, 74, 76, 78, 80, 82, or 84. In other embodiments, the DGAT1 gene is substantially identical to SEQ ID NO: 2, 4, 6, 8, 10, 12, 14, 72, 74, 76, 78, 80, 82, or 84, and the nucleotide sequence encodes a protein that retains the functional activity of a protein encoded by SEQ ID NO: 2, 4, 6, 8, 10, 12, 14, 72, 74, 76, 78, 80, 82, or 84, yet differs in nucleotide sequence due to natural allelic variation or mutagenesis. In another embodiment, the DGAT1 gene comprises a nucleotide sequence at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO: 2, 4, 6, 8, 10, 12, 14, 72, 74, 76, 78, 80, 82, or 84.

The DGA2 protein may have an amino acid sequence set forth in SEQ ID NO: 1, 3, 5, 7, 9, 11, 13, 71, 73, 75, 77, 79, 81, or 83. In other embodiments, the DGA2 protein is substantially identical to SEQ ID NO: 1, 3, 5, 7, 9, 11, 13, 71, 73, 75, 77, 79, 81, or 83, and retains the functional activity of the protein of SEQ ID NO: 1, 3, 5, 7, 9, 11, 13, 71, 73, 75, 77, 79, 81, or 83, yet differs in amino acid sequence due to natural allelic variation or mutagenesis. In another embodiment, the DGA2 protein comprises an amino acid sequence at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO: 1, 3, 5, 7, 9, 11, 13, 71, 73, 75, 77, 79, 81, or 83.

In some embodiments, the type 3 diacylglycerol acyltransferase is DGA3. For example, the diacylglycerol acyltransferase may be a DGA3 protein encoded by a DGAT3 gene found in an organism selected from the group consisting of *Ricinus communis* and *Arachis hypogaea*.

The DGAT3 gene may have a nucleotide sequence set forth in SEQ ID NO: 88 or 90. In other embodiments, the DGAT3 gene is substantially identical to SEQ ID NO: 88 or 90, and the nucleotide sequence encodes a protein that retains the functional activity of a protein encoded by SEQ ID NO: 87 or 89, yet differs in nucleotide sequence due to natural allelic variation or mutagenesis. In another embodiment, the DGAT3 gene comprises a nucleotide sequence at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO: 88 or 90.

The DGA3 protein may have an amino acid sequence set forth in SEQ ID NO: 87 or 89. In other embodiments, the DGA3 protein is substantially identical to SEQ ID NO: 87 or 89, and retains the functional activity of the protein of SEQ ID NO: 87 or 89, yet differs in amino acid sequence due to natural allelic variation or mutagenesis. In another embodiment, the DGA3 protein comprises an amino acid sequence at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO: 87 or 89.

The DGAT1, DGAT2, or DGA3 genes may comprise conservative substitutions, deletions, and/or insertions while still encoding a protein that has functional diacylglycerol acyltransferase activity. For example, the DGAT1, DGAT2, or DGA3 codons may be optimized for a particular host cell, different codons may be substituted for convenience, such as to introduce a restriction site or create optimal PCR primers, or codons may be substituted for another purpose. Similarly, the nucleotide sequence may be altered to create conservative amino acid substitutions, deletions, and/or insertions.

The DGA1, DGA2, and DGA3 polypeptides may comprise conservative substitutions, deletions, and/or insertions while still maintaining functional diacylglycerol acyltransferase activity. Conservative substitution tables are well known in the art (Creighton, *Proteins* (2d. ed., 1992)).

Amino acid substitutions, deletions and/or insertions may readily be made using recombinant DNA manipulation techniques. Methods for the manipulation of DNA sequences to produce substitution, insertion or deletion variants of a protein are well known in the art. These methods include M13 mutagenesis, T7-Gen in vitro mutagenesis (USB, Cleveland, OHIO), Quick Change Site Directed mutagenesis (Stratagene, San Diego, Calif.), PCR-mediated site-directed mutagenesis, and other site-directed mutagenesis protocols.

To determine the percent identity of two amino acid sequences or of two nucleic acid sequences, the sequences can be aligned for optimal comparison purposes (e.g., gaps can be introduced in one or both of a first and a second amino acid or nucleic acid sequence for optimal alignment and non-identical sequences can be disregarded for comparison purposes). The length of a reference sequence aligned for comparison purposes can be at least 95% of the length of the reference sequence. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences can be determined using the Needleman and Wunsch (J. Molecular Biology 48:444-453 (1970)) algorithm which has been incorporated into the GAP program in the GCG software package (available at the World Wide Web at gcg.com), using either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences can be determined using the GAP program in the GCG software package (available at the World Wide Web at gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences can be determined using the algorithm of E. Meyers and W. Miller (Computer Applications in the Biosciences 4:11-17 (1988)) which has been incorporated into the ALIGN program (version 2.0 or 2.0U), using a PAM120 weight residue table, a gap length penalty of 12 and a gap penalty of 4.

Exemplary computer programs which can be used to determine identity between two sequences include, but are not limited to, the suite of BLAST programs, e.g., BLASTN, MEGABLAST, BLASTX, TBLASTN, TBLASTX, and BLASTP, and Clustal programs, e.g., ClustalW, ClustalX, and Clustal Omega.

Sequence searches are typically carried out using the BLASTN program, when evaluating a given nucleic acid sequence relative to nucleic acid sequences in the GenBank DNA Sequences and other public databases. The BLASTX program is effective for searching nucleic acid sequences that have been translated in all reading frames against amino acid sequences in the GenBank Protein Sequences and other public databases.

An alignment of selected sequences in order to determine "% identity" between two or more sequences is performed using for example, the CLUSTAL-W program.

A "coding sequence" or "coding region" refers to a nucleic acid molecule having sequence information necessary to produce a protein product, such as an amino acid or polypeptide, when the sequence is expressed. The coding sequence may comprise and/or consist of untranslated sequences (including introns or 5' or 3' untranslated regions) within translated regions, or may lack such intervening untranslated sequences (e.g., as in cDNA).

The abbreviation used throughout the specification to refer to nucleic acids comprising and/or consisting of nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, unless otherwise specified, the nucleic acid sequences presented herein is the 5'→3' direction.

As used herein, the term "complementary" and derivatives thereof are used in reference to pairing of nucleic acids by the well-known rules that A pairs with T or U and C pairs with G. Complement can be "partial" or "complete". In partial complement, only some of the nucleic acid bases are matched according to the base pairing rules; while in complete or total complement, all the bases are matched according to the pairing rule. The degree of complement between the nucleic acid strands may have significant effects on the efficiency and strength of hybridization between nucleic acid strands as well known in the art. The efficiency and strength of said hybridization depends upon the detection method.

As used herein, "DGA1" means a diacylglycerol acyltransferase type 2 (DGAT2). DGA1 is an integral membrane protein that catalyzes the final enzymatic step in oil biosynthesis and the production of triacylglycerols in plants, fungi, and mammals. The DGA1 may play a key role in altering the quantity of long-chain polyunsaturated fatty acids produced in oils of oleaginous organisms. DGA1 is related to the acyl-coenzyme A:cholesterol acyltransferase ("ACAT"). This enzyme is responsible for transferring an acyl group from acyl-coenzyme-A to the sn-3 position of 1,2-diacylglycerol ("DAG") to form triacylglycerol ("TAG") (thereby involved in the terminal step of TAG biosynthesis). DGA1 is associated with membrane and lipid body fractions in plants and fungi, particularly, in oilseeds where it contributes to the storage of carbon used as energy reserves. TAG is believed to be an important chemical for storage of energy in cells. DGA1 is known to regulate TAG structure and direct TAG synthesis.

The DGA1 polynucleotide and polypeptide sequences may be derived from highly oleaginous organisms having very high, native levels of lipid accumulation. (Bioresource Technology 144:360-69 (2013); Progress Lipid Research 52:395-408 (2013); Applied Microbiology & Biotechnology 90:1219-27 (2011); European Journal Lipid Science & Technology 113:1031-51 (2011); Food Technology & Biotechnology 47:215-20 (2009); Advances Applied Microbiology 51:1-51 (2002); Lipids 11:837-44 (1976)). A list of organisms with a reported lipid content of about 50% and higher is shown in Table 1. *R. toruloides* and *L. starkeyi* have the highest lipid content. Among the organisms in Table 1, five have publicly accessible sequence for DGA1, *R. toruloides, L. starkeyi, A. limacinum, A. terreus*, and *C. purpurea* (bolded in Table 1).

TABLE 1

| List of oleaginous fungi with reported lipid contents of about 50% and above. Organisms with publicly accessible sequences for DGA1 gene are in bold. |
|---|
| ***Aspergillus terreus*** |
| ***Aurantiochytrium limacinum*** |
| ***Claviceps purpurea*** |
| *Cryptococcus albidus* |
| *Cryptococcus curvatus* |
| *Cryptococcus ramirezgomezianus* |
| *Cryptococcus terreus* |
| *Cryptococcus wieringae* |
| *Cunninghamella echinulata* |
| *Cunninghamella japonica* |
| *Leucosporidiella creatinivora* |
| *Lipomyces lipofer* |
| ***Lipomyces starkeyi*** |
| *Lipomyces tetrasporus* |
| *Mortierella isabellina* |
| *Prototheca zopfii* |
| *Rhizopus arrhizus* |
| *Rhodosporidium babjevae* |
| *Rhodosporidium paludigenum* |
| ***Rhodosporidium toruloides*** |
| *Rhodotorula glutinis* |
| *Rhodotorula mucilaginosa* |
| *Tremella enchepala* |
| *Trichosporon cutaneum* |
| *Trichosporon fermentans* |

Nucleic acid constructs for increasing the activity of DGA1 were described in U.S. Ser. No. 61/943,664, and PCT Patent Application No. PCT/US15/017227 (hereby incorporated by reference). FIG. 1 shows expression construct pNC243 used for expression of the *Rhodosporidium toruloides* DGA1 gene NG66 (SEQ ID NO:20) in *Y. lipolytica*. DGA1 expression constructs were linearized before transformation by a PacI/NotI restriction digest. The linear expression constructs each included the expression cassette for DGA1 and for the Nat1 gene, used as marker for selection with nourseothricin (NAT).

Figure 3:
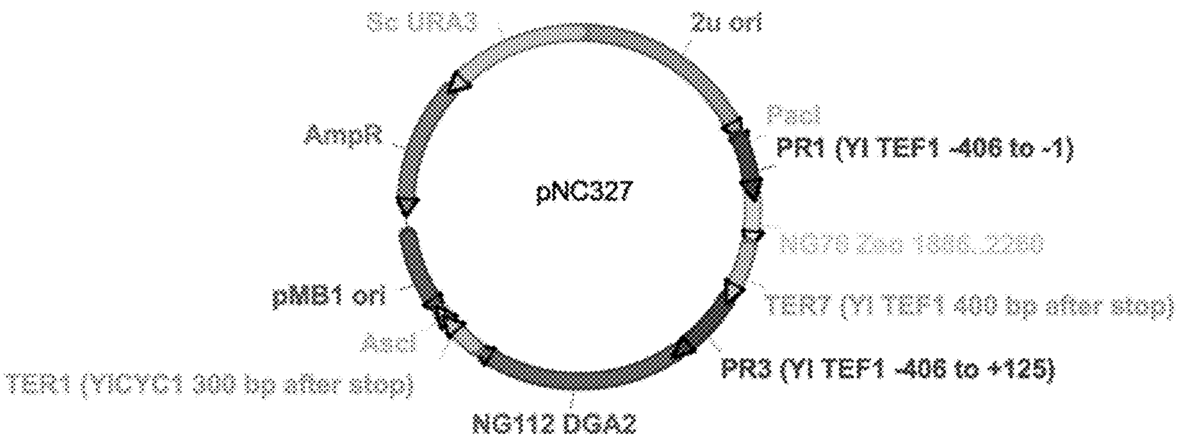
FIG. 3 depicts a map of the pNC327 construct used to express the NG112 gene (*C. purpurea* DGA2) in *Y. lipolytica*. Vector pNC327 was linearized by a PacI/AscI restriction digest before transformation. "2u ori" denotes the *S. cerevisiae origin of replication from the* 2 μm circle plasmid; "pMB1 ori" denotes the *E. coli* pMB1 origin of replication from the pBR322 plasmid; "AmpR" denotes the bla gene used as a marker for selection with ampicillin; "PR3" denotes the *Y. lipolytica* TEF1 promoter −406 to +125; "NG112" denotes the *C. purpurea* DGA2 gene synthetized by GenScript; "TER1" denotes the *Y. lipolytica* CYC1 terminator 300 bp after stop; "PR1" denotes the *Y. lipolytica* TEF1 promoter −406 to −1; "NG76" denotes the *Streptoalloteichus hindustanus* BLE gene used as a marker for selection with Zeocin; "TER7" denotes the *Y. lipolytica* TEF1 terminator 400 bp after stop; and "Sc URA3" denotes the *S. cerevisiae* URA3 auxotrophic marker for selection in yeast.

Nucleic acid constructs for increasing the activity of DGA2 and/or other diacylglycerol acyltransferases may be created using the methods described above and/or other methods known in the art. FIG. 3 shows expression construct pNC327 used for expression of the *Claviceps purpurea* DGA2 gene NG112 (SEQ ID NO:9) in *Y. lipolytica*. DGA2 expression constructs were linearized before transformation by a PacI/AscI restriction digest. The linear expression constructs each included the expression cassette for DGA2 and for the BLE gene, used as marker for selection with Zeocin.

Nucleic acid constructs for increasing the activity of DGA3 and/or other diacylglycerol acyltransferases may be created using the methods described above and/or other methods known in the art.

B. Triacylglycerol Lipase Nucleic Acid Molecules and Vectors

Triacylglycerol lipase depletes a cell's triacylglycerol by removing one or more fatty acid chains. Thus, decreasing the net triacylglycerol lipase activity of a cell may increase the cell's triacylglycerol. This decrease may be accomplished by reducing the efficiency of the enzyme, e.g., by mutating amino acids in its active site, or by reducing the expression of the enzyme. For example, a TGL3 knockout mutation will decrease the activity of a triacylglycerol lipase because it prevents the cell from transcribing TGL3. Triacylglycerol lipase knockouts are described in U.S. Ser. No. 61/987,098 and PCT Patent Application No. PCT/US15/28760 (hereby incorporated by reference).

In some embodiments, the triacylglycerol lipase is TGL3. In other embodiments, the triacylglycerol lipase is TGL3/4 or TGL4.

The TGL3 gene in *Y. lipolytica* encodes the triacylglycerol lipase protein TGL3 (SEQ ID NO:41), and the TGL4 gene in *Y. lipolytica* encodes the triacylglycerol lipase protein TGL4 (SEQ ID NO:85). SEQ ID NO:42 contains the TGL3 nucleotide sequence, 100 upstream nucleotides, and 100 downstream nucleotides. Thus, the SEQ ID NO:42 nucleotide sequence may be used to design a nucleic acid capable of recombining with a nucleic acid sequence in a native *Y. lipolytica* triacylglycerol lipase gene. Similarly, SEQ ID NO:86 contains the TGL4 nucleotide sequence. Thus, the SEQ ID NO:86 nucleotide sequence may be used to design a nucleic acid capable of recombining with a nucleic acid sequence in a native *Y. lipolytica* triacylglycerol lipase gene.

Knockout cassettes SEQ ID NOs: 49 and 50 are capable of recombining with the native TGL3 gene in *Y. lipolytica*. Thus, in some embodiments, the nucleic acids encoded by SEQ ID NOs: 49 and 50 may be used to generate a triacylglycerol lipase knockout mutation in *Y. lipolytica*. SEQ ID NOs: 49 and 50 each contain portions of a hygromycin resistance gene hph. Neither isolated sequence encodes a functional protein, but the two sequences are capable of encoding a functional kinase that confers hygromycin resistance upon successful recombination. Further, neither SEQ ID NO:49 nor SEQ ID NO:50 contains a promoter or terminator, and thus, they rely on homologous recombination with the *Y. lipolytica* TGL3 gene in order for the hph gene to be transcribed and translated. In this way, successfully transformed oleaginous cells may be selected by growing the cells on medium containing hygromycin.

Knockout cassette SEQ ID NO:49 may be prepared by amplifying a hygromycin resistance gene hph (SEQ ID NO:44) with primer NP1798 (SEQ ID NO:47) and primer NP656 (SEQ ID NO:46). Knockout cassette SEQ ID NO:50 may be prepared by amplifying a hygromycin resistance gene hph (SEQ ID NO:44) with primer NP655 (SEQ ID NO:45) and primer NP1799 (SEQ ID NO:48).

Different approaches may be used to design nucleic acids that reduce the activity of TGL3 in *Y. lipolytica* (Biochimica Biophysica Acta 1831:1486-95 (2013)). The methods disclosed herein and other methods known in the art may be used to reduce triacylglycerol lipase activity in other species. For example, these methods may be used to reduce the activity of the TGL3 gene of *Arxula adeninivorans* (SEQ ID NO:36), the TGL3/4 gene of *Arxula adeninivorans* (SEQ ID NO:38), or the TGL4 gene of *Arxula adeninivorans* (SEQ ID NO:40).

C. Transformed Cell

In some embodiments, the transformed cell is a prokaryotic cell, such as a bacterial cell. In some embodiments, the cell is a eukaryotic cell, such as a mammalian cell, a yeast cell, a filamentous fungi cell, a protist cell, an algae cell, an avian cell, a plant cell, or an insect cell.

The cell may be selected from the group consisting of *Arxula, Aspergillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces*, and *Yarrowia*.

In some embodiments, the cell is selected from the group consisting of *Arxula adeninivorans, Aspergillus niger, Aspergillus orzyae, Aspergillus terreus, Aurantiochytrium*

*limacinum*, *Candida utilis*, *Claviceps purpurea*, *Cryptococcus albidus*, *Cryptococcus curvatus*, *Cryptococcus ramirezgomezianus*, *Cryptococcus terreus*, *Cryptococcus wieringae*, *Cunninghamella echinulata*, *Cunninghamella japonica*, *Geotrichum fermentans*, *Hansenula polymorpha*, *Kluyveromyces lactis*, *Kluyveromyces marxianus*, *Kodamaea ohmeri*, *Leucosporidiella creatinivora*, *Lipomyces lipofer*, *Lipomyces starkeyi*, *Lipomyces tetrasporus*, *Mortierella isabellina*, *Mortierella alpina*, *Ogataea polymorpha*, *Pichia ciferrii*, *Pichia guilliermondii*, *Pichia pastoris*, *Pichia stipites*, *Prototheca zopfii*, *Rhizopus arrhizus*, *Rhodosporidium babjevae*, *Rhodosporidium toruloides*, *Rhodosporidium paludigenum*, *Rhodotorula glutinis*, *Rhodotorula mucilaginosa*, *Saccharomyces cerevisiae*, *Schizosaccharomyces pombe*, *Tremella enchepala*, *Trichosporon cutaneum*, *Trichosporon fermentans*, *Wickerhamomyces ciferrii*, and *Yarrowia lipolytica*.

In certain embodiments, the transformed cell is a high-temperature tolerant yeast cell. In some embodiments the transformed cell is *Kluyveromyces marxianus*.

In certain embodiments, the cell is *Yarrowia lipolytica* or *Arxula adeninivorans*.

D. Increasing the Activity of a Diacylglycerol Acyltransferase in a Cell

A protein's activity may be increased by overexpressing the protein. Proteins may be overexpressed in a cell using a variety of genetic modifications. In some embodiments, the genetic modification increases the expression of a native diacylglycerol acyltransferase. A native diacylglycerol acyltransferase may be overexpressed by modifying the upstream transcription regulators of a native diacylglycerol acyltransferase gene, for example, by increasing the expression of a transcription activator or decreasing the expression of a transcription repressor. Alternatively, the promoter of a native diacylglycerol acyltransferase gene may be substituted with a constitutively active or inducible promoter by recombination with an exogenous nucleic acid.

In some embodiments, the genetic modification encodes at least one copy of a type 1 diacylglycerol acyltransferase gene. The type 1 diacylglycerol acyltransferase gene may be a gene native to the cell or from a different species. In certain embodiments, the gene is inheritable to the progeny of a transformed cell. In some embodiments, the gene is inheritable because it resides on a plasmid. In certain embodiments, the gene is inheritable because it is integrated into the genome of the transformed cell.

In certain embodiments, the DGAT1 gene is the type 1 diacylglycerol acyltransferase gene from *Arxula adeninivorans*, *Aspergillus terreus*, *Chaetomium globosum*, *Claviceps purpurea*, *Lipomyces starkeyi*, *Metarhizium acridum*, *Ophiocordyceps sinensis*, *Phaeodactylum tricornutum*, *Pichia guilliermondii*, *Rhodosporidium toruloides*, *Rhodotorula graminis*, *Trichoderma virens*, or *Yarrowia lipolytica*. In certain embodiments, diacylglycerol acyltransferase is expressed by transforming a cell with a gene encoding a diacylglycerol acyltransferase gene. The genetic modification may encode one or more than one copy of a diacylglycerol acyltransferase gene. In certain embodiments, the genetic modification encodes at least one copy of the DGA2 protein from *Chaetomium globosum*, *Claviceps purpurea*, *Ophiocordyceps sinensis*, or *Yarrowia lipolytica*. In some embodiments, the genetic modification encodes at least one copy of the DGA2 protein from *Chaetomium globosum*, *Claviceps purpurea*, or *Ophiocordyceps sinensis* and the transformed cell is *Y. lipolytica*. In some embodiments, the genetic modification encodes at least one copy of the DGA2 protein from *Chaetomium globosum*, *Claviceps purpurea*, or *Yarrowia lipolytica*, and the transformed cell is *Arxula adeninivorans*.

In some embodiments, the genetic modification encodes at least one copy of a type 2 diacylglycerol acyltransferase gene. The type 2 diacylglycerol acyltransferase gene may be a gene native to the cell or from a different species. In certain embodiments, the gene is inheritable to the progeny of a transformed cell. In some embodiments, the gene is inheritable because it resides on a plasmid. In certain embodiments, the gene is inheritable because it is integrated into the genome of the transformed cell.

In certain embodiments, the DGAT2 gene is the type 2 diacylglycerol acyltransferase gene from *Arxula adeninivorans*, *Aspergillus terreus*, *Aurantiochytrium limacinum*, *Claviceps purpurea*, *Gloeophyllum trabeum*, *Lipomyces starkeyi*, *Microbotryum violaceum*, *Pichia guilliermondii*, *Phaeodactylum tricornutum*, *Puccinia graminis*, *Rhodosporidium diobovatum*, *Rhodosporidium toruloides*, *Rhodotorula graminis*, or *Yarrowia lipolytica*. In certain embodiments, diacylglycerol acyltransferase is expressed by transforming a cell with a gene encoding a diacylglycerol acyltransferase gene. The genetic modification may encode one or more than one copy of a diacylglycerol acyltransferase gene. In certain embodiments, the genetic modification encodes at least one copy of the DGA1 protein from *R. toruloides*. In some embodiments, the genetic modification encodes at least one copy of the DGA1 protein from *R. toruloides* and the transformed cell is *Y. lipolytica*. In some embodiments, the genetic modification encodes at least one copy of the DGA1 protein from *R. toruloides*, and the transformed cell is *Arxula adeninivorans*.

In some embodiments, the DGA1 protein is from *R. toruloides* and the DGA2 protein is from *Chaetomium globosum*, *Claviceps purpurea*, *Ophiocordyceps sinensis*, or *Yarrowia lipolytica*. In some embodiments, the DGA1 protein is from *R. toruloides*, the DGA2 protein is from *Claviceps purpurea*, *Chaetomium globosum*, or *Ophiocordyceps sinensis*, and the transformed cell is *Y. lipolytica*. In some embodiments, the DGA1 protein is from *R. toruloides*, the DGA2 protein is from *Claviceps purpurea*, *Chaetomium globosum*, or *Yarrowia lipolytica*, and the transformed cell is *Arxula adeninivorans*.

In some embodiments, the genetic modification encodes at least one copy of a type 3 diacylglycerol acyltransferase gene. The type 3 diacylglycerol acyltransferase gene may be a gene native to the cell or from a different species. In certain embodiments, the gene is inheritable to the progeny of a transformed cell. In some embodiments, the gene is inheritable because it resides on a plasmid. In certain embodiments, the gene is inheritable because it is integrated into the genome of the transformed cell.

In certain embodiments, the DGAT3 gene is the type 3 diacylglycerol acyltransferase gene from *Ricinus communis* or *Arachis hypogaea*. In certain embodiments, diacylglycerol acyltransferase is expressed by transforming a cell with a gene encoding a diacylglycerol acyltransferase gene. The genetic modification may encode one or more than one copy of a diacylglycerol acyltransferase gene. In certain embodiments, the genetic modification encodes at least one copy of the DGA3 protein from *Ricinus communis* or *Arachis hypogaea*. In some embodiments, the genetic modification encodes at least one copy of the DGA3 protein from *Ricinus communis* or *Arachis hypogaea*, and the transformed cell is *Y. lipolytica*. In some embodiments, the genetic modification encodes at least one copy of the DGA1 protein from *Ricinus communis* or *Arachis hypogaea*, and the transformed cell is *Arxula adeninivorans*.

In certain embodiments, the diacylglycerol acyltransferase gene is inheritable to the progeny of a transformed cell. In some embodiments, the diacylglycerol acyltransferase gene is inheritable because it resides on a plasmid. In certain embodiments, the diacylglycerol acyltransferase gene is inheritable because it is integrated into the genome of the transformed cell.

E. Decreasing Triacylglycerol Lipase Activity in a Cell

In some embodiments, the transformed oleaginous cell comprises a genetic modification that decreases the activity of a native triacylglycerol lipase. Such genetic modifications may affect a protein that regulates the transcription of a triacylglycerol lipase gene, including modifications that decrease the expression of a transcription activator and/or increase the expression of a transcription repressor. Modifications that affect a regulator protein may both decrease the expression of triacylglycerol lipase and alter other gene expression profiles that shift the cellular equilibrium toward increased lipid accumulation or modified lipid composition. Alternatively, the genetic modification may be the introduction of a small interfering RNA, or a nucleic acid that encodes a small interfering RNA. In other embodiments, the genetic modification consists of the homologous recombination of a nucleic acid and the regulatory region of a native triacylglycerol lipase gene, including an operator, promoter, sequences upstream from the promoter, enhancers, and sequences downstream of the gene.

In some embodiments the transformed oleaginous cell comprises a genetic modification consisting of a homologous recombination event. In certain embodiments, the transformed cell comprises a genetic modification consisting of a homologous recombination event between a native triacylglycerol lipase gene and a nucleic acid. Thus, the genetic modification deletes the triacylglycerol lipase gene, prevents its transcription, or prevents the transcription of a gene that can be transcribed into a fully-active protein. A homologous recombination event may mutate or delete a portion of a native triacylglycerol lipase gene. For example, the homologous recombination event may mutate one or more residues in the active site of a native triacylglycerol lipase, thereby reducing the efficiency of the lipase or rendering it inactive. Alternatively, the homologous recombination event may affect post-translational modification, folding, stability, or localization within the cell. In some embodiments, the homologous recombination event replaces the promoter with a promoter that drives less transcription. In other embodiments, the homologous recombination event mutates the promoter to impair its ability to drive transcription. In certain embodiments, the genetic modification is a triacylglycerol lipase knockout mutation. Knockout mutations are preferable because they eliminate a pathway that depletes a cell's triacylglycerol content, thereby increasing the triacylglycerol content of a cell.

A knockout mutation may delete one or more triacylglycerol lipase genes. Additionally, the knockout mutation may substitute a triacylglycerol lipase gene with a gene that encodes a different protein. The gene may be operably linked to an exogenous promoter. In certain embodiments, the gene is not linked to an exogenous promoter, and instead, the gene is configured to recombine with the triacylglycerol lipase gene such that the triacylglycerol lipase gene's promoter drives transcription of the gene. Thus, the gene is less likely to be expressed if it randomly integrates into the cell's genome. Methods for creating knockouts are well-known in the art (See, e.g., Fickers et al., J. Microbiological Methods 55:727 (2003)).

In certain embodiments, the genetic modification comprises two homologous recombination events. In the first event, a nucleic acid encoding a portion of a gene recombines with the triacylglycerol lipase gene, and in the second event, a nucleic acid encoding the remaining portion of the gene recombines with the triacylglycerol lipase gene. The two portions of the gene are designed such that neither portion is functional unless they recombine with each other. These two events further reduce the likelihood that the gene can be expressed following random integration events.

In certain embodiments, the gene encodes a dominant selectable marker. Thus, knockout cells may be selected by screening for the marker. In some embodiments, the dominant selectable marker is a drug resistance marker. A drug resistance marker is a dominant selectable marker that, when expressed by a cell, allows the cell to grow and/or survive in the presence of a drug that would normally inhibit cellular growth and/or survival. Cells expressing a drug resistance marker can be selected by growing the cells in the presence of the drug. In some embodiments, the drug resistance marker is an antibiotic resistance marker. In some embodiments, the drug resistance marker confers resistance to a drug selected from the group consisting of Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, Micafungin, Benzoic acid, Ciclopirox, Flucytosine, 5-fluorocytosine, Griseofulvin, Haloprogin, Polygodial, Tolnaftate, Crystal violet, Amikacin, Gentamicin, Kanamycin, Neomycin, Netilmicin, Tobramycin, Paromomycin, Spectinomycin, Geldanamycin, Herbimycin, Rifaximin, Streptomycin, Loracarbef, Ertapenem, Doripenem, Imipenem, Meropenem, Cefadroxil, Cefazolin, Cefalotin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Teicoplanin, Vancomycin, Telavancin, Clindamycin, Lincomycin, Daptomycin, Azithromycin, Clarithromycin, Dirithromycin, Erythromycin, Roxithromycin, Troleandomycin, Telithromycin, Spiramycin, Aztreonam, Furazolidone, Nitrofurantoin, Linezolid, Posizolid, Radezolid, Torezolid, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, clavulanate, sulbactam, tazobactam, clavulanate, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole, Co-trimoxazole, Sulfonamidochrysoidine, Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin, Rifabutin, Rifapentine, Streptomycin, Arsphenamine, Chloramphenicol, Fosfomycin, Fusidic acid, Metronidazole, Mupirocin, Platensimycin, Quinupristin, Dalfopristin, Thiamphenicol, Tigecycline, Tinidazole, Trimethoprim, Geneticin, Nourseothricin, Hygromycin, Bleomycin, and Puromycin.

In some embodiments, the dominant selectable marker is a nutritional marker. A nutritional marker is a dominant selectable marker that, when expressed by the cell, enables the cell to grow or survive using one or more particular nutrient sources. Cells expressing a nutritional marker can be selected by growing the cells under limiting nutrient conditions in which cells expressing the nutritional marker can survive and/or grow, but cells lacking the nutrient marker cannot. In some embodiments, the nutritional marker is selected from the group consisting of Orotidine 5-phosphate decarboxylase, Phosphite specific oxidoreductase, Alpha-ketoglutarate-dependent hypophosphite dioxygenase, Alkaline phosphatase, Cyanamide hydratase, Melamine deaminase, Cyanurate amidohydrolase, Biuret hydrolyase, Urea amidolyase, Ammelide aminohydrolase, Guanine deaminase, Phosphodiesterase, Phosphotriesterase, Phosphite hydrogenase, Glycerophosphodiesterase, Parathion hydrolyase, Phosphite dehydrogenase, Dibenzothiophene desulfurization enzyme, Aromatic desulfinase, NADH-dependent FMN reductase, Aminopurine transporter, Hydroxylamine oxidoreductase, Invertase, Beta-glucosidase, Alpha-glucosidase, Beta-galactosidase, Alpha-galactosidase, Amylase, Cellulase, and Pullulonase.

Different approaches may be used to knockout the TGL3 gene in *Y. lipolytica* (See, e.g., Dulermo et al., Biochimica Biophysica Acta 1831:1486 (2013)). The methods disclosed herein and other methods known in the art may be used to knockout different triacylglycerol lipase genes in other species. For example, these methods may be used to knockout the TGL3 gene of *Arxula adeninivorans* (SEQ ID NO:36), the TGL3/4 gene of *Arxula adeninivorans* (SEQ ID NO:38), or the TGL4 gene of *Arxula adeninivorans* (SEQ ID NO:40).

In some embodiments, a genetic modification decreases the expression of a native triacylglycerol lipase gene by 0.1, 0.2, 0.3, 0.4, 0.5, 0.6, 0.7, 0.8, 0.9, 1, 2, 3, 4, 5, 6, 7, 8, 9, 10, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, 99.9, or 100 percent.

In some embodiments, a genetic modification decreases the efficiency of a native triacylglycerol lipase gene by 0.1, 0.2, 0.3, 0.4, 0.5, 0.6, 0.7, 0.8, 0.9, 1, 2, 3, 4, 5, 6, 7, 8, 9, 10, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, 99.9, or 100 percent.

In some embodiments, a genetic modification decreases the activity of a native triacylglycerol lipase gene by 0.1, 0.2, 0.3, 0.4, 0.5, 0.6, 0.7, 0.8, 0.9, 1, 2, 3, 4, 5, 6, 7, 8, 9, 10, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, 99.9, or 100 percent.

F. Decreasing Triacylglycerol Lipase Activity in a Cell with Concomitant Expression of Diacylglycerol Acyltransferase In some embodiments, the transformed oleaginous cell comprises a triacylglycerol lipase knockout mutation and a genetic modification that increase the expression of a native diacylglycerol acyltransferase. In certain embodiments, the transformed oleaginous cell comprises a triacylglycerol lipase knockout mutation and a genetic modification that encodes at least one copy of a diacylglycerol acyltransferase gene that is either native to the cell or from a different species of cell. In some embodiments, a triacylglycerol acyltransferase gene is disrupted and DGA1 and DGA2 proteins are expressed.

In some embodiments, one nucleic acid increases the expression of a native diacylglycerol acyltransferase or encodes at least one copy of a diacylglycerol acyltransferase gene and a second nucleic acid decreases the activity of a triacylglycerol lipase in the cell. In some embodiments the same nucleic acid encodes at least one copy of a diacylglycerol acyltransferase gene and decreases the activity of a triacylglycerol lipase in the cell. For example, the nucleic acid designed to knock out a triacylglycerol lipase gene may also contain a copy of a diacylglycerol acyltransferase gene.

G. Triacylglycerol Production

In certain embodiments, the transformed cells are grown in the presence of exogenous fatty acids, glucose, ethanol, xylose, sucrose, starch, starch dextrin, glycerol, cellulose, and/or acetic acid. These substrates may be added during cultivation to increase lipid production. The exogenous fatty acids may include stearate, oleic acid, linoleic acid, γ-linolenic acid, dihomo-γ-linolenic acid, arachidonic acid, α-linolenic acid, stearidonic acid, eicosatetraenoic acid, eicosapenteaenoic acid, docosapentaenoic acid, eicosadienoic acid, and/or eicosatrienoic acid.

In certain embodiments, the present invention relates to a product produced by a modified host cell described herein. In certain embodiments, the product is an oil, lipid, or triacylglycerol. In some embodiments, the product is palmitic acid, palmitoleic acid, stearic acid, oleic acid, or linoleic acid. In certain embodiments, the product is a saturated fatty acid. Thus, the product may be caprylic acid, capric acid, lauric acid, myristic acid, palmitic acid, stearic acid, arachidic acid, behenic acid, lignoceric acid, or cerotic acid. In some embodiments, the product is an unsaturated fatty acid. Thus, the product may be myristoleic acid, palmitoleic acid, sapienic acid, oleic acid, elaidic acid, vaccenic acid, linoleic acid, linoelaidic acid, α-linolenic acid, arachidonic acid, eicosapenteaenoic acid, erucic acid, or docosahexaenoic acid.

The product may be selected from the group consisting of lipids, triacylglycerides, fatty alcohols, fatty acids, alkanes, alkenes, isoprenoids, isoprene, squalene, farnasene, alcohols, isopropanol, n-propanol, n-butanol, isobutanol, 2-butanol, butadiene, diols, 1,3 propanediol, 1,4 propanediol, succinic acid, adipic acid, nylon precursors, citric acid, malic acid, polyols, and erythritol.

Genetic Modifications Related to DGA1 and DGA2

In some embodiments, the invention relates to a transformed cell, comprising a first genetic modification and second genetic modification, wherein said first genetic modification increases the activity of a native type 1 diacylglycerol acyltransferase or encodes at least one copy of a type 1 diacylglycerol acyltransferase gene native to the cell or from a different species, and said second genetic modification increases the activity of a native type 2 diacylglycerol acyltransferase or encodes at least one copy of a type 2 diacylglycerol acyltransferase gene native to the cell or from a different species. In some embodiments, the cell comprises a third genetic modification, wherein said third genetic modification decreases the activity of a triacylglycerol lipase in the cell.

In some embodiments, the invention relates to a transformed cell, wherein a first genetic modification encodes at least one copy of a type 1 diacylglycerol acyltransferase gene native to the cell or from a different species. In some embodiments, at least one copy of a type 1 diacylglycerol acyltransferase gene is integrated into the genome of said cell.

The type 1 diacylglycerol acyltransferase gene may be a type 1 diacylglycerol acyltransferase gene from *Arxula adeninivorans, Aspergillus terreus, Chaetomium globosum, Claviceps purpurea, Lipomyces starkeyi, Metarhizium acridum, Ophiocordyceps sinensis, Phaeodactylum tricornutum, Pichia guilliermondii, Rhodosporidium toruloides, Rhodotorula graminis, Trichoderma vixens*, or *Yarrowia lipolytica*. In some embodiments, the type 1 diacylglycerol acyltransferase gene is a type 1 diacylglycerol acyltransferase gene from *Claviceps purpurea, Chaetomium globosum, Ophiocordyceps sinensis*, or *Yarrowia lipolytica*.

In some embodiments, the invention relates to a transformed cell, wherein a second genetic modification encodes at least one copy of a type 2 diacylglycerol acyltransferase gene native to the cell or from a different species. In some embodiments, at least one copy of a type 2 diacylglycerol acyltransferase gene is integrated into the genome of said cell.

The type 2 diacylglycerol acyltransferase gene may be a type 2 diacylglycerol acyltransferase gene from *Arxula adeninivorans, Aspergillus terreus, Aurantiochytrium limacinum, Claviceps purpurea, Gloeophyllum trabeum, Lipomyces starkeyi, Microbotryum violaceum, Pichia guilliermondii, Phaeodactylum tricornutum, Puccinia graminis, Rhodosporidium diobovatum, Rhodosporidium toruloides, Rhodotorula graminis*, or *Yarrowia lipolytica*. In some embodiments, the type 2 diacylglycerol acyltransferase gene is a type 2 diacylglycerol acyltransferase gene from *Lipomyces starkeyi* or *Rhodosporidium toruloides*.

In some embodiments, the invention relates to a transformed cell, wherein a third genetic modification is a triacylglycerol lipase knockout mutation. The triacylglycerol lipase may be encoded by a TGL3, TGL3/4, or TGL4 gene.

In some embodiments, the cell is *Arxula adeninivorans*; and said triacylglycerol lipase comprises the amino acid sequence set forth in SEQ ID NO:35, SEQ ID NO:37, or SEQ ID NO:39. In some embodiments, the cell is *Arxula adeninivorans*; and said triacylglycerol lipase is encoded by the nucleotide sequence set forth in SEQ ID NO:36, SEQ ID NO:38, or SEQ ID NO:40. In other embodiments, the cell is *Yarrowia lipolytica*; and said triacylglycerol lipase comprises the amino acid sequence set forth in SEQ ID NO:41 or SEQ ID NO:85. In some embodiments, the cell is *Yarrowia lipolytica*; and said triacylglycerol lipase is encoded by the nucleotide sequence set forth in SEQ ID NO:42 or SEQ ID NO:86.

Genetic Modifications Related to DGA2

In some embodiments, the invention relates to a transformed cell, comprising a genetic modification, wherein said genetic modification increases the activity of a native type 1 diacylglycerol acyltransferase or encodes at least one copy of a type 1 diacylglycerol acyltransferase gene native to the cell or from a different species. For example, the genetic modification may encode at least one copy of a type 1 diacylglycerol acyltransferase gene native to the cell or from a different species. In some embodiments, at least one copy of a type 1 diacylglycerol acyltransferase gene is integrated into the genome of said cell.

Genetic Modifications Related to DGA3

In some embodiments, the invention relates to a transformed cell, comprising a genetic modification, wherein said genetic modification increases the activity of a native type 3 diacylglycerol acyltransferase or encodes at least one copy of a type 3 diacylglycerol acyltransferase gene native to the cell or from a different species. For example, the genetic modification may encode at least one copy of a type 3 diacylglycerol acyltransferase gene native to the cell or from a different species. In some embodiments, at least one copy of a type 3 diacylglycerol acyltransferase gene is integrated into the genome of said cell. The type 3 diacylglycerol acyltransferase gene may be a type 3 diacylglycerol acyltransferase gene from *Ricinus communis* or *Arachis hypogaea*.

Species of Transformed Cell

In some embodiments, the invention relates to a transformed cell, wherein said cell is selected from the group consisting of algae, bacteria, molds, fungi, plants, and yeasts. The cell may be a yeast. The cell may be selected from the group consisting of *Arxula, Aspergillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces*, and *Yarrowia*. For example, the cell may be selected from the group consisting of *Arxula adeninivorans, Aspergillus niger, Aspergillus orzyae, Aspergillus terreus, Aurantiochytrium limacinum, Candida utilis, Claviceps purpurea, Cryptococcus albidus, Cryptococcus curvatus, Cryptococcus ramirezgomezianus, Cryptococcus terreus, Cryptococcus wieringae, Cunninghamella echinulata, Cunninghamella japonica, Geotrichum fermentans, Hansenula polymorpha, Kluyveromyces lactis, Kluyveromyces marxianus, Kodamaea ohmeri, Leucosporidiella creatinivora, Lipomyces lipofer, Lipomyces starkeyi, Lipomyces tetrasporus, Mortierella isabellina, Mortierella alpina, Ogataea polymorpha, Pichia ciferrii, Pichia guilliermondii, Pichia pastoris, Pichia stipites, Prototheca zopfii, Rhizopus arrhizus, Rhodosporidium babjevae, Rhodosporidium toruloides, Rhodosporidium paludigenum, Rhodotorula glutinis, Rhodotorula mucilaginosa, Saccharomyces cerevisiae, Schizosaccharomyces pombe, Tremella enchepala, Trichosporon cutaneum, Trichosporon fermentans, Wickerhamomyces ciferrii*, and *Yarrowia lipolytica*.

Products

In some aspects, the invention relates to a product derived from an aforementioned cell. In some embodiments the product is an oil, lipid, or triacylglycerol. The product may be palmitic acid, palmitoleic acid, stearic acid, oleic acid, or linoleic acid.

Methods Related to DGA1 and DGA2

In some aspects, the invention provides a method of increasing the triacylglycerol content of a cell, comprising: (a) providing a cell, comprising (i) a first genetic modification, wherein said first genetic modification increases the activity of a native type 1 diacylglycerol acyltransferase or encodes at least one copy of a type 1 diacylglycerol acyltransferase gene native to the cell or from a different species; and (ii) a second genetic modification, wherein said second genetic modification increases the activity of a native type 2 diacylglycerol acyltransferase or encodes at least one copy of a type 2 diacylglycerol acyltransferase gene native to the cell or from a different species; (b) growing said cell under conditions whereby the first and second genetic modifications are expressed, thereby producing a triacylglycerol; and (c) optionally recovering the triacylglycerol. The aforementioned method may also be used to modify the lipid composition of a cell. The cell may further comprise a third genetic modification, wherein said third genetic modification decreases the activity of a triacylglycerol lipase in the cell.

In some aspects, the invention provides a method of increasing the lipid content of a cell, comprising transforming a parent cell with a first nucleotide sequence and second nucleotide sequence, wherein said first nucleotide sequence increases the activity of a native type 1 diacylglycerol acyltransferase or encodes at least one copy of a type 1 diacylglycerol acyltransferase gene and said second nucleotide sequence increases the activity of a native type 2 diacylglycerol acyltransferase or encodes at least one copy of a type 2 diacylglycerol acyltransferase gene. The method may further comprise transforming said cell with a third nucleotide sequence, wherein said third nucleotide sequence decreases the activity of a triacylglycerol lipase.

The first nucleotide sequence may comprise a type 1 diacylglycerol acyltransferase gene. In certain embodiments, the first nucleotide sequence encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence homology with the amino acid sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:71, SEQ ID NO:73, SEQ ID NO:75, SEQ ID NO:77, SEQ ID NO:79, SEQ ID NO:81, or SEQ ID NO:83, or a biologically-active portion of any one of them. In some embodiments, the first nucleotide sequence encodes an amino acid sequence having at least 80% sequence homology with the amino acid sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:71, SEQ ID NO:73, SEQ ID NO:75, SEQ ID NO:77, SEQ ID NO:79, SEQ ID NO:81, or SEQ ID NO:83, or a biologically-active portion of any one of them. In some embodiments, the first nucleotide sequence encodes an amino acid sequence having at least 95% sequence homology with the amino acid sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:71, SEQ ID NO:73, SEQ ID NO:75, SEQ ID NO:77, SEQ ID NO:79, SEQ ID NO:81, or SEQ ID NO:83, or a biologically-active portion of any one of them. In some embodiments, the first nucleotide sequence encodes the amino acid sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:71, SEQ ID NO:73, SEQ ID NO:75, SEQ ID NO:77, SEQ ID NO:79, SEQ ID NO:81, or SEQ ID NO:83, or a biologically-active portion of any one of them. In some embodiments, the first nucleotide sequence encodes the amino acid sequence set forth in SEQ ID NO:1, SEQ ID NO:9, SEQ ID NO:11, or SEQ ID NO:81, or a biologically-active portion of any one of them.

In some embodiments, the first nucleotide sequence has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence homology with the nucleotide sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:72, SEQ ID NO:74, SEQ ID NO:76, SEQ ID NO:78, SEQ ID NO:80, SEQ ID NO:82, or SEQ ID NO: 84. In some embodiments, the first nucleotide sequence has at least 70% sequence homology with the nucleotide sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:72, SEQ ID NO:74, SEQ ID NO:76, SEQ ID NO:78, SEQ ID NO:80, SEQ ID NO:82, or SEQ ID NO: 84. In some embodiments, the first nucleotide sequence has at least 95% sequence homology with the nucleotide sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:72, SEQ ID NO:74, SEQ ID NO:76, SEQ ID NO:78, SEQ ID NO:80, SEQ ID NO:82, or SEQ ID NO: 84. In some embodiments, the first nucleotide sequence comprises the nucleotide sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:72, SEQ ID NO:74, SEQ ID NO:76, SEQ ID NO:78, SEQ ID NO:80, SEQ ID NO:82, or SEQ ID NO: 84. In some embodiments, the first nucleotide sequence comprises the nucleotide sequence set forth in SEQ ID NO:2, SEQ ID NO:10, SEQ ID NO:12, or SEQ ID NO:82.

The second nucleotide sequence may comprise a type 2 diacylglycerol acyltransferase gene. In some embodiments, the first nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence homology with the nucleotide sequence set forth in SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, or SEQ ID NO:69 or a biologically-active portion of any one of them. In some embodiments, the second nucleotide sequence encodes an amino acid sequence having at least 80% sequence homology with the amino acid sequence set forth in SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, or SEQ ID NO:69 or a biologically-active portion of any one of them. In some embodiments, the second nucleotide sequence encodes an amino acid sequence having at least 95% sequence homology with the amino acid sequence set forth in SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, or SEQ ID NO:69 or a biologically-active portion of any one of them. In some embodiments, the second nucleotide sequence encodes the amino acid sequence set forth in SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, or SEQ ID NO:69 or a biologically-active portion of any one of them. In some embodiments, the second nucleotide sequence encodes the amino acid sequence set forth in SEQ ID NO:19, SEQ ID NO:21, or SEQ ID NO:23, or a biologically-active portion of any one of them. In some embodiments, the second nucleotide sequence encodes the amino acid sequence set forth in SEQ ID NO:19, or a biologically-active portion thereof.

In some embodiments, the second nucleotide sequence has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence homology with the nucleotide sequence set forth in SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, or SEQ ID NO:70. In some embodiments, the second nucleotide sequence has at least 70% sequence homology with the nucleotide sequence set forth in SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, or SEQ ID NO:70. In some embodiments, the second nucleotide sequence has at least 95% sequence homology with the nucleotide sequence set forth in SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, or SEQ ID NO:70. In some embodiments, the second nucleotide sequence comprises the nucleotide sequence set forth in SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, or SEQ ID NO:70. In some embodiments, the second nucleotide sequence comprises the nucleotide sequence set forth in SEQ ID NO:20, SEQ ID NO:22, or SEQ ID NO:24. In some embodiments, the second nucleotide sequence comprises the nucleotide sequence set forth in SEQ ID NO:20.

In certain embodiments, the third nucleotide sequence is capable of recombining with a nucleotide sequence in a triacylglycerol lipase gene and/or a nucleotide sequence in the regulatory region of a triacylglycerol lipase gene. For example, the triacylglycerol lipase may be encoded by a TGL3, TGL3/4, or TGL4 gene. In some embodiments, the cell is *Arxula adeninivorans*; and said triacylglycerol lipase comprises the amino acid sequence set forth in SEQ ID NO:35, SEQ ID NO:37, or SEQ ID NO:39. In some embodiments, the cell is *Arxula adeninivorans*; and said triacylglycerol lipase is encoded by the nucleotide sequence set forth in SEQ ID NO:36, SEQ ID NO:38, or SEQ ID NO:40. In other embodiments, the cell is *Yarrowia lipolytica*; and said triacylglycerol lipase comprises the amino acid sequence set forth in SEQ ID NO:41 or SEQ ID NO:85. In some embodiments, the cell is *Yarrowia lipolytica*; and said triacylglycerol lipase is encoded by the nucleotide sequence set forth in SEQ ID NO:42 or SEQ ID NO:86.

In some embodiments, the third nucleotide sequence comprises a gene encoding a protein or a portion of a protein. The protein may confer resistance to a drug. The protein may enable the cell to grow or proliferate more quickly on a nutrient source than a cell of the same species that does not express the protein.

In some embodiments, the parent cell is transformed with a first nucleic acid that encodes the first nucleotide sequence and a second nucleic acid that encodes the second nucleotide sequence. In other embodiments, the parent cell is transformed with a first nucleic acid that encodes the first nucleotide sequence and the second nucleotide sequence. The cell may be transformed with a third nucleic acid that encodes the third nucleotide sequence, or either the first nucleic acid or second nucleic acid may encode the third nucleotide sequence. Still, in other embodiments, the parent cell is transformed with a nucleic acid that encodes the first nucleotide sequence, second nucleotide sequence, and third nucleotide sequence.

Methods Related to DGA2

In some aspects, the invention provides a method of increasing the triacylglycerol content of a cell, comprising: (a) providing a cell comprising a genetic modification, wherein said genetic modification increases the activity of a native type 1 diacylglycerol acyltransferase or encodes at least one copy of a type 1 diacylglycerol acyltransferase gene native to the cell or from a different species; (b) growing said cell under conditions whereby the genetic modification is expressed, thereby producing a triacylglycerol; and (c) optionally recovering the triacylglycerol. The aforementioned method may also be used to modify the lipid composition of a cell.

In some aspects, the invention provides a method of increasing the lipid content of a cell, comprising transforming a parent cell with a nucleotide sequence, wherein said nucleotide sequence increase the activity of a native type 1 diacylglycerol acyltransferase or encodes at least one copy of a type 1 diacylglycerol acyltransferase gene.

The nucleotide sequence may comprise a type 1 diacylglycerol acyltransferase gene. In certain embodiments, the nucleotide sequence encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence homology with the amino acid sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:71, SEQ ID NO:73, SEQ ID NO:75, SEQ ID NO:77, SEQ ID NO:79, SEQ ID NO:81, or SEQ ID NO:83, or a biologically-active portion of any one of them. In some embodiments, the nucleotide sequence encodes an amino acid sequence having at least 80% sequence homology with the amino acid sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:71, SEQ ID NO:73, SEQ ID NO:75, SEQ ID NO:77, SEQ ID NO:79, SEQ ID NO:81, or SEQ ID NO:83, or a biologically-active portion of any one of them. In some embodiments, the nucleotide sequence encodes an amino acid sequence having at least 95% sequence homology with the amino acid sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:71, SEQ ID NO:73, SEQ ID NO:75, SEQ ID NO:77, SEQ ID NO:79, SEQ ID NO:81, or SEQ ID NO:83, or a biologically-active portion of any one of them. In some embodiments, the nucleotide sequence encodes the amino acid sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:71, SEQ ID NO:73, SEQ ID NO:75, SEQ ID NO:77, SEQ ID NO:79, SEQ ID NO:81, or SEQ ID NO:83, or a biologically-active portion of any one of them. In some embodiments, the nucleotide sequence encodes the amino acid sequence set forth in SEQ ID NO:1, SEQ ID NO:9, SEQ ID NO:11, or SEQ ID NO:81, or a biologically-active portion of any one of them.

In some embodiments, the nucleotide sequence has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence homology with the nucleotide sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:72, SEQ ID NO:74, SEQ ID NO:76, SEQ ID NO:78, SEQ ID NO:80, SEQ ID NO:82, or SEQ ID NO: 84. In some embodiments, the first nucleotide sequence has at least 70% sequence homology with the nucleotide sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:72, SEQ ID NO:74, SEQ ID NO:76, SEQ ID NO:78, SEQ ID NO:80, SEQ ID NO:82, or SEQ ID NO: 84. In some embodiments, the nucleotide sequence has at least 95% sequence homology with the nucleotide sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:72, SEQ ID NO:74, SEQ ID NO:76, SEQ ID NO:78, SEQ ID NO:80, SEQ ID NO:82, or SEQ ID NO: 84. In some embodiments, the nucleotide sequence comprises the nucleotide sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:72, SEQ ID NO:74, SEQ ID NO:76, SEQ ID NO:78, SEQ ID NO:80, SEQ ID NO:82, or SEQ ID NO: 84. In some embodiments, the nucleotide sequence comprises the nucleotide sequence set forth in SEQ ID NO:2, SEQ ID NO:10, SEQ ID NO:12, or SEQ ID NO:82.

Methods Related to DGA3

In some aspects, the invention provides a method of increasing the triacylglycerol content of a cell, comprising: (a) providing a cell comprising a genetic modification, wherein said genetic modification increases the activity of a native type 3 diacylglycerol acyltransferase or encodes at least one copy of a type 3 diacylglycerol acyltransferase gene native to the cell or from a different species; (b) growing said cell under conditions whereby the genetic modification is expressed, thereby producing a triacylglycerol; and (c) optionally recovering the triacylglycerol. The aforementioned method may also be used to modify the lipid composition of a cell.

In some aspects, the invention provides a method of increasing the lipid content of a cell, comprising transforming a parent cell with a nucleotide sequence, wherein said nucleotide sequence increase the activity of a native type 3 diacylglycerol acyltransferase or encodes at least one copy of a type 3 diacylglycerol acyltransferase gene.

The nucleotide sequence may comprise a type 3 diacylglycerol acyltransferase gene. In certain embodiments, the nucleotide sequence encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence homology with the amino acid sequence set forth in SEQ ID NO:87 or SEQ ID NO:89, or a biologically-active portion of either one of them. In some embodiments, the nucleotide sequence encodes an amino acid sequence having at least 80% sequence homology with the amino acid sequence set forth in SEQ ID NO:87 or SEQ ID NO:89, or a biologically-active portion of either one of them. In some embodiments, the nucleotide sequence encodes an amino acid sequence having at least 95% sequence homology with the amino acid sequence set forth in SEQ ID NO:87 or SEQ ID NO:89, or a biologically-active portion of any one of them. In some embodiments, the nucleotide sequence encodes the amino acid sequence set forth in SEQ ID NO:87 or SEQ ID NO:89, or a biologically-active portion of either one of them.

In some embodiments, the nucleotide sequence has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence homology with the nucleotide sequence set forth in SEQ ID NO:88 or SEQ ID NO:90. In some embodiments, the first nucleotide sequence has at least 70% sequence homology with the nucleotide sequence set forth in SEQ ID NO:88 or SEQ ID NO:90. In some embodiments, the nucleotide sequence has at least 95% sequence homology with the nucleotide sequence set forth in SEQ ID NO:88 or SEQ ID NO:90. In some embodiments, the nucleotide sequence comprises the nucleotide sequence set forth in SEQ ID NO:88 or SEQ ID NO:90.

One skilled in the art will readily appreciate that the present invention is well adapted to carry out the objects and obtain the ends and advantages mentioned, as well as those inherent therein. The embodiments described herein are not intended as limitations on the scope of the invention. These and other features, aspects, and advantages of the present invention will become better understood with reference to the following description, drawings, and claims.

The present description is further illustrated by the following examples, which should not be construed as limiting in any way. The contents of all cited references (including literature references, issued patents, published patent applications and GenBank Accession numbers as cited throughout this application) are hereby expressly incorporated by reference. When definitions of terms in documents that are incorporated by reference herein conflict with those used herein, the definitions used herein govern.

EXEMPLIFICATION

Example 1

Method to Increase the Activity of a DGA1 Protein (DGAT2 Gene)

Nucleic acid constructs for expressing DGA1 were described in U.S. Ser. No. 61/943,664 and PCT Patent Application No. PCT/US15/017227 (hereby incorporated by reference). FIG. 1 shows expression construct pNC243 used for expression of the *R. toruloides* DGA1 gene NG66 (SEQ ID NO:20) in *Y. lipolytica*. DGA1 expression constructs were linearized before transformation by a PacI/NotI restriction digest. The linear expression constructs each included an expression cassette for the DGAT2 gene and for the Nat1 gene, used as a marker for selection with nourseothricin (NAT).

DGA1 expression constructs were randomly integrated into the genome of *Y. lipolytica* strain NS18 (obtained from ARS Culture Collection, NRRL #YB 392) using a transformation protocol as described in Chen (Applied Microbiology & Biotechnology 48:232-35 (1997)). Transformants were selected on YPD plates with 500 μg/mL NAT and screened for the ability to accumulate lipids by a fluorescent staining lipid assay as described in Example 2 below. For each expression construct, eight transformants were analyzed.

For most constructs, there was significant colony variation between the transformants, likely due to the lack of a functional DGA1 expression cassette in cells that only obtained a functional Nat1 cassette, or due to a negative effect of the site of DGA1 integration on DGA1 expression. Nevertheless, all transformants had a significant increase in lipid content.

Overexpression of native *Y. lipolytica* DGA1 (NG15) under a strong promoter increased the transformant's lipid content by about 2-fold compared to the parental strain NS18 as measured by the fluorescence assay described in Example 2. Transformants that demonstrated the highest fluorescence (about 3-fold higher compared to NS18) were generated by the expression of *R. toruloides* DGA1 (NG66, NG67) and *L. starkeyi* DGA1 (NG68).

In certain experiments, the effect of native *R. toruloides* DGA1 (NG49) expression on lipid production in *Y. lipolytica* was not as high as the effect of synthetic versions of *R. toruloides* DGAT2 genes that did not contain introns. This result may indicate that the gene splicing of the *R. toruloides* DGAT2 gene in *Y. lipolytica* was not very efficient. In certain experiments, codon optimization of the *R. toruloides* DGA1 gene for expression in *Y. lipolytica* did not have a positive effect on lipid production.

Example 2

Lipid Assay

Each well of an autoclaved, multi-well plate was filled with filter-sterilized media containing 0.5 g/L urea, 1.5 g/L yeast extract, 0.85 g/L casamino acids, 1.7 g/L YNB (without amino acids and ammonium sulfate), 100 g/L glucose, and 5.11 g/L potassium hydrogen phthalate (25 mM). Yeast strains that had been incubated for 1-2 days on YPD-agar plates at 30° C. were used to inoculate each well of the multiwall plate. 1.5 mL of media was used per well for 24-well plates and 300 μL of media was used per well for 96-well plates. Alternatively, the yeast cultures were used to inoculate 50 mL of sterilized media in an autoclaved 250 mL flask.

Multi-well plates were covered with a porous cover and incubated at 30° C., 70-90% humidity, and 900 rpm in an Infors Multitron ATR shaker. Alternatively, flasks were covered with aluminum foil and incubated at 30° C., 70-90% humidity, and 900 rpm in a New Brunswick Scientific shaker. After 96 hours, 20 μL of 100% ethanol was added to 20 μl of cells in an analytical microplate and incubated at 4° C. for 30 minutes. 20 μL of cell/ethanol mix was then added to 80 μl of a pre-mixed solution containing 50 μL 1 M potassium iodide, 1 mM μL Bodipy 493/503, 0.5 μL 100% DMSO, 1.5 μL 60% PEG 4000, and 27 μL water in a Costar 96-well, black, clear-bottom plate and covered with a transparent seal. Bodipy fluorescence was monitored with a SpectraMax M2 spectrophotometer (Molecular Devices) kinetic assay at 30° C., and normalized by dividing fluorescence by absorbance at 600 nm. Data was averaged in triplicate growth experiments.

Example 3

Analysis and Screening of *Y. lipolytica* Strains that Express DGA1

In order to select strains with the highest lipid production level, *Y. lipolytica* strain NS18 transformants expressing NG15 (*Y. lipolytica* DGA1) or NG66 (*R. toruloides* DGA1) were screened. For NG15, about 50 colonies were screened by the lipid assay described in Example 2 for the highest lipid accumulation, and the best transformant was named NS249. For NG66, 80 colonies were screened, and the 8 best colonies were selected for further analysis.

Strain NS249 and the 8 selected NG66 transformants were grown in shake flasks and analyzed by the lipid assay for lipid content and by HPLC for glucose consumption. *Y. lipolytica* strains expressing *R. toruloides* DGA1 had significantly higher lipid contents than *Y. lipolytica* strains with a native *Y. lipolytica* DGAT2 gene expressed under the same promoter as *R. toruloides* DGAT2. At the same time, NG66 transformants used significantly more glucose than NS249, demonstrating that NG66 was more efficient in converting glucose to lipids. The difference in efficiency between the two DGAT2 genes may be attributed to either a higher level of expression of *R. toruloides* DGA1 in *Y. lipolytica* or a higher level of *R. toruloides* DGA1 specific activity, or both.

Figure 2:
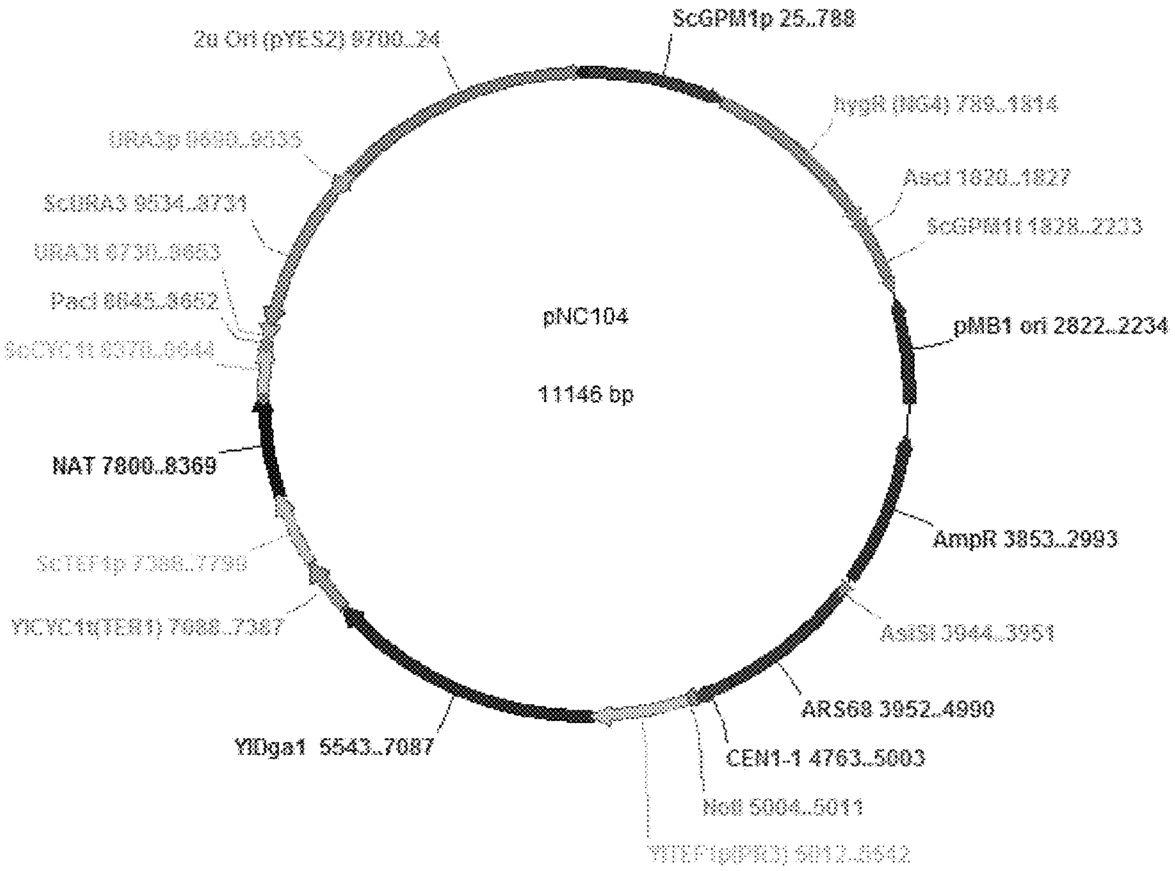
FIG. 2 depicts a map of the pNC104 construct used to overexpress the NG15 gene (YlDga1) in *Y. lipolytica* strain NS18. Vector pNC104 was linearized by a PacI/NotI restriction digest before transformation. "2u ori" denotes the *S. cerevisiae* origin of replication from the 2 μm circle plasmid; "pMB1 ori" denotes the *E. coli* pMB1 origin of replication from the pBR322 plasmid; "AmpR" denotes the bla gene used as a marker for selection with ampicillin; "ScGPM1p" denotes the *Y. lipolytica* GPD1 promoter −764 to −1; "hygR" denotes the *Escherichia coli* hph gene expression cassette used as a marker for selection with hygromycin B; "ScGPM1t" denotes the *S. cerevisiae* GPD1 terminator 406 bp after stop codon; "ARS68" and "CEN1-1" denote *Y. lipolytica* chromosomal origins of replication; "Y1TEF1p" denotes the *Y. lipolytica* TEF promoter −406 to +125; "Y1DGA1" denotes the *Y. lipolytica* DGA1 gene ORF (NG15); "Y1CYC1t" denotes the *Y. lipolytica* CYC1 terminator 300 base pairs after stop; "ScTEF1p" denotes the *S. cerevisiae* TEF1 promoter −412 to −1; "NAT" denotes the *Streptomyces noursei* Nat1 gene used as a marker for selection with nourseothricin; "ScCYC1t" denotes the *S. cerevisiae* CYC1 terminator 275 base pairs after stop; and "URA3p-ScURA3-URA3t" denotes the *S. cerevisiae* URA3 auxotrophic marker for selection in yeast.

Strain NS125 is a derivative of *Y. lipolytica* strain NS18 (obtained from ARS Culture Collection, NRRL #YB 392) that was transformed with a *Y. lipolytica* DGA1 expression cassette from the pNC104 vector (FIG. 2). The pNC104 construct was linearized by a PacI/NotI restriction digest prior to transformation. The linear expression construct included the expression cassette for the *Y. lipolytica* DGAT2 gene and for the Nat1 gene used as a marker for selection with nourseothricin (NAT). The expression construct was randomly integrated into the genome of *Y. lipolytica* strain NS18 using the transformation protocol as described in Chen (Applied Microbiology & Biotechnology 48:232-35 (1997)). Transformants were selected on YPD plates with 500 μg/mL NAT and screened for the ability to accumulate lipids by a fluorescent staining lipid assay as described in Example 2. The best transformant out of about 100 transformants screened was named NS125.

The NS281 strain was obtained using a similar process as strain NS125, except that the pNC243 construct was used for the transformation of the NS18 strain (FIG. 1). The pNC243 construct contained the *Rhodosporidium toruloides* DGAT2 gene (NG66) instead of *Y. lipolytica* DGAT2 gene used to make NS125. The NS281 strain contains a *Rhodosporidium toruloides* DGAT2 gene that is integrated into the *Y. lipolytica* genome.

Example 4

Method to Knockout Triacylglycerol Lipase Knockout Gene in *Y. lipolytica*

Nucleic acid constructs for knocking out the *Y. lipolytica* TGL3 gene while expressing the DGAT2 gene were described in U.S. Ser. No. 61/987,098 and PCT Patent Application No. PCT/US15/28760 (both hereby incorporated by reference). The TGL3 gene was knocked out of *Y. lipolytica* wild-type strain NS18 (obtained from NRLL #YB-392) and its DGA1 expressing derivative NS281. NS281 expresses the DGA1 gene from *Rhodosporidium toruloides* as described above. The *Y. lipolytica* TGL3 gene (YALI0D17534g, SEQ ID NO: 42) was deleted as follows: A two-fragment deletion cassette was amplified by PCR from a plasmid containing the hygromycin resistance gene ("hph," SEQ ID NO: 44) using primer pairs NP1798-NP656 and NP655-NP1799 (SEQ ID NOs: 45-48). The resulting PCR fragments (SEQ ID NOs: 49 & 50) were co-transformed into NS18 and NS281 according to the protocol developed in U.S. Ser. No. 61/819,746 and PCT Patent Application Publication No. WO 14/182657 (both hereby incorporated by reference). The omission of a promoter and terminator in the hph cassette and the splitting of the hph coding sequence into two PCR fragments reduce the probability that random integration of these pieces will confer hygromycin resistance. The hph gene should only be expressed if it integrates at the TGL3 locus by homologous recombination so that the TGL3 promoter and terminator can direct its transcription. Hygromycin resistant colonies were screened by PCR to confirm the absence of TGL3 and the presence of a tgl3::hyg specific product. Deletion of TGL3 in NS18 resulted in strain NS421. Deletion of TGL3 in NS281 resulted in strain NS377.

Example 5

Cells that Overexpress Both DGA1 and DGA2 and that Contain a TGL3 Deletion Accumulate More TAGs than Cells that do not Overexpress DGA2

In order to test the idea that combining DGA1 and DGA2 expression with TGL3 deletion leads to higher lipid accumulation in *Y. lipolytica*, DGA2 from *Claviceps purpurea* was expressed in strain NS377. Strain NS377 contains a deletion of TGL3 and expresses DGA1 from *Rhodosporidium toruloides* as described in Example 4 and U.S. Ser. No. 61/987,098 and PCT Patent Application No. PCT/US15/28760 (both hereby incorporated by reference). DGA2 from *Claviceps purpurea* was selected based on experiments that demonstrate that this gene increases the lipid content of *Y. lipolytica* in combination with DGA1 from *Rhodosporidium toruloides*.

FIG. 3 shows the map of pNC327, the expression construct used to express *C. purpurea* DGA2 in NS377. The construct was linearized prior to transformation with a PacI/AscI restriction digest. The linear expression construct included an expression cassette for the *C. purpurea* DGA2 gene and for the BLE gene used as a marker for selection with Zeocin (ZEO). Transformants were analyzed by the fluorescent lipid assay described in Example 2, and the top lipid producer was designated NS432.

Figure 4:
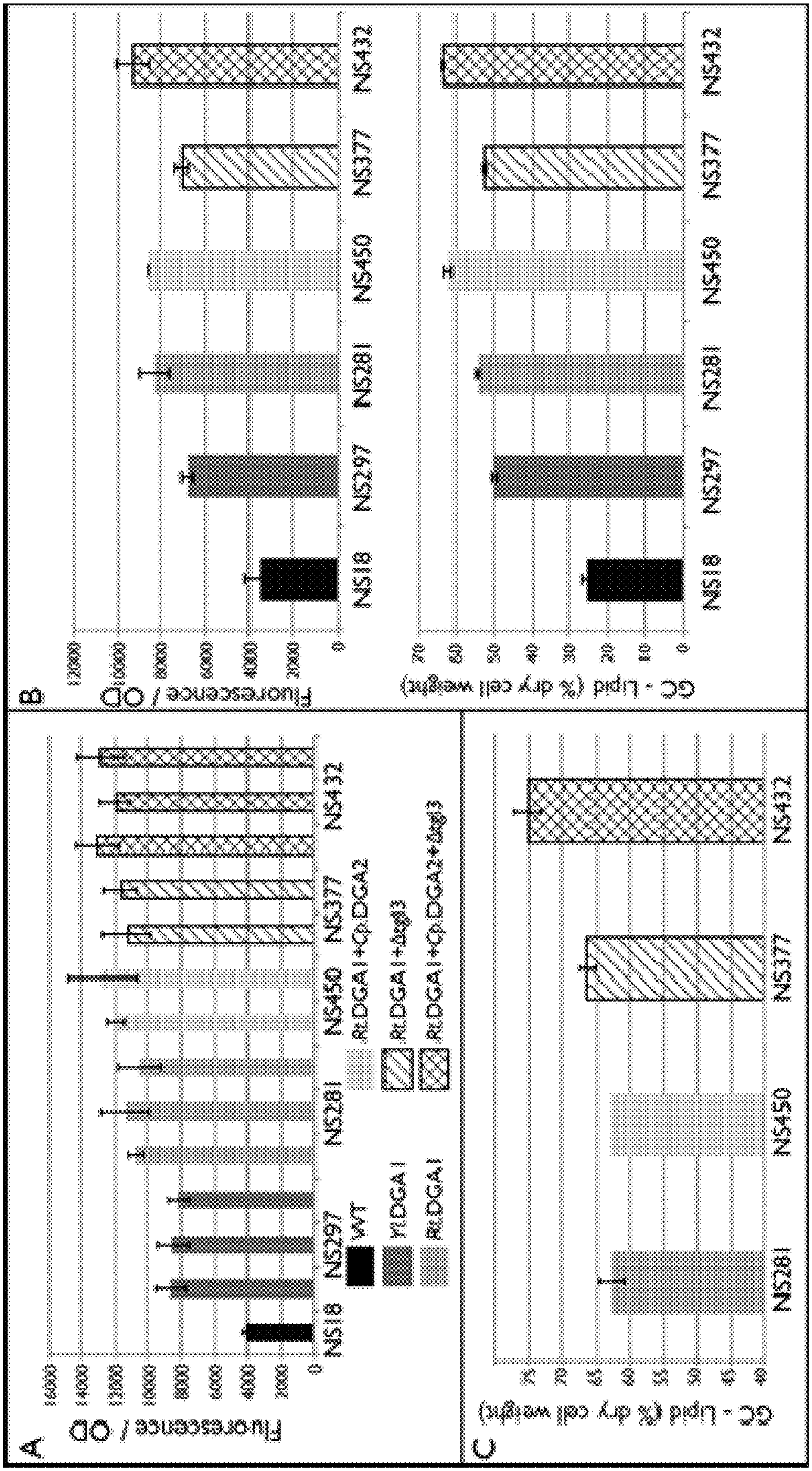
FIG. 4 comprises three panels, labeled (A), (B), and (C). The figure depicts lipid accumulation measured by a fluorescence-based assay or a percentage of the dry cell weight as determined by gas chromatography for *Yarrowia lipolytica* strains NS297, NS281, NS450, NS377, and NS432. NS297 expresses an additional copy of *Y. lipolytica* DGA1; NS281 expresses *Rhodosporidium toruloides* DGA1; NS450 expresses *R. toruloides* DGA1 and *Claviceps purpurea* DGA2; NS377 expresses *R. toruloides* DGA1 and carries a deletion of *Y. lipolytica* TGL3; NS432 expresses *R. toruloides* DGA1 and *C. purpurea* DGA2 and carries a deletion of *Y. lipolytica* TGL3. In panel (A), strains were analyzed by fluorescence assay after 96 hours of fermentation in a 48-well plate where two or three transformants were analyzed for each construct. In panel (B), strains were analyzed by fluorescence assay and gas chromatography after 96 hours of fermentation in 50-mL flasks. In panel (C), strains were analyzed by gas chromatography after 140 hours of fermentation in 1-L bioreactors. Data for NS281, NS377, and NS432 are averages obtained from duplicate bioreactor fermentations. Data for NS450 represents the value obtained from a single bioreactor fermentation.

The lipid production of strains NS297, NS281, NS412, NS450, NS377, and NS432 were compared. A subset of these strains were either grown using a batch glucose process (in 48-well plates or 50-ml flasks) or using a high cell density fed-batch glucose process (in 1-L bioreactors). Lipid content was analyzed by fluorescence assay or gas chromatography, and strain NS432 was found to have a higher lipid content than its parent strain NS377 and the strains without the TGL3 knockout (FIG. 4). These results demonstrate the advantage of DGA1 and DGA2 expression in a TGL3 knockout.

Example 6

Increasing the Activity of DGA1, DGA2, or DGA3 in *Arxula adeninivorans*

Figure 5:
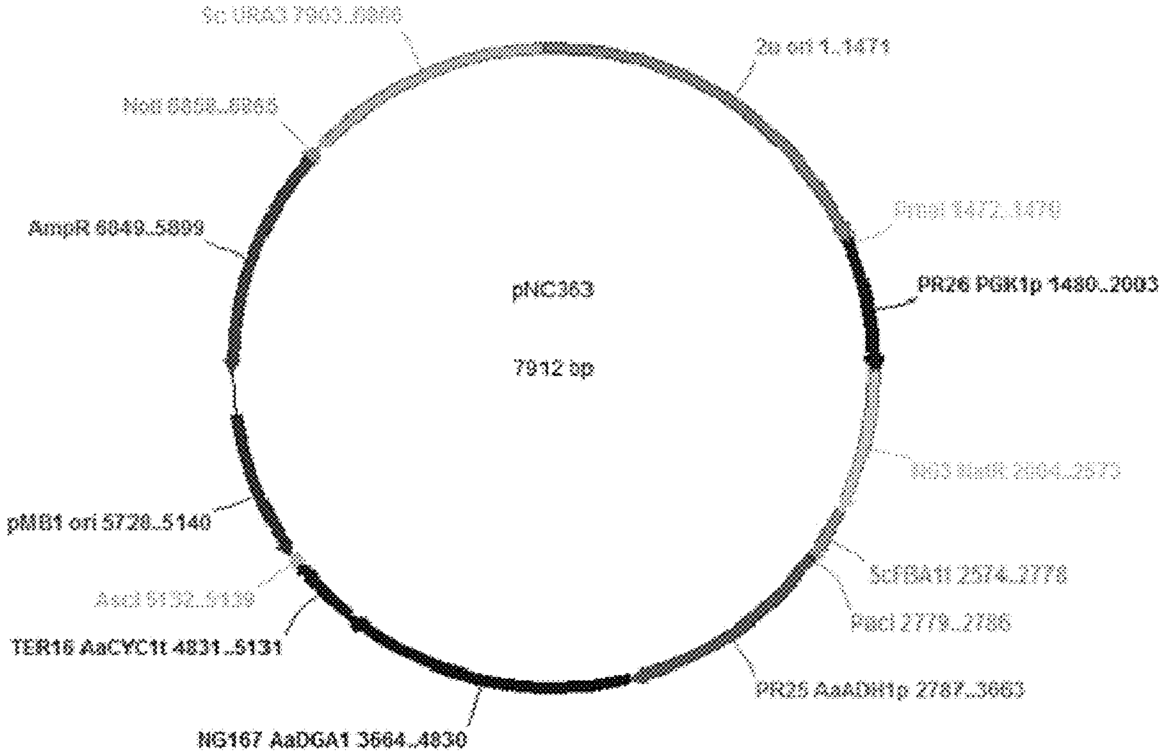
FIG. 5 depicts a map of the pNC363 construct used to overexpress the NG167 gene (AaDga1) in *A. adeninivorans* strain NS252 (ATCC 76597). Vector pNC363 was linearized by a PmeI/AscI restriction digest before transformation. "2u ori" denotes the *S. cerevisiae* origin of replication from the 2 μm circle plasmid; "pMB1 ori" denotes the *E. coli* pMB1 origin of replication from the pBR322 plasmid; "AmpR" denotes the bla gene used as a marker for selection with ampicillin; "Sc URA3" denotes the *S. cerevisiae* URA3 auxotrophic marker for selection in yeast; "PR26 PGK1p" denotes the *A. adeninivorans PGK*1 promoter −524 to −1; "NG3 NatR" denotes the *Streptomyces noursei* Nat1 gene used as a marker for selection with nourseothricin; "ScFBA1t" denotes the *S. cerevisiae* FBA1 terminator 205 bp after stop; "PR25 AaADH1p" denotes the *A. adeninivorans* ADH1 promoter −877 to −1; "NG167 AaDGA1" denotes the *A. adeninivorans* DGA1 gene ORF (NG167); "TER16 CYC1t" denotes the *A. adeninivorans* CYC1 terminator 301 bp after stop codon.

Twenty nine genes encoding for diacylglycerol acyltransferase (DGA) type 1 (DGA2), type 2 (DGA1) and type 3 (DGA3) from various donors were selected for expression in *Arxula adeninivorans* strain NS252 (Table 2). The map of the expression construct used to express the DGAs in *A. adeninivorans* is shown in the FIG. 5, with NG167 target as an example. The constructs for all other DGAs were the same except for the target open reading frames (ORFs). The negative control comprised the *E. coli* hph gene, which encodes for a phosphotransferase that confers resistance to Hygromycin B, in place of a DGA.

TABLE 2

Diacylglycerol acyltransferase genes used for expression in *Arxula adeninivorans* and *Yarrowia lipolytica*.

| Gene ID | Donor Organism | Gene | SEQ ID NO |
|---|---|---|---|
| NG15 | *Yarrowia lipolytica* | DGA1 | 16 |
| NG16 | *Yarrowia lipolytica* | DGA2 | 2 |
| NG66 | *Rhodosporidium toruloides* | DGA2 | 20 |
| NG69 | *Lipomyces starkeyi* | DGA1 | 26 |
| NG70 | *Aspergillus terreus* | DGA1 | 28 |
| NG71 | *Claviceps purpurea* | DGA1 | 30 |
| NG72 | *Aurantiochytrium limacinum* | DGA1 | 32 |
| NG109 | *Rhodosporidium toruloides* | DGA2 | 4 |
| NG110 | *Lipomyces starkeyi* | DGA2 | 6 |
| NG111 | *Aspergillus terreus* | DGA2 | 8 |
| NG112 | *Claviceps purpurea* | DGA2 | 10 |
| NG113 | *Chaetomium globosum* | DGA2 | 12 |
| NG167 | *Arxula adeninivorans* | DGA1 | 34 |
| NG168 | *Arxula adeninivorans* | DGA2 | 14 |
| NG286 | *Rhodotorula graminis* | DGA1 | 52 |
| NG287 | *Microbotryum violaceum* | DGA1 | 56 |
| NG288 | *Puccinia graminis* | DGA1 | 58 |
| NG289 | *Gloeophyllum trabeum* | DGA1 | 60 |
| NG290 | *Rhodosporidium diobovatum* | DGA1 | 62 |
| NG291 | *Phaeodactylum tricornutum* | DGA1A | 64 |
| NG292 | *Phaeodactylum tricornutum* | DGA1B | 66 |
| NG293 | *Phaeodactylum tricornutum* | DGA1C | 68 |
| NG294 | *Phaeodactylum tricornutum* | DGA1D | 70 |
| NG295 | *Phaeodactylum tricornutum* | DGA2 | 78 |
| NG296 | *Metarhizium acridum* | DGA2 | 80 |
| NG297 | *Ophiocordyceps sinensis* | DGA2 | 82 |
| NG298 | *Trichoderma virens* | DGA2 | 84 |
| NG299 | *Ricinus communis* | DGA3 | 88 |
| NG300 | *Arachis hypogaea* | DGA3 | 90 |

The expression constructs were assembled by yeast mediated ligation. Next, the full-length constructs were linearized by a PmeI/AscI restriction digest before transformation. The linear expression constructs included an expression cassette for a DGA and an expression cassette for the *Streptomyces noursei* Nat1 gene, used as marker for selection with nourseothricin (NAT). The expression contracts were randomly integrated into the genome of *A. adeninivorans* NS252 (ATCC #76597) using a protocol specifically adapted to *A. adeninivorans*. Briefly, 2 mL of YPD was inoculated with the parent *A. adeninivorans* culture and grown overnight at 37° C. in a rotary shaker. 0.5 mL of the overnight culture was then used to inoculate 25 mL of fresh YPD in a 250 flask, which was then grown at 37° C. for 3.5 to 4 hours. The cells were pelleted at 3000 rpm for 2 minutes, and the supernatant was discarded. The cells were washed in sterile water, and pelleted again at 3000 rpm for 2 minutes. The pellet was suspended in 2 mL of 100 mM lithium acetate comprising 40 μM dithiothreitol and transferred into a microcentrifuge tube. The suspension was incubated for one hour at 37° C. on a rotary shaker. The cells were pelleted at 10,000 rpm for 10 seconds and the supernatant was discarded. The cells were resuspended in 1 mL of water with gentle pipetting, centrifuged again at 10,000 rpm for 10 seconds, and the water was discarded. The cells were washed by pipetting with 1 M cold sorbitol, then centrifuged again at 10,000 rpm for 10 seconds, and the supernatant discarded. 2 mL of cold 1 M sorbitol was added to the pellet, and the tube was placed on ice. 40 μL of the cells were then added to pre-chilled 0.2 cm electroporation cuvettes along with 5 μL of DNA. The cells were electroporated at 25 μF, 200 ohms, 1.5 kV, with a ~4.9-5.0 ms time constant. The cells were added to 1 mL of YPD, incubated at 37° C. overnight, and 100 μL to 500 μL of cells were plated onto YPD agar.

Figure 6:
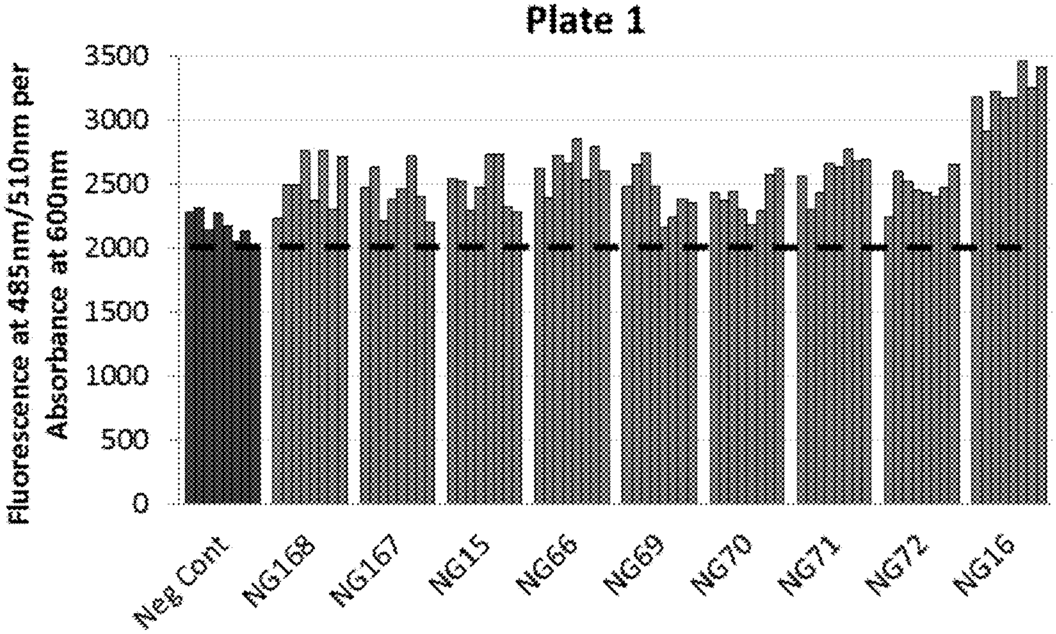
FIG. 6 comprises four graphs, labeled "Plate 1", "Plate 2", "Plate 3", and "Plate 4". Each graph displays results from a fluorescence-based lipid assay, wherein fluorescence at 485 nm/510 nm per absorbance at 600 nm correlates with the lipid content of a cell. The x-axis labels correspond to DGA expression constructs that were used to transform cells, which are defined in Table 2, infra. For each expression construct eight transformants were analyzed. NG168, which corresponds to the *A. adeninivorans* DGA2 gene, was used as a positive control. DGA2s from *Y. lipolytica* (NG16) and *Chaetomium globosum* (NG113) displayed the most significant effect on lipid content.
Figure 6:
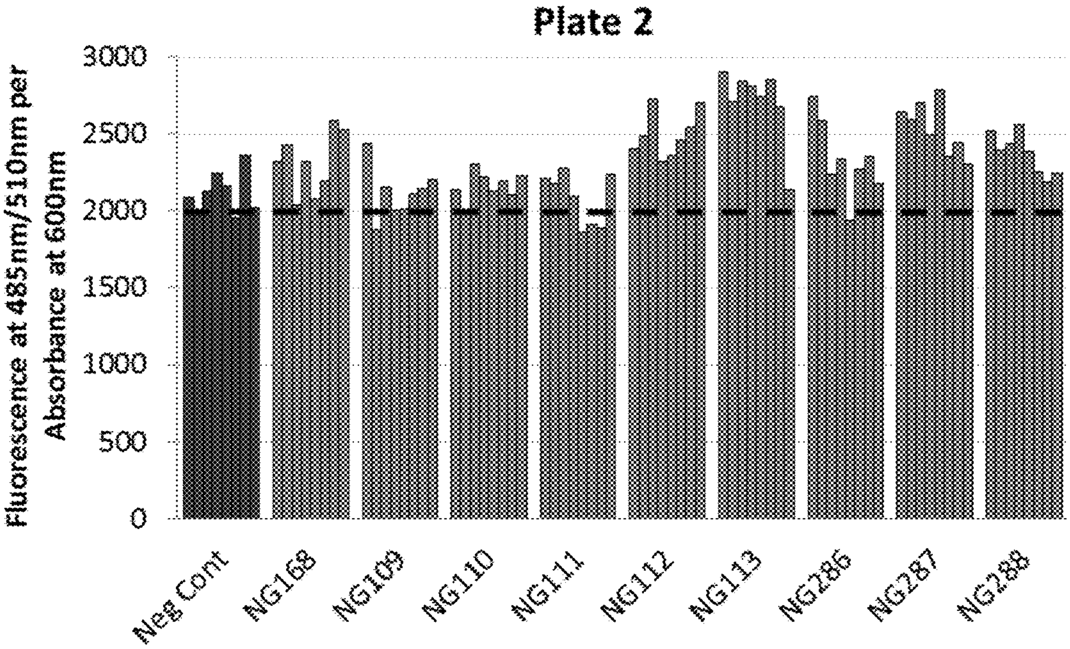
Figure 6:
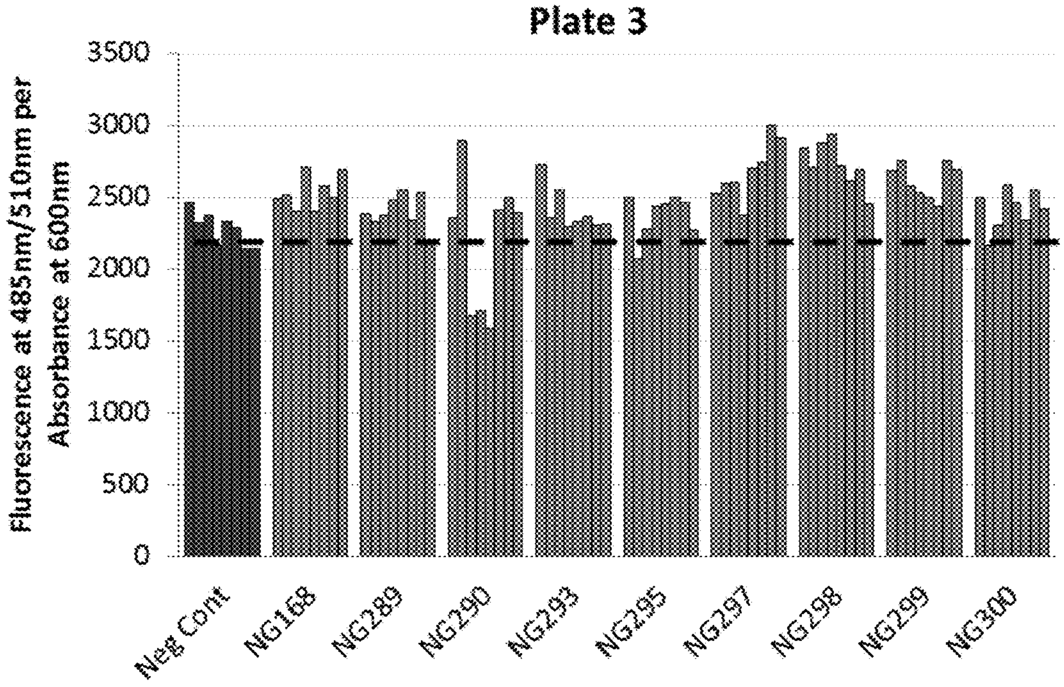
Figure 6:
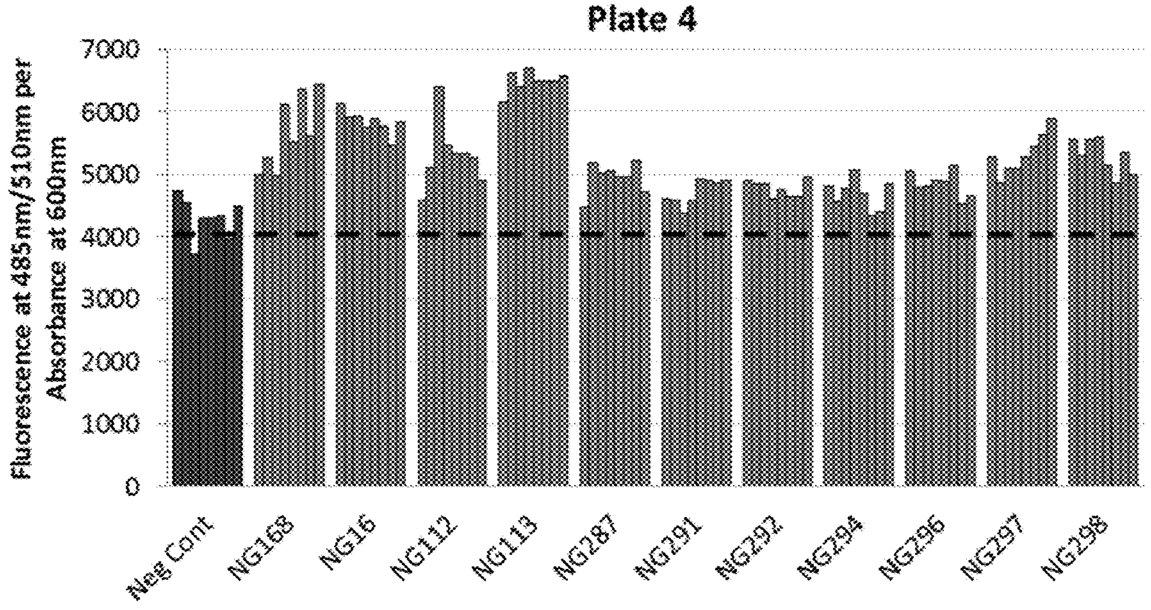

*A. adeninivorans* transformants were selected on YPD plates with 50 µg/mL NAT. The transformants were screened for an ability to accumulate lipids by the fluorescent staining lipid assay described in Example 2. The results of the lipid assays are shown in the FIG. 6. For each expression construct, eight transformants were analyzed. Transformants expressing phosphotransferase instead of DGA were used as negative controls ("Neg Cont"). The assays were carried out in 4 plates with the same negative control and NG168, used as a positive control, in each plate to discount for assay variability between plates. FIG. 6 demonstrates that most of the DGAs tested displayed a positive effect on lipid content in *A. adeninivorans*. DGA2s displayed more significant positive effects on lipid content in *A. adeninivorans* relative to DGA1 s and DGA3s. DGA2s from *Y. lipolytica* (NG16) and *Chaetomium globosum* (NG113) displayed the most significant effect on lipid content in *A. adeninivorans*.

Example 7

Increasing the Activity of DGA1, DGA2, or DGA3 in *Yarrowia lipolytica*

Eighteen genes encoding diacylglycerol acyltransferase type 1, type 2 and type 3 from various donors, listed in Table 2, were expressed in *Yarrowia lipolytica* strain NS598. Strain NS598 is a derivative of *Y. lipolytica* strain NS18 (obtained from ARS Culture Collection, NRRL #YB 392) with two genetic modifications: 1) the native Δ9 desaturase gene was replaced with a Δ9 desaturase gene from *A. adeninivorans*; and 2) the native Δ12 desaturase gene was deleted and replaced with expression cassettes for *E. coli* phosphotransferase, which confers resistance to Hygromycin B, and Herpes Simplex Virus thymidine kinase, which confers sensitivity to 5-Fluoro-2'-deoxyuridine (see U.S. Provisional Patent Application No. 62/090,169, hereby incorporated by reference).

Figure 7:
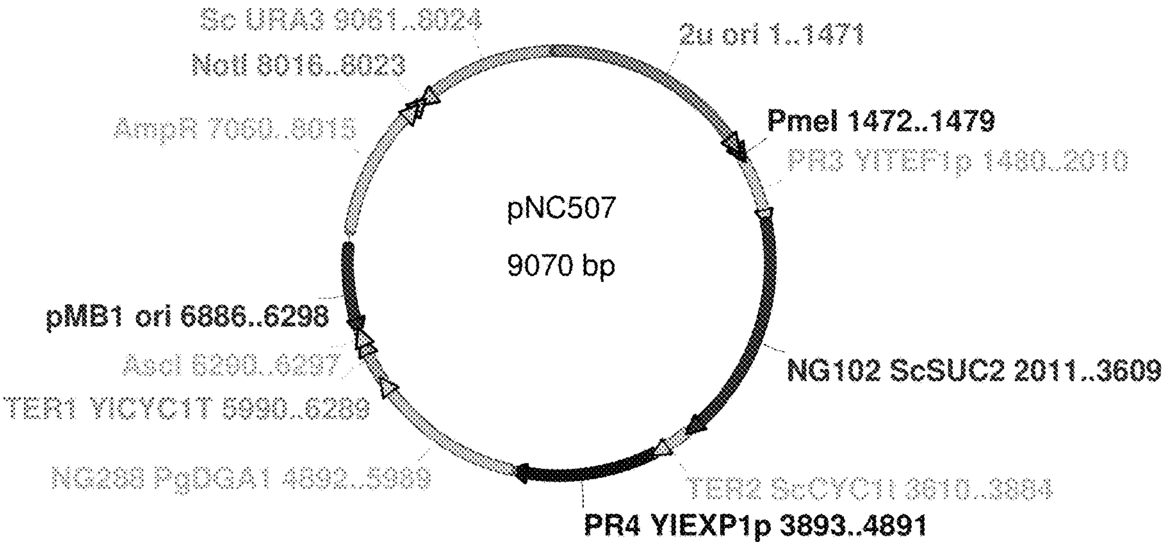
FIG. 7 is a map of the pNC507 vector used to express the NG288 gene in *Y. lipolytica* strain NS598. Vector pNC507 was linearized by a PmeI/AscI restriction digest before transformation. "2u ori" denotes the *S. cerevisiae* origin of replication from the 2 μm circle plasmid; "PR3" denotes the *Y. lipolytica* TEF1 promoter −406 to +125; "NG102" denotes the *S. cerevisiae* SUC2 gene, which encodes an invertase; "TER2" denotes the *S. cerevisiae* CYC1 terminator 275 bp after stop; "PR4" denotes the *Y. lipolytica* EXP1 promoter −999 to −1; "NG288" denotes the *Puccinia graminis* DGA1 cDNA synthetized by GenScript; "TER1" denotes the *Y. lipolytica* CYC1 terminator 300 bp after stop; "pMB1 ori" denotes the *E. coli* pMB1 origin of replication from the pBR322 plasmid; and "AmpR" denotes the bla gene used as a marker for selection with ampicillin.

The map of the expression construct used to express the DGAs in *Y. lipolytica* is shown in FIG. 7, with the NG288 target as example. The constructs for all other DGAs (except for NG112) were the same, except for the target open reading frames. The expression construct used to express NG112 in NS589 is shown in FIG. 3. The expression constructs were assembled by yeast mediated ligation as described below, except for the NG112 gene, which is described in Example 3, supra.

Figure 8:
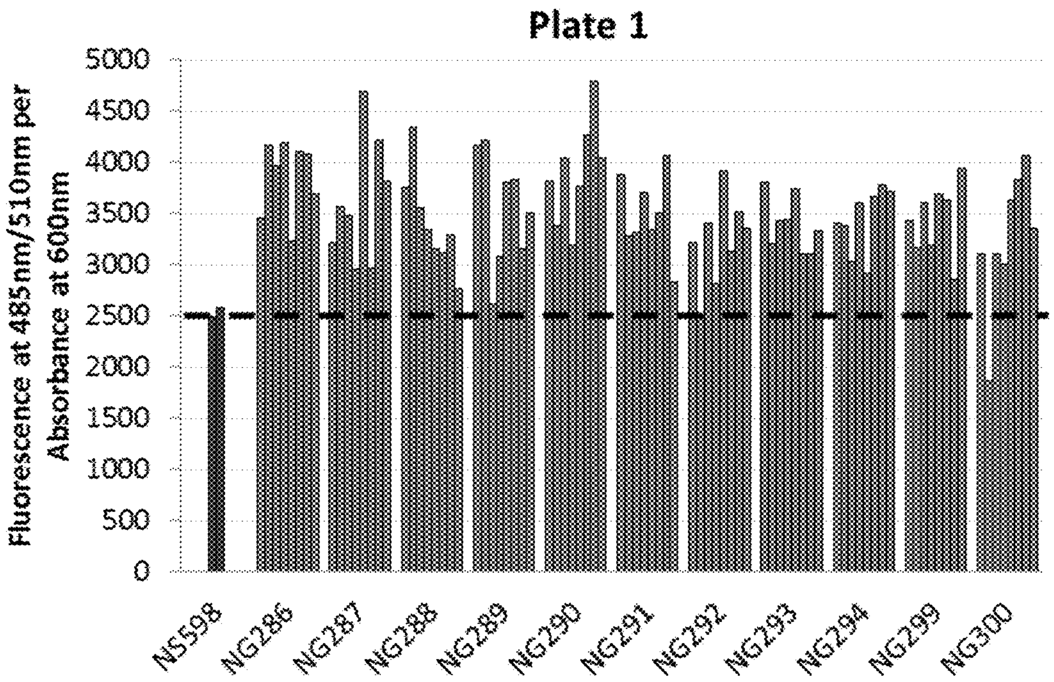
FIG. 8 comprises three graphs, labeled "Plate 1", "Plate 2", and "Plate 3". Each graph displays results from a fluorescence-based lipid assay, wherein fluorescence at 485 nm/510 nm per absorbance at 600 nm correlates with the lipid content of a cell. The x-axis labels correspond to DGA expression constructs that were used to transform cells, which are defined in Table 2, infra. For each expression construct eight transformants were analyzed. The parental strain NS598 was used as a negative control.
Figure 8:
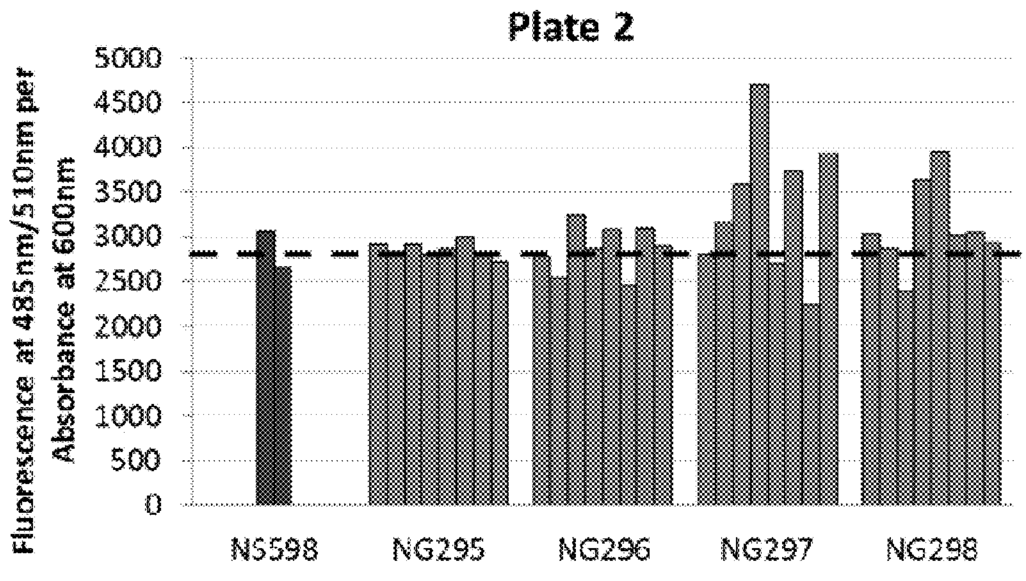
Figure 8:
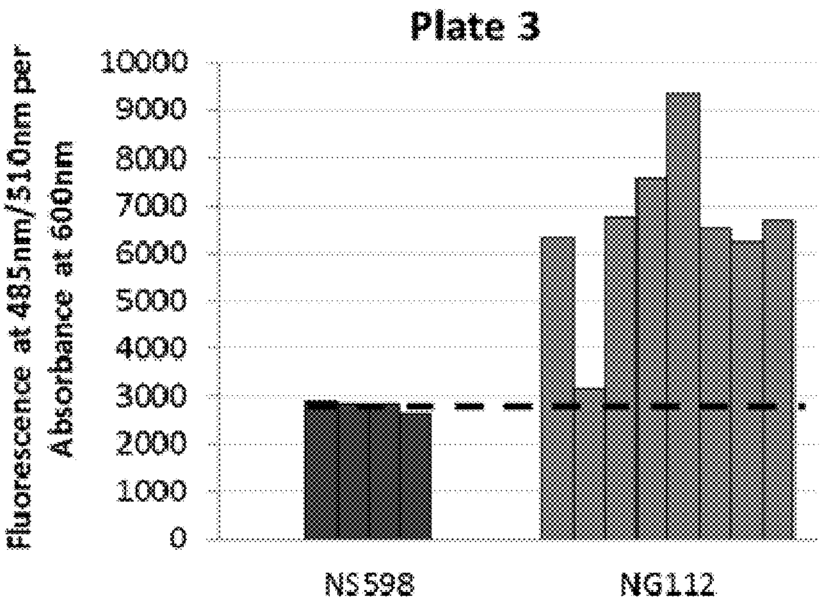

The constructs were linearized by PmeI/AscI restriction digest before transformation. Each linear expression construct included an expression cassette for a DGA gene and for the *S. cerevisiae* SUC2 gene encoding invertase, used as marker for selection with sucrose. The expression constructs were randomly integrated into the genome of NS598 using the transformation protocol described by Chen et al. (Applied Microbiology & Biotechnology 48:232-35 (1997)). The *Y. lipolytica* transformants were selected on YNB plates with 2% sucrose. The transformants were screened for an ability to accumulate lipids by the fluorescent staining lipid assay described in Example 2. Results for the lipid assays are shown in the FIG. 8. For each expression construct, eight transformants were analyzed. The parental strain NS598 was used as negative control. The assays were carried out in 3 plates. The data in FIG. 8 demonstrates that each DGA1 and DGA3 tested displayed a significant positive effect on the lipid content of *Y. lipolytica*. Some DGA2s also displayed a positive effect on the lipid content of *Y. lipolytica*, with *Claviceps purpurea* DGA2 (NG112) showing the largest increase. These results vary from the DGA screen described for *A. adeninivorans* in Example 6, supra, which suggests that the effect of different DGAs on lipid content is host organism specific.

INCORPORATION BY REFERENCE

All of the patents, published patent applications, and other references cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of modifying the lipid content or composition of a yeast cell, the method comprising transforming the yeast cell with at least two nucleotide sequences, wherein the yeast cell is a *Yarrowia* cell that does not express an endogenous triacylglycerol lipase gene; and the at least two nucleotide sequences comprise:

a first nucleotide sequence encoding a type 1 diacylglycerol acyltransferase protein from *Claviceps*; and a second nucleotide sequence encoding a type 2 diacylglycerol acyltransferase protein from *Rhodosporidium.*

2. The method of claim 1, wherein the type 1 diacylglycerol acyltransferase is a *Claviceps purpurea* diacylglycerol acyltransferase.

3. The method of claim 1, wherein the type 2 diacylglycerol acyltransferase is from *Rhodosporidium toruloides* diacylglycerol acyltransferase.

4. The method of claim 1, wherein the yeast cell is a *Yarrowia lipolytica* cell.

5. The method of claim 1, wherein the cell further comprises a Δ9 fatty acid desaturase gene from another species.

6. The method of claim 5, wherein the Δ9 fatty acid desaturase gene is from *Arxula*.

7. The method of claim 6, wherein the Δ9 fatty acid desaturase is from *Arxula adeninivorans*.

* * * * *

SEQUENCE LISTING

```
<160> NUMBER OF SEQ ID NOS: 90

<210> SEQ ID NO 1
<211> LENGTH: 526
<212> TYPE: PRT
<213> ORGANISM: Yarrowia lipolytica

<400> SEQUENCE: 1

Met Glu Val Arg Arg Arg Lys Ile Asp Val Leu Lys Ala Gln Lys Asn
1               5                   10                  15

Gly Tyr Glu Ser Gly Pro Pro Ser Arg Gln Ser Ser Gln Pro Ser Ser
            20                  25                  30

Arg Ala Ser Ser Arg Thr Arg Asn Lys His Ser Ser Ser Thr Leu Ser
        35                  40                  45

Leu Ser Gly Leu Thr Met Lys Val Gln Lys Lys Pro Ala Gly Pro Pro
    50                  55                  60

Ala Asn Ser Lys Thr Pro Phe Leu His Ile Lys Pro Val His Thr Cys
65                  70                  75                  80

Cys Ser Thr Ser Met Leu Ser Arg Asp Tyr Asp Gly Ser Asn Pro Ser
```

-continued

```
                85                  90                  95

Phe Lys Gly Phe Lys Asn Ile Gly Met Ile Ile Leu Ile Val Gly Asn
            100                 105                 110

Leu Arg Leu Ala Phe Glu Asn Tyr Leu Lys Tyr Gly Ile Ser Asn Pro
        115                 120                 125

Phe Phe Asp Pro Lys Ile Thr Pro Ser Glu Trp Gln Leu Ser Gly Leu
    130                 135                 140

Leu Ile Val Val Ala Tyr Ala His Ile Leu Met Ala Tyr Ala Ile Glu
145                 150                 155                 160

Ser Ala Ala Lys Leu Leu Phe Leu Ser Ser Lys His His Tyr Met Ala
                165                 170                 175

Val Gly Leu Leu His Thr Met Asn Thr Leu Ser Ser Ile Ser Leu Leu
            180                 185                 190

Ser Tyr Val Val Tyr Tyr Tyr Leu Pro Asn Pro Val Ala Gly Thr Ile
        195                 200                 205

Val Glu Phe Val Ala Val Ile Leu Ser Leu Lys Leu Ala Ser Tyr Ala
    210                 215                 220

Leu Thr Asn Ser Asp Leu Arg Lys Ala Ala Ile His Ala Gln Lys Leu
225                 230                 235                 240

Asp Lys Thr Gln Asp Asp Asn Glu Lys Glu Ser Thr Ser Ser Ser Ser
                245                 250                 255

Ser Ser Asp Asp Ala Glu Thr Leu Ala Asp Ile Asp Val Ile Pro Ala
            260                 265                 270

Tyr Tyr Ala Gln Leu Pro Tyr Pro Gln Asn Val Thr Leu Ser Asn Leu
        275                 280                 285

Leu Tyr Phe Trp Phe Ala Pro Thr Leu Val Tyr Gln Pro Val Tyr Pro
    290                 295                 300

Lys Thr Glu Arg Ile Arg Pro Lys His Val Ile Arg Asn Leu Phe Glu
305                 310                 315                 320

Leu Val Ser Leu Cys Met Leu Ile Gln Phe Leu Ile Phe Gln Tyr Ala
                325                 330                 335

Tyr Pro Ile Met Gln Ser Cys Leu Ala Leu Phe Phe Gln Pro Lys Leu
            340                 345                 350

Asp Tyr Ala Asn Ile Ser Glu Arg Leu Met Lys Leu Ala Ser Val Ser
        355                 360                 365

Met Met Val Trp Leu Ile Gly Phe Tyr Ala Phe Phe Gln Asn Gly Leu
    370                 375                 380

Asn Leu Ile Ala Glu Leu Thr Cys Phe Gly Asn Arg Thr Phe Tyr Gln
385                 390                 395                 400

Gln Trp Trp Asn Ser Arg Ser Ile Gly Gln Tyr Trp Thr Leu Trp Asn
                405                 410                 415

Lys Pro Val Asn Gln Tyr Phe Arg His His Val Tyr Val Pro Leu Leu
            420                 425                 430

Ala Arg Gly Met Ser Arg Phe Asn Ala Ser Val Val Val Phe Phe Phe
        435                 440                 445

Ser Ala Val Ile His Glu Leu Leu Val Gly Ile Pro Thr His Asn Ile
    450                 455                 460

Ile Gly Ala Ala Phe Phe Gly Met Met Ser Gln Val Pro Leu Ile Met
465                 470                 475                 480

Ala Thr Glu Asn Leu Gln His Ile Asn Ser Ser Leu Gly Pro Phe Leu
                485                 490                 495

Gly Asn Cys Ala Phe Trp Phe Thr Phe Phe Leu Gly Gln Pro Thr Cys
            500                 505                 510
```

-continued

```
Ala Phe Leu Tyr Tyr Leu Ala Tyr Asn Tyr Lys Gln Asn Gln
        515                 520                 525
```

<210> SEQ ID NO 2
<211> LENGTH: 1581
<212> TYPE: DNA
<213> ORGANISM: Yarrowia lipolytica

<400> SEQUENCE: 2

```
atggaagtcc gacgacgaaa aatcgacgtg ctcaaggccc agaaaaacgg ctacgaatcg     60

ggcccaccat ctcgacaatc gtcgcagccc tcctcaagag catcgtccag aacccgcaac    120

aaacactcct cgtccaccct gtcgctcagc ggactgacca tgaaagtcca gaagaaacct    180

gcgggacccc cggcgaactc caaaacgcca ttcctacaca tcaagcccgt gcacacgtgc    240

tgctccacat caatgctttc gcgcgattat gacggctcca accccagctt caagggcttc    300

aaaaacatcg gcatgatcat tctcattgtg ggaaatctac ggctcgcatt cgaaaactac    360

ctcaaatacg gcatttccaa cccgttcttc gaccccaaaa ttactccttc cgagtggcag    420

ctctcaggct tgctcatagt cgtggcctac gcacatatcc tcatggccta cgctattgag    480

agcgctgcca agctgctgtt cctctctagc aaacaccact acatggccgt ggggcttctg    540

cataccatga acactttgtc gtccatctcg ttgctgtcct acgtcgtcta ctactacctg    600

cccaaccccg tggcaggcac aatagtcgag tttgtggccg ttattctgtc tctcaaactc    660

gcctcatacg ccctcactaa ctcggatctc cgaaaagccg caattcatgc ccagaagctc    720

gacaagacgc aagacgataa cgaaaaggaa tccacctcgt cttcctcttc ttcagatgac    780

gcagagactt tggcagacat tgacgtcatt cctgcatact acgcacagct gccctacccc    840

cagaatgtga cgctgtcgaa cctgctgtac ttctggtttg ctcccacact ggtctaccag    900

cccgtgtacc ccaagacgga gcgtattcga cccaagcacg tgatccgaaa cctgtttgag    960

ctcgtctctc tgtgcatgct tattcagttt ctcatcttcc agtacgccta ccccatcatg   1020

cagtcgtgtc tggctctgtt cttccagccc aagctcgatt atgccaacat ctccgagcgc   1080

ctcatgaagt tggcctccgt gtctatgatg gtctggctca ttggattcta cgctttcttc   1140

cagaacggtc tcaatcttat tgccgagctc acctgttttg gaaacagaac cttctaccag   1200

cagtggtgga attcccgctc cattggccag tactggactc tatggaacaa gccagtcaac   1260

cagtacttta gacaccacgt ctacgtgcct cttctcgctc ggggcatgtc gcggttcaat   1320

gcgtcggtgg tggttttctt tttctccgcc gtcatccatg aactgcttgt cggcatcccc   1380

actcacaaca tcatcggagc cgccttcttc ggcatgatgt cgcaggtgcc tctgatcatg   1440

gctactgaga accttcagca tattaactcc tctctgggcc ccttccttgg caactgtgca   1500

ttctggttca ccttttttcct gggacaaccc acttgtgcat tcctttatta tctggcttac   1560

aactacaagc agaaccagta g                                               1581
```

<210> SEQ ID NO 3
<211> LENGTH: 697
<212> TYPE: PRT
<213> ORGANISM: Rhodosporidium toruloides

<400> SEQUENCE: 3

```
Met Thr Glu Arg Ser Leu Pro Val Thr Leu Pro Leu Pro Arg Asn Phe
1               5                   10                  15

Ala Leu Thr Pro His Gln Met Ala Ser Pro Asp Pro Pro Leu Pro Gly
            20                  25                  30
```

```
Pro Ala Asn Leu Val Asp Asp Ala Leu Arg His Pro Asp Ser Ala Pro
        35                  40                  45

Pro Ile Ser Pro Asp Ser Ala Pro Pro Ser Thr Ala Thr Arg Pro Ser
    50                  55                  60

Ala Leu Ser Arg Gly Glu Leu Ser Thr Ala Ser Ser Tyr Ala Ser Glu
65                  70                  75                  80

Val Ser Thr Arg Glu Gly Thr Pro Asp Leu Ala Asn Gly Gln Gly Val
                85                  90                  95

Thr Thr Thr Ile Thr Thr Val Thr Gly Lys Gly Gly Lys Ala Val Thr
            100                 105                 110

Gln Thr Leu Thr His Val Gly Ala Ala Ser Val Asp Ala Arg Phe Ser
        115                 120                 125

Ser Thr Thr Asn Ser Ile Thr Leu Arg Pro Ile Pro Ala Arg Gly Gly
    130                 135                 140

Asp Pro Lys Lys Ile Lys Val Leu Arg Ser Arg Arg Thr His Phe Ala
145                 150                 155                 160

Pro Arg Thr Ser His Phe Asp Arg His Asn Leu Thr Ser Ala Ser Asp
                165                 170                 175

Pro Phe Arg Gly Leu Tyr Thr Leu Phe Trp Ile Val Ile Phe Val Gly
            180                 185                 190

Ala Leu Lys Thr Val Tyr His Arg Phe Ala Glu Gln Gly Gly Trp Gly
        195                 200                 205

Gly Glu Trp Arg Phe Ala Ala Leu Ile Ser Arg Asp Gly Trp Val Leu
    210                 215                 220

Ala Val Ser Asp Ala Val Leu Val Ser Ala Ser Leu Leu Cys Val Pro
225                 230                 235                 240

Tyr Ala Lys Leu Leu Val His Gly Trp Ile Arg Tyr His Gly Ala Gly
                245                 250                 255

Val Ile Ile Gln His Ile Cys Gln Thr Leu Tyr Leu Ala Ile Ala Ile
            260                 265                 270

Arg Trp Thr Phe His Arg Asn Trp Pro Trp Val Gln Ser Gly Phe Met
        275                 280                 285

Thr Leu His Ala Leu Ser Met Leu Met Lys Ile His Ser Tyr Cys Ser
    290                 295                 300

Leu Asn Gly Glu Leu Ser Glu Arg Arg Arg Gln Leu Lys Lys Asp Glu
305                 310                 315                 320

Lys Arg Leu Glu Glu Val Leu Glu Glu Met Gly Gly Arg Arg Lys Ala
                325                 330                 335

Glu Arg Glu Ala Arg Glu Glu Trp Glu Arg Gln Cys Gly Glu Ala Ala
            340                 345                 350

Arg Ala Lys Glu Gly Glu Ala Gly Val Ser Glu Gly Glu Lys Glu Ala
        355                 360                 365

Ala Ala Thr Leu Ser Ser Thr Asp Ala Ser Asn Ser Ala Leu Ser Ser
    370                 375                 380

Glu Asp Glu Ala Ala Ala Ala Leu Leu Arg His Arg Gln Pro Thr Ala
385                 390                 395                 400

Arg Arg Arg Ser Ile Ser Pro Ser Ala Ser Arg Thr Gly Ser Ser Ser
                405                 410                 415

Ala Pro Ser Ala Thr Leu Ala Pro Ser Arg Ala Glu Glu Pro Gln Glu
            420                 425                 430

Gly Val Glu Thr Leu Thr Trp His Pro Ser Asp Gln Val Ser Lys Leu
        435                 440                 445
```

```
Ala Ile Ala Ile Cys Glu Ala Lys Asp Leu Leu Thr Ser Asn Gly Lys
    450                 455                 460

Lys Pro Val Thr Phe Pro Glu Asn Val Thr Phe Ala Asn Phe Ile Asp
465                 470                 475                 480

Tyr Leu Leu Val Pro Thr Leu Val Tyr Glu Leu Glu Tyr Pro Arg Thr
                485                 490                 495

Asp Ser Ile Arg Pro Leu Tyr Ile Leu Glu Lys Thr Leu Ala Thr Phe
            500                 505                 510

Gly Thr Phe Ser Ile Leu Val Leu Ile Val Asp Ser Phe Ile Leu Pro
        515                 520                 525

Val Thr Ser Arg Thr Asp Thr Pro Leu Phe Gly Phe Val Leu Asp Leu
    530                 535                 540

Ala Leu Pro Phe Thr Leu Ala Tyr Leu Leu Ile Phe Tyr Val Ile Phe
545                 550                 555                 560

Glu Gly Val Cys Asn Gly Phe Ala Glu Leu Thr Arg Phe Ala Asp Arg
                565                 570                 575

Asn Phe Phe Asp Asp Trp Trp Asn Ser Cys Thr Phe Asp Glu Phe Ser
            580                 585                 590

Arg Lys Trp Asn Arg Pro Val His Ala Phe Leu Leu Arg His Val Tyr
        595                 600                 605

Ala Glu Thr Met Ala Ser Tyr Lys Leu Ser Lys Leu Ser Ala Ala Phe
    610                 615                 620

Val Thr Phe Leu Phe Ser Ala Cys Val His Glu Leu Val Met Ala Val
625                 630                 635                 640

Val Thr Lys Lys Leu Arg Leu Tyr Leu Phe Ser Met Gln Met Ala Gln
                645                 650                 655

Leu Pro Leu Ile Met Val Gly Arg Ala Lys Ile Phe Arg Gln Tyr Pro
            660                 665                 670

Ala Leu Gly Asn Leu Phe Phe Trp Leu Ala Leu Leu Ser Gly Phe Pro
        675                 680                 685

Leu Leu Gly Thr Leu Tyr Leu Arg Tyr
    690                 695
```

<210> SEQ ID NO 4
<211> LENGTH: 2094
<212> TYPE: DNA
<213> ORGANISM: Rhodosporidium toruloides

<400> SEQUENCE: 4

```
atgacggagc gatcccttcc agtgacgctc cctcttcctc gaaactttgc gctcacaccg      60

caccagatgg cctcgccaga cccgccactc ccaggcccag ccaacctcgt cgacgacgca     120

ctccgacacc cagactcggc gccgcccatc tcgcccgact ccgcgcctcc ttcgactgcg     180

actcggccct ctgctctctc gcgcggagag ctctcgaccg cttcgagcta cgcgagcgag     240

gtgtcgacga gggaggggac accggatctg gcgaatgggc aaggggttac gacgaccatc     300

acgactgtca caggcaaagg cggaaaggcc gtcacccaga ccctcaccca cgtcggcgcc     360

gcctccgtcg acgcccgctt ctcctccacc acaaactcca tcactctccg ccctatcccc     420

gcccgtggcg gcgacccgaa aaagatcaaa gtcctccgct ctcgtcggac ccacttcgcc     480

ccacgcacct cacacttcga ccgtcacaac ctcacctccg cctctgaccc gttccgcgga     540

ctgtacacgt tgttctggat cgtgatcttc gttggggcac tcaagactgt gtatcatcgg     600

tttgcggaac agggtgggtg gggtggagaa tggaggtttg cggcgttgat tagtcgcgat     660

gggtgggttc tggcggttag tgatgcggtg ttggttagcg cgtcgttgtt gtgcgtgccg     720
```

```
tatgcaaagc tcctcgtaca cggctggatc cggtaccacg gcgcaggcgt catcatccaa    780

cacatctgtc aaacgctcta cctcgccatc gcgatccgct ggaccttcca ccgcaactgg    840

ccctgggtcc aaagcggttt catgaccctc cacgccctct cgatgctcat gaagatccat    900

agctactgtt ctctgaacgg cgagctttcg gagcggcgga gacagttgaa gaaggacgag    960

aagcggttgg aggaggtgct ggaggagatg ggtggacgga ggaaggcgga gagggaggcg   1020

agggaggagt gggagaggca gtgtggggag gcggcgaggg ccaaggaggg tgaggcggga   1080

gtgagcgagg gggagaagga ggcggcggcg actctatctt cgacggatgc gtcgaattcg   1140

gccctttcgt cggaggacga ggcggctgcg gcgctgttgc ggcatcgaca gccgactgct   1200

cgacgacgat ccatctcgcc ctctgcctca cgcaccggtt cctcctccgc cccctccgct   1260

accctcgccc cctctcgcgc cgaagaaccc caagaaggcg ttgagacgct cacctggcac   1320

ccatccgacc aagtcagcaa actcgctatc gccatctgcg aggcaaagga cctcctcacg   1380

agtaacggca agaagcccgt cacgttcccc gagaacgtca cctttgcgaa ctttatcgac   1440

tacttgcttg tgccgacgtt ggtgtacgag ttggagtacc ctcggacgga ttccatccgg   1500

cccctctaca tcctcgaaaa gaccctcgca accttcggca ccttctccat tctcgtcctc   1560

atcgtcgact cgttcatcct ccccgtcacc tcgcgcaccg acacgcccct cttcgggttc   1620

gtcctcgacc tcgccctgcc gttcacgctc gcgtacctcc tcatcttcta cgtcatcttt   1680

gagggcgtgt gcaatgggtt tgcggagttg acgaggtttg cggatcggaa tttcttcgac   1740

gattggtgga actcgtgcac gttcgacgag ttctcgcgca agtggaatcg ccccgtccac   1800

gccttcctcc tccgccacgt ttacgccgaa acgatggctt cttacaagct ctcgaagctc   1860

tcggctgcgt tcgtcacgtt cttgttcagc gcctgcgtgc acgaactcgt catggcggtc   1920

gtgacgaaga agcttcggct gtacctgttc tcgatgcaga tggcccagct cccgctcatc   1980

atggtgggcc gcgccaagat cttccgacag tatccagcgc tcggcaacct cttcttctgg   2040

ctcgcccttc tctcgggatt cccgcttctc gggacgctgt atctgcggta ctga         2094
```

<210> SEQ ID NO 5
<211> LENGTH: 555
<212> TYPE: PRT
<213> ORGANISM: Lipomyces starkeyi

<400> SEQUENCE: 5

```
Met Ser Thr Ala Ala Gln Ser Asp Thr Asp Asn Glu Asp Ile Ser Thr
1               5                   10                  15

Val Asp Leu Val Asp Ser Arg Ala Asp Thr His Thr Ser Ser Asn Val
            20                  25                  30

Met Leu Gln Gln Gln Lys Ser Arg Arg Arg Leu Ile Gly Lys Asp Ala
        35                  40                  45

Glu Pro Arg Thr Gln His Pro Ser Gly Gly Lys Ser Glu Lys Glu Glu
    50                  55                  60

Leu Thr Lys Pro Asp Asp Ser Lys Gly Pro Ile Lys Leu Ser His Ile
65                  70                  75                  80

Tyr Pro Ile His Ala Val Ser Arg Gly Ser Ile Leu Ser Arg Glu Ser
                85                  90                  95

Thr Thr Pro Thr Pro Ser Phe Val Gly Phe Arg Asn Leu Ala Met Ile
            100                 105                 110

Val Leu Gly Lys Leu Gln Tyr Ser Leu Phe Phe Trp Cys Asp Arg Ala
        115                 120                 125
```

-continued

```
Asn Ile Pro Thr Ala Val Ser Asn Leu Arg Leu Val Ile Glu Asn Tyr
    130                 135                 140

Ser Lys Tyr Gly Val Leu Ile Arg Phe Ala Arg Leu Gly Ile Ser Gln
145                 150                 155                 160

Lys Asp Ile Leu Tyr Cys Ile Phe Leu Thr Ala Thr Ile Pro Leu His
                165                 170                 175

Leu Phe Ile Ala Ile Val Ile Glu Arg Leu Val Ala Ile Pro Thr Val
            180                 185                 190

Asn Tyr Val Ala Ser Leu Ser Glu Ser Glu Asp Lys Lys Arg Ser Asn
        195                 200                 205

Pro Lys Met Gly Arg Lys Gly Gly Ser Ile Ser Ile Leu Arg Pro Lys
    210                 215                 220

Pro Lys Tyr Met Trp Arg Leu Ile Val Leu Leu His Ser Ile Asn Ala
225                 230                 235                 240

Met Ala Cys Leu Trp Val Thr Thr Val Val Val Tyr Asn Ser Ile Tyr
                245                 250                 255

His Pro Leu Ile Gly Thr Ala Cys Glu Phe His Ala Val Ile Val Cys
            260                 265                 270

Leu Lys Val Ala Ser Phe Ala Leu Thr Asn Arg Asp Leu Arg Glu Ser
        275                 280                 285

Met Leu Asn Ser Gln Pro Val Pro Ala Ile Tyr Asn Leu Ala Pro Tyr
    290                 295                 300

Pro Lys Asn Leu Thr Leu Lys Asn Leu Ser Tyr Phe Trp Trp Ala Pro
305                 310                 315                 320

Thr Leu Val Tyr Gln Pro Val Tyr Pro Arg Ser Pro Ser Phe Arg Pro
                325                 330                 335

Leu Phe Phe Val Lys Arg Ile Leu Glu Met Val Gly Leu Ser Phe Leu
            340                 345                 350

Ile Trp Phe Leu Ser Ala Gln Tyr Ala Val Pro Thr Leu Glu Asn Ser
        355                 360                 365

Leu Val His Phe His Ser Leu Gln Phe Met Gly Ile Met Glu Arg Leu
    370                 375                 380

Met Lys Leu Ala Ser Ile Ser Met Ala Ile Trp Leu Ala Gly Phe Phe
385                 390                 395                 400

Cys Ile Phe Gln Ser Gly Leu Asn Ala Leu Ala Glu Val Met Arg Phe
                405                 410                 415

Gly Asp Arg Ala Phe Tyr Asp Asp Trp Trp Asn Ser Lys Ser Val Gly
            420                 425                 430

Glu Tyr Trp Arg Leu Trp Asn Lys Pro Val Thr Asn Tyr Phe Arg Arg
        435                 440                 445

His Ile Tyr Val Pro Leu Val Arg Arg Gly Trp Asn Ser Ala Thr Ala
    450                 455                 460

Ser Val Met Val Phe Phe Val Ser Ala Val Leu His Glu Leu Val Val
465                 470                 475                 480

Gly Val Pro Thr His Asn Val Ile Gly Val Ala Phe Ser Ser Met Ile
                485                 490                 495

Leu Gln Ile Pro Leu Ile Gln Val Thr Ala Pro Leu Glu Lys Met His
            500                 505                 510

Gly Pro Thr Ser Gly Ile Ile Gly Asn Cys Ile Phe Trp Phe Ser Phe
        515                 520                 525

Phe Ile Gly Gln Pro Leu Gly Val Leu Leu Tyr Tyr Phe Ala Trp Asn
    530                 535                 540

Val Ser Met Ser Lys Val Lys Met Val Glu Ser
```

-continued 545 550 555

<210> SEQ ID NO 6
<211> LENGTH: 1668
<212> TYPE: DNA
<213> ORGANISM: Lipomyces starkeyi

<400> SEQUENCE: 6
atgtcgaccg ctgcacaatc tgatacagac aacgaggata tatcgactgt cgatttggtt 60
gactctcgtg cagatactca cacatcttca aatgttatgt tgcaacagca aaaatcgcgt 120
cggagactaa tcgggaaaga cgccgagcca agaacacagc atccgtctgg aggcaaatcg 180
gagaaggagg agttgacgaa gccggatgac tcaaagggac ccataaaatt aagtcacata 240
tacccgatac atgccgttag ccgaggcagt attctgtcac gagagtcgac aactcctaca 300
ccgagttttg ttgggtttcg aaacttagcc atgatagtgc tagggaagtt acagtattca 360
ttattctttt ggtgcgatcg ggctaacatt ccgacagccg tcagcaatct tcgattggtg 420
attgaaaatt actcaaagta cggcgttctg atccgattcg cccgactcgg tatttcacaa 480
aaggacattc tgtattgcat attcttgacc gctaccatcc cgctgcacct atttattgct 540
attgtcattg aaagactagt tgcgattccg acggtaaact acgtcgcttc gctcagcgag 600
agcgaggata aaaaacgctc caaccccaaa atgggacgga agggggcag tatatcgatt 660 ttgcgtccta agccaaaata tatgtggcgc ctgatcgtcc tattgcattc aataaacgca 720
atggcttgct tgtgggttac gactgttgtt gtttacaatt ctatttatca tccccttatt 780
gggacagctt gtgaatttca tgcagtgatt gtgtgtctta aggtcgcatc gtttgcgctt 840
accaatcgcg atcttcggga gtcgatgctg aactctcaac ctgtgccagc catatacaac 900
ttggcccctt atccaaaaaa cttaaccctc aagaacttgt catacttttg gtgggcgccg 960
actcttgttt atcaacctgt ctatccgcga tcgccttcat tccggccttt gttttttgtc 1020
aagcggattc tggagatggt gggcctatca tttttaatat ggttcttgtc agctcaatat 1080
gctgtgccga cgctagaaaa tagtttggtg cattttcaca gtttgcaatt catgggaatt 1140
atggagcgac tcatgaagct tgctagcatt agcatggcta tttggcttgc tggtttttc 1200 tgcatttttc agtctggact caatgcgctt gcggaggtaa tgcggtttgg tgacagagcc 1260
ttttacgacg actggtggaa cagcaaatct gtgggagagt attggcgtct gtggaataag 1320
ccggttacga attacttccg gcgtcatatt tacgtaccgc ttgtgcgccg cgggtggaat 1380
tctgcgacag ccagtgtcat ggtatttttc gtcagcgcgg tgttgcatga gctagttgtt 1440
ggagttccga cgcataacgt aattggagtt gcattctcgt cgatgattct acaaatccca 1500
ctcatacaag taaccgcgcc tctggagaag atgcatggac ctacatctgg aataataggg 1560
aactgtatct tttggtttag cttcttcatc ggtcagcctc tgggcgtgct actttactat 1620
tttgcgtgga acgttagtat gagcaaagta aagatggtcg agagctag 1668

<210> SEQ ID NO 7
<211> LENGTH: 517
<212> TYPE: PRT
<213> ORGANISM: Aspergillus terreus

<400> SEQUENCE: 7

Met Val Met Asp Thr Gln Thr Thr Ala Ser Ala Thr Ser Thr Ala Leu
1 5 10 15

Thr Thr Asp His Thr Val Ala Ser Arg Thr Ser Arg Ser Glu Pro Asn
20 25 30

```
Gly Gly Val His Asn Val Ser Ser Pro Pro Thr Ser Glu Pro Thr Gly
        35                  40                  45

Gly Asn Gly Gly Gly Arg Arg Arg Ser Lys Tyr Arg His Val Ala Ala
    50                  55                  60

Tyr His Ser Glu Val Arg His Ser Ser Leu Ser Arg Glu Ser Asn Thr
65                  70                  75                  80

Ser Pro Ser Phe Leu Gly Phe Arg Asn Leu Met Val Ile Val Leu Gly
                85                  90                  95

Glu Cys Pro Ser Ala Leu Leu Arg Phe Val Asn Pro Thr Glu Asn Ser
            100                 105                 110

Tyr Gly Ser Arg Leu Val Ala Met Asn Leu Arg Leu Val Ile Glu Asn
        115                 120                 125

Tyr Val Lys Tyr Gly Val Leu Ile Cys Ile Arg Cys His Asp Tyr Arg
    130                 135                 140

Lys Gln Asp Val Val Leu Gly Ser Met Leu Phe Ala Leu Val Pro Cys
145                 150                 155                 160

Gln Leu Phe Ile Ala Tyr Leu Leu Glu Leu Ala Ala Ala Gly Arg Ala
                165                 170                 175

Lys Gln Thr Val Gly Arg Lys Lys Lys Asp Gly Ser Ala Glu Glu Gly
            180                 185                 190

Glu Arg Glu Ala Arg Ala Phe Arg His Ile Trp Arg Phe Ala Leu Ser
        195                 200                 205

Phe His Ile Leu Asn Ile Val Leu Asn Leu Ala Val Thr Ser Phe Val
    210                 215                 220

Val Tyr Tyr Tyr Ile His His Pro Gly Ile Gly Thr Leu Cys Glu Val
225                 230                 235                 240

His Ala Ile Val Val Ala Leu Lys Asn Trp Ser Tyr Ala Phe Thr Asn
                245                 250                 255

Arg Asp Leu Arg Glu Ala Met Leu Asn Pro Ser Ala Glu Ser Ala Leu
            260                 265                 270

Pro Glu Ile Tyr Ser Ser Leu Pro Tyr Pro Lys Asn Ile Thr Leu Gly
        275                 280                 285

Asn Leu Thr Tyr Phe Trp Leu Ala Pro Thr Leu Leu Tyr Gln Pro Val
    290                 295                 300

Tyr Pro Arg Ser Pro Ser Ile Arg Trp Pro Phe Val Ala Lys Arg Leu
305                 310                 315                 320

Ser Glu Phe Ala Cys Leu Ser Val Phe Ile Trp Leu Leu Ser Ala Gln
                325                 330                 335

Tyr Ala Ala Pro Val Leu Arg Asn Ser Ile Asp Lys Ile Arg Asp Met
            340                 345                 350

Ala Tyr Ala Ser Ile Phe Glu Arg Val Met Lys Leu Ser Thr Ile Ser
        355                 360                 365

Leu Val Ile Trp Leu Ala Gly Phe Phe Ala Ile Phe Gln Ser Leu Leu
    370                 375                 380

Asn Ala Leu Ala Glu Ile Met Lys Phe Gly Asp Arg Glu Phe Tyr Thr
385                 390                 395                 400

Asp Trp Trp Asn Ser Pro Ser Leu Gly Val Tyr Trp Arg Ser Trp Asn
                405                 410                 415

Arg Pro Val Tyr Gln Phe Met Lys Arg His Val Tyr Ser Pro Leu Ile
            420                 425                 430

Gly Arg Gly Tyr Ser Pro Phe Val Ala Ser Thr Val Val Phe Thr Ile
        435                 440                 445
```

```
Ser Ala Leu Leu His Glu Leu Leu Val Gly Ile Pro Thr His Asn Met
    450                 455                 460

Ile Gly Val Ala Leu Val Gly Met Leu Phe Gln Leu Pro Leu Ile Ala
465                 470                 475                 480

Ile Thr Ala Pro Leu Glu Lys Met Lys Asp Pro Leu Gly Lys Pro Leu
                485                 490                 495

Gly Ala Leu Leu Tyr Phe Phe Ala Trp Gln Ala Lys Tyr Gly Ser Val
            500                 505                 510

Ser Arg Met Gly Asn
        515


<210> SEQ ID NO 8
<211> LENGTH: 1554
<212> TYPE: DNA
<213> ORGANISM: Aspergillus terreus

<400> SEQUENCE: 8

atggtgatgg acacacaaac cacagcatcc gccaccagca cggcgctcac gaccgaccac      60

actgttgcct ctcggacgtc ccgctctgag ccgaacggtg gtgtgcataa tgtatcgtca     120

cctccaacga gcgaaccgac tgggggaaat ggcggaggcc ggcgaaggag taaataccgg     180

catgtcgcag cgtaccattc cgaagtgcgc cattccagtc tcagtcggga atcgaatact     240

tctccgagtt tcctcggatt ccggaacctc atggtaatcg tattaggtga gtgccctagt     300

gctctcctac gttttgtgaa cccgacggag aactcatacg ggtcgcgact agttgctatg     360

aatcttcgat tggttatcga gaattacgtg aagtatgggg tcttgatctg catcagatgc     420

cacgattatc gaaagcagga cgttgtcctg ggctcaatgt tatttgctct cgtcccatgc     480

cagctattca tcgcctacct cctggaattg gccgcagcgg gtagggccaa acagactgtg     540

ggccgaaaga aaaaggacgg atcagccgag gagggcgaac gtgaagcacg tgcttttcga     600

cacatctggc ggtttgcatt gtcctttcac atcctcaaca ttgttctcaa tctcgccgtc     660

acgagcttcg ttgtgtatta ctacatccac catcccggca ttggtacgct ctgtgaagtg     720

catgcgatcg ttgtcgcgtt gaaaaactgg tcctatgcgt tcaccaatcg ggatctgcga     780

gaggcgatgc ttaatccctc ggcggagtcg gcgcttcccg agatctattc cagcctcccg     840

tacccgaaaa acatcacgtt aggaaatcta acgtacttct ggcttgcacc gacactgttg     900

tatcagccag tataccccag gtcgccttcc atccgatggc cattcgtggc caaacgcttg     960

tcggaatttg cgtgcttgtc ggtgttcatt tggctacttt cggcccaata cgctgcgcca    1020

gttttgcgca actccattga caagattcgt gatatggcat atgcatccat ttttgagcgc    1080

gttatgaagc tatccaccat ctctctcgtc atttggctgg ctgggttctt tgcgattttc    1140

caatcactct tgaatgcttt ggcggagatc atgaagtttg gcgatcggga attctacacc    1200

gattggtgga atagcccaag tctcggtgtt tactggcggt catggaatcg gccagtgtac    1260

cagttcatga agcggcacgt atattctccg ttgatagggc gggggtacag cccgtttgtg    1320

gcaagcactg tcgtattcac catctccgct ctccttcatg agctcctcgt ggggataccc    1380

acgcacaaca tgataggcgt cgcgcttgtt ggaatgctgt tccagctccc gttgatcgcc    1440

atcactgccc cattggaaaa gatgaaagat ccattgggta agcccctggg agcactgctg    1500

tatttctttg cctggcaggc aaaatatggc agtgtgagca ggatgggcaa ctga          1554


<210> SEQ ID NO 9
<211> LENGTH: 506
<212> TYPE: PRT
```

<213> ORGANISM: Claviceps purpurea

<400> SEQUENCE: 9

```
Met Ser Ala Thr Gly Val Asp Val Ala Asn Gly Arg Ser Gly Ala Arg
1               5                   10                  15

Arg Arg Asn Asp Thr Ala Val Asp Glu Thr Ile Ser Ala Val Thr Ala
            20                  25                  30

Glu Met Arg Ser Ser Ser His Pro Thr Tyr Arg His Val Ser Ala Val
        35                  40                  45

His Ser Thr Ser Arg Pro Ser Cys Leu Ser His Asp Ser Asp Ala Ala
    50                  55                  60

Pro Ser Phe Ile Gly Phe Arg Asn Leu Met Val Ile Val Leu Val Val
65                  70                  75                  80

Gly Asn Val Arg Leu Met Ile Glu Asn Leu Lys Lys Tyr Gly Val Leu
                85                  90                  95

Ile Cys Leu Arg Cys His Ser Tyr Lys Asn Glu Asp Ile Ile Ile Gly
            100                 105                 110

Gly Leu Leu Tyr Phe Leu Ile Pro Cys His Leu Leu Val Ala Tyr Gly
        115                 120                 125

Ile Glu Leu Ala Ala Ala Arg Gln Ala Arg Glu Ser Arg Thr Arg Pro
    130                 135                 140

Pro Gly Gln Ser Asp Thr Ala Ser Lys Ser Thr Glu Asp Asp Asn Lys
145                 150                 155                 160

His Phe His Ser Thr Trp Val Leu Ala Ala Trp Ala His Ile Ile Asn
                165                 170                 175

Met Thr Leu Ser Phe Ile Leu Thr Thr Phe Val Val Tyr Tyr Tyr Val
            180                 185                 190

His His Pro Leu Val Gly Thr Leu Thr Glu Met His Ala Val Ile Val
        195                 200                 205

Ser Leu Lys Thr Ala Ser Tyr Ala Phe Thr Asn Arg Asp Leu Arg His
    210                 215                 220

Ala Tyr Leu His Pro Asp Lys Arg Lys His Ile Pro Glu Leu Tyr Leu
225                 230                 235                 240

Glu Cys Pro Tyr Pro Gln Asn Leu Thr Phe Gly Asn Leu Val Tyr Phe
                245                 250                 255

Trp Trp Ala Pro Thr Leu Val Tyr Gln Pro Val Tyr Pro Arg Thr Asp
            260                 265                 270

Lys Ile Arg Trp Val Phe Val Phe Lys Arg Leu Gly Glu Val Cys Cys
        275                 280                 285

Leu Ser Ala Phe Ile Trp Phe Ala Ser Phe Gln Tyr Ala Ala Pro Val
    290                 295                 300

Leu Arg Asn Ser Leu Asp Lys Ile Ala Ser Leu Asp Phe Ile Met Ile
305                 310                 315                 320

Phe Glu Arg Leu Leu Lys Leu Ser Thr Ile Ser Leu Val Ile Trp Leu
                325                 330                 335

Ala Gly Phe Phe Ala Leu Phe Gln Ser Phe Leu Asn Ala Leu Ala Glu
            340                 345                 350

Val Leu Arg Phe Gly Asp Arg Cys Phe Tyr Asp Asp Trp Trp Asn Ser
        355                 360                 365

Glu Ser Leu Gly Ala Tyr Trp Arg Thr Trp Asn Arg Pro Val Tyr Thr
    370                 375                 380

Tyr Phe Lys Arg His Val Tyr Val Pro Met Ile Gly Arg Gly Trp Ser
385                 390                 395                 400
```

-continued

```
Pro Trp Thr Ala Ser Cys Thr Val Phe Phe Val Ser Ala Val Leu His
                405                 410                 415

Glu Val Leu Val Gly Val Pro Thr His Asn Ile Ile Gly Val Ala Phe
            420                 425                 430

Val Gly Met Phe Leu Gln Leu Pro Leu Ile Ala Leu Thr Ala Pro Met
        435                 440                 445

Glu Lys Lys Lys Trp Gly His Thr Gly Arg Val Met Gly Asn Val Ile
    450                 455                 460

Phe Trp Val Ser Phe Thr Ile Phe Gly Gln Pro Phe Ala Ala Leu Met
465                 470                 475                 480

Tyr Phe Tyr Ala Trp Gln Ala Lys Tyr Gly Ser Val Ser Arg Gln Ile
                485                 490                 495

Val Leu Val Asn Pro Val Glu Glu Ala Ser
            500                 505
```

<210> SEQ ID NO 10
<211> LENGTH: 1521
<212> TYPE: DNA
<213> ORGANISM: Claviceps purpurea

<400> SEQUENCE: 10

```
atgtccgcca cgggcgttga tgtggccaac ggccgcagcg gcgcgcgacg acgcaacgat     60
actgccgtcg acgagactat atccgccgtc acggccgaga tgcgttcctc gtcgcatcca    120
acataccgcc atgtgtctgc tgtgcactcc acgagccggc cctcgtgtct gagccatgat    180
tctgacgctg cgccgagctt cattggcttt cgaaatctca tggtcattgt tctggtcgtt    240
ggcaatgttc gattaatgat tgaaaatcta aaaaagtacg gcgtactgat atgcctccga    300
tgtcactcgt ataaaaacga agacatcatt atcggcggac tgctctactt cctgatcccc    360
tgccacttgc ttgtcgccta cggaatcgag ttagccgccg ccagacaagc acgcgaatct    420
cgaactcgtc caccaggcca gtccgacacg gcgtcgaaat caacagaaga tgacaacaag    480
cacttccact caacatgggt gctcgctgcc tgggcacaca tcatcaacat gacactttcc    540
ttcatcctca ccaccttcgt cgtctactac tacgtgcacc atcccctcgt cggcaccctg    600
accgagatgc acgccgtcat cgtctctctc aaaacagctt cctacgcatt caccaaccga    660
gatcttcgcc acgcatacct ccatcctgac aagcgcaagc acatccccga gctatatctc    720
gaatgtccct acccccagaa cctcaccttt ggcaatctcg tgtatttctg gtgggccccc    780
acgctggtat accagcccgt gtatccgcgc accgacaaga tcagatgggt ttttgttttt    840
aaaagactag gcgaagtctg ctgtctcagc gcattcatct ggttcgccag cttccagtac    900
gccgcgcccg tgttgcggaa ctccctggac aagattgcgt ctctcgactt catcatgatc    960
tttgagcgcc ttctcaagct atccaccatt tctctcgtca tctggctcgc cggcttcttc   1020
gccctgttcc agtctttcct gaatgccctg gctgaggtat tgcgctttgg ggaccggtgc   1080
ttctacgacg attggtggaa tagcgagagt ctgggggcgt attggaggac gtggaacagg   1140
cctgtgtata cctacttcaa gcgccatgtg tatgtgccca tgattgggag gggatggagt   1200
ccctggactg ctagttgtac tgtttttttt gtgtcggcgg tgctgcacga ggttcttgtt   1260
ggggtgccca cccacaatat cattggtgtc gcctttgtgg gcatgtttct gcagcttccc   1320
ctaatagccc tcaccgctcc catggaaaag aagaaatggg gccacaccgg ccgtgtgatg   1380
ggcaatgtta ttttctgggt gtcctttaca atctttgggc agccctttgc agcgctcatg   1440
tacttttatg cctggcaggc caagtacggg agcgtgagtc ggcaaattgt gctggtgaat   1500
```

ccggtggagg aggcgtcttg a 1521

<210> SEQ ID NO 11
<211> LENGTH: 551
<212> TYPE: PRT
<213> ORGANISM: Chaetomium globosum

<400> SEQUENCE: 11

Met Lys Ala Glu Thr Gly Thr Thr Met Ala Thr Ser Thr Ser Leu Glu
1 5 10 15

Thr Ser Gln Val Asn Gly Val Thr Asn Arg Ala Pro Val Gly Pro Ser
20 25 30

His Asp Pro His Ala Thr Thr Pro Thr His Glu Thr Thr Thr Thr Ile
35 40 45

Pro Ser Asp Val Leu Ala Asn Gly Ser Thr Asn Gly Thr Thr Asn Gly
50 55 60

Thr Thr Asp Asp Ser Leu Asp Ile Ser Glu Leu Arg Lys Ala Phe Arg
65 70 75 80

Asn Lys Tyr Arg His Val Glu Ala Val His Ser Glu Ser Lys Pro Ser
85 90 95

Cys Leu Ser His Asp Ala Thr Glu Thr Pro Ser Phe Ile Gly Phe Arg
100 105 110

Asn Leu Met Val Ile Val Leu Val Ala Ala Asn Leu Arg Leu Val Ile
115 120 125

Glu Asn Ile Gln Lys Tyr Gly Val Leu Ile Cys Ile Lys Cys His Asp
130 135 140

Phe Arg Pro Asn Asp Val Arg Leu Gly Leu Leu Leu Tyr Ile Leu Ile
145 150 155 160

Pro Trp His Leu Met Leu Ala Tyr Leu Ile Glu Leu Val Ala Ala Ala
165 170 175

Asn Ala Arg Asn Ser Arg Ala Lys Ala Lys Lys Arg Asp Gly Ser Thr
180 185 190

Ser Pro Thr Glu Asp Glu Ser Lys Gln Phe Leu Gln Thr Trp Arg Met
195 200 205

Leu Arg Ile Leu His Ala Val Asn Val Thr Ala Ala Leu Ala Val Thr
210 215 220

Ser Tyr Val Val Tyr Tyr Tyr Ile His His Pro Leu Ile Gly Thr Leu
225 230 235 240

Ser Glu Leu His Ala Ile Ile Val Trp Leu Lys Thr Ala Ser Tyr Ala
245 250 255

Leu Thr Asn Arg Asp Leu Arg His Ala Tyr Leu His Pro Val Arg Gly
260 265 270

Glu Arg Asp Ala Leu Pro Glu Ile Tyr Ala Gln Cys Pro Tyr Pro Ala
275 280 285

Asn Val Thr Phe Ser Asn Leu Thr Tyr Phe Trp Trp Ala Pro Thr Leu
290 295 300

Val Tyr Gln Pro Ala Tyr Pro Arg Thr Gln Arg Ile Arg Trp Val Phe
305 310 315 320

Val Ala Lys Arg Leu Gly Glu Val Val Cys Leu Ser Ala Phe Ile Trp
325 330 335

Phe Ala Ser Ala Gln Tyr Ala Thr Pro Val Leu Arg Asn Ser Leu Asp
340 345 350

Lys Ile Ala Thr Leu Asp Tyr Met Ser Ile Val Glu Arg Leu Leu Lys
355 360 365

-continued

```
Leu Ser Thr Ile Ser Leu Val Ile Trp Leu Ala Gly Phe Phe Ala Leu
    370                 375                 380

Phe Gln Ser Phe Leu Asn Ala Leu Ala Glu Val Met Arg Phe Gly Asp
385                 390                 395                 400

Arg Glu Phe Tyr Glu Ala Trp Trp Asn Ser Glu Ser Leu Gly Ala Tyr
                405                 410                 415

Trp Arg Thr Trp Asn Lys Pro Val Tyr Gln Phe Phe Arg Arg His Val
            420                 425                 430

Tyr Ser Pro Met Arg Ser Arg Gly Trp Ser His Leu Ser Ala Ser Leu
        435                 440                 445

Ala Val Phe Leu Leu Ser Ala Val Leu His Glu Leu Leu Val Gly Val
    450                 455                 460

Pro Thr His Asn Ile Ile Gly Val Ala Phe Leu Gly Met Phe Leu Gln
465                 470                 475                 480

Leu Pro Leu Ile Ala Met Thr Ala Arg Leu Gly Gly Arg Arg Gly Asn
                485                 490                 495

Thr Ala His Gly Arg Leu Leu Gly Asn Thr Ile Phe Trp Val Ser Phe
            500                 505                 510

Thr Ile Phe Gly Gln Pro Phe Ala Ala Leu Met Tyr Phe Tyr Ala Trp
        515                 520                 525

Gln Ala Lys Tyr Gly Ser Val Ser Lys Met Pro Leu Ala Gln Pro Gly
    530                 535                 540

Thr Cys Pro Ala Val Val Val
545                 550


<210> SEQ ID NO 12
<211> LENGTH: 1656
<212> TYPE: DNA
<213> ORGANISM: Chaetomium globosum

<400> SEQUENCE: 12

atgaaggcag aaacgggcac aacgatggca acgtcgacta gtctcgagac ttcccaagtc     60

aatggcgtca ccaaccgggc ccctgttggc cctagtcacg acccccacgc tacaactccg    120

actcatgaga cgacaaccac cataccgtcc gacgtcctcg ccaatggttc tacaaatggg    180

actacgaatg ggacgacaga tgattcattg gacatatccg aattgcgcaa agcgttccgc    240

aacaagtatc gccatgtcga ggctgtccac tccgaatcga aaccatcctg tctgagccat    300

gacgctacag agacacccag tttcatcggt tttaggaatc tcatggtgat tgtgttggtt    360

gctgccaatc ttcgcctggt catcgagaac attcaaaagt atggagttct gatctgcatc    420

aaatgccacg actttcgccc caacgatgta cgcctggggc tcctcctcta catcctgatc    480

ccatggcacc tcatgctcgc ctacctcatt gagctggtcg ccgccgccaa tgcccgcaac    540

tcccgggcca aggcgaagaa gcgggacggc agtaccagcc cgaccgaaga cgagtccaag    600

caattcctgc agacctggcg gatgctccgc attctccacg ccgtcaacgt cacggccgcc    660

ctggccgtca cctcctacgt ggtctactac tacattcacc acccgctgat cggcacgctc    720

tcggagctgc acgccatcat cgtgtggctc aagacggcgt cgtacgcgct caccaaccgc    780

gacctgcgcc acgcctacct acacccggtg cgcggcgagc gcgacgctct gcccgagatc    840

tacgcccagt gcccctaccc ggccaacgtg accttctcca acttgaccta cttctggtgg    900

gcgcccaccc tggtgtacca gccggcgtac ccgcgcactc agcgcatccg ctgggtcttt    960

gtggctaagc gcctcggcga ggtcgtctgc ttgagcgcct tcatctggtt cgccagcgcc   1020

cagtacgcta cccccgtgct gcgaaactcg ctcgacaaga tcgctaccct ggattacatg   1080
```

```
tccattgtcg agcgtctgtt gaagctgtcg accatctcgc tggtcatctg gctggcgggc   1140

ttctttgcgc tgtttcagag tttcctgaat gccttggccg aggtgatgcg gtttggagac   1200

cgcgagttct acgaagcatg gtggaacagc gaaagcctcg gcgcctactg gcgcacctgg   1260

aacaaacccg tgtaccaatt cttccggcgg cacgtctact cgccgatgcg gtcgcgcggg   1320

tggagccact tgtcggccag cctcgccgtg tttctgctct cggccgtgct acacgagctg   1380

ctggtggggg tgccgacgca caacatcatc ggcgtcgcct tcctgggcat gttcctgcag   1440

ctgccgctca tcgccatgac ggcgcgcctg ggcggccgcc gcgggaacac cgcccacggc   1500

cgcctgctcg gcaacactat cttttgggtg tcatttacca tttttggcca gccgtttgcc   1560

gcgctgatgt atttttatgc atggcaggcc aagtatggta gtgtgagcaa gatgccgctg   1620

gcgcagccgg ggacgtgtcc ggctgtggtt gtttga                             1656
```

<210> SEQ ID NO 13
<211> LENGTH: 515
<212> TYPE: PRT
<213> ORGANISM: Arxula adeninivorans

<400> SEQUENCE: 13

```
Met Ala Thr Ala Thr Ala Ile Ala Thr Val Thr Glu Gly Leu Gly Leu
1               5                   10                  15

Asp Lys Val Leu Ser Lys Glu Gln Pro Gly Leu Ser Lys Leu Ala Pro
            20                  25                  30

Arg Ala Asn Thr Asn Val Gln Pro Thr Gln Leu Gln Ser Pro Ser Pro
        35                  40                  45

Pro Gln Ser Arg Ser Ser Ser Pro Ile Ser Ala Ser Ser Ser Ser Glu
    50                  55                  60

Ser Leu Glu Leu Lys Val Pro Lys Ala Lys Ser Pro Ser Ser Ser Lys
65                  70                  75                  80

His Lys Pro His Tyr Arg Pro Val His Val Arg Ser Thr Ala Ser Ile
                85                  90                  95

Leu Ser Arg Asp Pro Ala Ala Arg Thr Glu Pro Pro Ser Tyr Ser Gly
            100                 105                 110

Phe Arg Asn Leu Ala Met Ile Ala Leu Ala Val Ser Asn Met Arg Leu
        115                 120                 125

Leu Leu Glu Asp Tyr Gln Asn Tyr Gly Val Phe His Thr Leu Asn Ile
    130                 135                 140

Met Gly Leu Ser Ala His Asp Val Arg Leu Thr Leu Ala Leu Thr Ala
145                 150                 155                 160

Ser Val Pro Phe His Leu Phe Val Ala Leu Ala Ile Glu Arg Ile Ala
                165                 170                 175

Val Leu Thr Met Pro Ser Lys Ser Thr Ala His Asn His Arg Ser Lys
            180                 185                 190

His Leu Trp Gly Leu Phe Ala Val Leu His Ala Leu Asn Ala Ala Ala
        195                 200                 205

Val Leu Ala Ile Ser Ser Tyr Thr Val Tyr Ser Arg Met Trp Ser Pro
    210                 215                 220

Ala Val Gly Thr Leu Cys Glu Cys His Ala Ile Val Val Cys Phe Lys
225                 230                 235                 240

Val Ala Ser Tyr Ala Leu Thr Asn Arg Asp Leu Arg Asp Ala Ala Ile
                245                 250                 255

Asp Gly Leu Glu Thr Thr Asp Pro Leu Leu Ser Lys Leu Pro Tyr Pro
            260                 265                 270
```

-continued

Ser Asn Leu Thr Leu Ser Asn Leu Val Tyr Phe Trp Trp Ala Pro Thr
        275                 280                 285

Leu Val Tyr Gln Pro Ile Tyr Pro Arg Trp Pro Leu His Arg Arg Trp
    290                 295                 300

Gly Phe Ile Phe Ser Arg Leu Leu Glu Ile Met Gly Ser Met Val Leu
305                 310                 315                 320

Ile Trp Phe Ile Ser Thr Gln Tyr Ala Asn Pro Ile Leu Glu Ser Ser
                325                 330                 335

Leu Gly His Phe Glu Gln Phe Asn Val Val Lys Ile Ser Glu Cys Leu
            340                 345                 350

Leu Lys Leu Ala Ser Val Ser Met Ala Ile Trp Leu Leu Gly Phe Phe
        355                 360                 365

Cys Leu Phe Gln Ser Phe Leu Asn Leu Leu Ala Glu Leu Val Arg Phe
    370                 375                 380

Gly Asp Arg Glu Phe Tyr Gln Asp Trp Trp Asn Ala Gly Ser Val Gly
385                 390                 395                 400

Thr Tyr Trp Arg Lys Trp Asn Arg Pro Val His Asn Tyr Phe Leu Arg
                405                 410                 415

His Phe Tyr Ile Pro Met Leu Lys Arg Gly Tyr Ser Gln Arg Thr Ala
            420                 425                 430

Ser Val Ile Val Phe Phe Leu Ser Ala Ile Leu His Glu Val Ala Val
        435                 440                 445

Gly Val Pro Thr Gln Ser Leu Ile Gly Val Ala Phe Val Gly Met Gly
    450                 455                 460

Ala Gln Ile Pro Leu Val Leu Ala Thr Ser Pro Leu Glu Lys Met Gly
465                 470                 475                 480

Glu Thr Gly Ala Thr Ile Gly Asn Cys Ile Phe Trp Leu Ser Phe Phe
                485                 490                 495

Leu Gly Gln Pro Met Gly Val Leu Leu Tyr Tyr Phe Ala Trp Asn Met
            500                 505                 510

Lys His Gln
        515

<210> SEQ ID NO 14
<211> LENGTH: 1548
<212> TYPE: DNA
<213> ORGANISM: Arxula adeninivorans

<400> SEQUENCE: 14
atggccaccg ctactgctat cgctacggtc acggagggcc tgggactaga taaggtgcta 60
tccaaggagc agccaggctt gtcgaagcta gctcctcgag cgaatacaaa tgtacaaccg 120
acccagttgc agtccccgtc tccaccacaa tctcgatctt cgtctccaat ttcggcctcc 180
tcatcatcag agtccctgga gctcaaggtg cccaaggcca aatcgccatc atcttccaaa 240
cacaaaccac actaccgccc cgtgcatgtg cggtcaacag catccatcct gtccagagac 300
ccggccgcca gaaccgagcc tccctcttac tctgggttca ggaacctagc catgattgca 360
ttggcggttt ctaatatgcg cctccttctc gaggactatc aaaactatgg cgtgttccac 420
actctcaaca ttatgggctt gagcgcacac gacgttcgcc tcacactggc attgacagct 480
tcggttccgt tccatctgtt tgtggccctg gccattgagc gcatcgcagt cctcactatg 540
ccctccaaat ctacagcaca caaccaccgc tcaaagcatc tctggggctt gtttgcagtt 600
ctgcatgctc tcaacgccgc tgctgtgcta gcaatcagct catacaccgt atacagtcgc 660

-continued

```
atgtggagtc ctgctgtggg aacattgtgc gaatgccacg caatcgtggt atgctttaag    720

gtggcatcgt atgcgcttac caaccgagac ttacgagatg ctgccattga tgggctagag    780

acaactgacc ctctgttgtc caagttgccc tacccatcca accttacctt gtcaaatctc    840

gtgtatttct ggtgggcccc aaccctagtg tatcagccaa tttaccctcg atggcccctg    900

catcgacgat ggggcttcat cttttctcgc ctgctcgaga ttatgggatc tatggtacta    960

atctggttca tttccaccca atacgccaac cccattttgg aatcatcctt ggggcacttt   1020

gaacagttta acgtggttaa aatctcagaa tgtctcctca aattagcatc ggtctccatg   1080

gccatctggc ttttgggttt cttttgtctc tttcaatcgt ttttgaactt gctggcagaa   1140

ttggttcgtt ttggcgaccg cgagttctac caagactggt ggaacgccgg ctcagtaggt   1200

acctactggc gcaaatggaa ccgaccagtg cacaactatt tcttgcgcca tttctacatc   1260

ccaatgctca agcgaggtta ttcacagcgc actgcctcgg tcattgtatt ctttttatct   1320

gccattctcc atgaagttgc tgttggcgtg cctactcagt ccttgattgg agttgcgttt   1380

gtaggcatgg gtgcccagat tcctctagtg ctggccacta gtcctttgga aaagatgggc   1440

gaaactggcg caactattgg caactgcatc ttttggctct ctttcttcct gggccagcca   1500

atgggggtac tgctttacta ctttgcgtgg aatatgaagc accagtag                1548
```

```
<210> SEQ ID NO 15
<211> LENGTH: 514
<212> TYPE: PRT
<213> ORGANISM: Yarrowia lipolytica

<400> SEQUENCE: 15

Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile
        35                  40                  45

Pro Thr Phe Leu Thr Ile Phe Met Leu Cys Cys Ala Ile Pro Leu Leu
    50                  55                  60

Trp Pro Phe Val Ile Ala Tyr Val Val Tyr Ala Val Lys Asp Asp Ser
65                  70                  75                  80

Pro Ser Asn Gly Gly Val Val Lys Arg Tyr Ser Pro Ile Ser Arg Asn
                85                  90                  95

Phe Phe Ile Trp Lys Leu Phe Gly Arg Tyr Phe Pro Ile Thr Leu His
            100                 105                 110

Lys Thr Val Asp Leu Glu Pro Thr His Thr Tyr Tyr Pro Leu Asp Val
        115                 120                 125

Gln Glu Tyr His Leu Ile Ala Glu Arg Tyr Trp Pro Gln Asn Lys Tyr
    130                 135                 140

Leu Arg Ala Ile Ile Thr Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
                165                 170                 175

Pro Leu Leu Ser Pro Val Ser Pro Ser Ser Pro Gly Ser Gln Pro Asp
            180                 185                 190

Lys Trp Ile Asn His Asp Ser Arg Tyr Ser Arg Gly Glu Ser Ser Gly
        195                 200                 205

Ser Asn Gly His Ala Ser Gly Ser Glu Leu Asn Gly Asn Gly Asn Asn
    210                 215                 220
```

-continued

```
Gly Thr Thr Asn Arg Arg Pro Leu Ser Ser Ala Ser Ala Gly Ser Thr
225                 230                 235                 240

Ala Ser Asp Ser Thr Leu Leu Asn Gly Ser Leu Asn Ser Tyr Ala Asn
                245                 250                 255

Gln Ile Ile Gly Glu Asn Asp Pro Gln Leu Ser Pro Thr Lys Leu Lys
            260                 265                 270

Pro Thr Gly Arg Lys Tyr Ile Phe Gly Tyr His Pro His Gly Ile Ile
        275                 280                 285

Gly Met Gly Ala Phe Gly Gly Ile Ala Thr Glu Gly Ala Gly Trp Ser
    290                 295                 300

Lys Leu Phe Pro Gly Ile Pro Val Ser Leu Met Thr Leu Thr Asn Asn
305                 310                 315                 320

Phe Arg Val Pro Leu Tyr Arg Glu Tyr Leu Met Ser Leu Gly Val Ala
                325                 330                 335

Ser Val Ser Lys Lys Ser Cys Lys Ala Leu Leu Lys Arg Asn Gln Ser
            340                 345                 350

Ile Cys Ile Val Val Gly Gly Ala Gln Glu Ser Leu Leu Ala Arg Pro
        355                 360                 365

Gly Val Met Asp Leu Val Leu Leu Lys Arg Lys Gly Phe Val Arg Leu
    370                 375                 380

Gly Met Glu Val Gly Asn Val Ala Leu Val Pro Ile Met Ala Phe Gly
385                 390                 395                 400

Glu Asn Asp Leu Tyr Asp Gln Val Ser Asn Asp Lys Ser Ser Lys Leu
                405                 410                 415

Tyr Arg Phe Gln Gln Phe Val Lys Asn Phe Leu Gly Phe Thr Leu Pro
            420                 425                 430

Leu Met His Ala Arg Gly Val Phe Asn Tyr Asp Val Gly Leu Val Pro
        435                 440                 445

Tyr Arg Arg Pro Val Asn Ile Val Val Gly Ser Pro Ile Asp Leu Pro
    450                 455                 460

Tyr Leu Pro His Pro Thr Asp Glu Glu Val Ser Glu Tyr His Asp Arg
465                 470                 475                 480

Tyr Ile Ala Glu Leu Gln Arg Ile Tyr Asn Glu His Lys Asp Glu Tyr
                485                 490                 495

Phe Ile Asp Trp Thr Glu Glu Gly Lys Gly Ala Pro Glu Phe Arg Met
            500                 505                 510

Ile Glu


<210> SEQ ID NO 16
<211> LENGTH: 1545
<212> TYPE: DNA
<213> ORGANISM: Yarrowia lipolytica

<400> SEQUENCE: 16

atgactatcg actcacaata ctacaagtcg cgagacaaaa acgacacggc acccaaaatc      60

gcgggaatcc gatatgcccc gctatcgaca ccattactca accgatgtga gaccttctct     120

ctggtctggc acattttcag cattcccact ttcctcacaa ttttcatgct atgctgcgca     180

attccactgc tctggccatt tgtgattgcg tatgtagtgt acgctgttaa agacgactcc     240

ccgtccaacg gaggagtggt caagcgatac tcgcctattt caagaaactt cttcatctgg     300

aagctctttg gccgctactt ccccataact ctgcacaaga cggtggatct ggagcccacg     360

cacacatact accctctgga cgtccaggag tatcacctga ttgctgagag atactggccg     420
```

-continued

```
cagaacaagt acctccgagc aatcatcacc accatcgagt actttctgcc cgccttcatg    480

aaacggtctc tttctatcaa cgagcaggag cagcctgccg agcgagatcc tctcctgtct    540

cccgtttctc ccagctctcc gggttctcaa cctgacaagt ggattaacca cgacagcaga    600

tatagccgtg gagaatcatc tggctccaac ggccacgcct cgggctccga acttaacggc    660

aacggcaaca atggcaccac taaccgacga cctttgtcgt ccgcctctgc tggctccact    720

gcatctgatt ccacgcttct taacgggtcc ctcaactcct acgccaacca gatcattggc    780

gaaaacgacc cacagctgtc gcccacaaaa ctcaagccca ctggcagaaa atacatcttc    840

ggctaccacc cccacggcat tatcggcatg ggagcctttg gtggaattgc caccgaggga    900

gctggatggt ccaagctctt tccgggcatc cctgtttctc ttatgactct caccaacaac    960

ttccgagtgc ctctctacag agagtacctc atgagtctgg gagtcgcttc tgtctccaag   1020

aagtcctgca aggccctcct caagcgaaac cagtctatct gcattgtcgt tggtggagca   1080

caggaaagtc ttctggccag acccggtgtc atggacctgg tgctactcaa gcgaaagggt   1140

tttgttcgac ttggtatgga ggtcggaaat gtcgcccttg ttcccatcat ggcctttggt   1200

gagaacgacc tctatgacca ggttagcaac gacaagtcgt ccaagctgta ccgattccag   1260

cagtttgtca agaacttcct tggattcacc cttcctttga tgcatgcccg aggcgtcttc   1320

aactacgatg tcggtcttgt cccctacagg cgacccgtca acattgtggt tggttccccc   1380

attgacttgc cttatctccc acaccccacc gacgaagaag tgtccgaata ccacgaccga   1440

tacatcgccg agctgcagcg aatctacaac gagcacaagg atgaatattt catcgattgg   1500

accgaggagg gcaaaggagc cccagagttc cgaatgattg agtaa                   1545
```

<210> SEQ ID NO 17
<211> LENGTH: 348
<212> TYPE: PRT
<213> ORGANISM: Rhodosporidium toruloides

<400> SEQUENCE: 17

```
Met Gly Gln Gln Ala Thr Pro Glu Glu Leu Tyr Thr Arg Ser Glu Ile
1               5                   10                  15

Ser Lys Ile Lys Phe Ala Pro Phe Gly Val Pro Arg Ser Arg Arg Leu
            20                  25                  30

Gln Thr Phe Ser Val Phe Ala Trp Thr Thr Ala Leu Pro Ile Leu Leu
        35                  40                  45

Gly Val Phe Phe Leu Leu Cys Ser Phe Pro Pro Leu Trp Pro Ala Val
    50                  55                  60

Ile Ala Tyr Leu Thr Trp Val Phe Phe Ile Asp Gln Ala Pro Ile His
65                  70                  75                  80

Gly Gly Arg Ala Gln Ser Trp Leu Arg Lys Ser Arg Ile Trp Val Trp
                85                  90                  95

Phe Ala Gly Tyr Tyr Pro Val Ser Leu Ile Lys Ser Ala Asp Leu Pro
            100                 105                 110

Pro Asp Arg Lys Tyr Val Phe Gly Tyr His Pro His Gly Val Ile Gly
        115                 120                 125

Met Gly Ala Ile Ala Asn Phe Ala Thr Asp Ala Thr Gly Phe Ser Thr
    130                 135                 140

Leu Phe Pro Gly Leu Asn Pro His Leu Leu Thr Leu Gln Ser Asn Phe
145                 150                 155                 160

Lys Leu Pro Leu Tyr Arg Glu Leu Leu Leu Ala Leu Gly Ile Cys Ser
                165                 170                 175
```

-continued

```
Val Ser Met Lys Ser Cys Gln Asn Ile Leu Arg Gln Gly Pro Gly Ser
            180                 185                 190

Ala Leu Thr Ile Val Val Gly Gly Ala Ala Glu Ser Leu Ser Ala His
        195                 200                 205

Pro Gly Thr Ala Asp Leu Thr Leu Lys Arg Arg Lys Gly Phe Ile Lys
    210                 215                 220

Leu Ala Ile Arg Gln Gly Ala Asp Leu Val Pro Val Phe Ser Phe Gly
225                 230                 235                 240

Glu Asn Asp Ile Phe Gly Gln Leu Arg Asn Glu Arg Gly Thr Arg Leu
                245                 250                 255

Tyr Lys Leu Gln Lys Arg Phe Gln Gly Val Phe Gly Phe Thr Leu Pro
            260                 265                 270

Leu Phe Tyr Gly Arg Gly Leu Phe Asn Tyr Asn Val Gly Leu Met Pro
        275                 280                 285

Tyr Arg His Pro Ile Val Ser Val Val Gly Arg Pro Ile Ser Val Glu
    290                 295                 300

Gln Lys Asp His Pro Thr Thr Ala Asp Leu Glu Glu Val Gln Ala Arg
305                 310                 315                 320

Tyr Ile Ala Glu Leu Lys Arg Ile Trp Glu Glu Tyr Lys Asp Ala Tyr
                325                 330                 335

Ala Lys Ser Arg Thr Arg Glu Leu Asn Ile Ile Ala
            340                 345
```

<210> SEQ ID NO 18
<211> LENGTH: 1858
<212> TYPE: DNA
<213> ORGANISM: Rhodosporidium toruloides

<400> SEQUENCE: 18

```
atgggccagc aggcgacgcc cgaggagcta tacacacgct cagagatctc caagatcaag      60

caagtcgagc cagctcttct cctcaccacc ccacaacata ccccgcagcc cacgacagcc     120

ctcccacagc acctgcagcc tgctgaccag ctcgagaaca cccacagatt cgcacccttt     180

ggcgtcccgc ggtcgcgccg gctgcagacc ttctccgtct ttgcctggac gacggcactg     240

cccatcctac tcggcgtctt cttcctcctc tggtgcgtca ggcttggcgt gatctgagag     300

tagcgggcgg atcatctgac ctgcttcttc gctgcagctc gttcccaccg ctctggccgg     360

ctgtcattgc ctacctcacc tgggtctttt tcattgacca ggcgccgatt cacggtggac     420

gggcgcagtc ttggctgcgg aagagtcgga tatgggtctg gtttgcagga tactatcccg     480

tcaggtgcgt cctctttcca agcctgcgtc tcgaggcctc gctcacggcc aactcgcccg     540

accggctacc tccgaacttt ccgtcaacag cttgatcaag gtcagtctgc gcgtctctcg     600

acttcagtgc tctgtggagg agctgcgcca ttgggcccga cctgcggagg gcctcaaagg     660

acgatgccgc tgacttcctt tcctccgaca gagcgccgac ttgccgcctg accggaagta     720

cgtctttggc taccacccgc acggcgtcat aggcatgggc gccatcgcca acttcgcgac     780

cgacgcaacc ggcttctcga cactcttccc cggcttgaac cctcacctcc tcaccctcca     840

aagcaacttc aagctcccgc tctaccgcga gttgctgctc gctctcggca tatgctccgt     900

ctcgatgaag agctgtcaga acattctgcg acaaggtgag cggtatgcgc aagacgggcg     960

gtcaagcgtg aacgcagtga acgagaagag ctgaccttcc gccttactcc atccgtgcag    1020

gtcctggctc ggctctcact atcgtcgtcg gtggcgccgc cgagagcttg agtgcgcatc    1080

ccggaaccgc cgatcttacg ctcaagcgac gaaaaggctt catcaaactc gcgatccggc    1140
```

```
aaggcgccga ccttgtgccc gtcttttcgt tcggcgagaa cgacgtgcgc acgctctccg   1200

agtctctaaa ccggaagcga atgctgaccg ctgcccaatt ctctctccag atctttggcc   1260

agctgcgaaa cgagcgagga acgcggctgt acaagttgca gaagcgtttc caaggcgtgt   1320

ttggcttcac cctccgtacg tctcaccgcg ccgtcttgcc gaactgctcg ttcagtcgct   1380

cacgcagctt tcactcgcgc agctctcttc tacggccggg gactcttcaa ctgtgcgctc   1440

gagttcaccg cttcgccaac agcgaggaat gcctccgagt acagcccagc tgacgcccca   1500

tctcttctca tagacaacgt cggattgatg ccgtatcgcc atccgatcgt ctctgtcggt   1560

gtgaacccgc tctgtcgctc ctacctgcgt tccttaggct gacaccactc gcgtcaaaca   1620

gtcggtcgac caatctcggt agagcagaag gaccacccga ccacggcgga cctcgaagaa   1680

gttcaggcgc ggtatatcgc agaactcaag cggtacgttc caagtcgtct gcctccgctt   1740

gccgcctcaa ataagctgag gcgtgctgac cgtatctgcc gaaccgtaca gcatctggga   1800

agaatacaag gacgcctacg ccaaaagtcg cacgcgggag ctcaatatta tcgcctga     1858


<210> SEQ ID NO 19
<211> LENGTH: 348
<212> TYPE: PRT
<213> ORGANISM: Rhodosporidium toruloides

<400> SEQUENCE: 19

Met Gly Gln Gln Ala Thr Pro Glu Glu Leu Tyr Thr Arg Ser Glu Ile
1               5                   10                  15

Ser Lys Ile Lys Phe Ala Pro Phe Gly Val Pro Arg Ser Arg Arg Leu
            20                  25                  30

Gln Thr Phe Ser Val Phe Ala Trp Thr Thr Ala Leu Pro Ile Leu Leu
        35                  40                  45

Gly Val Phe Phe Leu Leu Cys Ser Phe Pro Pro Leu Trp Pro Ala Val
    50                  55                  60

Ile Ala Tyr Leu Thr Trp Val Phe Phe Ile Asp Gln Ala Pro Ile His
65                  70                  75                  80

Gly Gly Arg Ala Gln Ser Trp Leu Arg Lys Ser Arg Ile Trp Val Trp
                85                  90                  95

Phe Ala Gly Tyr Tyr Pro Val Ser Leu Ile Lys Ser Ala Asp Leu Pro
            100                 105                 110

Pro Asp Arg Lys Tyr Val Phe Gly Tyr His Pro His Gly Val Ile Gly
        115                 120                 125

Met Gly Ala Ile Ala Asn Phe Ala Thr Asp Ala Thr Gly Phe Ser Thr
    130                 135                 140

Leu Phe Pro Gly Leu Asn Pro His Leu Leu Thr Leu Gln Ser Asn Phe
145                 150                 155                 160

Lys Leu Pro Leu Tyr Arg Glu Leu Leu Leu Ala Leu Gly Ile Cys Ser
                165                 170                 175

Val Ser Met Lys Ser Cys Gln Asn Ile Leu Arg Gln Gly Pro Gly Ser
            180                 185                 190

Ala Leu Thr Ile Val Val Gly Gly Ala Ala Glu Ser Leu Ser Ala His
        195                 200                 205

Pro Gly Thr Ala Asp Leu Thr Leu Lys Arg Arg Lys Gly Phe Ile Lys
    210                 215                 220

Leu Ala Ile Arg Gln Gly Ala Asp Leu Val Pro Val Phe Ser Phe Gly
225                 230                 235                 240

Glu Asn Asp Ile Phe Gly Gln Leu Arg Asn Glu Arg Gly Thr Arg Leu
                245                 250                 255
```

```
Tyr Lys Leu Gln Lys Arg Phe Gln Gly Val Phe Gly Phe Thr Leu Pro
            260                 265                 270

Leu Phe Tyr Gly Arg Gly Leu Phe Asn Tyr Asn Val Gly Leu Met Pro
        275                 280                 285

Tyr Arg His Pro Ile Val Ser Val Val Gly Arg Pro Ile Ser Val Glu
    290                 295                 300

Gln Lys Asp His Pro Thr Thr Ala Asp Leu Glu Glu Val Gln Ala Arg
305                 310                 315                 320

Tyr Ile Ala Glu Leu Lys Arg Ile Trp Glu Glu Tyr Lys Asp Ala Tyr
                325                 330                 335

Ala Lys Ser Arg Thr Arg Glu Leu Asn Ile Ile Ala
            340                 345
```

<210> SEQ ID NO 20
<211> LENGTH: 1047
<212> TYPE: DNA
<213> ORGANISM: Rhodosporidium toruloides

<400> SEQUENCE: 20

```
atgggccagc aggcgacgcc cgaggagcta tacacacgct cagagatctc caagatcaag      60

ttcgcaccct ttggcgtccc gcggtcgcgc cggctgcaga ccttctccgt ctttgcctgg     120

acgacggcac tgcccatcct actcggcgtc ttcttcctcc tctgctcgtt cccaccgctc     180

tggccggctg tcattgccta cctcacctgg gtctttttca ttgaccaggc gccgattcac     240

ggtggacggg cgcagtcttg gctgcggaag agtcggatat gggtctggtt tgcaggatac     300

tatcccgtca gcttgatcaa gagcgccgac ttgccgcctg accggaagta cgtctttggc     360

taccacccgc acggcgtcat aggcatgggc gccatcgcca acttcgcgac cgacgcaacc     420

ggcttctcga cactcttccc cggcttgaac cctcacctcc tcaccctcca aagcaacttc     480

aagctcccgc tctaccgcga gttgctgctc gctctcggca tatgctccgt ctcgatgaag     540

agctgtcaga acattctgcg acaaggtcct ggctcggctc tcactatcgt cgtcggtggc     600

gccgccgaga gcttgagtgc gcatcccgga accgccgatc ttacgctcaa gcgacgaaaa     660

ggcttcatca aactcgcgat ccggcaaggc gccgaccttg tgcccgtctt ttcgttcggc     720

gagaacgaca tctttggcca gctgcgaaac gagcgaggaa cgcggctgta caagttgcag     780

aagcgtttcc aaggcgtgtt tggcttcacc ctccctctct tctacggccg gggactcttc     840

aactacaacg tcggattgat gccgtatcgc catccgatcg tctctgtcgt cggtcgacca     900

atctcggtag agcagaagga ccacccgacc acggcggacc tcgaagaagt tcaggcgcgg     960

tatatcgcag aactcaagcg gatctgggaa gaatacaagg acgcctacgc caaaagtcgc    1020

acgcgggagc tcaatattat cgcctga                                         1047
```

<210> SEQ ID NO 21
<211> LENGTH: 348
<212> TYPE: PRT
<213> ORGANISM: Rhodosporidium toruloides

<400> SEQUENCE: 21

```
Met Gly Gln Gln Ala Thr Pro Glu Glu Leu Tyr Thr Arg Ser Glu Ile
1               5                   10                  15

Ser Lys Ile Lys Phe Ala Pro Phe Gly Val Pro Arg Ser Arg Arg Leu
            20                  25                  30

Gln Thr Phe Ser Val Phe Ala Trp Thr Thr Ala Leu Pro Ile Leu Leu
        35                  40                  45
```

```
Gly Val Phe Phe Leu Leu Cys Ser Phe Pro Pro Leu Trp Pro Ala Val
    50                  55                  60

Ile Ala Tyr Leu Thr Trp Val Phe Phe Ile Asp Gln Ala Pro Ile His
65                  70                  75                  80

Gly Gly Arg Ala Gln Ser Trp Leu Arg Lys Ser Arg Ile Trp Val Trp
                85                  90                  95

Phe Ala Gly Tyr Tyr Pro Val Ser Leu Ile Lys Ser Ala Asp Leu Pro
            100                 105                 110

Pro Asp Arg Lys Tyr Val Phe Gly Tyr His Pro His Gly Val Ile Gly
        115                 120                 125

Met Gly Ala Ile Ala Asn Phe Ala Thr Asp Ala Thr Gly Phe Ser Thr
    130                 135                 140

Leu Phe Pro Gly Leu Asn Pro His Leu Leu Thr Leu Gln Ser Asn Phe
145                 150                 155                 160

Lys Leu Pro Leu Tyr Arg Glu Leu Leu Leu Ala Leu Gly Ile Cys Ser
                165                 170                 175

Val Ser Met Lys Ser Cys Gln Asn Ile Leu Arg Gln Gly Pro Gly Ser
            180                 185                 190

Ala Leu Thr Ile Val Val Gly Gly Ala Ala Glu Ser Leu Ser Ala His
        195                 200                 205

Pro Gly Thr Ala Asp Leu Thr Leu Lys Arg Arg Lys Gly Phe Ile Lys
    210                 215                 220

Leu Ala Ile Arg Gln Gly Ala Asp Leu Val Pro Val Phe Ser Phe Gly
225                 230                 235                 240

Glu Asn Asp Ile Phe Gly Gln Leu Arg Asn Glu Arg Gly Thr Arg Leu
                245                 250                 255

Tyr Lys Leu Gln Lys Arg Phe Gln Gly Val Phe Gly Phe Thr Leu Pro
            260                 265                 270

Leu Phe Tyr Gly Arg Gly Leu Phe Asn Tyr Asn Val Gly Leu Met Pro
        275                 280                 285

Tyr Arg His Pro Ile Val Ser Val Val Gly Arg Pro Ile Ser Val Glu
    290                 295                 300

Gln Lys Asp His Pro Thr Thr Ala Asp Leu Glu Glu Val Gln Ala Arg
305                 310                 315                 320

Tyr Ile Ala Glu Leu Lys Arg Ile Trp Glu Glu Tyr Lys Asp Ala Tyr
                325                 330                 335

Ala Lys Ser Arg Thr Arg Glu Leu Asn Ile Ile Ala
            340                 345
```

<210> SEQ ID NO 22
<211> LENGTH: 1047
<212> TYPE: DNA
<213> ORGANISM: Rhodosporidium toruloides

<400> SEQUENCE: 22

```
atgggacagc aggctacccc cgaggagctc tacacccgat ccgagatttc taagattaag      60

ttcgcccctt ttggagtgcc ccgatcccga cgactccaga ccttctccgt ttttgcctgg     120

accactgctc tgcccattct gctcggcgtc ttctttctgc tctgctcttt ccccccctctc     180

tggcccgccg tcatcgctta cctgacctgg gtgttcttta tcgaccaggc ccctattcac     240

ggcggtcgag ctcagtcctg gctgcgaaag tctcgaattt gggtttggtt cgccggttac     300

taccccgtct ctctcatcaa gtcggctgac ctgccccctg atcgaaagta cgtgttcggc     360

taccaccctc atggtgttat cggtatggga gccattgcta actttgccac cgatgctact     420
```

```
ggtttctcca ccctctttcc cggactgaac cctcacctgc tcactctcca gtctaacttc    480

aagctccccc tgtaccgaga gctgctcctg gccctgggta tctgctccgt ctctatgaag    540

tcttgtcaga acattctccg acagggacct ggttcggctc tgaccatcgt cgtgggagga    600

gctgctgagt cgctctccgc ccatcctgga accgctgacc tcactctgaa gcgacgaaag    660

ggcttcatca agctcgccat tcgacagggt gctgacctgg tgcccgtttt ctcctttgga    720

gagaacgata ttttcggcca gctgcgaaac gagcgaggaa cccgactcta caagctgcag    780

aagcgatttc agggtgtgtt cggcttcacc ctccctctgt tctacggacg aggcctcttt    840

aactacaacg ttggactgat gccctaccga caccctatcg tctcggttgt cggccgaccc    900

atttccgtgg agcagaagga ccatcctacc actgccgatc tcgaggaggt gcaggcccga    960

tacatcgctg agctgaagcg aatttgggag gagtacaagg acgcctacgc taagtctcga   1020

acccgagagc tgaacatcat tgcctaa                                       1047
```

```
<210> SEQ ID NO 23
<211> LENGTH: 410
<212> TYPE: PRT
<213> ORGANISM: Lipomyces starkeyi

<400> SEQUENCE: 23

Met Ser Glu Lys Ala Glu Ile Glu Val Pro Pro Gln Lys Ser Thr Phe
1               5                   10                  15

Pro Arg Ser Val His Phe Ala Pro Leu His Ile Pro Leu Glu Arg Arg
            20                  25                  30

Leu Gln Thr Leu Ala Val Leu Phe His Thr Val Ala Leu Pro Tyr Cys
        35                  40                  45

Ile Gly Leu Phe Phe Leu Met Leu Ala Phe Pro Pro Phe Trp Pro Leu
    50                  55                  60

Leu Val Met Tyr Val Ile Tyr Ala Tyr Gly Phe Asp His Ser Ser Ser
65                  70                  75                  80

Asn Gly Glu Ile Ser Arg Arg Arg Ser Pro Leu Phe Arg Arg Leu Pro
                85                  90                  95

Leu Phe Arg Leu Tyr Cys Asp Tyr Phe Pro Ile His Ile His Arg Glu
            100                 105                 110

Val Pro Leu Glu Pro Thr Phe Pro Gly Arg Leu Arg Glu Pro Ser Gly
        115                 120                 125

Leu Val Glu Arg Trp Ile Ala Lys Met Phe Gly Val Gln Asp Ala Val
    130                 135                 140

Val Glu Gly Asn Glu Ser Asp Val Lys Ala Thr Ala Asn Gly Asn Gly
145                 150                 155                 160

Thr Thr Lys Glu Ile Gly Pro Thr Tyr Val Phe Gly Tyr His Pro His
                165                 170                 175

Gly Ile Val Ser Leu Gly Ala Phe Gly Ala Ile Gly Thr Glu Gly Ala
            180                 185                 190

Gly Trp Glu Lys Leu Phe Pro Gly Ile Pro Val Ser Leu Leu Thr Leu
        195                 200                 205

Glu Thr Asn Phe Ser Leu Pro Phe Tyr Arg Glu Tyr Leu Leu Ser Leu
    210                 215                 220

Gly Ile Ala Ser Val Ser Arg Arg Ser Cys Thr Asn Leu Leu Lys His
225                 230                 235                 240

Asp Gln Ser Ile Cys Ile Val Ile Gly Gly Ala Gln Glu Ser Leu Leu
                245                 250                 255
```

-continued

```
Ala Glu Pro Gly Thr Leu Asp Leu Ile Leu Val Lys Arg Arg Gly Phe
            260                 265                 270

Val Lys Leu Ala Met Ser Thr Ala Arg Val Ser Asp Gln Pro Ile Cys
        275                 280                 285

Leu Val Pro Ile Leu Ser Phe Gly Glu Asn Asp Val Tyr Asp Gln Val
    290                 295                 300

Arg Gly Asp Arg Ser Ser Lys Leu Tyr Lys Ile Gln Thr Phe Ile Lys
305                 310                 315                 320

Lys Ala Ala Gly Phe Thr Leu Pro Leu Met Tyr Ala Arg Gly Ile Phe
                325                 330                 335

Asn Tyr Asp Phe Gly Leu Met Pro Tyr Arg Arg Gln Met Thr Leu Val
            340                 345                 350

Val Gly Lys Pro Ile Ala Val Pro Tyr Val Ala Gln Pro Thr Glu Ala
        355                 360                 365

Glu Ile Glu Val Tyr His Lys Gln Tyr Met Asp Glu Leu Arg Arg Leu
    370                 375                 380

Trp Asp Thr Tyr Lys Asp Asp Tyr Phe Val Asp His Lys Gly Lys Gly
385                 390                 395                 400

Val Lys Asn Ser Glu Met Arg Phe Val Glu
                405                 410
```

<210> SEQ ID NO 24
<211> LENGTH: 1233
<212> TYPE: DNA
<213> ORGANISM: Lipomyces starkeyi

<400> SEQUENCE: 24

```
atgagtgaga aggcagagat cgaggttccg ccgcaaaaat cgacattccc tcgcagtgtg     60

cacttcgctc cacttcatat tccactggag agacgcctac agactttggc agtcttattc    120

cacactgtcg cgctaccata ctgcatcggt ctgttctttc tcatgctcgc gttccctcct    180

ttttggccat tattggtaat gtatgtcata tacgcatacg ggttcgacca ctcgagctcg    240

aacggagaga tctcccgccg gcgatcgccg ctgtttcgaa gactcccgtt gttcaggctg    300

tattgtgatt acttccccat ccacattcac cgggaggttc cgctcgagcc gacgtttcct    360

ggtcgccttc gcgaaccgag tggccttgtc gagcggtgga ttgcgaagat gttcggcgtg    420

caggacgctg ttgtcgaggg aaatgaatct gacgttaagg ccacggccaa cggcaatggg    480

acgacgaaag aaatcggacc gacgtatgtt ttcggctatc atccgcatgg aattgttagc    540

ttgggtgcgt ttggtgctat tggtacggaa ggcgctggat gggagaagct ctttcctggg    600

atcccggtgt cactgctgac tctcgaaaca aatttcagcc ttccatttta cagagagtat    660

ttgctgtcac ttgggattgc ttcagtatct cgacggtctt gtaccaatct cctcaaacac    720

gaccaatcca tctgcatcgt tatcggcggc gcccaagagt cgctcttagc ggaaccaggc    780

actctagatc tgatcctcgt taaacgtcgc ggttttgtca aacttgcaat gtcaacggcg    840

cgggtatctg accaaccgat ttgtcttgtt ccgatcctca gtttcggcga gaacgacgtg    900

tacgaccaag tccgcgggga ccgatcgtcg aagttgtata agatccagac ttttatcaag    960

aaagcggccg ggtttacgct accattgatg tatgcgcgcg gtatatttaa ttacgacttt   1020

gggctgatgc cgtaccgcag gcaaatgacg ctcgtggtcg gcaagccgat tgcagtgccg   1080

tacgtggccc agcctacgga ggctgaaatc gaagtgtatc acaagcagta catggatgaa   1140

ttgaggaggt tatgggacac gtataaggac gactattttg tagaccacaa gggcaagggg   1200

gtcaagaatt ccgagatgcg ttttgtggag taa                                1233
```

<210> SEQ ID NO 25
<211> LENGTH: 410
<212> TYPE: PRT
<213> ORGANISM: Lipomyces starkeyi

<400> SEQUENCE: 25

```
Met Ser Glu Lys Ala Glu Ile Glu Val Pro Pro Gln Lys Ser Thr Phe
1               5                   10                  15

Pro Arg Ser Val His Phe Ala Pro Leu His Ile Pro Leu Glu Arg Arg
            20                  25                  30

Leu Gln Thr Leu Ala Val Leu Phe His Thr Val Ala Leu Pro Tyr Cys
        35                  40                  45

Ile Gly Leu Phe Phe Leu Met Leu Ala Phe Pro Pro Phe Trp Pro Leu
    50                  55                  60

Leu Val Met Tyr Val Ile Tyr Ala Tyr Gly Phe Asp His Ser Ser Ser
65                  70                  75                  80

Asn Gly Glu Ile Ser Arg Arg Arg Ser Pro Leu Phe Arg Arg Leu Pro
                85                  90                  95

Leu Phe Arg Leu Tyr Cys Asp Tyr Phe Pro Ile His Ile His Arg Glu
            100                 105                 110

Val Pro Leu Glu Pro Thr Phe Pro Gly Arg Leu Arg Glu Pro Ser Gly
        115                 120                 125

Leu Val Glu Arg Trp Ile Ala Lys Met Phe Gly Val Gln Asp Ala Val
    130                 135                 140

Val Glu Gly Asn Glu Ser Asp Val Lys Ala Thr Ala Asn Gly Asn Gly
145                 150                 155                 160

Thr Thr Lys Glu Ile Gly Pro Thr Tyr Val Phe Gly Tyr His Pro His
                165                 170                 175

Gly Ile Val Ser Leu Gly Ala Phe Gly Ala Ile Gly Thr Glu Gly Ala
            180                 185                 190

Gly Trp Glu Lys Leu Phe Pro Gly Ile Pro Val Ser Leu Leu Thr Leu
        195                 200                 205

Glu Thr Asn Phe Ser Leu Pro Phe Tyr Arg Glu Tyr Leu Leu Ser Leu
    210                 215                 220

Gly Ile Ala Ser Val Ser Arg Arg Ser Cys Thr Asn Leu Leu Lys His
225                 230                 235                 240

Asp Gln Ser Ile Cys Ile Val Ile Gly Gly Ala Gln Glu Ser Leu Leu
                245                 250                 255

Ala Glu Pro Gly Thr Leu Asp Leu Ile Leu Val Lys Arg Arg Gly Phe
            260                 265                 270

Val Lys Leu Ala Met Ser Thr Ala Arg Val Ser Asp Gln Pro Ile Cys
        275                 280                 285

Leu Val Pro Ile Leu Ser Phe Gly Glu Asn Asp Val Tyr Asp Gln Val
    290                 295                 300

Arg Gly Asp Arg Ser Ser Lys Leu Tyr Lys Ile Gln Thr Phe Ile Lys
305                 310                 315                 320

Lys Ala Ala Gly Phe Thr Leu Pro Leu Met Tyr Ala Arg Gly Ile Phe
                325                 330                 335

Asn Tyr Asp Phe Gly Leu Met Pro Tyr Arg Arg Gln Met Thr Leu Val
            340                 345                 350

Val Gly Lys Pro Ile Ala Val Pro Tyr Val Ala Gln Pro Thr Glu Ala
        355                 360                 365

Glu Ile Glu Val Tyr His Lys Gln Tyr Met Asp Glu Leu Arg Arg Leu
```

370 375 380

Trp Asp Thr Tyr Lys Asp Asp Tyr Phe Val Asp His Lys Gly Lys Gly
385 390 395 400

Val Lys Asn Ser Glu Met Arg Phe Val Glu
405 410

<210> SEQ ID NO 26
<211> LENGTH: 1233
<212> TYPE: DNA
<213> ORGANISM: Lipomyces starkeyi

<400> SEQUENCE: 26
atgtccgaga aggctgagat tgaggtgccc ccccagaagt ctactttccc tcgatccgtt 60
catttcgccc ccctgcatat ccccctggag cgacgactcc agaccctggc tgtgctcttc 120
cacactgttg ccctgcctta ctgcatcgga ctcttctttc tgatgctcgc tttccccccct 180 ttttggcccc tgctcgtgat gtacgttatc tacgcctacg gattcgacca ttcctcttcg 240
aacggcgaga tctctcgacg acgatcgcct ctgttccgac gactgcccct ctttcgactc 300
tactgtgatt acttccctat ccacattcat cgagaggtcc ccctggagcc tacctttcct 360
ggtcgactgc gagagccttc cggactcgtt gagcgatgga ttgctaagat gttcggtgtc 420
caggacgccg tcgtggaggg aaacgagtct gatgtgaagg ccaccgctaa cggaaacggc 480
accactaagg agatcggccc tacttacgtc ttcggatacc acccccatgg cattgtgtcc 540
ctgggagcct ttggcgctat cggtaccgag ggtgctggat gggagaagct cttccctggt 600
attcccgtct cgctgctcac cctggagact aacttctccc tcccctttta ccgagagtac 660
ctgctctctc tgggaatcgc ctcggtgtcc cgacgatcgt gcaccaacct gctcaagcac 720
gaccagtcta tctgtattgt tatcggaggt gctcaggagt ccctgctcgc tgagcctgga 780
accctggacc tcattctggt caagcgacga ggcttcgtga agctggccat gtccactgct 840
cgagtgtctg atcagcctat ttgcctggtt cccatcctct ctttcggcga gaacgacgtt 900
tacgatcagg tccgaggtga ccgatcctct aagctgtaca agattcagac cttcatcaag 960
aaggccgctg gctttactct ccctctgatg tacgcccgag gcatcttcaa ctacgacttt 1020
ggtctgatgc cctaccgacg acagatgacc ctcgttgtcg gcaagcctat tgccgtcccc 1080
tacgtggctc agcccactga ggccgagatc gaggtctacc acaagcagta catggacgag 1140
ctgcgacgac tctgggatac ctacaaggac gattacttcg ttgaccataa gggcaagggt 1200
gtcaagaact ctgagatgcg atttgtggag taa 1233

<210> SEQ ID NO 27
<211> LENGTH: 380
<212> TYPE: PRT
<213> ORGANISM: Aspergillus terreus

<400> SEQUENCE: 27

Met Pro Arg Asn Thr His Pro Pro Ala Asn Asn Ala Gly Pro Asn Ala
1 5 10 15

Ser His Lys Lys Asp Arg Lys Arg Gln Gly Arg Leu Phe Gln His Thr
20 25 30

Val Pro Asn Lys Tyr Ser Arg Ile Arg Trp Ala Pro Leu Asn Ile Gly
35 40 45

Leu Glu Arg Arg Leu Gln Thr Leu Val Val Leu Cys His Thr Leu Thr
50 55 60

Ile Ala Leu Phe Leu Ala Phe Phe Phe Phe Thr Cys Ala Ile Pro Leu

```
65                  70                  75                  80

Thr Trp Pro Leu Leu Phe Pro Tyr Leu Val Tyr Ile Thr Leu Phe Ser
                85                  90                  95

Thr Ala Pro Thr Ser Gly Thr Leu Lys Gly Arg Ser Asp Phe Leu Arg
            100                 105                 110

Ser Leu Pro Ile Trp Lys Leu Tyr Thr Ala Tyr Phe Pro Ala Lys Leu
        115                 120                 125

His Arg Ser Glu Pro Leu Leu Pro Thr Arg Lys Tyr Ile Phe Gly Tyr
    130                 135                 140

His Pro His Gly Ile Ile Ser His Gly Ala Phe Ala Ala Phe Ala Thr
145                 150                 155                 160

Asp Ala Leu Gly Phe Ser Lys Leu Phe Pro Gly Ile Thr Asn Thr Leu
                165                 170                 175

Leu Thr Leu Asp Ser Asn Phe Arg Ile Pro Phe Tyr Arg Glu Tyr Ala
            180                 185                 190

Met Ala Met Gly Val Ala Ser Val Ser Arg Glu Ser Cys Glu Asn Leu
        195                 200                 205

Leu Thr Lys Gly Gly Ala Asp Gly Glu Gly Met Gly Arg Ala Ile Thr
    210                 215                 220

Ile Val Val Gly Gly Ala Arg Glu Ser Leu Asp Ala Leu Pro His Thr
225                 230                 235                 240

Met Arg Leu Val Leu Lys Arg Arg Lys Gly Phe Ile Lys Leu Ala Ile
                245                 250                 255

Arg Thr Gly Ala Asp Leu Val Pro Val Leu Ala Phe Gly Glu Asn Asp
            260                 265                 270

Leu Tyr Glu Gln Val Arg Ser Asp Gln His Pro Leu Ile Tyr Lys Val
        275                 280                 285

Gln Met Leu Val Lys Arg Phe Leu Gly Phe Thr Val Pro Leu Phe His
    290                 295                 300

Ala Arg Gly Ile Phe Asn Tyr Asp Val Gly Leu Met Pro Tyr Arg Arg
305                 310                 315                 320

Pro Leu Asn Ile Val Val Gly Arg Pro Ile Gln Val Val Arg Gln Gln
                325                 330                 335

Asp Arg Asp Lys Ile Asp Asp Glu Tyr Ile Asp Arg Leu His Ala Glu
            340                 345                 350

Tyr Val Arg Glu Leu Glu Ser Leu Trp Asp Gln Trp Lys Asp Val Tyr
        355                 360                 365

Ala Lys Asp Arg Ile Ser Glu Leu Glu Ile Val Ala
    370                 375                 380
```

<210> SEQ ID NO 28
<211> LENGTH: 1143
<212> TYPE: DNA
<213> ORGANISM: Aspergillus terreus

<400> SEQUENCE: 28

```
atgccccgaa acacccaccc ccccgccaac aacgccggac ctaacgcctc tcacaagaag      60

gaccgaaagc gacagggacg actctttcag cacaccgttc ctaacaagta ctctcgaatc     120

cgatgggccc ccctcaacat tggcctggag cgacgactgc agaccctcgt cgtgctgtgc     180

catacccctca ctatcgccct gttcctcgct ttctttttct ttacttgtgc cattcccctg    240

acctggcctc tgctcttccc ctacctcgtg tacatcaccc tgttttcgac cgctcctact     300

tccggtaccc tgaagggacg atctgacttc ctccgatcgc tgcctatttg gaagctctac     360
```

-continued

```
actgcctact ttcccgctaa gctgcaccga tccgagcctc tgctccctac ccgaaagtac    420

atcttcggct accaccccca tggtatcatt tcccatggag ccttcgccgc ttttgccact    480

gacgctctcg gcttctctaa gctgtttcct ggtatcacca acactctgct caccctggat    540

tcgaacttcc gaattccctt ttaccgagag tacgccatgg ctatgggagt ggcttccgtt    600

tctcgagagt cgtgcgagaa cctgctcact aagggaggtg ctgacggaga gggaatgggc    660

cgagctatca ccattgttgt cggaggcgcc cgagagtccc tcgatgctct gcctcacact    720

atgcgactgg tcctcaagcg acgaaagggt ttcatcaagc tggccattcg aaccggagct    780

gacctcgttc ccgtcctggc cttcggcgag aacgacctct acgagcaggt gcgatctgat    840

cagcaccctc tgatctacaa ggtccagatg ctcgtgaagc gattcctggg ttttaccgtg    900

cccctgttcc atgctcgagg aatttttaac tacgacgttg gcctcatgcc ttaccgacga    960

cccctgaaca tcgtggttgg tcgacccatt caggtcgtgc gacagcagga ccgagataag   1020

atcgacgatg agtacattga ccgactccac gccgagtacg tccgagagct cgagtccctg   1080

tgggaccagt ggaaggatgt ttacgccaag gaccgaatct ctgagctgga gattgtcgct   1140

taa                                                                 1143
```

<210> SEQ ID NO 29
<211> LENGTH: 437
<212> TYPE: PRT
<213> ORGANISM: Claviceps purpurea

<400> SEQUENCE: 29

```
Met Ala Ala Val Gln Val Ala Arg Pro Val Pro Pro His His His Asp
1               5                   10                  15

Gly Ala Gly Arg Glu His Lys Gly Glu Arg Ala His Ser Pro Glu Arg
            20                  25                  30

Gly Glu Lys Thr Val His Asn Gly Tyr Gly Leu Ala Glu Thr His Glu
        35                  40                  45

Pro Leu Glu Leu Asn Gly Ser Ala Val Gln Asp Gly Lys His Asp Ser
    50                  55                  60

Asp Glu Thr Ile Thr Asn Gly Asp Tyr Ser Pro Tyr Pro Glu Leu Asp
65                  70                  75                  80

Cys Gly Lys Glu Arg Ala Ala His Glu Lys Glu Ala Trp Thr Ala Gly
                85                  90                  95

Gly Val Arg Phe Ala Pro Leu Arg Val Pro Phe Lys Arg Arg Met Gln
            100                 105                 110

Thr Ala Ala Val Leu Phe His Cys Met Ser Ile Ile Leu Ile Ser Ser
        115                 120                 125

Cys Phe Trp Phe Ser Leu Ala Asn Pro Ile Thr Trp Pro Ile Leu Val
    130                 135                 140

Pro Tyr Leu Val His Leu Ser Leu Ser Asn Ala Ser Thr Asp Gly Lys
145                 150                 155                 160

Leu Ser Tyr Arg Ser Glu Trp Leu Arg Ser Leu Pro Leu Trp Arg Leu
                165                 170                 175

Phe Ala Gly Tyr Phe Pro Ala Lys Leu His Lys Thr Phe Asp Leu Pro
            180                 185                 190

Pro Asn Arg Lys Tyr Ile Phe Gly Tyr His Pro His Gly Ile Ile Ser
        195                 200                 205

His Gly Ala Trp Cys Ala Phe Ala Thr Asn Ala Leu Gly Phe Val Glu
    210                 215                 220

Lys Phe Pro Gly Ile Thr Asn Ser Leu Leu Thr Leu Asp Ser Asn Phe
```

```
225                 230                 235                 240

Arg Val Pro Phe Tyr Arg Asp Trp Ile Leu Ala Met Gly Ile Arg Ser
                245                 250                 255

Val Ser Arg Glu Ser Ile Arg Asn Ile Leu Ser Lys Gly Gly Pro Asp
            260                 265                 270

Ser Asn Gly Gln Gly Arg Ala Val Thr Ile Val Ile Gly Gly Ala Arg
        275                 280                 285

Glu Ser Leu Glu Ala Gln Pro Gly Thr Leu Arg Leu Ile Leu Gln Gly
    290                 295                 300

Arg Lys Gly Phe Ile Lys Val Ala Leu Arg Ala Gly Ala Asp Leu Val
305                 310                 315                 320

Pro Val Ile Gly Phe Gly Glu Asn Asp Leu Tyr Asp Gln Leu Ser Pro
                325                 330                 335

Lys Thr His Pro Leu Val His Lys Ile Gln Met Phe Phe Leu Lys Val
            340                 345                 350

Phe Lys Phe Thr Ile Pro Ala Leu His Gly Arg Gly Leu Leu Asn Tyr
        355                 360                 365

Asp Val Gly Leu Leu Pro Tyr Arg Arg Ala Val Asn Ile Val Val Gly
    370                 375                 380

Arg Pro Ile Gln Ile Asp Glu Thr Tyr Gly Glu Gln Pro Pro Gln Glu
385                 390                 395                 400

Val Ile Asp Arg Tyr His Glu Leu Tyr Val Gln Glu Val Glu Arg Leu
                405                 410                 415

Tyr Ala Ala Tyr Lys Glu Gln Phe Ser Asn Gly Lys Lys Thr Pro Glu
            420                 425                 430

Leu Gln Ile Leu Ser
        435

<210> SEQ ID NO 30
<211> LENGTH: 1314
<212> TYPE: DNA
<213> ORGANISM: Claviceps purpurea

<400> SEQUENCE: 30
atggctgctg ttcaggttgc ccgacccgtt cccccccacc accacgatgg cgctggccga     60
gagcacaagg gagagcgagc ccattcccct gagcgaggag agaagaccgt ccacaacggc    120
tacggtctgg ccgagactca tgagcccctg gagctcaacg gttctgctgt gcaggacgga    180
aagcacgact cggatgagac catcactaac ggtgactact ctccctaccc tgagctcgat    240
tgcggaaagg agcgagccgc tcatgagaag gaggcttgga ccgctggagg tgtgcgattc    300
gctcctctgc gagttccttt taagcgacga atgcagactg ccgctgtcct cttccactgc    360
atgtccatca ttctgatttc ctcttgtttc tggttttctc tcgccaaccc catcacctgg    420
cctattctcg ttccctacct ggtccacctg tcgctctcca acgcttctac tgacggcaag    480
ctctcctacc gatctgagtg gctgcgatcc ctgcctctct ggcgactgtt cgccggttac    540
tttcccgcta agctccacaa gaccttcgat ctgcccccta accgaaagta catctttggt    600
taccaccccc atggaatcat ttcccatggc gcctggtgtg ccttcgctac caacgctctg    660
ggcttcgttg agaagtttcc tggtattacc aactcgctgc tcactctcga ctccaacttc    720
cgagtgccct tttaccgaga ttggatcctg gccatgggca ttcgatctgt ttcgcgagag    780
tctatccgaa acattctctc gaagggagga cctgactcca acggacaggg ccgagctgtg    840
accatcgtta ttggtggagc ccgagagtct ctggaggctc agcccggaac tctgcgactc    900
```

-continued

```
attctgcagg gccgaaaggg cttcattaag gtggctctcc gagctggagc tgacctggtt     960

cccgtcatcg gtttcggaga gaacgacctc tacgatcagc tgtcccctaa gacccacccc    1020

ctcgttcata agatccagat gttctttctg aaggtcttca agtttactat tcctgctctg    1080

cacggacgag gtctgctcaa ctacgacgtc ggtctgctcc cttaccgacg agctgtgaac    1140

atcgtcgtgg gacgacccat ccagattgac gagacctacg gcgagcagcc ccctcaggag    1200

gtcatcgatc gataccacga gctctacgtc caggaggtgg agcgactgta cgccgcttac    1260

aaggagcagt tctcgaacgg aaagaagacc cccgagctcc agatcctgtc ctaa          1314


<210> SEQ ID NO 31
<211> LENGTH: 351
<212> TYPE: PRT
<213> ORGANISM: Aurantiochytrium limacinum

<400> SEQUENCE: 31

Met Leu Ala Trp Met Pro Val Leu Ile Ala Leu Pro Arg Arg Lys Gln
1               5                   10                  15

Thr Ala Val Val Leu Leu Phe Val Met Leu Leu Pro Met Ile Met Val
            20                  25                  30

Val Tyr Ser Trp Thr Leu Ile Leu Leu Ile Phe Pro Leu Thr Thr Leu
        35                  40                  45

Pro Thr Leu Ser Tyr Leu Ile Trp Ile Met Tyr Ile Asp Lys Ser His
    50                  55                  60

Glu Thr Gly Lys Arg Lys Pro Phe Met Arg Tyr Trp Lys Met Trp Arg
65                  70                  75                  80

His Phe Ala Asn Tyr Phe Pro Leu Arg Leu Ile Arg Thr Thr Pro Leu
                85                  90                  95

Asp Pro Arg Arg Lys Tyr Val Phe Cys Tyr His Pro His Gly Ile Ile
            100                 105                 110

Ser Leu Gly Ala Phe Gly Asn Phe Ala Thr Asp Ser Thr Gly Phe Ser
        115                 120                 125

Arg Lys Phe Pro Gly Ile Asp Leu Arg Leu Leu Thr Leu Gln Ile Asn
    130                 135                 140

Phe Tyr Cys Pro Ile Ile Arg Glu Leu Leu Leu Tyr Met Gly Leu Cys
145                 150                 155                 160

Ser Ala Ala Lys Lys Ser Cys Asn Gln Ile Leu Gln Arg Gly Pro Gly
                165                 170                 175

Ser Ala Ile Met Leu Val Val Gly Gly Ala Ala Glu Ser Leu Asp Ser
            180                 185                 190

Gln Pro Gly Thr Tyr Arg Leu Thr Leu Gly Arg Lys Gly Phe Val Arg
        195                 200                 205

Val Ala Leu Asp Asn Gly Ala Asp Leu Val Pro Val Leu Gly Phe Gly
    210                 215                 220

Glu Asn Asp Val Phe Asp Thr Val Tyr Leu Pro Pro Asn Ser Trp Ala
225                 230                 235                 240

Arg Asn Val Gln Glu Phe Val Arg Lys Lys Leu Gly Phe Ala Thr Pro
                245                 250                 255

Ile Phe Ser Gly Arg Gly Ile Phe Gln Tyr Asn Met Gly Leu Met Pro
            260                 265                 270

His Arg Lys Pro Ile Ile Val Val Val Gly Lys Pro Ile Lys Ile Pro
        275                 280                 285

Lys Ile Pro Asp Glu Leu Lys Gly Arg Ala Leu Ser Thr Thr Ala Glu
    290                 295                 300
```

-continued

Gly Val Ala Leu Val Asp Lys Tyr His Glu Lys Tyr Val Arg Ala Leu
305 310 315 320

Arg Glu Leu Trp Asn Leu Tyr Lys Glu Glu Tyr Ala Thr Glu Pro Lys
325 330 335

Ala Ala Tyr Leu Glu Pro Asn Ser Ile Arg Lys Asn Gln Asn Val
340 345 350

<210> SEQ ID NO 32
<211> LENGTH: 1056
<212> TYPE: DNA
<213> ORGANISM: Aurantiochytrium limacinum

<400> SEQUENCE: 32
atgctcgcct ggatgcctgt cctcattgcc ctcccccgac gaaagcagac cgctgttgtt 60
ctcctgtttg tgatgctcct ccctatgatc atggtcgtgt actcctggac cctgatcctg 120
ctcattttcc ccctcaccac tctgcctact ctctcctacc tgatctggat tatgtacatt 180
gacaagtctc acgagaccgg aaagcgaaag ccctttatgc gatactggaa gatgtggcga 240
catttcgcca actactttcc tctccgactg atccgaacca ctcccctgga ccctcgacga 300
aagtacgtgt tctgctacca cccccatggc atcatttccc tcggagcctt cggcaacttt 360
gctaccgact cgactggctt ctcccgaaag tttcccggta tcgatctgcg actgctcacc 420
ctccagatta acttctactg tcctatcatt cgagagctgc tcctgtacat gggtctgtgc 480
tctgccgcta agaagtcgtg taaccagatc ctccagcgag gacccggctc tgctattatg 540
ctggttgtcg gcggtgccgc tgagtccctc gactctcagc ctggcaccta ccgactcact 600
ctgggtcgaa agggattcgt gcgagttgcc ctggacaacg gtgctgatct ggtccccgtg 660
ctcggtttcg gagagaacga cgtgtttgat accgtttacc tgccccctaa ctcgtgggcc 720
cgaaacgtcc aggagttcgt gcgaaagaag ctcggattcg ctacccccat cttttccggc 780
cgaggtattt ttcagtacaa catgggtctg atgccccacc gaaagcctat cattgtggtt 840
gtcggaaagc ccatcaagat tcccaagatc cctgacgagc tgaagggacg agccctctct 900
accactgccg agggcgttgc tctggtcgat aagtaccatg agaagtacgt tcgagccctc 960
cgagagctgt ggaacctcta caaggaggag tacgctaccg agcccaaggc cgcttacctc 1020
gagcctaact cgattcgaaa gaaccagaac gtctaa 1056

<210> SEQ ID NO 33
<211> LENGTH: 388
<212> TYPE: PRT
<213> ORGANISM: Arxula adeninivorans

<400> SEQUENCE: 33

Met Val Arg Phe Ala Pro Leu Asn Val Pro Leu His Arg Arg Leu Glu
1 5 10 15

Thr Phe Ala Leu Thr Tyr His Ile Leu Ser Ile Pro Val Trp Met Ser
20 25 30

Phe Phe Leu Leu Cys Cys Ala Ile Pro Leu Met Trp Pro Leu Val Ile
35 40 45

Ile Tyr Leu Leu Tyr Tyr Ala Ser Asp Asn Ser Ser Glu Asn Gly Gly
50 55 60

Val Ala Ser Arg Tyr Ser Pro Lys Phe Arg Ser Val Pro Leu Trp Lys
65 70 75 80

Tyr Phe Ala Asn Tyr Phe Pro Ile Thr Leu His Arg Thr Gln Glu Leu
85 90 95

```
Pro Pro Ala Phe Val Tyr Gln Gly Glu Asp Leu Asp Pro Glu Thr Pro
            100                 105                 110

Asp Asp Ser Asp Asp Gly His Ala Lys Ser Lys Ser Ile Val Leu Lys
        115                 120                 125

Leu Trp Lys Val Ala Phe Trp Trp Tyr Tyr Leu Pro Lys His Phe Leu
    130                 135                 140

Arg Lys Pro Glu Val Arg Pro Thr Gly Arg Arg Tyr Ile Phe Gly Tyr
145                 150                 155                 160

His Pro His Gly Ile Ile Gly Met Gly Ala Ile Gly Ala Ile Ala Thr
                165                 170                 175

Glu Gly Ala Gly Trp Ser Lys Leu Phe Pro Gly Ile Pro Val Ser Leu
            180                 185                 190

Leu Thr Leu Ala Asn Asn Phe Arg Ile Pro Leu Tyr Arg Glu Tyr Leu
        195                 200                 205

Met Ser Leu Gly Ile Ala Ser Val Ser Arg Arg Ser Cys Glu Ala Leu
    210                 215                 220

Leu Lys Arg Gly Gln Ser Ile Cys Ile Val Ile Gly Gly Ala Gln Glu
225                 230                 235                 240

Ser Leu Leu Ala His Pro Gly His Met Asp Leu Val Leu Lys Arg Arg
                245                 250                 255

Lys Gly Phe Ile Lys Leu Ala Leu Glu Val Gly Asn Thr Asp Leu Val
            260                 265                 270

Pro Val Met Ala Phe Gly Glu Asn Asp Leu Tyr Gln Gln Val Asn Ser
        275                 280                 285

Ser Lys Ser Ser Arg Leu Tyr Lys Leu Gln Ser Leu Val Lys Asn Ala
    290                 295                 300

Leu Gly Phe Thr Leu Pro Leu Met His Ala Arg Gly Val Phe Asn Tyr
305                 310                 315                 320

Asp Val Gly Ile Ile Pro Tyr Arg Arg Pro Ile Asn Val Val Val Gly
                325                 330                 335

Lys Pro Ile Pro Ile Pro His Ile Pro Asn Pro Ser Ala Asp Gln Val
            340                 345                 350

Asn Arg Tyr Gln Ile Gln Tyr Met Thr Glu Leu Lys Glu Leu Tyr Asp
        355                 360                 365

Lys Tyr Lys Asp Lys Cys Ser Asn Lys Asp Leu Pro Val Pro Glu Leu
    370                 375                 380

Thr Phe Val Glu
385


<210> SEQ ID NO 34
<211> LENGTH: 1167
<212> TYPE: DNA
<213> ORGANISM: Arxula adeninivorans

<400> SEQUENCE: 34

atggttcggt tcgctccttt aaatgttcct cttcatcgga ggttagagac gttcgcgctc      60

acctaccata tcctgtcgat tccagtatgg atgtccttct ttttgctatg ctgtgccatt     120

cctttaatgt ggccgttggt tatcatctac ctgctgtact atgcttccga caacagctct     180

gagaatggag gggttgcgag caggtattcg ccaaagttca ggtccgtgcc tctttggaag     240

tactttgcaa actactttcc aatcaccctt caccgtactc aagagctacc gcccgcattc     300

gtgtaccaag gcgaagactt ggaccctgag acgcccgatg acagtgacga cgggcatgca     360

aagtcaaagt ctattgtatt aaagctgtgg aaagttgcat tctggtggta ctacttgccc     420
```

-continued

```
aagcatttc ttcgcaaacc agaggttcgt cctacgggtc gaagatacat ctttggatat    480

cacccccatg gaatcattgg catgggtgcc attggcgcaa ttgctactga aggtgcgggg    540

tggtccaagc tcttccccgg gatccctgtc agtttgctca ctctggcaaa caactttcga    600

atccccctgt accgggaata tctcatgtct ctgggcattg cctcggtatc tagacggtcc    660

tgtgaagctt tattaaaaag aggacagtca atttgcattg taattggagg cgctcaggaa    720

agtcttcttg cacatccagg gcacatggat ttggtgctca agcgacgcaa gggattcatt    780

aaactagctc ttgaagttgg caacaccgac ttggtgccag ttatggcatt tggagaaaac    840

gatctctacc agcaagtgaa cagtagcaaa tcctcccgtc tatacaagct ccagagccta    900

gttaagaatg ccttgggatt cacgcttccg ctgatgcacg ctcgaggagt gttcaattat    960

gacgtgggca taatacccta tcgaagacca attaacgttg tagtgggcaa gcccatcccc   1020

attccacaca ttccaaaccc atctgccgac caggtcaatc ggtaccagat ccagtacatg   1080

actgaactca aagaattgta cgacaagtac aaagacaagt gcagtaacaa ggatcttcca   1140

gttccggagc ttacatttgt agagtag                                       1167
```

<210> SEQ ID NO 35
<211> LENGTH: 579
<212> TYPE: PRT
<213> ORGANISM: Arxula adeninivorans

<400> SEQUENCE: 35

```
Met Ile Arg Ala Ala Tyr Gly Ser Val Ser Arg Ala Arg Asp Ser Leu
1               5                   10                  15

Thr Leu Arg Ala Pro Ser Phe Pro Thr Thr Ala Val Glu Val Arg Asp
            20                  25                  30

Lys Ile Leu Trp Ile Leu Tyr Ala Trp Ile Glu Met Phe Thr Asp Val
        35                  40                  45

Phe Ser Phe Trp Thr Glu Lys Val Trp Gly Tyr Val Ser Thr Pro Thr
    50                  55                  60

Lys Glu Ser Ile Leu Arg Lys Gln Leu Asp Glu Ala Lys Ser Tyr His
65                  70                  75                  80

Glu Trp Glu Glu Leu Ser Tyr Lys Leu Asp Ser Ile Leu Gly Asn Asp
                85                  90                  95

Ile Trp Arg Gln Asn Pro Val Ser Arg Lys Tyr Asp Tyr Arg Leu Ile
            100                 105                 110

Ser Thr Arg Leu Lys Glu Leu Val Ala Ala Arg Asp Asn Arg Asn Ile
        115                 120                 125

Glu Leu Leu Met Asp Arg Leu Arg Ser Gly Leu Leu Arg Asn Ile Gly
    130                 135                 140

Ser Ile Ala Ser Thr His Leu Tyr Asn Arg Ala Tyr Ser Gly Thr Lys
145                 150                 155                 160

Leu Leu Ile Glu Asp Tyr Ile Asn Val Val Ile Gln Cys Leu Glu Tyr
                165                 170                 175

Val Glu Arg Gly Gly Arg Pro Leu Thr Ala Ser Ala Ser Lys Ile Pro
            180                 185                 190

Asn Gly Gly Glu Pro Pro Ser Pro Arg Thr Tyr His Lys Pro Met Ile
        195                 200                 205

Thr Arg Gln Arg Lys Leu Asn Phe Phe Asn Asp Thr Arg Gln Ser Phe
    210                 215                 220

Gly Ser Thr Ala Val Val Leu His Gly Gly Ser Leu Phe Gly Leu Cys
225                 230                 235                 240
```

-continued

```
His Ile Gly Met Ile Lys Thr Leu Phe Asn Gln Gly Leu Leu Pro Arg
                245                 250                 255

Ile Val Cys Gly Ser Thr Val Gly Ala Leu Val Ala Ser Leu Val Cys
            260                 265                 270

Ser Cys Val Asp Glu Glu Val Tyr Glu Thr Leu Asp Asn Val Ser Ser
        275                 280                 285

Glu Met Ser Pro Leu Arg Gln Gly Tyr Thr Asp Ile Lys Tyr His Ser
    290                 295                 300

Val Ala Glu Gly Val Ile Ser Ser Met Cys Pro Pro Glu Ile Leu Ile
305                 310                 315                 320

Phe Glu Gln Tyr Ile Arg Glu Lys Leu Gly Asp Leu Thr Phe Glu Glu
                325                 330                 335

Ala Tyr Gln Arg Thr Gly Arg Ile Leu Asn Ile Pro Val Thr Pro Lys
            340                 345                 350

Ala Lys Pro Gly Gln Val Ala Pro Pro Val Pro Thr Leu Leu Asn Tyr
        355                 360                 365

Leu Ser Ser Pro Asn Val Val Val Trp Ser Ala Ala Gln Cys Ser Ile
    370                 375                 380

Gly Thr Gly Ile Ile His Lys Lys Val Glu Leu Leu Val Lys Gly Leu
385                 390                 395                 400

Asp Gly Gln Leu Lys Pro Tyr Leu Asp Ala Asp Asp Ile Glu Tyr Thr
                405                 410                 415

Pro Ala Asn Gln Ala Val Tyr Ala Ala Asp Arg Glu Ser Pro Tyr Thr
            420                 425                 430

Arg Leu Ser Glu Leu Phe Asn Val Asn Asn Tyr Ile Val Ser Val Ala
        435                 440                 445

Arg Pro Tyr Phe Ala Pro Ile Leu Leu Ser Asp Phe Lys Tyr Arg Ala
    450                 455                 460

Ala Lys Ser Phe Lys Thr Arg Phe Leu Lys Leu Thr Arg Leu Glu Leu
465                 470                 475                 480

Gln Tyr Arg Leu Asn Gln Leu Ser Gln Leu Gly Leu Val Pro Pro Met
                485                 490                 495

Ile Gln Gln Trp Phe Val Asp Gly Asn Ile Pro Ala Gly Phe Gln Val
            500                 505                 510

Thr Val Val Pro Glu Leu Pro Ser Leu Ile Arg Asp Ile Gly Lys Val
        515                 520                 525

Phe Asp Ser Asp Asn Ile Lys Glu Lys Val Asp Tyr Trp Ile Lys Ile
    530                 535                 540

Gly Glu Arg Ser Val Trp Pro Val Leu Asn Ile Ile Trp Ala Arg Cys
545                 550                 555                 560

Ala Ile Glu Phe Val Leu Asp Asp Leu Tyr His Ser Arg Arg Lys Asp
                565                 570                 575

Glu Leu Asp
```

<210> SEQ ID NO 36
<211> LENGTH: 1740
<212> TYPE: DNA
<213> ORGANISM: Arxula adeninivorans

<400> SEQUENCE: 36

```
atgattaggg ctgcctacgg gtcagtgtcc agggcccgag attctttaac gttgagggct      60

ccatcttttc ctaccactgc tgtggaggtc cgtgacaaga ttctatggat tctgtatgcc     120

tggattgaaa tgttcacgga cgtctttagc ttctggacgg agaaggtgtg gggttatgtt     180
```

```
tctactccta ctaaagaaag cattcttaga aagcaactcg acgaggcaaa atcataccat    240

gaatgggagg agctcagcta caaactagac tcaattttag ggaacgatat ttggcgacag    300

aaccctgtta gccgaaagta tgactatcgc ctgatttcta cccgcctcaa ggaattggtt    360

gctgctaggg ataatcgcaa cattgaattg ctaatggatc ggctaaggtc aggcctgctt    420

cgtaatattg gatcgattgc aagtactcat ctctacaacc gagcgtattc gggcacaaaa    480

ctgttaattg aggattacat taatgtagtg attcaatgcc tggagtatgt tgaacggggc    540

ggcaggccat tgactgcttc agcatccaag attcccaatg gcggtgaacc cccttctcca    600

cgaacctacc ataagcccat gattaccaga cagcgcaagc tcaacttctt caatgataca    660

cgccagtcgt ttggaagtac agctgtggta cttcacggcg ggtccttgtt tggactttgc    720

catattggca tgattaaaac attgttcaac cagggtctac ttcctcgcat agtctgtggc    780

tccacagtgg gagcactagt agcgagtcta gtatgctcct gtgtggatga agaggtgtat    840

gagactttgg ataatgtgtc ttcggaaatg tctcctctcc gccaaggata cactgatata    900

aagtaccatt cggtagccga aggggtcatt tcatcaatgt gtccgccaga gatttttgatt    960

tttgaacagt acatccgaga aaaactcgga gacctgacat ttgaagaagc atatcaacgc   1020

accggccgca ttcttaatat cccagtgaca ccaaaggcaa aaccaggtca ggtagcacca   1080

ccagtcccga cgctcctgaa ttatttgtcg agcccgaatg ttgtagtatg gtcagcagcg   1140

caatgcagca ttggaacggg gattattcac aagaaggttg aacttttagt aaaaggtctg   1200

gatggtcaat taaaacctta tttggatgcg gatgatattg aatacactcc tgcaaatcaa   1260

gctgtatacg ctgctgatcg cgagagtccc tatacaagat tgtctgagct gttcaatgtg   1320

aacaattaca ttgtatcagt agctcgcccc tactttgccc caattctgct ttcggatttc   1380

aagtaccgtg cagctaaaag cttcaagacc cggttcctca aactaacccg tctggagtta   1440

cagtatcgtc tcaatcagct gtctcaattg ggggctggttc cgcccatgat tcaacaatgg   1500

tttgtggacg gtaacattcc cgccgggttc caagttaccg tggtgcctga attaccctca   1560

cttattagag acatcggcaa ggttttcgat tcggataata taaaggagaa ggtcgactac   1620

tggattaaga tcggtgagcg cagtgtgtgg ccagtgctga atattatctg ggcaaggtgc   1680

gcaattgagt ttgtgctcga cgatctatat cacagccgac gtaaagacga actcgactag   1740
```

<210> SEQ ID NO 37
<211> LENGTH: 633
<212> TYPE: PRT
<213> ORGANISM: Arxula adeninivorans

<400> SEQUENCE: 37

```
Met Asn Pro Phe Asp Val Asp Tyr Thr Asn Arg Asp His Leu Val Asp
1               5                   10                  15

Phe Glu Arg Ala Leu His Glu Asp Glu Ala Ser His Ile Ile Ser Val
            20                  25                  30

Asn Asp Trp Ala Pro Val His Ala Pro Leu Lys Arg Arg Leu Arg Arg
        35                  40                  45

Lys Pro Thr Asp Ser Asp Pro Gly Thr Gly Leu Gly Tyr Thr Leu Leu
    50                  55                  60

Arg Trp Pro Ile Leu Val Ala Ile Ala Leu Trp Leu Ala Leu Leu Ala
65                  70                  75                  80

Phe Val Tyr Ala Ile Val Arg Phe Trp Val Ala Leu Phe Glu Tyr Phe
                85                  90                  95

Val Thr Trp Arg Gly Pro Arg Arg Asn Leu Arg Glu Lys Leu Arg Ser
```

-continued

```
            100                 105                 110

Ala Arg Ser Tyr Glu Glu Trp Ile Ser Ala Ala Lys Val Leu Asp Asp
        115                 120                 125

His Leu Gly Asn Thr Ser Trp Lys His Asn Pro Lys Phe Ser Arg Tyr
    130                 135                 140

Asp Tyr Arg Thr Ile Asp Arg Ile Thr Asn Ser Leu Arg Gln Leu Arg
145                 150                 155                 160

Asn Gln Asn Lys Ala Glu Glu Val Gly Ser Ile Leu Gln Gly Cys Val
                165                 170                 175

Lys His Asn Phe Ala Gly Thr Gln Gly Gln Pro Leu Tyr Ser Gln Cys
            180                 185                 190

Tyr Tyr Gly Thr Lys Asp Leu Val Glu Glu Phe Asn Ser Glu Ile Val
        195                 200                 205

Lys Ser Leu Asp Tyr Leu Ala Thr His Pro Asp Leu Ser Pro Gln Ser
    210                 215                 220

Arg Arg Leu Leu Phe Lys Met Phe Ser Lys Asn Phe Gly Lys Thr Ala
225                 230                 235                 240

Leu Cys Leu Ser Gly Gly Ala Thr Phe Ala Tyr Arg His Phe Gly Val
                245                 250                 255

Val Lys Ala Leu Leu Glu Gln Gly Leu Leu Pro Asn Ile Ile Ser Gly
            260                 265                 270

Thr Ser Gly Gly Gly Leu Val Ala Ala Leu Val Gly Thr Arg Thr Asn
        275                 280                 285

Ser Glu Leu Arg Glu Leu Leu Thr Pro Gln Leu Ala Asp Lys Ile Thr
    290                 295                 300

Ala Cys Trp Glu Lys Phe Pro Lys Trp Val Tyr Arg Phe Tyr Ser Thr
305                 310                 315                 320

Gly Ala Arg Phe Asp Ala Val Asp Trp Ala Glu Arg Ser Cys Trp Phe
                325                 330                 335

Thr Leu Gly Ser Leu Thr Phe Arg Glu Ala Tyr Asp Arg Thr Gly Lys
            340                 345                 350

Ile Leu Asn Ile Ser Thr Val Pro Ala Asp Pro Asn Ser Pro Ser Ile
        355                 360                 365

Leu Cys Asn Tyr Ile Thr Ser Pro Asp Cys Val Ile Trp Ser Ala Leu
    370                 375                 380

Leu Ala Ser Ala Ala Val Pro Gly Ile Leu Asn Pro Val Val Leu Met
385                 390                 395                 400

Met Lys Thr Lys Lys Gly Asn Leu Val Pro Tyr Ser Phe Gly Asn Lys
                405                 410                 415

Trp Lys Asp Gly Ser Leu Arg Thr Asp Ile Pro Val His Ala Leu Asn
            420                 425                 430

Val Tyr Phe Asn Val Asn Phe Thr Ile Val Ser Gln Val Asn Pro His
        435                 440                 445

Ile Ser Leu Phe Met Tyr Ala Pro Arg Gly Thr Val Gly Arg Pro Val
    450                 455                 460

Ser His Arg Gln Gly Lys Gly Trp Arg Gly Gly Phe Leu Gly Ser Ala
465                 470                 475                 480

Leu Glu Asp Met Leu Lys Leu Glu Ile Arg Lys Trp Leu Lys Leu Met
                485                 490                 495

Lys Asn Leu Ser Leu Met Pro Arg Phe Phe Asn Gln Asp Trp Ser Ser
            500                 505                 510

Val Trp Leu Gln Thr Phe Glu Gly Ser Val Thr Leu Trp Pro Arg Ile
        515                 520                 525
```

-continued

```
Arg Leu Lys Asp Phe Tyr Tyr Ile Leu Ser Asp Pro Thr Arg Glu Gln
    530                 535                 540

Met Glu Thr Met Ile Ile Ser Gly Gln Arg Cys Thr Phe Pro Lys Leu
545                 550                 555                 560

Leu Phe Ile Lys His Gln Val Asn Ile Glu Arg Ala Ile Asp Arg Gly
                565                 570                 575

Arg Lys His Asn Ala Lys Ala Arg Glu Glu Asn Gly Pro Gln Leu Arg
            580                 585                 590

Arg Val Asn Pro Phe Leu His Asp Leu Asp Asp Arg Val Tyr His Ser
        595                 600                 605

Ser Ser Ser Val Asp Pro Arg Glu Phe Gln Asp Asp His Asp Asp Glu
    610                 615                 620

Asp Asp Asp Ser Thr Asp Ser Ser Met
625                 630


<210> SEQ ID NO 38
<211> LENGTH: 1902
<212> TYPE: DNA
<213> ORGANISM: Arxula adeninivorans

<400> SEQUENCE: 38

atgaacccgt ttgatgtaga ttacacaaac agggaccatc tggtcgactt tgaacgagct     60

ttgcacgaag atgaggcttc ccatattata tcggtaaacg actgggctcc agtgcatgct    120

cctctcaagc gacggttgag acgcaagccg acagattcgg atcctgggac aggattagga    180

tacactttgc ttagatggcc tattctggtg gcaattgcgc tgtggctggc cctgttagca    240

tttgtgtacg ccatagtgag gttttgggtc gctctgtttg agtactttgt tacctggcga    300

ggaccccggc gcaatcttcg tgaaaagcta cgcagcgctc gtagttacga ggaatggatt    360

agtgctgcca aagttcttga tgaccatcta ggaaatactt cttggaagca caacccaaag    420

ttctctcgat acgactaccg tactattgat cgcatcacta actcactgcg gcaactgcga    480

aaccagaaca aggccgagga ggttggctct attctacaag gatgcgtcaa gcacaacttt    540

gctggaactc agggccaacc tttgtactct cagtgctact atggcacaaa ggacctggta    600

gaggagttca attctgaaat tgtgaaatcg ctcgattacc tggcaaccca tccagacctg    660

agtcctcaat ctagacgtct tttgttcaaa atgttttcca agaattttgg aaagacggca    720

ttgtgcctct ctggaggggc aacatttgcc tatagacatt tcggagttgt taaagcgctc    780

ttggaacagg gcttgctgcc taatattatt tctggtactt ctggcggagg attggtagct    840

gcgctagttg gtaccagaac aaatagtgaa ctccgtgagc ttctcactcc tcaactggcc    900

gacaagatca ccgcctgctg ggaaaagttc ccaaaatggg tttatagatt ctacagcacc    960

ggcgctcgat tcgatgccgt cgactgggct gaacggtctt gctggtttac actaggaagc   1020

ctgactttta gagaggccta cgatcgaact ggaaagatcc tcaacatttc cactgttcct   1080

gctgacccta attccccttc aatcctctgc aattacatta cttctcccga ctgtgtcatc   1140

tggtcggctt tacttgcttc tgctgcagta ccgggaattc tgaacccagt ggtgctcatg   1200

atgaagacga aaaagggcaa tctggtacct tacagctttg gtaacaagtg gaaggatggt   1260

tctctccgaa ctgatattcc tgtccacgca ctcaacgtgt actttaacgt caacttcacc   1320

atcgtgtccc aggtcaaccc tcacatttct ctgttcatgt atgccccgcg gggaactgtg   1380

ggtaggccag tatctcaccg tcagggtaaa ggctggcgag gtgggttcct aggctcagct   1440

ttggaagaca tgctgaagct ggaaattcgt aaatggctca aactcatgaa aaaccttagt   1500
```

```
cttatgccac ggtttttcaa tcaagattgg tcttcagtat ggcttcaaac gttcgaggga   1560

tccgtcacct tgtggccaag gatcaggcta aaggactttt attatattct gtctgatccc   1620

actcgggaac aaatggaaac catgatcatt agtggacagc gatgcacatt cccaaagctc   1680

ttgttcatca agcaccaagt caacatagag cgggcaattg accgtggaag aaagcacaat   1740

gcaaaagcca gggaggaaaa tggtccccag cttagacggg taaacccatt cctgcacgac   1800

ttggatgacc gtgtatacca ttccagctct agcgtggacc ctcgcgagtt tcaggatgat   1860

cacgatgatg aagacgacga cagcactgat tctagcatgt aa                      1902


<210> SEQ ID NO 39
<211> LENGTH: 662
<212> TYPE: PRT
<213> ORGANISM: Arxula adeninivorans

<400> SEQUENCE: 39

Met Gln Ser Leu Asp Leu Leu Asp Asp Arg Ser Trp Val Pro Asn Tyr
1               5                   10                  15

Ala Arg Val Gly Leu Lys Ser Leu Lys Glu Tyr Leu Val Ser His Arg
            20                  25                  30

Tyr Gln Ser Glu Glu Ala Arg Lys His Ala Glu Ala Leu Glu Arg Trp
        35                  40                  45

Thr Lys Ser Gln Ala Gln Ala Glu Thr Tyr Glu Gln Trp Leu Phe Ala
    50                  55                  60

Ser Glu Gln Leu Asp Lys Leu Ser Gly Asn Asp Lys Trp Lys Glu Asp
65                  70                  75                  80

Pro Val Ser Pro Tyr Tyr Asp Ser Val Leu Val Gln Gln Arg Leu Gln
                85                  90                  95

Gln Leu Arg Asp Ala Arg Val Asn Ser Asn Met Asp Glu Leu Leu Tyr
            100                 105                 110

Leu Val Arg Thr Ser Leu Gln Arg Asn Leu Gly Asn Met Gly Asp Pro
        115                 120                 125

Arg Leu Tyr Val Arg Thr His Thr Gly Ser Lys Thr Leu Ile Glu Gln
    130                 135                 140

Tyr Ile Ala Glu Val Glu Leu Ala Leu Asp Thr Leu Leu Ser Cys Gly
145                 150                 155                 160

Pro Gly Thr Phe Ser Pro Lys Val Leu Leu Ser Asn Leu Ile Gln Thr
                165                 170                 175

Arg Lys Ala Phe Gly Arg Thr Ala Leu Val Leu Ser Gly Gly Ser Thr
            180                 185                 190

Phe Gly Ile Leu His Ile Gly Val Met Arg Glu Leu His Arg Ala His
        195                 200                 205

Leu Leu Pro Gln Val Ile Ser Gly Ser Ser Ala Gly Ser Ile Phe Ala
    210                 215                 220

Ser Met Leu Cys Ile His Leu Glu Asp Glu Ile Glu Glu Leu Leu Gln
225                 230                 235                 240

Leu Pro Leu His Lys Glu Ser Phe Glu Ile Phe Glu Pro Ala Gly Glu
                245                 250                 255

Arg Glu Gly Leu Met Val Arg Leu Ala Arg Phe Leu Lys His Gly Thr
            260                 265                 270

Trp Phe Asp Asn Lys Tyr Leu Ser Thr Thr Met Arg Glu Leu Leu Gly
        275                 280                 285

Asp Leu Thr Phe Gln Glu Ala Tyr Tyr Arg Thr Gln Arg Ile Leu Asn
    290                 295                 300
```

```
Val Thr Val Ser Pro Ser Ser Met His Glu Met Pro Lys Ile Leu Asn
305                 310                 315                 320

Tyr Leu Thr Ala Pro Asn Val Leu Ile Trp Ser Ala Val Cys Ala Ser
                325                 330                 335

Cys Ser Val Pro Phe Val Phe Asp Ser His Asp Ile Leu Ala Lys Asn
            340                 345                 350

Pro Arg Thr Gly Glu Phe Tyr Ser Trp Asn Ala Ser Thr Phe Ile Asp
        355                 360                 365

Gly Ser Val Tyr Asn Asp Leu Pro Leu Ser Arg Leu Ala Glu Met Phe
    370                 375                 380

Asn Val Asn His Phe Ile Ala Cys Gln Val Asn Pro His Val Val Pro
385                 390                 395                 400

Phe Val Lys Phe Ala Glu Thr Met Ser Leu Val Glu Ala Arg Pro Thr
                405                 410                 415

Thr Thr Glu Pro Gly Ser Leu Thr Lys Leu Trp His Ser Thr Gln Leu
            420                 425                 430

Ala Leu Ser Ser Glu Ile Ser His Tyr Leu Asp Leu Ala Ala Glu Met
        435                 440                 445

Gly Leu Phe Lys Asn Ile Ser Ser Lys Leu Arg Ser Val Leu Asp Gln
    450                 455                 460

Gln Tyr Ser Gly Asp Ile Thr Ile Leu Pro Glu Leu Tyr Leu Ser Glu
465                 470                 475                 480

Phe Gly Gln Ile Phe Lys Asn Pro Ser Lys Glu Phe Phe Gln Lys Ala
                485                 490                 495

Glu Leu Arg Ala Ala Arg Ala Thr Trp Pro Lys Met Ser His Ile His
            500                 505                 510

Asn Arg Val Ala Ile Glu Leu Ala Leu Val Lys Ala Ile His Lys Leu
        515                 520                 525

Arg Ala Arg Ile Val Ser Gln Ser Val His Glu Pro Gly Ser Ser Leu
    530                 535                 540

Gln Val His Ala Ala Asn Asp Glu Gly Thr Leu Ala Pro Ile Arg Arg
545                 550                 555                 560

Arg His Ser Ser Thr Lys Leu His His Arg Arg Gln Arg Ser Asp Gly
                565                 570                 575

Met Ala Val Lys Tyr Leu Val Arg Arg His Ser Leu Gln Tyr Phe Gly
            580                 585                 590

Thr Glu Gly Pro Gly Pro Ala Ala Leu Ser Arg Lys Lys Ser Ser Ala
        595                 600                 605

Gly Leu Thr Gln Ala His Thr Pro Thr Pro Ser Leu Thr Asn Ser Val
    610                 615                 620

Ser Val Gly Gly Ser Pro Arg His Arg Arg Phe Thr Thr Ser Ser Arg
625                 630                 635                 640

Gln Ser Ser Gly Asp His Leu Glu Met Phe Ser Gln Asn His Pro Leu
                645                 650                 655

Glu Arg Ile Ser Thr Gly
            660
```

<210> SEQ ID NO 40
<211> LENGTH: 1989
<212> TYPE: DNA
<213> ORGANISM: Arxula adeninivorans

<400> SEQUENCE: 40

```
atgcaatccc tggacctatt agacgacagg tcctgggtcc ccaattatgc gcgtgtgggc     60
```

```
ctgaaatcgc taaaagaata cttggttagc catagatatc agtctgaaga agctcgaaag    120
catgccgaag cgttagaaag atggacaaag tctcaggctc aggcggagac atacgaacag    180
tggctatttg cttcggagca gctcgacaag ctgtctggga acgacaagtg gaaagaggac    240
ccggtgtccc catattatga cagtgtgcta gtacaacagc ggttacagca gctccgagat    300
gctagggtga atagtaacat ggacgagctg ctgtatttgg tccgcactag cttgcaaaga    360
aacttgggta acatgggtga tcctcgacta tacgtgagga cccatactgg ctctaagacg    420
ctcattgaac aatatattgc tgaggtagaa ctggcattag acactctgct gagctgcgga    480
ccggggacgt tttcacccaa agttctgtta tccaatctta ttcagacaag aaaggcgttt    540
ggacgaacag ccctggtgct ttctggaggt agtacgtttg gaattttaca tattggtgta    600
atgcgagagc ttcaccgagc ccatctgtta ccgcaggtca tttctggatc gtcggccgga    660
tccatctttg cgtccatgct atgtattcac ttagaagacg agattgaaga actactgcaa    720
ctgcctctac acaaggaaag ctttgaaatc ttcgaacctg ctggagaacg agaaggacta    780
atggttcggc tggcacggtt cctcaaacat ggcacttggt tcgacaacaa gtatcttagc    840
acaactatgc gagagcttct aggagacctc actttccagg aggcctacta ccgaacgcag    900
cgaattctaa atgtcactgt gtctccttcg agtatgcacg aaatgccgaa gattctcaac    960
tatctgaccg ctcctaacgt gctcatttgg tcggcagtgt gtgcatcgtg ctcagtacca   1020
tttgtgtttg attctcacga cattctggca aaaaaccctc gaactgggga gttttattca   1080
tggaacgctt ctactttcat cgacgggagt gtgtataatg atctgccatt gtctcgacta   1140
gcggaaatgt ttaacgtgaa ccattttatt gcgtgccagg taaacccgca tgtggttcca   1200
ttcgtcaaat ttgccgagac aatgtcattg gtggaagctc gtcccactac tactgaaccg   1260
ggatcgttga caaagctatg gcacagtact cagctcgcgc tttctagtga gatctcacac   1320
tatctggatt tggctgctga aatgggcttg ttcaagaaca ttagttccaa gctgcgatcg   1380
gtgctagatc aacaatattc cggcgacatt actattcttc ccgaattata cctgtctgag   1440
tttggtcaga ttttcaaaaa cccatcaaag gagttcttcc agaaggcaga gcttcgagct   1500
gccagagcga catggcccaa gatgtcccac attcacaacc gtgtggccat cgagttggct   1560
ttagtaaagg caattcacaa gcttcgtgcc cgtattgtat ctcagagcgt ccatgagcct   1620
ggcagttctc tacaagtaca tgctgctaat gacgaaggca ccctagcacc tattcgccgt   1680
cgccattctt cgaccaagct tcaccataga cgacaacggt ccgatggaat ggccgtgaaa   1740
tacttggtcc gcagacattc gctacagtac tttggcactg agggccctgg tcccgctgcg   1800
ctatctcgta aaaagagttc ggccgggctt acccaggctc atactcctac gccttcactg   1860
accaacagcg ttagtgtagg gggcagtcca aggcaccgtc gcttcactac tagctctaga   1920
cagtcctcag gagaccattt ggaaatgttc tctcaaaatc atccgctaga acgtatctct   1980
accggctga                                                           1989
```

<210> SEQ ID NO 41
<211> LENGTH: 666
<212> TYPE: PRT
<213> ORGANISM: Yarrowia lipolytica

<400> SEQUENCE: 41

```
Met Lys Ser Arg Val Ala Val Val Leu Ala Pro Val Leu Ala Pro Phe
1               5                   10                  15

Val Ala Ile Leu Lys Asn Leu Trp Val Phe Phe Thr Ala Leu Leu Glu
```

-continued

```
            20                  25                  30

Leu Leu Phe Asp Val Ser Trp His Trp Met Leu Gln Ser Trp His Trp
        35                  40                  45

Trp Cys Ser Thr Asp Gln Lys Thr Leu Leu Gln Leu Gln Leu Asp Gln
    50                  55                  60

Ala Asp Thr Tyr Glu Glu Trp Glu Ser Ile Ala Ser Glu Leu Asp Glu
65                  70                  75                  80

Leu Leu Gly Asn Asp Val Trp Arg Gln Thr Ala Ala Ser Lys Arg Tyr
                85                  90                  95

Asp Tyr Arg Leu Ile Ala Gly Arg Leu Arg Asp Phe Ile Glu Cys Arg
            100                 105                 110

Ala Val Gly Asp Ile Ala Thr Leu Ile Ser Arg Leu Arg Ser Gly Leu
        115                 120                 125

Leu Arg Asn Leu Gly Ser Ile Ser Ser Leu Gln Leu Tyr Thr Arg Ser
    130                 135                 140

Tyr Leu Gly Ser Lys Leu Leu Ile Glu Glu Tyr Ile Thr Glu Val Ile
145                 150                 155                 160

Asp Cys Leu Lys Tyr Ile Lys Asp Tyr Gly Thr Thr Gly Gly Leu Asp
                165                 170                 175

Thr Lys Gly Val His Phe Phe Pro Lys Ser Glu Gln Arg Gln Leu Asp
            180                 185                 190

Ser Glu Gln Leu Thr Arg Gln Lys Lys His Lys Leu Phe Tyr Asp Thr
        195                 200                 205

Arg Gln Ser Phe Gly Arg Thr Ala Leu Val Leu Gln Gly Gly Thr Ile
    210                 215                 220

Phe Gly Leu Thr His Leu Gly Thr Ile Lys Ala Leu Thr Leu Gln Gly
225                 230                 235                 240

Leu Leu Pro Gly Ile Val Thr Gly Phe Lys Glu Gly Ala Phe Ile Ala
                245                 250                 255

Ala Leu Thr Gly Ile Tyr Val Ser Asp Leu Glu Leu Leu Glu Thr Ile
            260                 265                 270

Asp Ser Leu Pro Asp Thr Leu Asn Asp Leu Tyr Gln Lys Tyr Lys Glu
        275                 280                 285

Arg Leu Ala Glu Glu Asn Lys His Lys Asp His Ser Phe Ser Asn Ser
    290                 295                 300

Asn Ser Asp Tyr Asp Phe Asp Tyr Ala Phe Asp Phe Glu Gln Phe Ala
305                 310                 315                 320

Asn Thr Tyr Asn Val Thr Phe Ser Ser Val Thr Asp Lys Val Leu Arg
                325                 330                 335

Ser Glu Tyr Pro Pro Glu Val Lys Met Tyr Glu Glu Phe Ile Glu Asn
            340                 345                 350

Gln Leu Gly Asp Leu Thr Phe Glu Glu Ala Phe Asn Lys Ser Asp Arg
        355                 360                 365

Val Leu Asn Ile Val Ala His Ser His Asp Ser Ser Phe Pro Thr Leu
    370                 375                 380

Met Asn Tyr Leu Thr Thr Pro Asn Val Leu Ile Arg Ser Ala Cys Arg
385                 390                 395                 400

Ala Ser Met Val Thr Ala His Asp Glu Pro Gln Thr Lys Lys Ala Cys
                405                 410                 415

Ala His Leu Leu Val Lys Asp Asp Asp Asn Ser Val Ile Pro Tyr Asp
            420                 425                 430

Ala Cys Lys Ser Arg Arg Gly Ser Ser Thr Asp Val Ile Leu Gly Pro
        435                 440                 445
```

```
Val Gln Glu Glu Val Asp Pro Leu Asp Ser Thr Ala Asn Gly Thr Asn
    450                 455                 460

Ser Ser Gly Pro Pro Lys Leu Glu Ile Thr Thr Asp Thr Trp Lys Arg
465                 470                 475                 480

Asn Asn Ala Asp Asp Glu Asp His Val Asp Thr Leu Pro Gly Arg Val
                485                 490                 495

Ser Ala Leu Pro Thr Pro Ser Tyr Ser Met Ile Asn Gln Gly Lys Ile
            500                 505                 510

Val Ser Pro Tyr Ala Arg Leu Ser Glu Leu Phe Asn Val Asn His Phe
        515                 520                 525

Ile Val Ser Leu Ser Arg Pro Tyr Leu Ala Pro Leu Leu Ala Ile Glu
    530                 535                 540

Gly Arg His Arg Gly Tyr His Gly Trp Arg Val Asn Leu Ile Arg Val
545                 550                 555                 560

Leu Lys Leu Glu Phe Glu His Arg Leu Ala Gln Phe Asp Tyr Ile Gly
                565                 570                 575

Leu Leu Pro Thr Ile Phe Arg Arg Phe Phe Ile Asp Asp Lys Ile Pro
            580                 585                 590

Gly Ile Gly Pro Asn Ala Glu Val Leu Ile Val Pro Glu Leu Ala Ala
        595                 600                 605

Gly Met Ile Ser Asp Phe Lys Lys Ala Phe Ser Asn His Asp Ile Pro
    610                 615                 620

Glu Lys Val Arg Tyr Trp Thr Thr Val Gly Glu Arg Ala Thr Trp Pro
625                 630                 635                 640

Leu Val Ala Ala Ile Trp Ala Arg Thr Ala Ile Glu Tyr Thr Leu Asn
                645                 650                 655

Asp Met Tyr Asn Gln Thr Lys Arg Gln Asn
            660                 665
```

<210> SEQ ID NO 42
<211> LENGTH: 2201
<212> TYPE: DNA
<213> ORGANISM: Yarrowia lipolytica

<400> SEQUENCE: 42

```
cttttacgag tgtgtatcat cacatgatta tgcagcaaga tcagtatcat ttcggctatc     60

cagctctctt cccccgttca gctccttttc taccgcgatt atgaaaagcc gcgtggccgt    120

tgtcttggcg ccggttctgg caccatttgt ggcgattttg aaaaacctgt gggtcttctt    180

cacagctcta ctggagctct tattcgacgt tagctggcac tggatgttac aatcatggca    240

ctggtggtgc tccaccgacc aaaaaacact gctacaactg cagctggacc aggcagacac    300

ctacgaggaa tgggaaagca ttgcatcgga gctggacgag ctgctgggca acgacgtgtg    360

gcgtcagacc gcagcctcga aacgatacga ctaccggctg attgcaggcc gtctgagaga    420

ctttatcgag tgccgggcgg tcggcgacat tgcgacgctg atttctcgtc tgcgaagcgg    480

actgctgcgg aatttgggct cgatttcgtc gctccagctg tacactcgct cgtacctcgg    540

ctctaaactg ctcatcgaag agtacatcac cgaggtcatt gactgtctca agtacatcaa    600

ggactatggg acgacgggcg gactggacac caagggagtg catttcttcc caaagtccga    660

acagcgacaa ctggacagtg aacagctgac tcgacaaaag aaacacaagt tattctacga    720

cacacgacaa tcttttggcc gaacggccct cgtgttgcag ggaggaacta ttttcggact    780

tactcatctc ggaacaatca aggctcttac tctccagggt ctgctaccgg gtattgtcac    840
```

-continued

```
cggtttcaag gagggggcgt ttattgccgc tctcacaggc atctacgtat ccgacctgga     900
gctgctcgaa accattgact ctttgccaga cactctcaat gacctgtacc aaaaatacaa     960
ggagcgactg gcggaggaaa acaaacacaa ggaccactcg ttcagtaact ccaattcgga    1020
ctacgacttt gactacgcat ttgactttga acagtttgca aacacctata atgtgacctt    1080
ctcgtctgtc actgacaaag tattgcgatc ggagtacccc ccggaagtca aaatgtacga    1140
ggagttcatc gagaatcaac tcggagacct cacgttcgaa gaggccttca acaaaagcga    1200
ccgcgtgctc aacattgtcg cccattccca tgactcttcc ttcccgacac tgatgaacta    1260
cctcaccact cccaatgtgc tcatcagaag cgcatgtaga gcttccatgg tgaccgccca    1320
cgacgagccc caaacgaaaa aggcatgtgc ccatctgctg gtcaaggatg acgacaacag    1380
cgtcattccc tatgacgcct gcaaatccag gcgaggaagc tcgaccgacg tgattctggg    1440
acctgtccag gaggaggtgg atccattaga ttcaacagct aacggtacta actcttctgg    1500
acctcccaaa ctcgaaatca caactgacac ctggaaacga aacaatgcag acgacgagga    1560
ccacgtggat actctcccgg gccgcgtgag tgctctacct acaccttcgt actccatgat    1620
taaccagggc aagattgtct ctccctacgc tcgcctttcc gaactcttta acgtcaacca    1680
cttcatcgtc tctctctcaa gaccctacct ggcgcctctt ctggccatcg aaggccgaca    1740
tagaggctac cacggctgga gagtgaacct gatccgagta ctgaaactag aattcgaaca    1800
cagactcgcc cagttcgact acataggcct gctgccgacc atcttccgtc ggttcttcat    1860
cgacgataag atccctggca tcggtcccaa cgccgaggtg ctcattgttc ctgagctagc    1920
ggctggcatg atctccgact tcaaaaaggc cttttcgaac cacgacattc ccgagaaggt    1980
ccgctactgg accactgtgg gcgaacgagc cacctggcct ctagtcgccg ccatctgggc    2040
cagaacagca atcgagtaca ccctcaacga catgtacaac cagaccaagc gacaaaacta    2100
gaccccgagc agagcacata actactaacg atgagactaa agtatgtact gtatgtacta    2160
aacatacgct cgtaaacagt tgtatttatt ctttttcagc a                        2201
```

<210> SEQ ID NO 43
<211> LENGTH: 341
<212> TYPE: PRT
<213> ORGANISM: Escherichia coli

<400> SEQUENCE: 43

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
```

```
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340
```

<210> SEQ ID NO 44
<211> LENGTH: 1026
<212> TYPE: DNA
<213> ORGANISM: Escherichia coli

<400> SEQUENCE: 44

```
atgaagaagc ccgagctgac cgctacctct gttgagaagt tcctgattga gaagtttgat      60

tccgtttccg acctgatgca gctgtccgag ggcgaggagt ctcgagcctt ctcctttgac     120

gtgggcggac gaggttacgt tctgcgagtg aactcgtgtg ccgacggctt ctacaaggat     180

cgatacgtct accgacactt tgcttctgcc gctctgccca tccctgaggt tctcgacatt     240

ggcgagttct ctgagtccct cacctactgc atctctcgac gagctcaggg agtcaccctg     300

caggacctcc ctgagactga gctgcctgct gtcctccagc ctgttgctga ggccatggac     360

gctatcgctg ctgctgatct gtcccagacc tcgggtttcg gccccttttgg acctcaggga     420

attggacagt acaccacttg gcgagacttc atctgtgcta ttgccgatcc tcacgtctac     480

cattggcaga ccgttatgga cgatactgtg tcggcttctg tcgctcaggc tctggacgag     540

ctgatgctct gggccgagga ttgccccgag gttcgacacc tggtgcatgc tgacttcggt     600

tccaacaacg ttctcaccga caacggccga atcactgccg tgattgactg gtccgaggct     660

atgtttggcg actcgcagta cgaggtggcc aacatcttct tttggcgacc ctggctggct     720

tgtatggagc agcagacccg atacttcgag cgacgacatc ctgagctcgc tggatcccct     780

cgactgcgag cttacatgct ccgaattggt ctggaccagc tctaccagtc gctggtggat     840

ggcaactttg acgatgctgc ctgggctcag ggacgatgtg acgccatcgt gcgatctggc     900
```

gctggaaccg tcggacgaac tcagattgcc cgacgatccg ctgctgtctg gaccgacgga 960
tgcgtggagg tcctggctga ttcgggtaac cgacgaccct ctactcgacc tcgagctaag 1020
gagtaa 1026

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
accacttggc gagacttcat ctgt 24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
agcatcgtca aagttgccat ccac 24

<210> SEQ ID NO 47
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
cagctctctt cccccgttca gctccttttc taccgcgatt atgaagaagc ccgagctgac 60

<210> SEQ ID NO 48
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
tttagtctca tcgttagtag ttatgtgctc tgctcggggt tactccttag ctcgaggtcg 60

<210> SEQ ID NO 49
<211> LENGTH: 898
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49
cagctctctt cccccgttca gctccttttc taccgcgatt atgaagaagc ccgagctgac 60
cgctacctct gttgagaagt tcctgattga gaagtttgat tccgtttccg acctgatgca 120
gctgtccgag ggcgaggagt ctcgagcctt ctcctttgac gtgggcggac gaggttacgt 180
tctgcgagtg aactcgtgtg ccgacggctt ctacaaggat cgatacgtct accgacactt 240
tgcttctgcc gctctgccca tccctgaggt tctcgacatt ggcgagttct ctgagtccct 300

```
cacctactgc atctctcgac gagctcaggg agtcaccctg caggacctcc ctgagactga    360

gctgcctgct gtcctccagc ctgttgctga ggccatggac gctatcgctg ctgctgatct    420

gtcccagacc tcgggtttcg gccccttttgg acctcaggga attggacagt acaccacttg   480

gcgagacttc atctgtgcta ttgccgatcc tcacgtctac cattggcaga ccgttatgga    540

cgatactgtg tcggcttctg tcgctcaggc tctggacgag ctgatgctct gggccgagga    600

ttgccccgag gttcgacacc tggtgcatgc tgacttcggt tccaacaacg ttctcaccga    660

caacggccga atcactgccg tgattgactg gtccgaggct atgtttggcg actcgcagta    720

cgaggtggcc aacatcttct tttggcgacc ctggctggct tgtatggagc agcagacccg    780

atacttcgag cgacgacatc ctgagctcgc tggatcccct cgactgcgag cttacatgct    840

ccgaattggt ctggaccagc tctaccagtc gctggtggat ggcaactttg acgatgct      898
```

<210> SEQ ID NO 50
<211> LENGTH: 633
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 50

```
accacttggc gagacttcat ctgtgctatt gccgatcctc acgtctacca ttggcagacc     60

gttatggacg atactgtgtc ggcttctgtc gctcaggctc tggacgagct gatgctctgg    120

gccgaggatt gccccgaggt tcgacacctg gtgcatgctg acttcggttc caacaacgtt    180

ctcaccgaca acggccgaat cactgccgtg attgactggt ccgaggctat gtttggcgac    240

tcgcagtacg aggtggccaa catcttcttt tggcgaccct ggctggcttg tatggagcag    300

cagacccgat acttcgagcg acgacatcct gagctcgctg gatcccctcg actgcgagct    360

tacatgctcc gaattggtct ggaccagctc taccagtcgc tggtggatgg caactttgac    420

gatgctgcct gggctcaggg acgatgtgac gccatcgtgc gatctggcgc tggaaccgtc    480

ggacgaactc agattgcccg acgatccgct gctgtctgga ccgacggatg cgtggaggtc    540

ctggctgatt cgggtaaccg acgaccctct actcgacctc gagctaagga gtaaccccga    600

gcagagcaca taactactaa cgatgagact aaa                                 633
```

<210> SEQ ID NO 51
<211> LENGTH: 346
<212> TYPE: PRT
<213> ORGANISM: Rhodotorula graminis

<400> SEQUENCE: 51

```
Met Gly Ala Gln Glu Glu Val Asp Tyr Asp Gln Ser Asp His Thr Lys
1               5                   10                  15

Ile Lys Phe Val Pro Phe Val Val Pro Arg His Arg Arg Leu Gln Thr
            20                  25                  30

Phe Ser Val Phe Leu Trp Thr Thr Ala Leu Pro Ile Ser Leu Gly Ile
        35                  40                  45

Phe Cys Ile Leu Cys Ser Phe Pro Pro Leu Trp Pro Leu Val Ile Gly
    50                  55                  60

Tyr Leu Thr Trp Val Phe Leu Ile Asp Gln Ala Pro Met Arg Gly Gly
65                  70                  75                  80

Arg Pro Gln Ala Trp Leu Arg Lys Ser Arg Val Trp Glu Trp Phe Ala
                85                  90                  95
```

-continued

```
Gly Tyr Tyr Pro Val Ser Leu Ile Lys Ser Ala Asp Leu Pro Pro Asp
            100                 105                 110

Gln Arg Tyr Val Phe Gly Tyr His Pro His Gly Val Ile Gly Met Gly
        115                 120                 125

Ala Ile Ala Asn Phe Gly Thr Asp Ala Thr Gly Phe Ser Arg Leu Phe
    130                 135                 140

Pro Gly Ile Thr Pro His Leu Leu Thr Leu Ala Ser Asn Phe Lys Leu
145                 150                 155                 160

Pro Val Tyr Arg Glu Leu Leu Leu Ala Leu Gly Ile Ser Ser Val Ser
                165                 170                 175

Met Lys Ser Cys Gln Asn Ile Leu Arg Gln Gly Pro Gly Ser Ser Ile
            180                 185                 190

Thr Ile Val Val Gly Gly Ala Ala Glu Ser Leu Ser Ala His Pro Gly
        195                 200                 205

Thr Ala Asp Leu Thr Leu Lys Arg Arg Lys Gly Phe Ile Lys Leu Ala
    210                 215                 220

Ile Arg Thr Gly Ala Ser Leu Val Pro Val Phe Ser Phe Gly Glu Asn
225                 230                 235                 240

Asp Ile Phe Asn Gln Leu Ser Asn Glu Arg Gly Thr Arg Leu Tyr Lys
                245                 250                 255

Leu Gln Lys Arg Phe Gln Ala Val Phe Gly Phe Thr Leu Pro Ile Phe
            260                 265                 270

Phe Gly Arg Gly Leu Phe Asn Tyr Asn Met Gly Leu Met Pro Tyr Arg
        275                 280                 285

His Pro Ile Val Ser Val Val Gly Arg Pro Ile Lys Val Lys Gln Lys
    290                 295                 300

Asp His Pro Ser Thr Ala Asp Leu Glu Glu Val Gln Glu Arg Tyr Ile
305                 310                 315                 320

Ala Glu Leu Lys Arg Ile Trp Glu Asp Tyr Lys Glu Val Tyr Ala Lys
                325                 330                 335

Ser Arg Thr Lys Glu Leu Thr Ile Ile Ala
            340                 345
```

<210> SEQ ID NO 52
<211> LENGTH: 1041
<212> TYPE: DNA
<213> ORGANISM: Rhodotorula graminis

<400> SEQUENCE: 52

```
atgggcgcac aagaagaggt cgactacgac cagtcggacc acaccaagat caagttcgtg      60

ccctttgtcg tcccgcggca ccgtcgcctc cagacgttct cggtcttcct gtggacgacg     120

gccctcccta tctcgctcgg catcttctgc atcctgtgct ccttccctcc tctttggccg     180

ctcgtcatcg ggtacctcac ctgggtcttc ctcattgacc aggcgccgat gcgcggcggg     240

aggccacaag cctggctgcg aaagtcgcgc gtgtgggagt ggttcgccgg ctactatccc     300

gtcagcctca tcaagagcgc cgacctcccg cccgaccagc gttacgtctt tggctaccac     360

cctcacggcg tcatcggcat gggcgccatc gccaactttg gcaccgacgc gaccgggttc     420

tcgcgcctgt tcccgggcat cacgccgcac ctcctcacgc tcgcgagcaa cttcaagctc     480

ccagtctacc gagagctcct cctcgccctc ggcatctcgt ccgtctcgat gaagagctgc     540

cagaacatcc tgcggcaagg tcccggctcg tccatcacga tcgtcgtcgg cggcgccgcc     600

gagagcctga gcgcgcaccc tggcacggcc gacctgacgc tcaagcgccg caagggcttc     660

atcaagctcg ccatccgcac cggcgcctcg ctcgtgcccg tcttttcctt tggcgagaac     720
```

gacatcttca accagctgtc gaacgagcga gggacgcgcc tgtacaagct gcagaagcgg 780
ttccaggccg tctttggctt cacattgccc atcttcttcg gccgaggcct gttcaactac 840
aacatgggct tgatgccgta ccgacacccg atcgtctcgg tcgtcggccg cccgatcaag 900
gtcaagcaga aggaccaccc gtcgactgcc gacctcgaag aagtccagga gcggtacatc 960
gccgagctca aaaggatctg ggaggactac aaggaggtgt acgccaagag tcgcaccaag 1020
gagctcacca tcatcgcctg a 1041

<210> SEQ ID NO 53
<211> LENGTH: 635
<212> TYPE: PRT
<213> ORGANISM: Pichia guilliermondii

<400> SEQUENCE: 53

Met Thr Lys Glu Val Asp Glu Ser Thr Gly Gly Ala Ser Asp Ile Pro
1 5 10 15

Asn Met Val Glu Glu Ala Lys Ser Ser Ser Phe Asp Arg Glu Thr Glu
20 25 30

Glu Asn Leu Leu Leu Glu Thr Thr Lys Pro Asp Glu Asn Leu Val Pro
35 40 45

Glu Ser Thr Lys His Asp Glu Lys Leu Val Pro Glu Ile Thr Lys His
50 55 60

Glu Asp Asn Pro Met Glu Asn Asp Gln Val Ser Gln Asn Thr Ala Thr
65 70 75 80

Ser Pro Met Thr Gly Ala Gly Ser Glu Glu Thr Arg Asp Leu Ile Thr
85 90 95

Glu Asn Ile Glu Lys Pro Asp Glu Gly Asp Leu Leu Ile Glu Leu Ile
100 105 110

Ser Lys Asp Asn Asp Gly Asp Gly Asp Asp Gly Leu Lys Asn Arg Lys
115 120 125

Gln Lys Arg Ser Ser Ser Glu Val Lys Arg Leu Arg Met Ser Ser Leu
130 135 140

Ala Pro Lys Gly Pro Thr Pro Gln Lys His Glu Arg Pro Lys Tyr Ile
145 150 155 160

Asn Val Ala Pro Leu Asn Ile Pro Ile Arg Arg Arg Leu Glu Met Val
165 170 175

Gly Ile Ile Trp His Thr Ile Cys Ile Pro Thr Phe Val Ser Leu Phe
180 185 190

Phe Leu Thr Leu Ser Leu Gly Pro Phe Ala Trp Val Gly Val Ile Leu
195 200 205

Pro Tyr Phe Leu Trp Trp Tyr Leu Ile Asp Leu His Thr Pro Thr Asn
210 215 220

Gly Lys Val Ala Tyr Arg Ser Arg Asp Trp Met Lys Asn Phe Ile Val
225 230 235 240

Trp Asp Trp Phe Val Asp Tyr Phe Pro Ile Arg Val His Lys Ser Cys
245 250 255

Glu Leu Glu Pro Thr Phe Ser Asp Val Ile Ile Glu Asp Asp Val Val
260 265 270

Pro Asp Asp Glu Glu Asp Leu Ile Ser Glu Gln Ser Arg Thr Gly Val
275 280 285

Asp Lys Leu Phe Lys Phe Leu Gly Leu Arg Lys Arg Leu Asn Asp Asp
290 295 300

Ser Asp Ala Ser Ser Gln Cys Ser Leu Leu Gln Glu Ser Leu Ser Thr

-continued

```
305                 310                 315                 320

Arg Arg Lys Val Lys Arg Met Ser Thr Gly Pro Arg Tyr Ile Phe Gly
                325                 330                 335

Tyr His Pro His Gly Val Ile Ser Met Gly Val Phe Gly Thr Phe Ala
            340                 345                 350

Thr Asn Ala Leu Arg Asn Glu Pro Tyr Glu Pro Pro Leu Arg Leu Leu
        355                 360                 365

Lys Pro Phe Phe His Asp Ser Ser Lys Gly Glu Arg Leu Phe Pro Gly
    370                 375                 380

Ile Gly Thr Val Phe Pro Leu Thr Leu Thr Thr Gln Phe Ile Val Pro
385                 390                 395                 400

Tyr Tyr Arg Asp Tyr Ile Leu Gly Met Gly Leu Thr Ser Ala Ser Ala
                405                 410                 415

Lys Asn Ile Lys Ser Leu Ile Ser Asn Gly Asp Asn Ser Ile Cys Val
            420                 425                 430

Val Val Gly Gly Ala Gln Glu Ser Leu Leu Asn Asp Met Val Ala Ala
        435                 440                 445

Thr Thr Val Pro Gly Arg Tyr Gly Lys Ser Asn Leu Pro Asn Asp Ser
    450                 455                 460

Asp Thr Asp Ser Glu Phe Asp Pro Gln Arg Lys Ile Glu Glu Asn Lys
465                 470                 475                 480

Glu Glu Thr Gly Val Lys Lys Ile Glu Leu Val Leu Asn Lys Arg Lys
                485                 490                 495

Gly Phe Val Lys Ile Ala Ile Glu Leu Gly Asn Val Ser Leu Val Pro
            500                 505                 510

Thr Phe Gly Phe Gly Glu Ala Asp Ile Tyr Arg Ile Thr Lys Pro Lys
        515                 520                 525

Pro Gly Ser Phe Gly Glu Met Phe Gln Ser Trp Met Lys Arg Thr Phe
    530                 535                 540

Gln Phe Thr Val Pro Phe Phe Ser Ala Arg Gly Val Phe Ile Tyr Asp
545                 550                 555                 560

Phe Gly Phe Leu Pro Tyr Arg Asn Pro Ile Asn Val Cys Phe Gly Arg
                565                 570                 575

Pro Ile His Ile Pro Ala Gly Leu Leu Asp Gln Tyr Lys Glu Pro Glu
            580                 585                 590

Thr Glu Lys Asp Glu Lys Glu Lys Glu Lys Asn Val Phe Gln Phe Thr
        595                 600                 605

Gln Asp Lys Gln Ala Pro Ala Phe Asn Ile Gln Ser Ile Gln Val Phe
    610                 615                 620

Gln Gly Glu Ala Thr Ile Lys Glu Glu Thr Ser
625                 630                 635
```

<210> SEQ ID NO 54
<211> LENGTH: 1908
<212> TYPE: DNA
<213> ORGANISM: Pichia guilliermondii

<400> SEQUENCE: 54

```
atgaccaagg aggttgatga aagcactggg ggtgccagtg atataccaaa tatggttgaa      60

gaagcgaaat catcgagttt tgaccgtgaa actgaagaga atctgctact ggagaccact     120

aaacctgacg agaatctggt accggagagt actaaacatg acgagaaact tgtaccggag     180

atcactaaac atgaagacaa tcccatggaa aatgaccaag tttcccaaaa cacagccacc     240

agtcctatga caggagctgg ttccgaagaa acccgtgatt tgattacaga gaacattgag     300
```

```
aaaccagatg agggtgatct gctaattgag cttatttcca aagataacga tggtgatgga    360

gatgatgggt tgaaaaatag aaaacaaaaa cgatcttctt ctgaagtgaa aaggctgcgc    420

atgtcgtctc tggctcctaa aggtccaact cctcaaaagc atgaacgtcc caagtatata    480

aatgtggcac ctcttaatat ccccattcga cggcgcttgg agatggtggg gataatctgg    540

cacaccattt gtattcccac gtttgtcagt ttgtttttct tgactttgtc gttgggtccg    600

tttgcttggg taggggtgat attgccgtac tttttatggt ggtatcttat cgatttacat    660

actcctacaa acggtaaggt tgcgtatcgg tctcgcgact ggatgaagaa tttcattgtg    720

tgggattggt tcgttgacta ttttcctatc agggtccaca agtcttgtga gttggagcct    780

acctttagcg atgttattat tgaagacgat gtggtgcccg atgatgaaga agaccttatc    840

tcagagcaat cacgaactgg agtcgataaa cttttcaaat ttttggggct tcgaaaacgc    900

ttaaatgacg actcggatgc ttcgtcgcag tgctcactgc tgcaagagtc tttaagcaca    960

agacgtaaag tgaaacgtat gtctactggt cctcgctaca tctttggata ccatccccat   1020

ggagtaattt cgatgggtgt ttttggaact ttcgctacca atgcgttgcg taacgagccg   1080

tacgaacctc ccttgcgttt gctaaagcca tttttccacg actcttccaa gggagaacgg   1140

ttgtttcccg gtattggcac cgtctttcca ttgacattga caacccaatt tattgtgccg   1200

tactaccgtg actatatctt gggcatggga ctcaccagtg cttcggctaa aaacatcaag   1260

agccttataa gcaacggaga caactcgata tgtgtcgttg ttggaggtgc tcaggaatcg   1320

ctcctaaacg atatggtagc cgcaaccaca gttcccggtc gttacggaaa gagcaatttg   1380

cccaatgaca gtgataccga tagcgagttt gatcctcagc gtaagattga agaaaacaag   1440

gaagaaaccg gcgtaaagaa aattgaactt gtacttaata agagaaaggg tttcgtcaag   1500

atagcgattg agttgggcaa cgtttcactc gtgcctacgt ttggttttgg agaagctgac   1560

atctacagaa tcaccaaacc caaaccaggt tcatttggag aaatgttcca atcttggatg   1620

aaacgcacat ttcaattcac ggttccattt ttcagcgcta gaggtgtgtt catttacgac   1680

tttgggtttc ttccttacag aaatcccatc aatgtctgct ttggacggcc cattcatatt   1740

ccagccggct tattggatca atacaaagag cccgaaactg agaaagatga aaaagaaaag   1800

gaaaaaaacg tcttccagtt cactcaagac aaacaagcgc cagccttcaa tatccaatct   1860

attcaagttt tccaagggga agcaaccatc aaagaggaaa cgagttag                1908
```

<210> SEQ ID NO 55
<211> LENGTH: 370
<212> TYPE: PRT
<213> ORGANISM: Microbotryum violaceum

<400> SEQUENCE: 55

```
Met Thr Ser Leu Arg Asp Val Asn Pro Thr Ser Thr Gln Ala Ser Leu
1               5                   10                  15

Tyr Lys Asp Glu Gly Lys Asp Lys Glu Asp Val Ala Pro Gln Glu Lys
            20                  25                  30

Tyr Thr Gln Ser Leu Arg Thr Asn Ile Lys Phe Ala Pro Leu Ala Val
        35                  40                  45

Pro Arg His Arg Arg Leu Gln Thr Met Ala Val Leu Gly Trp Thr Thr
    50                  55                  60

Ala Leu Pro Leu Met Leu Gly Leu Phe Phe Leu Leu Cys Ser Ile Pro
65                  70                  75                  80

Leu Leu Trp Pro Ile Ile Val Pro Tyr Leu Phe Trp Ile His Leu Ile
```

```
                85                  90                  95

Asp Asn Ser Pro Thr Gln Gly Gly Arg Ala Ser Lys Trp Leu Arg Gln
            100                 105                 110

Ser Arg Phe Trp Val Trp Phe Thr Gly Tyr Tyr Pro Ile Ser Leu Val
        115                 120                 125

Lys Thr Val Asp Leu Pro Pro Asp Arg Lys Tyr Val Phe Gly Tyr His
    130                 135                 140

Pro His Gly Ile Ile Gly Met Gly Ala Ile Ala Asn Phe Gly Thr Asp
145                 150                 155                 160

Ala Thr Gly Phe Ser Glu Leu Phe Pro Gly Leu Asn Pro His Leu Leu
                165                 170                 175

Thr Leu Ala Ser Asn Phe Lys Leu Pro Ile Tyr Arg Asp Phe Leu Leu
            180                 185                 190

Ala Leu Gly Ile Cys Ser Val Ser Met Lys Ser Cys Gln Asn Ile Leu
        195                 200                 205

Lys Gln Gly Pro Gly Ser Ala Leu Thr Ile Val Val Gly Gly Ala Ala
    210                 215                 220

Glu Ser Leu Ser Ala His Pro Gly Thr Ala Asn Leu Thr Leu Arg Arg
225                 230                 235                 240

Arg Met Gly Phe Ile Lys Leu Ala Met Arg Gln Gly Ala Asp Leu Val
                245                 250                 255

Pro Val Phe Ser Phe Gly Glu Asn Asp Ile Phe Glu Gln Met Pro Asn
            260                 265                 270

Glu Arg Gly Thr Lys Leu Tyr Lys Met Gln Lys Lys Phe Gln Thr Ala
        275                 280                 285

Phe Gly Phe Thr Leu Pro Ile Phe His Gly Arg Gly Ile Phe Asn Tyr
    290                 295                 300

Asn Leu Gly Ile Leu Pro Tyr Arg His Pro Ile Val Ser Val Val Gly
305                 310                 315                 320

Arg Pro Ile Arg Val Ser Gln Arg Asp Asn Pro Thr Lys Glu Glu Leu
                325                 330                 335

Glu Glu Val Gln Glu Arg Tyr Ile Glu Glu Leu Lys Arg Ile Trp Asp
            340                 345                 350

Asp Tyr Lys Asn Gln His Ala Ile Lys Arg Lys Gly Glu Leu Arg Ile
        355                 360                 365

Ile Ala
    370


<210> SEQ ID NO 56
<211> LENGTH: 1113
<212> TYPE: DNA
<213> ORGANISM: Microbotryum violaceum

<400> SEQUENCE: 56

atgacgtcgc tgcgagacgt gaacccgacc tcgacccaag catcgttgta caaagacgag      60

ggcaaggaca aggaggatgt cgcaccgcag gagaaataca cgcagtcgct ccggaccaac     120

atcaaatttg cacctctagc tgtaccacgc catcgacgac tgcagaccat ggcagtgttg     180

ggatggacga ccgcactgcc actcatgctt ggtttgttct ttctattgtg ctcaatcccc     240

cttctatggc ccatcatcgt gccctatctc ttctggatcc acctcatcga caactcgccg     300

acgcagggag gacgagcgag caaatggctt cgccaaagtc ggttctgggt gtggttcaca     360

gggtactatc ctatcagtct cgtcaagacg gtcgatttac ctccagatcg gaaatacgtc     420

ttcggttacc acccccatgg cataattgga atgggtgcaa ttgccaattt tgggaccgac     480
```

```
gccactgggt tctctgagct cttcccagga ctcaaccctc atctcctcac acttgccagc    540

aacttcaaat tgccgatata tcgagacttc ttgcttgcgc tcggcatctg ctcagtcagt    600

atgaaatctt gccaaaacat cctcaaacag ggcccggggt ctgctttgac cattgtcgtc    660

ggaggagctg cggaatccct ttcggcgcat cctggcacag ccaacttgac actccgtcgc    720

cgaatgggct tcatcaagct ggcgatgcgt caaggcgcgg atcttgtacc cgtcttttca    780

ttcggagaga acgatatctt cgaacagatg ccgaacgaga gagggacgaa gctgtacaag    840

atgcaaaaga agtttcagac cgcttttgga ttcactctac cgatcttcca cggccgagga    900

atttttaact ataaccttgg catcttgccg taccgtcatc cgatcgtgtc ggtcgtcggt    960

cggcccatcc gcgtttcgca gcgtgacaac cctactaagg aggaactcga ggaggtgcag   1020

gaacgataca tcgaggagtt gaagagaatc tgggacgatt acaaaaatca acatgccatc   1080

aagcgaaagg gcgaacttcg tattattgcc tga                                1113


<210> SEQ ID NO 57
<211> LENGTH: 365
<212> TYPE: PRT
<213> ORGANISM: Puccinia graminis

<400> SEQUENCE: 57

Met Lys Asp Asp Ser Arg Ser Pro Ser Gly Ser Glu Pro Glu Gly Asp
1               5                   10                  15

Asn His Lys Lys Glu Lys Arg Pro Ile Trp Ala Pro Ile Arg Val Pro
            20                  25                  30

Pro Tyr Arg Arg Ile Gln Thr Ala Ala Val Leu Leu Trp Thr Ser Gln
        35                  40                  45

Leu Ser Leu Cys Ile Ser Leu Phe Phe Phe Leu Met Ser Tyr Pro Ile
    50                  55                  60

Thr Trp Pro Ile Leu Leu Pro Tyr Val Ile Trp Ile Leu Val Ile Asp
65                  70                  75                  80

Pro Ala Pro Glu Lys Gly Gly Arg Leu Asn Gln Ser Val Arg Thr Trp
                85                  90                  95

Lys Phe Trp Asn Leu Phe Ala Ser Tyr Phe Pro Ile Ser Leu Ile Lys
            100                 105                 110

Thr Val Asp Leu Pro Ser Asp Arg Lys Tyr Val Phe Gly Tyr His Pro
        115                 120                 125

His Gly Ile Ile Gly Met Gly Ala Val Ala Asn Phe Gly Thr Glu Ala
    130                 135                 140

Thr Gly Phe Ser Glu Lys Phe Pro Gly Leu Asn Pro His Leu Leu Thr
145                 150                 155                 160

Leu Ser Thr Asn Phe Ile Ile Pro Phe Tyr Arg Asp Leu Ile Leu Ser
                165                 170                 175

Leu Gly Ile Cys Ser Val Ser Ile Lys Ser Cys Ile Ser Ile Leu Lys
            180                 185                 190

Ser Lys Asn Lys Arg Ser Ala Asp Val Lys Asn Asn Lys Gly Glu Gly
        195                 200                 205

Asn Cys Leu Val Ile Val Val Gly Gly Ala Ala Glu Ser Leu Ser Ala
    210                 215                 220

His Pro Gly Thr Ala Asp Leu Thr Leu Lys Arg Arg Leu Gly Phe Ile
225                 230                 235                 240

Lys Leu Ala Ile Arg Glu Gly Ala Asp Leu Val Pro Val Phe Ser Phe
                245                 250                 255
```

-continued

Gly Glu Asn Asp Ile Tyr Ala Gln Leu Ser Asn Ser Lys Gly Thr Ala
260 265 270

Leu Tyr Ser Leu Gln Lys Arg Phe Gln Ala Val Phe Gly Phe Thr Leu
275 280 285

Pro Val Phe His Gly Arg Gly Ile Phe Asn Tyr Ser Leu Gly Leu Leu
290 295 300

Pro Tyr Arg His Pro Ile Val Ser Val Val Gly Lys Pro Ile Arg Val
305 310 315 320

Glu Gln Asn Lys Asn Pro Gly Leu Glu Glu Ile Glu Lys Val Gln Lys
325 330 335

Glu Tyr Ile Ala Glu Leu Thr Ala Val Trp Asp Gln Tyr Lys Asp Leu
340 345 350

Tyr Ala Arg Asn Arg Lys Ser Glu Leu Thr Leu Ile Ala
355 360 365

<210> SEQ ID NO 58
<211> LENGTH: 1098
<212> TYPE: DNA
<213> ORGANISM: Puccinia graminis

<400> SEQUENCE: 58
atgaaggatg actccagaag cccgtctggg tccgaacccg agggcgataa tcacaagaag 60
gagaaaaggc caatctgggc tccgattcgt gtacctcctt acaggcgcat ccaaacggcc 120
gcagtactct tatggacttc tcaactctca ctatgcattt ccttattctt tttcttaatg 180
tcttacccga tcacctggcc gatcctcctt ccatacgtta tttggatctt ggtcatagat 240
cctgctcccg agaagggtgg ccggttgaat caatctgttc ggacctggaa gttttggaat 300
ctatttgcgt cgtatttccc aatcagttta atcaaaactg ttgatttgcc cagtgaccgc 360
aaatatgtct ttggttacca ccctcatggt atcatcggaa tgggcgcggt ggccaacttt 420
ggaacggaag cgacaggatt ttcggaaaaa ttccctggtc tcaatccaca tctactcaca 480
ttgagcacga actttatcat cccattctat cgagacctga tcctcagtct tggaatctgt 540
tcggtgtcga tcaaatcatg catctcgatc ctcaaatcca aaaacaaacg ctcagctgat 600
gtcaagaaca ataagggcga aggaaattgt ttggttatcg ttgtcggtgg ggctgcggaa 660
agtttgtctg ctcatcctgg aacagccgat ctcactctaa aacgacggct gggtttcatc 720
aaactggcca ttcgagaagg agccgatctc gtccctgtgt tctcctttgg agagaatgac 780
atttacgccc aattatcaaa ctcaaaaggc acggcactct actctcttca aaaacgattt 840
caagctgtat ttggctttac cttacctgtt ttccatggcc gaggtatctt caactactct 900
ctcggcttgc ttccctatcg acacccgatt gtttcagtag ttggtaaacc tattcgagtc 960
gagcaaaata aaaaccccgg gctcgaagaa atcgaaaagg ttcagaaaga atacattgct 1020
gaacttaccg cagtatggga tcagtataaa gatttatacg ctagaaatcg gaagagtgaa 1080
ttgactttga ttgcttag 1098

<210> SEQ ID NO 59
<211> LENGTH: 373
<212> TYPE: PRT
<213> ORGANISM: Gloeophyllum trabeum

<400> SEQUENCE: 59

Met Asp Ala Gly Arg Ala Phe Ser Ser Ala Ser Arg Ser Leu Ser Ser
1 5 10 15

Ser Ser Leu Lys Asp Lys Leu Ser Lys Val Ser Lys Leu Ser Thr Thr

```
            20                  25                  30

Pro Leu Arg Pro Val Ala Ala His Val Lys Asn Ile Asp Phe Val Pro
        35                  40                  45

Ser Lys Ile Pro Arg Lys Arg Arg Leu Gln Met Leu Ala Val Ala Val
    50                  55                  60

Trp Ala Leu Leu Ile Pro Ile Thr Thr Phe Leu Phe Leu Ile Leu Cys
65                  70                  75                  80

Ser Phe Pro Pro Leu Trp Pro Phe Leu Ala Ala Tyr Leu Ile Trp Ile
                85                  90                  95

Arg Trp Ile Asp Arg Ser Pro Glu His Gly Gly Arg Ile Ser Pro Trp
            100                 105                 110

Phe Arg Ser Met Arg Phe Trp Arg Tyr Phe Ala Asp Tyr Tyr Pro Ala
        115                 120                 125

Ser Phe Leu Lys Glu Cys Asp Leu Pro Pro Asp Arg Pro Tyr Val Phe
    130                 135                 140

Gly Tyr His Pro His Gly Ile Ile Gly Met Gly Ala Met Ala Thr Phe
145                 150                 155                 160

Ala Thr Glu Ala Thr Gly Phe Ser Glu Gln Phe Pro Gly Leu Thr Pro
                165                 170                 175

His Leu Leu Thr Leu Ala Thr Asn Phe Thr Met Pro Ile Tyr Arg Asp
            180                 185                 190

Ile Ile Leu Ala Leu Gly Ile Cys Ser Val Ser Lys Gln Ser Cys Ser
        195                 200                 205

Asn Ile Leu Ser Ser Gly Pro Gly Gln Ala Ile Thr Ile Val Val Gly
    210                 215                 220

Gly Ala Ala Glu Ser Leu Ser Ala Arg Pro Gly Thr Ala Asp Leu Thr
225                 230                 235                 240

Leu Lys Arg Arg Leu Gly Phe Ile Lys Ile Ala Ile Gln His Gly Ala
                245                 250                 255

Ala Leu Val Pro Val Phe Ser Phe Gly Glu Asn Asp Ile Tyr Gln Gln
            260                 265                 270

Met Pro Asn Glu Lys Gly Thr Thr Ile Tyr Ala Leu Gln Lys Lys Phe
        275                 280                 285

Gln Ser Val Phe Gly Phe Thr Leu Pro Leu Phe His Gly Arg Gly Met
    290                 295                 300

Leu Asn Tyr Asn Leu Gly Leu Met Pro Tyr Arg Arg Arg Ile Val Ser
305                 310                 315                 320

Val Ile Gly Arg Pro Ile Leu Cys Glu Lys Cys Glu Lys Pro Ser Met
                325                 330                 335

Glu Glu Val Thr Arg Val Gln Gln Glu Tyr Ile Ala Glu Leu Leu Arg
            340                 345                 350

Ile Trp Asp Thr Tyr Lys Asp Gln Phe Ala Arg Ser Arg Lys Arg Glu
        355                 360                 365

Leu Ser Ile Ile Asp
    370
```

<210> SEQ ID NO 60
<211> LENGTH: 1122
<212> TYPE: DNA
<213> ORGANISM: Gloeophyllum trabeum

<400> SEQUENCE: 60

```
atggacgctg gtcgcgcctt ctcctctgca tcccgctcgt tatcgtcctc gtccctgaag      60

gacaagctgt caaaggtctc gaagctcagc accactcctc tgcgaccggt cgctgcccat     120
```

```
gtcaagaata tcgacttcgt cccgtccaag atcccccgga aacggaggct gcagatgctc    180

gctgttgcag tatgggcgct cctgataccc atcacgacgt ttttgttcct catactatgt    240

tcttttccac cgctgtggcc atttttagcg gcgtatctta tatggataag atggatagac    300

cggagtcctg agcatggcgg gaggataagt ccgtggttcc gctcgatgag gttctggaga    360

tactttgccg actactaccc tgcatcgttc ttgaaggaat gcgacctccc cccagaccga    420

ccttacgtct tcgggtatca ccctcatggc atcattggca tgggtgccat ggccactttc    480

gccaccgaag ccactggatt cagcgaacag ttccctgggc tcactcccca cctgctcacc    540

ctagccacaa atttcaccat gcccatatac agagacatca tcctcgccct gggcatatgc    600

tccgtcagca agcagtcctg ctcgaacatc ctcagcagcg gccccgggca ggctatcaca    660

atcgtagtag gaggcgcagc agagagtctt agcgctcggc cgggcacggc cgacctcacg    720

ctcaaacgga ggcttggctt catcaagatt gctatacaac acggagcggc actggtccct    780

gtattttctt tcggcgagaa tgatatttat caacaaatgc ccaacgaaaa gggaaccaca    840

atatatgccc tacagaagaa attccagagc gtcttcggct tcacgttgcc cttgttccac    900

ggtcggggca tgctaaatta taaccttggt ttgatgccgt atcgacggcg gatcgtgtct    960

gtcatcggtc ggcccatatt atgcgagaag tgcgagaagc caagcatgga ggaggttacg   1020

cgggtgcaac aggagtacat cgcagagctg ctcagaatat gggacacgta caaagatcaa   1080

tttgctcggt cgcggaagag agaactgagt attattgatt ga                      1122
```

```
<210> SEQ ID NO 61
<211> LENGTH: 346
<212> TYPE: PRT
<213> ORGANISM: Rhodosporidium diobovatum

<400> SEQUENCE: 61

Met Gly Ala Leu Asp Ala Gly Asp His Glu Gly Thr Glu His Pro Lys
1               5                   10                  15

Ile Lys Phe Val Pro Phe Val Val Pro Arg His Arg Arg Leu Gln Thr
            20                  25                  30

Phe Ser Val Phe Leu Trp Thr Thr Ala Leu Pro Leu Ser Leu Gly Ile
        35                  40                  45

Phe Cys Ile Leu Cys Ser Phe Pro Pro Leu Trp Pro Leu Val Ile Gly
    50                  55                  60

Tyr Leu Thr Trp Val Phe Leu Ile Asp Gln Ala Pro Met Arg Gly Gly
65                  70                  75                  80

Arg Pro Gln Ala Trp Leu Arg Lys Ser Arg Val Trp Glu Trp Phe Ala
                85                  90                  95

Gly Tyr Tyr Pro Val Ser Leu Ile Lys Ser Ala Asp Leu Pro Pro Asp
            100                 105                 110

Gln Arg Tyr Val Phe Gly Tyr His Pro His Gly Val Ile Gly Met Gly
        115                 120                 125

Ala Ile Ala Asn Phe Gly Thr Asp Ala Thr Gly Phe Ser Arg Leu Phe
    130                 135                 140

Pro Gly Ile Lys Pro His Leu Leu Thr Leu Ala Ser Asn Phe Lys Leu
145                 150                 155                 160

Pro Leu Tyr Arg Glu Leu Leu Leu Ala Leu Gly Ile Ser Ser Val Ser
                165                 170                 175

Met Lys Ser Cys Gln Asn Ile Leu Arg Gln Gly Pro Gly Ser Ser Ile
            180                 185                 190
```

```
Thr Ile Val Val Gly Gly Ala Ala Glu Ser Leu Ser Ala His Pro Gly
        195                 200                 205

Thr Ala Asp Leu Thr Leu Lys Arg Arg Lys Gly Phe Ile Lys Leu Ala
    210                 215                 220

Ile Arg Ser Gly Ala Tyr Leu Val Pro Val Phe Ser Phe Gly Glu Asn
225                 230                 235                 240

Asp Ile Phe Asn Gln Leu Ser Asn Glu Arg Gly Thr Arg Leu Tyr Lys
                245                 250                 255

Leu Gln Lys Arg Phe Gln Ala Val Phe Gly Phe Thr Leu Pro Ile Phe
            260                 265                 270

Phe Gly Arg Gly Leu Phe Asn Tyr Asn Met Gly Leu Met Pro Tyr Arg
        275                 280                 285

His Pro Ile Val Ser Val Val Gly Arg Pro Ile Lys Val Thr Gln Lys
    290                 295                 300

Asp His Pro Ser Thr Ala Asp Leu Glu Glu Val Gln Asp Arg Tyr Ile
305                 310                 315                 320

Ala Glu Leu Lys Arg Ile Trp Glu Asp Tyr Lys Glu Val Tyr Ala Lys
                325                 330                 335

Ser Arg Thr Lys Glu Leu Thr Ile Ile Ala
            340                 345
```

<210> SEQ ID NO 62
<211> LENGTH: 1041
<212> TYPE: DNA
<213> ORGANISM: Rhodosporidium diobovatum

<400> SEQUENCE: 62

```
atgggagcac tagatgcggg cgaccacgag gggaccgaac accccaagat caagttcgtt     60

cctttcgttg tgccgcgaca ccgcaggctg cagacctttt cggtgtttct gtggacgacc    120

gcgctgcctc tgtcgctcgg catcttctgc attctctgct ccttcccccc actctggccc    180

ctcgtcatag ggtatctcac gtgggtattc ctcatcgacc aggcgcccat gcggggtggc    240

aggcctcagg cctggttgcg caagtcgcgt gtgtgggagt ggttcgccgg ctactaccct    300

gtcagcttga tcaagagcgc cgacctcccg cccgaccagc gctacgtctt tggctaccac    360

ccacacggcg tcattgggat gggcgccatc gccaactttg gtaccgacgc gaccggcttc    420

tcgcggctgt tccccggcat caagccgcac ctcctcacgc tcgccagcaa cttcaagctg    480

ccgctctacc gagaactgct cctcgccttg ggcatttcgt ccgtgtcgat gaagagctgc    540

cagaacatcc tgcgccaagg tcccggctcg tcgatcacga ttgtcgtcgg aggggcagca    600

gaaagcctca gcgcgcaccc gggaacggca gacctgacgc tcaagcggcg gaaggggttc    660

atcaagctcg cgatccgctc aggggcctac ctcgtcccgg tattttcctt tggcgagaat    720

gacatcttca accagctgtc gaatgagcgc ggcacccgac tctacaagct gcaaaagcgg    780

ttccaggccg tctttggctt caccttgccc atcttcttcg gtcgcggcct cttcaactac    840

aacatgggct tgatgccata tcgacacccg atcgtctcgg tcgtcggacg ccccatcaag    900

gtcacgcaga aggatcaccc gtcgacggcc gacctcgaag aggtacagga ccgctacatt    960

gccgagttga agaggatctg ggaggactac aaagaggtgt acgccaagag ccgcaccaag   1020

gagctcacca tcatcgcatg a                                             1041
```

<210> SEQ ID NO 63
<211> LENGTH: 359
<212> TYPE: PRT
<213> ORGANISM: Phaeodactylum tricornutum

<400> SEQUENCE: 63

```
Met Lys Glu Arg Arg Ser Gly Leu Asn Pro Ser Gly Ser Ser Val Tyr
1               5                   10                  15

Pro Leu His Pro Pro Asp Ser Arg Val Leu Val Arg Val Pro Ser Asp
            20                  25                  30

Ile Ser Phe Leu Asp Arg Leu Ile Val Ala Gly Ser Ser Ile Phe Ile
        35                  40                  45

Val Gly Ser Leu Val Trp Val Pro Leu Thr Ala Arg Trp Val Tyr Arg
    50                  55                  60

Arg Trp Lys Gln Ala Lys Asp Lys Arg Lys Arg Ala Met Tyr Ala Ser
65                  70                  75                  80

Leu Leu Val Ile Leu Ala Val Leu Val Ile Gly Gly Pro His Arg Ser
                85                  90                  95

Pro Arg Val Gly Lys Trp Leu Gln Val Arg Lys Trp Ser Leu Phe Gln
            100                 105                 110

Ala Trp Val Lys Phe Ile Ala Met Glu Val Ile Leu Asp Gln Pro Lys
        115                 120                 125

Gly Ile Thr Met Asp Val Gln Gln Asp Lys Ala Ile Phe Ala Phe Ala
    130                 135                 140

Pro His Gly Ile Phe Pro Phe Ala Phe Ala Phe Gly Val Leu Pro Asp
145                 150                 155                 160

Ile Ala Thr Gln Ser Phe Gly Tyr Val Arg Pro Val Val Ala Thr Ala
                165                 170                 175

Thr Arg Leu Phe Pro Val Val Arg Asp Phe Ile Ser Trp Ala Asn Pro
            180                 185                 190

Val Asp Ala Ser Lys Asp Ser Val Glu Arg Ala Leu Ala Leu Gly Asp
        195                 200                 205

Arg Ile Ala Val Ile Pro Gly Gly Ile Ala Glu Ile Phe Glu Gly Tyr
    210                 215                 220

Pro Lys Pro Asn Thr His Pro Asp Glu Glu Tyr Ala Ile Val Arg Ser
225                 230                 235                 240

Gly Phe Leu Arg Leu Ala Ile Lys His Gly Ile Pro Val Ile Pro Val
                245                 250                 255

Tyr Cys Phe Gly Ala Thr Lys Met Leu Lys Arg Leu Glu Leu Pro Gly
            260                 265                 270

Leu Glu Gln Leu Ser Leu Phe Leu Arg Val Ser Ile Cys Leu Phe Phe
        275                 280                 285

Gly Val Gly Gly Leu Pro Ile Pro Phe Arg Gln Arg Leu Ser Tyr Val
    290                 295                 300

Met Gly Gln Pro Ile Leu Pro Pro Val Arg Thr Thr Gly Ser Asp Ile
305                 310                 315                 320

Ser Asp Ala His Val Lys Glu Met Gln Asp Arg Phe Cys Ala Glu Val
                325                 330                 335

Gln Arg Leu Phe Asp Arg His Lys Glu Ala Tyr Gly Trp Ser Tyr Lys
            340                 345                 350

Thr Leu Lys Leu Leu Glu Gln
        355
```

<210> SEQ ID NO 64
<211> LENGTH: 1080
<212> TYPE: DNA
<213> ORGANISM: Phaeodactylum tricornutum

<400> SEQUENCE: 64

```
atgaaagaaa gaagatctgg cctaaatccg tcaggatcct ccgtgtatcc attgcaccct     60

cctgacagtc gcgttctcgt tcgagtcccc tccgatattt cctttcttga tcgtctcatc    120

gtcgctggca gcagtatctt tattgtcggt tcgctagtat gggttccatt gaccgcaaga    180

tgggtctaca ggcggtggaa gcaagctaaa gataaacgaa agcgggctat gtatgcctct    240

ctactcgtga ttctggcagt tctcgttatt ggcggacccc accgatctcc tcgtgtcggc    300

aaatggctcc aagtacgaaa gtggtccctc ttccaagcgt gggtaaagtt tattgccatg    360

gaagtgattt tggatcaacc gaaaggcatt actatggacg tccaacaaga caaggcgatt    420

tttgcattcg cgccacatgg aatctttccg tttgcgttcg cctttggagt gcttcccgat    480

attgccacac aatcgtttgg ctacgttcgt ccggtcgtgg caaccgccac aaggttgttt    540

cctgtagtcc gggatttcat ctcttgggcg aatccggtag acgcttccaa agattccgtt    600

gaacgtgctt tagcattggg cgatcgcatt gctgtaatac ctggaggaat tgcagaaatt    660

ttcgaaggat atccgaaacc gaacacgcat ccggatgaag agtacgctat cgtacggagt    720

ggatttttgc gtttggcaat aaaacacggt atcccagtga ttcccgtata ctgtttcggc    780

gctaccaaaa tgttgaagcg tctggagctt cccggcctgg agcaactgtc cctgtttcta    840

cgcgtgagca tttgcctctt ttttggagtc ggcgggttgc ccatcccttt ccgacaacga    900

ttgtcgtacg taatgggaca accaattttg ccacccgtaa ggacaacggg cagcgatatt    960

tcggacgcac acgtcaaaga aatgcaagat cgcttttgtg ctgaggtcca gcggctcttt   1020

gatcgacata aggaagctta tggttggtca tacaaaaacgc tgaaactatt ggaacagtga  1080
```

<210> SEQ ID NO 65
<211> LENGTH: 329
<212> TYPE: PRT
<213> ORGANISM: Phaeodactylum tricornutum

<400> SEQUENCE: 65

```
Met Glu Arg Thr Lys Ile Gln Asp Glu His Lys Ser Pro Pro Asn Pro
1               5                   10                  15

Ser Thr Phe Arg Trp Phe Leu Gly Leu Leu Val Ala Ser Thr Phe Ser
            20                  25                  30

Met Val Tyr Phe Val Ala Pro Phe Tyr Met Leu Thr Val Val Phe Ala
        35                  40                  45

Leu Val Phe Lys Tyr Pro Ser Val Glu Ile Ala Trp Met Tyr Ala Ile
    50                  55                  60

Pro Met Ile Val Ser Ala Ile Leu Pro Pro Met Ala Ser Pro Leu Ala
65                  70                  75                  80

Leu Arg Leu Ile Ser Pro Leu Ile Asp Tyr Phe Asp Tyr Glu Glu Ile
                85                  90                  95

His Glu Thr Ser Pro Val Asp Val Gln Lys Glu Ile Leu Ser Asn Asn
            100                 105                 110

Lys Asn Tyr Leu Leu Val Phe Gln Pro His Gly Ala Leu Ser Phe Thr
        115                 120                 125

Gly Ile Thr Ser Met Val Thr Ala Pro Gln Ala Met Lys Gly Lys Leu
    130                 135                 140

Pro Thr Ala Val Ala Asp Ala Leu Leu Tyr Thr Pro Ile Leu Lys His
145                 150                 155                 160

Val Leu Gly Ile Phe Gly Leu Ile Ser Ala Ser Lys Ser Ser Met Ile
                165                 170                 175

Arg Thr Leu Lys Lys Lys Gly Val Glu Gly Thr Ile Val Leu Tyr Val
```

```
            180                 185                 190

Gly Gly Ile Ala Glu Leu Phe Leu Thr Asp Glu Thr Asp Glu Arg Leu
        195                 200                 205

Tyr Leu Arg Lys Arg Lys Gly Phe Ile Lys Leu Ala Leu Gln Gln Gly
    210                 215                 220

Val Asp Val Val Pro Val Tyr Leu Phe Gly Asn Thr Asn Ala Leu Ser
225                 230                 235                 240

Val Leu Lys Thr Gly Phe Leu Ala Ala Ile Ser Arg Lys Leu Gln Ile
                245                 250                 255

Ser Leu Thr Tyr Ile Trp Gly Lys Trp Tyr Leu Pro Ile Pro Arg Asp
            260                 265                 270

Cys Lys Leu Leu Tyr Ala Ser Gly Gln Pro Leu Gly Met Pro His Ile
        275                 280                 285

Leu Asp Pro Ser Gln Ala Asp Ile Asp Lys Trp His Glu Lys Tyr Cys
    290                 295                 300

Ser Glu Val Met Arg Ile Phe Glu Lys Tyr Lys Glu Lys Val Pro Glu
305                 310                 315                 320

Tyr Lys His Lys Lys Leu Glu Ile Ile
                325
```

<210> SEQ ID NO 66
<211> LENGTH: 990
<212> TYPE: DNA
<213> ORGANISM: Phaeodactylum tricornutum

<400> SEQUENCE: 66

```
atggagagaa caaagataca agacgagcac aaaagtcccc ctaatccgtc gacatttcga      60

tggttcctcg gccttctagt ggcgtcgacg ttttccatgg tctattttgt ggctcccttt     120

tacatgctta cagtcgtgtt tgcactagtt ttcaaatatc cttcggtaga aattgcatgg     180

atgtacgcta ttccgatgat tgtctcggcc attttgccac caatggcttc tccactggcc     240

ttgcgactca tctccccgct cattgactac ttcgattacg aagagatcca cgaaacctca     300

ccggtggacg tccagaagga aatactaagc aacaacaaaa actatttgct agtctttcaa     360

ccgcatggag cactgtcgtt tacaggaatc acttcaatgg tgacagctcc acaagcaatg     420

aaaggcaaat tgccaacagc tgtggctgac gcactcttgt acacacctat actgaaacat     480

gtcttaggaa ttttcgggct gattagtgcc tccaaaagca gcatgatccg aactttaaaa     540

aagaagggtg tggaaggaac cattgttttg tacgttggtg ggattgccga gctcttttg      600

accgacgaga cggacgagcg cctctatctg cgaaagcgaa aagggtttat caaattagct     660

ctacaacagg gtgtcgatgt tgtacctgtg tatctatttg ggaacacaaa cgcgctgtcg     720

gtactaaaga cgggatttct cgcggcaatt tcgcgaaaat tacagatatc tctgacgtac     780

atttggggaa agtggtatct tccgattccc cgtgattgca aattgctgta tgcttccggt     840

cagccattag gaatgcctca tattttagac ccaagccaag ccgacattga taaatggcac     900

gaaaagtact gctccgaggt catgcggatc ttcgaaaaat acaaggaaaa ggttccggaa     960

tacaagcaca agaaattaga aattatttga                                      990
```

<210> SEQ ID NO 67
<211> LENGTH: 392
<212> TYPE: PRT
<213> ORGANISM: Phaeodactylum tricornutum

<400> SEQUENCE: 67

```
Met Arg Glu Arg Ser Cys Ala Asn Ala Ser Asp Asp Asp Ser Ile His
1               5                   10                  15

Lys Gln Ser Pro Glu Leu Glu Ala Glu Phe Leu His Thr Ser Lys Leu
            20                  25                  30

Thr Leu Ala Asp Met Arg Arg Leu Ala His Asp Pro Lys Asp Arg Gly
        35                  40                  45

Leu Ala Thr Lys Pro Ala Ala Gln Ala Thr Lys Glu Asp Val Leu Thr
    50                  55                  60

Val Gln Pro Met Ser Phe Val Glu His Thr Ala Cys Cys Leu Phe Leu
65                  70                  75                  80

Ala Phe Gly Val Pro Asn Gly Ala Leu Thr Ile Pro Ile Ala Thr Trp
                85                  90                  95

Leu Ile Gly Lys Phe Val Leu Arg Asn Val Phe Leu Ala Phe Leu Leu
            100                 105                 110

Ala Gly Cys Ile Leu Leu Pro Leu Ala Ile Leu Pro Gln Glu Tyr Val
        115                 120                 125

Pro Ala Arg Leu Gln Ser Trp Leu Ala Leu Gln Ile Leu Lys Tyr Phe
    130                 135                 140

Ser Phe Ser Leu Val Met Glu Glu Arg Pro Pro Thr Met Cys Thr Gly
145                 150                 155                 160

Lys Gln Leu Ile Glu Gln Pro Ala Arg Pro Arg Ile Val Thr Ala Tyr
                165                 170                 175

Pro His Gly Val Phe Pro Tyr Gly Asn Ala Leu Thr Val Val Thr Trp
            180                 185                 190

Pro Leu Leu Thr Gly His His Ile Val Gly Leu Ala Ala Asn Ala Ala
        195                 200                 205

Leu Arg Thr Pro Ile Phe Lys Gln Ile Leu Arg Ser Ile Gly Val Lys
    210                 215                 220

Asp Ala Ser Arg Ala Ser Val Arg Asn Ala Leu Glu Thr Trp Pro Phe
225                 230                 235                 240

Thr Val Gly Ile Ser Pro Gly Gly Val Ala Glu Val Phe Glu Thr Asn
                245                 250                 255

His Phe Asn Glu His Ile Leu Leu Lys Glu Arg Ile Gly Val Ile Lys
            260                 265                 270

Met Ala Ile Arg Thr Gly Ala Asp Leu Val Pro Gly Tyr Met Tyr Gly
        275                 280                 285

Asn Thr Asn Leu Tyr Trp Cys Trp Thr Gly Glu Gly Ile Pro Gly Ala
    290                 295                 300

Arg Trp Leu Leu Glu Tyr Val Ser Arg Lys Ile Leu Gly Phe Ala Leu
305                 310                 315                 320

Val Pro Ile Ala Gly Arg Trp Arg Leu Pro Ile Pro Tyr Arg Thr Pro
                325                 330                 335

Ile Leu Cys Val Val Gly Lys Pro Ile Pro Thr Ile His Leu Gln Thr
            340                 345                 350

Glu Glu Pro Ser Met Glu Gln Ile Val Asp Ile Gln Glu Gln Leu Ser
        355                 360                 365

Thr Glu Leu Lys Ser Met Phe Asp Arg Tyr Lys His Leu Tyr Gly Trp
    370                 375                 380

Glu Asp Arg Met Leu Val Ile Thr
385                 390
```

<210> SEQ ID NO 68
<211> LENGTH: 1179
<212> TYPE: DNA

<213> ORGANISM: Phaeodactylum tricornutum

<400> SEQUENCE: 68

```
atgcgtgagc gaagctgcgc caacgcttct gacgatgaca gcattcacaa gcagtcgcca      60
gaattggagg ctgagtttct tcataccagc aagttgacct tagccgacat gcgacgattg     120
gcgcacgatc cgaaggatcg ggggttggca acaaaacctg cggcgcaagc tacgaaagaa     180
gacgtcttga cggtacaacc catgagtttc gtagaacaca ctgcttgctg tctgtttctc     240
gcgtttggag tgcccaatgg cgctctgacg attcccatag caacgtggct gatcggaaaa     300
ttcgtgttgc gcaacgtttt cttggcgttt ctgttagcag gctgtatact tctaccgctt     360
gcgatactgc cgcaagaata tgtgcccgcc cgattgcaat cgtggcttgc tttgcagata     420
ctgaaatatt tttctttctc tttggtcatg gaggaacgcc ctccgacaat gtgtactggc     480
aagcagctga tcgagcagcc cgctcggcca cgaatcgtca cagcctatcc gcacggagtt     540
ttcccatacg gaaacgcgtt gactgtagtc acatggccgt tgttgacggg acaccatatt     600
gtgggtttgg cagcaaatgc cgctttgcgg acaccgatct ttaaacaaat cttgcggagc     660
attggcgtca aggacgcctc tcgagcgtcg gtacggaatg cgctggaaac atggcctttc     720
accgtcggga tttcgccagg tggcgtggcg gaagtttttg aaacaaacca cttcaatgag     780
cacattctgt tgaaagaacg tattggtgtc atcaagatgg ccattcgcac cggtgcggat     840
cttgtaccag gctatatgta tggtaatact aatctgtact ggtgctggac aggggaaggt     900
attcctggag ctcggtggct attggagtat gtttcgcgta aaatcctagg ttttgccctc     960
gtgcctatag cgggtagatg gagactacca ataccgtaca ggactccgat attgtgtgtc    1020
gtgggcaagc caataccaac cattcatttg caaaccgaag aaccatcaat ggagcaaatc    1080
gtggacattc aggaacaatt gtcaacagaa ttgaaatcaa tgttcgaccg ctataagcac    1140
ctgtacggat gggaagatcg aatgctagtg atcacataa                           1179
```

<210> SEQ ID NO 69
<211> LENGTH: 320
<212> TYPE: PRT
<213> ORGANISM: Phaeodactylum tricornutum

<400> SEQUENCE: 69

```
Met Thr Arg Ser Lys Phe Ile Gly Ser Ala Gly Ala Ile Gly Leu Phe
1               5                   10                  15

Cys Leu Met Ile Ile Pro Asn Val Gly Ile Leu Ile Ala Thr Phe Leu
            20                  25                  30

Tyr Pro Lys Val Leu Gly Leu Tyr Phe Leu Ile Pro Tyr Tyr Ala Tyr
        35                  40                  45

Asn Leu Ser Ile Gly Lys His Glu Ala Arg Asp Gly Asn Gly Trp Asn
    50                  55                  60

Trp Phe Ser Glu Asn Phe Phe Val Phe Asn Ile Val Arg Gly Tyr Leu
65                  70                  75                  80

Asn Leu Lys Ile Glu Ala Asp Ser Glu Leu Lys Glu Ala Glu Ala Lys
                85                  90                  95

Glu Gly Ala Gln Phe Val Phe Ala Val Ser Pro His Gly Thr Asn Ala
            100                 105                 110

Asp Tyr Arg Val Phe Ile Asp Gly Met Leu His Glu Ala Leu Pro Gln
        115                 120                 125

Thr Ala Ser Lys Ile Arg Thr Leu Ala Ala Thr Val Leu Phe His Ile
    130                 135                 140
```

-continued

```
Pro Leu Val Arg Glu Ile Ala Leu Trp Thr Gly Cys Val Asp Ala Ser
145                 150                 155                 160

Arg Ala Val Ala Val Glu Arg Leu Lys Glu Glu Gly Gly Ser Leu Leu
                165                 170                 175

Val Ile Pro Gly Gly Gln Ala Glu Gln Met Tyr Thr Gln Tyr Gly Arg
            180                 185                 190

Glu Arg Val Tyr Leu Lys Arg Arg Lys Gly Phe Leu Lys Leu Cys Leu
        195                 200                 205

Lys Tyr Glu Ile Pro Val Val Pro Ala Tyr Val Phe Gly Val Ser Asp
    210                 215                 220

Tyr Tyr Phe Thr Ser Ala Lys Leu Phe Gly Leu Arg Met Trp Leu Val
225                 230                 235                 240

Gln Asn Leu Gly Ile Ala Leu Pro Leu Cys Trp Gly Arg Tyr Gly Leu
                245                 250                 255

Pro Ile Cys Pro Arg Pro Val Asp Thr Thr Leu Val Phe Asp Lys Pro
            260                 265                 270

Leu Tyr Leu Ser Cys Gln Asn Pro Ser Asn Pro Ser Glu Asp Glu Val
        275                 280                 285

Asp Lys Ala His Leu Gln Phe Cys Gln Ala Leu Glu Lys Leu Phe Asp
    290                 295                 300

Thr His Lys Glu Arg Leu Gly Tyr Gly Asp Arg Lys Leu Glu Ile Ile
305                 310                 315                 320
```

<210> SEQ ID NO 70
<211> LENGTH: 963
<212> TYPE: DNA
<213> ORGANISM: Phaeodactylum tricornutum

<400> SEQUENCE: 70

```
atgaccagat cgaagtttat aggaagtgct ggagctattg gcttattttg tttgatgatc      60

ataccgaatg tgggaattct gatcgcaaca tttctttatc ccaaagtact tgggctctac     120

tttctgattc cgtactacgc atacaacttg tccattggca aacacgaagc tcgagacggc     180

aacggctgga attggttcag cgagaatttc tttgtcttta acattgtgag ggatatcta      240

aatcttaaga ttgaagctga ctccgagctc aaggaagccg aagcgaaaga aggcgcccaa     300

tttgtgttcg ccgttagccc tcacggaacg aacgcagact atcgagtttt tattgacggt     360

atgctacatg aggcactccc acagactgca agcaagatca gaacactagc ggcgacagta     420

ctgttccaca ttcccttggt tcgtgaaatc gcactttgga caggatgtgt cgatgccagc     480

cgcgcagttg ctgtcgagag attaaaagaa gaaggtggtt cactgcttgt gattcccggt     540

ggccaagcag aacaaatgta cacccaatat ggacgtgaaa gagtatatct gaaacggcgc     600

aaaggatttt tgaagctttg cttgaagtac gagattccgg tcgtcccagc ttatgttttt     660

ggcgtatctg actattactt cacgtccgca aagctctttg gtctgcgaat gtggctcgtt     720

cagaatcttg gcattgctct tccactgtgc tggggaagat atggtctacc aatctgtcct     780

agaccagtcg ataccaccct tgtctttgac aaacctttat acctatcctg ccagaatccg     840

tcgaatccct cggaagacga ggttgacaag gctcatctgc aattttgcca agccctcgag     900

aagctgtttg atacacacaa agagaggctt gggtacggcg atcgaaagct ggaaataatt     960

tag                                                                   963
```

<210> SEQ ID NO 71
<211> LENGTH: 663
<212> TYPE: PRT

<213> ORGANISM: Rhodotorula graminis

<400> SEQUENCE: 71

```
Met Ser Thr Ala Asp Leu Pro Pro Gly Pro Ala Gln Leu Leu Glu Asp
1               5                   10                  15

Ala Leu Arg Gln Pro Asp Gly Pro Pro Leu Leu Ser Thr Ser Ala Ala
            20                  25                  30

Asp Pro Ser Ser Pro Leu Gln Leu Asp His Asp His Arg Pro Gly Met
        35                  40                  45

Ala Ala Asp Ala Ala Ser Ser Ala Ser Asp Ser Ser Ile Ser Thr Val
    50                  55                  60

Ser Ser Val Leu Arg Gly Gln Gln Ala Thr Thr Thr Val Thr Thr Asn
65                  70                  75                  80

Arg Gly Glu Gly Gly Arg Glu Thr Thr Glu Thr Phe Thr His Val Gly
                85                  90                  95

Ala Ala Asn Val Asp Ala Glu Tyr Ser Ser Ser Thr Gly His Ile Thr
            100                 105                 110

Leu Arg Pro Val Val Ala Lys Gly Gly Asp Pro Arg Arg Ile Arg Leu
        115                 120                 125

Val Arg Ser Arg Arg Thr His Phe Glu Pro Arg Ile Ser His Phe Asp
    130                 135                 140

Arg His Asn Lys Thr Ser Ala Glu Asp Thr Phe Arg Gly Phe Phe Ser
145                 150                 155                 160

Leu Phe Trp Ile Val Ile Ala Val Gly Gly Thr Arg Thr Ile Tyr Asn
                165                 170                 175

Arg Val Ala Glu Thr Gly Gly Leu Leu Gly Gly Trp Gln Phe Ala Ala
            180                 185                 190

Leu Ile Ser Glu Asp Ala Trp Ala Leu Ala Leu Ser Asp Ala Val Leu
        195                 200                 205

Val Gly Ser Thr Ile Leu Cys Val Pro Phe Val Lys Leu Ile Val Asn
    210                 215                 220

Gly Trp Val Arg Tyr Tyr Tyr Thr Gly Leu Val Leu Gln His Leu Ala
225                 230                 235                 240

Gln Thr Leu Tyr Leu Gly Ile Ala Val Arg Trp Thr Phe His Arg His
                245                 250                 255

Trp Pro Trp Val Gln Ser Gly Phe Met Thr Leu His Ala Leu Ser Met
            260                 265                 270

Leu Met Lys Ile His Ser Tyr Cys Ser Leu Asn Gly Glu Leu Ser Glu
        275                 280                 285

Arg Val Arg Gln Leu Glu Lys Asp Glu Arg Lys Leu His Glu Ala Val
    290                 295                 300

Glu Glu Leu Gly Gly Gln Asp Ala Leu Glu Arg Glu Gly Arg Val Ala
305                 310                 315                 320

Trp Glu Lys Ala Cys Ala Glu Ala Ala Glu Gln Lys Ala Ala Glu Glu
                325                 330                 335

Ala Ala Gly Gly Arg Gly Lys Ala Ser Ala Ser Ser Leu Ala Pro Pro
            340                 345                 350

Pro Ala Thr Gly Pro Gln Pro Ser Ser Asp Glu Glu Ala Val Ser Thr
        355                 360                 365

Thr Leu Arg Gln Arg Pro Ser Ala Ala Arg Arg Arg Ser Leu Ser Pro
    370                 375                 380

Ser Ala Ala Arg Thr His Val Thr Pro Pro Ser Arg Lys Ala Glu Pro
385                 390                 395                 400
```

```
His Asp Val Glu Thr Leu Thr Trp Ser Pro Asn Glu Arg Val Ser His
                405                 410                 415

Leu Ala Ile Ala Ile Cys Glu Ala Arg Glu Ala Leu Ser Ser Ser Gly
            420                 425                 430

Ala Ala Lys Val Ser Phe Pro Asp Asn Val Thr Val Leu Asn Phe Val
        435                 440                 445

Asp Tyr Leu Leu Val Pro Thr Leu Val Tyr Glu Leu Glu Tyr Pro Arg
    450                 455                 460

Thr Asp Ser Ile Arg Pro Leu Tyr Ile Leu Glu Lys Thr Leu Ala Thr
465                 470                 475                 480

Phe Gly Thr Phe Ser Val Leu Leu Leu Ile Val Glu His Phe Ile Tyr
                485                 490                 495

Pro Val Met Pro Gly Pro Asp Ser Ser Phe Ile Ser Ser Leu Leu Asp
            500                 505                 510

Leu Ala Leu Pro Phe Thr Ile Cys Tyr Leu Leu Ile Phe Tyr Ile Ile
        515                 520                 525

Phe Glu Cys Ile Cys Asn Ala Phe Ala Glu Ile Thr Arg Phe Ser Asp
    530                 535                 540

Arg Ala Phe Tyr Ser Asp Trp Trp Asn Ser Ile Ser Phe Asp Glu Phe
545                 550                 555                 560

Ser Arg Lys Trp Asn Arg Pro Val His Thr Phe Leu Leu Arg His Val
                565                 570                 575

Tyr Ala Thr Thr Ile Ser Thr Tyr Lys Leu Ser Lys Phe Ser Ala Ala
            580                 585                 590

Phe Val Thr Phe Leu Leu Ser Ala Leu Val His Glu Leu Val Met Val
        595                 600                 605

Val Val Thr His Lys Ile Arg Met Tyr Leu Phe Met Ala Gln Leu Pro
    610                 615                 620

Leu Ile Met Leu Gly Arg Ala Ser Ile Phe Lys Arg His Pro Ala Leu
625                 630                 635                 640

Gly Asn Leu Phe Phe Trp Phe Gly Leu Leu Ser Gly Phe Pro Leu Leu
                645                 650                 655

Ala Val Ala Tyr Leu Lys Phe
            660
```

<210> SEQ ID NO 72
<211> LENGTH: 1992
<212> TYPE: DNA
<213> ORGANISM: Rhodotorula graminis

<400> SEQUENCE: 72

```
atgagcaccg ccgatcttcc accaggtcct gcccagctgc tcgaagacgc cctgcgccag      60

ccagacggcc cccctctcct gtcgacctcc gccgccgatc cctcctcccc acttcaactc     120

gaccacgacc accgccccgg catggctgca gacgccgcca gctcagcttc agacagctct     180

atcagcacgg tgtccagtgt cctgcgcggt cagcaagcca cgacaacggt gacgaccaac     240

aggggagaag gcgggcgaga aacgaccgag accttcaccc acgtcggcgc cgccaatgtc     300

gacgccgagt actcgtcctc gaccggccac atcacgctcc gacccgtcgt ggcaaagggc     360

ggtgaccctc gccggatccg cctcgtccgc tcgcgccgca cccacttcga gccgcgcatc     420

tcgcacttcg accgccacaa caagacgtcg gccgaggaca cgttccgcgg cttcttctcg     480

ctcttctgga tcgtcatcgc cgtcggcggc acgaggacca tctacaaccg cgtcgccgag     540

acgggcggtc tcctcggcgg gtggcagttt gcggcgctca tctccgagga cgcatgggct     600
```

-continued

```
ctggcgctga gcgatgcggt cctcgtcggg tcgacgatac tctgcgtccc gttcgtcaag     660

ctcatcgtca acggctgggt ccggtactac tacacgggcc tcgtcctcca gcacctcgcc     720

cagacgctct acctcggcat cgccgtccga tggacgttcc accgtcactg gccctgggtc     780

cagagcggct tcatgacgct gcacgccctg agcatgctca tgaagatcca ctcgtactgc     840

tcgctcaacg gcgagctgtc cgagcgcgtg cggcagctcg agaaggacga gcgcaagctg     900

cacgaggcgg tcgaggagct tggcggccag gacgcgctcg agcgcgaggg gcgcgtggcg     960

tgggagaagg cgtgcgccga ggcggccgag cagaaggcgg ccgaggaggc ggcaggcggt    1020

cgcggcaaag cttcggcgtc ctcgctcgcc ccgccgccgg cgacagggcc gcagccctcg    1080

tccgacgagg aggccgtctc gacgacgctc cgacagcgac cgtcggccgc tcgccgccgc    1140

tcgctctcgc cgtcggccgc acggacccac gtcacgccgc cgtcgcgcaa ggccgagccg    1200

cacgacgtcg agacgctcac ctggtcgccc aacgagcgcg tgtcgcacct cgccatcgcc    1260

atctgcgagg cacgcgaggc cctgtcgtcg agcggcgccg ccaaggtctc gttcccggac    1320

aacgtcacgg tcctcaactt tgtcgactac cttctcgtcc cgacgctcgt gtacgagctt    1380

gagtacccga ggaccgactc tatccgaccc ttgtacatcc tcgagaagac cctcgccacg    1440

ttcggcacat tctcggtcct cctcctcatc gtcgagcact tcatctaccc ggtcatgccc    1500

gggcccgaca gctcgttcat ctcgtccctc ctcgacctcg ccctcccatt caccatctgc    1560

tacctcctca tcttctacat catcttcgag tgtatctgca acgccttcgc cgagatcacg    1620

cgcttctcgg accgggcctt ctacagcgac tggtggaact cgatctcgtt cgacgagttc    1680

tcgcgcaagt ggaaccggcc cgtgcacacg ttcctcctgc gccacgtgta cgcgacgacc    1740

atctcgacct acaagctcag caagttctcg gccgcctttg tcacgttcct cctgagcgcg    1800

ctcgtgcacg agctcgtcat ggtagtcgtg acgcacaaga tccgcatgta tctctttatg    1860

gcgcagctcc ccctcatcat gctcggccga gcaagcatct tcaagcgtca ccctgcgctc    1920

ggcaacctct tcttctggtt cggcctcttg agcggtttcc ctctgctagc tgtagcgtac    1980

ctcaagttct ag                                                        1992
```

<210> SEQ ID NO 73
<211> LENGTH: 597
<212> TYPE: PRT
<213> ORGANISM: Pichia guilliermondii

<400> SEQUENCE: 73

```
Met Ser Lys Glu Asn Leu Leu Lys Ile Ser Gln Tyr Asn Thr Glu Arg
1               5                   10                  15

Arg Pro Ser Leu Ala Thr Asp Val Asp Tyr Ser Ser Thr Asp Leu Ser
            20                  25                  30

Ser Arg Leu Asp Ser Ala Asn Thr Thr Asn Gly Thr Pro Thr Val Thr
        35                  40                  45

Leu His Lys Arg Gln Ser Ser Thr Glu Leu Leu Ser Glu Ser Pro Glu
    50                  55                  60

Gln Lys Arg Phe Leu Lys Thr Ile Asp Thr Leu Asn Arg Thr Thr Asn
65                  70                  75                  80

Ser Arg Leu Arg Gln Arg Leu Asn Arg Glu Gly Asp Lys His Lys Lys
                85                  90                  95

Glu His Lys Glu His Glu Lys His Lys Asp Asp His Ser Lys Tyr Lys
            100                 105                 110

Ser Arg Phe Gly Asp Ile His Phe Tyr Ser Asn Met Thr Thr Ile Phe
        115                 120                 125
```

```
Asp Ala Asp Tyr Phe Lys Glu Ser Gln Phe Phe Gly Val Tyr Ile Leu
    130                 135                 140

Phe Trp Leu Gly Thr Ala Phe Leu Ile Leu Asn Asn Leu Val His Thr
145                 150                 155                 160

Phe Leu Glu Asn Gly Asp Asn Leu Leu Asp Gly Pro Val Val Arg Thr
                165                 170                 175

Phe Lys Lys Asp Leu Leu Lys Ile Ala Leu Thr Asp Leu Gly Met Tyr
            180                 185                 190

Leu Thr Met Tyr Val Ser Val Phe Ile Gln Leu Gly Ile Arg Lys Gly
        195                 200                 205

Trp Tyr Ser Trp Ser Ser Thr Gly Ala Thr Leu Gln Asn Ile Tyr Ser
    210                 215                 220

Phe Val Tyr Phe Phe Ala Trp Ser Tyr Phe Ala Ser Pro Lys Tyr Met
225                 230                 235                 240

Asp Tyr Pro Trp Ile Gly Lys Val Phe Leu Ala Leu His Ser Leu Val
                245                 250                 255

Phe Leu Met Lys Met His Ser Tyr Ala Thr Tyr Asn Gly Tyr Leu Trp
            260                 265                 270

Asn Ile Phe Asn Glu Leu Gln Val Ser Arg Lys Tyr Leu Lys Ile Leu
        275                 280                 285

Asp Glu Thr Asp Glu Ser Met Ile Glu Gly Lys Ser Val Ser Asp Leu
    290                 295                 300

Arg Lys Ala Leu Val Asp Ser Ile Gly Phe Cys Ser Tyr Glu Leu Glu
305                 310                 315                 320

Tyr Gln Ser Lys Ser Thr Ser Val Asn Thr Asp Val Glu Ile Thr Gly
                325                 330                 335

Asp Lys Asn Lys Leu Asn Thr Thr Lys Ser Thr Ser Ser Leu Asp Asp
            340                 345                 350

Asp Tyr Val Ser Phe Pro Asn Asn Ile Thr Phe Phe Asp Phe Phe Arg
        355                 360                 365

Tyr Ser Met Phe Pro Thr Val Val Tyr Ser Leu Lys Phe Pro Arg Thr
    370                 375                 380

Lys Arg Ile Arg Trp Gly Tyr Val Met Glu Lys Ser Phe Ala Val Phe
385                 390                 395                 400

Gly Ile Ile Phe Leu Met Ile Thr Val Ala Gln Asn Trp Met Tyr Pro
                405                 410                 415

Ile Val Val Arg Ala Gln Glu Ala Ser Lys Leu Pro Met Ser Arg Glu
            420                 425                 430

Lys Val Leu Gln Tyr Cys Leu Val Leu Leu Asp Met Ile Pro Pro Phe
        435                 440                 445

Leu Met Glu Tyr Leu Phe Thr Phe Phe Leu Ile Trp Asp Val Ile Leu
    450                 455                 460

Asn Ala Ile Ala Glu Leu Ser Arg Phe Ala Asp Arg Asp Phe Tyr Gly
465                 470                 475                 480

Pro Trp Trp Ser Cys Thr Asp Trp Ser Glu Phe Ala Arg Ile Trp Asn
                485                 490                 495

Arg Pro Val His Lys Phe Leu Leu Arg His Val Tyr Gln Ser Thr Ile
            500                 505                 510

Ser Thr Phe Lys Leu Asn Lys Asn Gln Ala Ser Leu Val Thr Phe Ile
        515                 520                 525

Ile Leu Ser Phe Val His Glu Phe Val Met Phe Val Ile Phe Arg Lys
    530                 535                 540
```

```
Val Arg Phe Tyr Met Leu Ala Leu Gln Met Ser Gln Leu Pro Leu Ile
545                 550                 555                 560

Met Ile Ser Arg Thr Lys Phe Met Arg Asp Lys Lys Val Leu Gly Asn
                565                 570                 575

Val Ile Cys Trp Val Gly Phe Ile Ser Gly Pro Ser Met Ile Cys Thr
            580                 585                 590

Leu Tyr Leu Val Phe
        595


<210> SEQ ID NO 74
<211> LENGTH: 1794
<212> TYPE: DNA
<213> ORGANISM: Pichia guilliermondii

<400> SEQUENCE: 74

atgtccaagg aaaacttact taagatcagc cagtataata ctgagagaag accgtcgttg      60

gccacagacg ttgactactc ttccaccgat ttatccagtc gtctggattc ggccaacacg     120

acaaacggaa caccgaccgt aactcttcac aagaggcaat cgtctacaga gctcttgtct     180

gagtcacctg aacagaaaag gttcttgaaa acgatagaca ctttgaatcg aaccacaaat     240

tctagattac gccagaggtt aaaccgtgag ggcgataagc ataaaaagga acacaaagaa     300

catgaaaaac ataaagatga ccattctaaa tacaagtctc ggtttggaga tatccatttc     360

tactcaaaca tgacaaccat cttcgatgct gattacttta aggaatcgca gttctttgga     420

gtttacattc tcttttggct cggaacggca ttcttaattc tcaacaactt ggtccataca     480

tttttggaga acggagacaa tcttctcgat ggaccagttg tcagaacgtt taaaaaggac     540

ttacttaaaa ttgctcttac agacttggga atgtacttga cgatgtacgt ctctgtcttt     600

attcaattgg gcatccgcaa aggatggtat agctggagct caacaggagc caccttgcaa     660

aacatatact cattcgtgta cttctttgcc tggagttact ttgcgtcgcc aaagtacatg     720

gactaccctt ggattggaaa ggtgtttctt gcacttcaca gcttggtgtt tctcatgaaa     780

atgcattctt atgccacata caacggctat ctttggaaca tcttcaacga gcttcaagtg     840

tcacgaaagt acttgaagat attggacgag accgatgaat ccatgattga gggtaagagt     900

gtttccgatt tgcgaaaggc tttggtagac agcattggtt tctgctcata cgagttggag     960

taccagtcca aatcaacgag cgtgaacacg gatgtcgaaa tcaccggcga caagaacaaa    1020

ttgaacacaa ccaagtctac cagttcactc gatgacgact atgtgagttt ccccaataac    1080

attacgtttt tcgatttttt caggtattca atgtttccaa cagtggtgta ttctctcaag    1140

ttcccacgta caaagcgtat tagatggggt tacgtcatgg aaaagtcatt tgcagtgttt    1200

ggcatcatct tcttgatgat caccgtcgct caaaactgga tgtatcctat cgttgtacga    1260

gcacaagagg ctagcaaact cccaatgtca agagaaaagg tattgcagta ctgtttggtt    1320

ttactagaca tgattccacc atttctcatg gaatatcttt tcaccttttt cttgatttgg    1380

gacgtgatcc taaatgcgat agccgaattg agtaggtttg cagatcggga cttttatggt    1440

ccttggtggt cttgtaccga ttggtcggaa tttgcaagaa tttggaatcg tcctgttcac    1500

aaatttttgc ttcgtcatgt gtaccagtca actatcagta ctttcaaact caataaaaac    1560

caagcgtcgt tggtgacgtt tatcattctg agttttgttc atgagtttgt catgtttgtc    1620

atttttagaa aggtgagatt ctacatgttg gcgctccaga tgtctcagct tccattgata    1680

atgattagtc gaacaaaatt catgagagac aaaaaagtgt tgggaaatgt tatctgctgg    1740

gtaggattca tttctggacc atcgatgatc tgtactttgt atttagtatt ttaa          1794
```

<210> SEQ ID NO 75
<211> LENGTH: 515
<212> TYPE: PRT
<213> ORGANISM: Arxula adeninivorans

<400> SEQUENCE: 75

```
Met Ala Thr Ala Thr Ala Ile Ala Thr Val Thr Glu Gly Leu Gly Leu
1               5                   10                  15

Asp Lys Val Leu Ser Lys Glu Gln Pro Gly Leu Ser Lys Leu Ala Pro
            20                  25                  30

Arg Ala Asn Thr Asn Val Gln Pro Thr Gln Leu Gln Ser Pro Ser Pro
        35                  40                  45

Pro Gln Ser Arg Ser Ser Ser Pro Ile Ser Ala Ser Ser Ser Ser Glu
    50                  55                  60

Ser Leu Glu Leu Lys Val Pro Lys Ala Lys Ser Pro Ser Ser Ser Lys
65                  70                  75                  80

His Lys Pro His Tyr Arg Pro Val His Val Arg Ser Thr Ala Ser Ile
                85                  90                  95

Leu Ser Arg Asp Pro Ala Ala Arg Thr Glu Pro Pro Ser Tyr Ser Gly
            100                 105                 110

Phe Arg Asn Leu Ala Met Ile Ala Leu Ala Val Ser Asn Met Arg Leu
        115                 120                 125

Leu Leu Glu Asp Tyr Gln Asn Tyr Gly Val Phe His Thr Leu Asn Ile
    130                 135                 140

Met Gly Leu Ser Ala His Asp Val Arg Leu Thr Leu Ala Leu Thr Ala
145                 150                 155                 160

Ser Val Pro Phe His Leu Phe Val Ala Leu Ala Ile Glu Arg Ile Ala
                165                 170                 175

Val Leu Thr Met Pro Ser Lys Ser Thr Ala His Asn His Arg Ser Lys
            180                 185                 190

His Leu Trp Gly Leu Phe Ala Val Leu His Ala Leu Asn Ala Ala Ala
        195                 200                 205

Val Leu Ala Ile Ser Ser Tyr Thr Val Tyr Ser Arg Met Trp Ser Pro
    210                 215                 220

Ala Val Gly Thr Leu Cys Glu Cys His Ala Ile Val Val Cys Phe Lys
225                 230                 235                 240

Val Ala Ser Tyr Ala Leu Thr Asn Arg Asp Leu Arg Asp Ala Ala Ile
                245                 250                 255

Asp Gly Leu Glu Thr Thr Asp Pro Leu Leu Ser Lys Leu Pro Tyr Pro
            260                 265                 270

Ser Asn Leu Thr Leu Ser Asn Leu Val Tyr Phe Trp Trp Ala Pro Thr
        275                 280                 285

Leu Val Tyr Gln Pro Ile Tyr Pro Arg Trp Pro Leu His Arg Arg Trp
    290                 295                 300

Gly Phe Ile Phe Ser Arg Leu Leu Glu Ile Met Gly Ser Met Val Leu
305                 310                 315                 320

Ile Trp Phe Ile Ser Thr Gln Tyr Ala Asn Pro Ile Leu Glu Ser Ser
                325                 330                 335

Leu Gly His Phe Glu Gln Phe Asn Val Val Lys Ile Ser Glu Cys Leu
            340                 345                 350

Leu Lys Leu Ala Ser Val Ser Met Ala Ile Trp Leu Leu Gly Phe Phe
        355                 360                 365

Cys Leu Phe Gln Ser Phe Leu Asn Leu Leu Ala Glu Leu Val Arg Phe
```

```
    370                 375                 380

Gly Asp Arg Glu Phe Tyr Gln Asp Trp Trp Asn Ala Gly Ser Val Gly
385                 390                 395                 400

Thr Tyr Trp Arg Lys Trp Asn Arg Pro Val His Asn Tyr Phe Leu Arg
                405                 410                 415

His Phe Tyr Ile Pro Met Leu Lys Arg Gly Tyr Ser Gln Arg Thr Ala
            420                 425                 430

Ser Val Ile Val Phe Phe Leu Ser Ala Ile Leu His Glu Val Ala Val
        435                 440                 445

Gly Val Pro Thr Gln Ser Leu Ile Gly Val Ala Phe Val Gly Met Gly
    450                 455                 460

Ala Gln Ile Pro Leu Val Leu Ala Thr Ser Pro Leu Glu Lys Met Gly
465                 470                 475                 480

Glu Thr Gly Ala Thr Ile Gly Asn Cys Ile Phe Trp Leu Ser Phe Phe
                485                 490                 495

Leu Gly Gln Pro Met Gly Val Leu Leu Tyr Tyr Phe Ala Trp Asn Met
            500                 505                 510

Lys His Gln
        515


<210> SEQ ID NO 76
<211> LENGTH: 1548
<212> TYPE: DNA
<213> ORGANISM: Arxula adeninivorans

<400> SEQUENCE: 76

atggccaccg ctactgctat cgctacggtc acggagggcc tgggactaga taaggtgcta     60

tccaaggagc agccaggctt gtcgaagcta gctcctcgag cgaatacaaa tgtacaaccg    120

acccagttgc agtccccgtc tccaccacaa tctcgatctt cgtctccaat ttcggcctcc    180

tcatcatcag agtccctgga gctcaaggtg cccaaggcca aatcgccatc atcttccaaa    240

cacaaaccac actaccgccc cgtgcatgtg cggtcaacag catccatcct gtccagagac    300

ccggccgcca gaaccgagcc tccctcttac tctgggttca ggaacctagc catgattgca    360

ttggcggttt ctaatatgcg cctccttctc gaggactatc aaaactatgg cgtgttccac    420

actctcaaca ttatgggctt gagcgcacac gacgttcgcc tcacactggc attgacagct    480

tcggttccgt tccatctgtt tgtggccctg gccattgagc gcatcgcagt cctcactatg    540

ccctccaaat ctacagcaca caaccaccgc tcaaagcatc tctggggctt gtttgcagtt    600

ctgcatgctc tcaacgccgc tgctgtgcta gcaatcagct catacaccgt atacagtcgc    660

atgtggagtc ctgctgtggg aacattgtgc gaatgccacg caatcgtggt atgctttaag    720

gtggcatcgt atgcgcttac caaccgagac ttacgagatg ctgccattga tgggctagag    780

acaactgacc ctctgttgtc caagttgccc tacccatcca accttacctt gtcaaatctc    840

gtgtatttct ggtgggcccc aaccctagtg tatcagccaa tttaccctcg atggcccctg    900

catcgacgat ggggcttcat cttttctcgc ctgctcgaga ttatgggatc tatggtacta    960

atctggttca tttccaccca atacgccaac cccattttgg aatcatcctt ggggcacttt   1020

gaacagttta acgtggttaa aatctcagaa tgtctcctca aattagcatc ggtctccatg   1080

gccatctggc ttttgggttt cttttgtctc tttcaatcgt ttttgaactt gctggcagaa   1140

ttggttcgtt ttggcgaccg cgagttctac caagactggt ggaacgccgg ctcagtaggt   1200

acctactggc gcaaatggaa ccgaccagtg cacaactatt tcttgcgcca tttctacatc   1260
```

-continued ccaatgctca agcgaggtta ttcacagcgc actgcctcgg tcattgtatt ctttttatct 1320
gccattctcc atgaagttgc tgttggcgtg cctactcagt ccttgattgg agttgcgttt 1380
gtaggcatgg gtgcccagat tcctctagtg ctggccacta gtcctttgga aaagatgggc 1440
gaaactggcg caactattgg caactgcatc ttttggctct ctttcttcct gggccagcca 1500
atgggggtac tgctttacta ctttgcgtgg aatatgaagc accagtag 1548

<210> SEQ ID NO 77
<211> LENGTH: 564
<212> TYPE: PRT
<213> ORGANISM: Phaeodactylum tricornutum

<400> SEQUENCE: 77

Met Asp Glu Thr Glu Ile Thr Pro Leu Leu Arg Phe Ser Thr Pro Ser
1 5 10 15

Arg Ala Glu His Ser Ser Trp Ile Lys Leu Ala Ser Glu Ser Cys Ala
20 25 30

Tyr Ser Glu Thr Asp Glu Phe Leu Ala Asp Glu Ala Ala Arg Ala Thr
35 40 45

Gln Arg Ala Leu Gln His Gln Glu Ala Leu Gln Met Ala Gln Ala Met
50 55 60

Pro Gly Ala Lys Pro Gly Thr Leu Pro Pro Leu Tyr Phe Ala Pro Thr
65 70 75 80

Ile Lys Arg Ser Arg Ser Phe Ala Lys Leu Gln Glu His His Gly Asp
85 90 95

Gly Met Pro Arg Val Asn Met Arg Arg Thr Lys Ser Arg Asp Phe Asn
100 105 110

Ala Asp Lys Leu Asp Ala Arg Ser Thr Lys Gly Tyr Pro Pro Ser Lys
115 120 125

Pro Met His Arg Ala Ala Glu Pro Ser Tyr Leu Ser Ala Asp Ala Pro
130 135 140

Ile Gln Asn Tyr Arg Gly Phe Leu Asn Leu Gly Val Ile Ile Leu Ile
145 150 155 160

Val Ser Asn Phe Arg Leu Ile Leu Gly Thr Ile Arg Ser Asn Gly Phe
165 170 175

Val Leu Thr Thr Ala Val Lys His Tyr Lys Asn Leu Asn His Leu Lys
180 185 190

Glu Asp Pro Trp Gln Glu Phe Pro Phe Val Ser Gly Phe Leu Leu Gln
195 200 205

Leu Val Phe Val Ser Ile Ala Phe Gly Ile Glu Trp Met Leu Cys Arg
210 215 220

Lys Tyr Phe Asn Glu Asn Phe Gly Met Ile Leu His His Phe Asn Ala
225 230 235 240

His Ser Ala Leu Leu Ile Pro Leu Gly Ile Val Trp Asn Leu Ile Asp
245 250 255

Arg Pro Ala Val Gly Ala Ile Leu Leu Leu His Ala Thr Ile Thr Trp
260 265 270

Met Lys Leu Ile Ser Tyr Met Leu Ala Asn Glu Asp Tyr Arg Leu Ser
275 280 285

Ser Arg Arg Val Gly Gly Asn Pro His Leu Ala Thr Leu Ala Leu Val
290 295 300

Glu Asn Leu Asp Ser Asp Glu Ala Asn Ile Asn Tyr Pro Gln Asn Val
305 310 315 320

Thr Leu Arg Asn Ile Phe Tyr Phe Trp Cys Ala Pro Thr Leu Thr Tyr

```
                325                 330                 335

Gln Ile Ala Phe Pro Lys Ser Pro Arg Val Arg Tyr Trp Lys Ile Ala
            340                 345                 350

Asp Ile Leu Met Arg Met Thr Val Ser Ile Ala Leu Phe Thr Phe Leu
        355                 360                 365

Leu Ala Gln Ile Val Gln Pro Ala Leu Glu Glu Leu Val Ser Asp Leu
    370                 375                 380

Asp Glu Thr Asn Gly Ser Tyr Thr Ala Ala Ile Phe Ala Glu Tyr Trp
385                 390                 395                 400

Leu Lys Leu Ser Ile Ala Asn Thr Tyr Leu Trp Leu Leu Met Phe Tyr
                405                 410                 415

Thr Tyr Phe His Leu Tyr Leu Asn Leu Phe Ala Glu Leu Leu Arg Phe
            420                 425                 430

Gly Asp Arg Val Phe Tyr Lys Asp Trp Trp Asn Ser Ser Glu Val Ser
        435                 440                 445

Ala Tyr Trp Arg Leu Trp Asn Met Pro Val His Tyr Trp Leu Ile Arg
    450                 455                 460

His Val Tyr Phe Pro Cys Val Arg Leu Lys Met Pro Lys Val Ala Ala
465                 470                 475                 480

Thr Phe Val Val Phe Phe Leu Ser Ala Val Met His Glu Val Leu Val
                485                 490                 495

Ser Val Pro Phe His Ile Ile Arg Pro Trp Ser Phe Ile Gly Met Met
            500                 505                 510

Met Gln Ile Pro Leu Val Ala Phe Thr Lys Tyr Leu Tyr Arg Lys Phe
        515                 520                 525

Pro Gly Gly Ser Ile Gly Asn Val Leu Phe Trp Met Thr Phe Cys Val
    530                 535                 540

Ile Gly Gln Pro Met Ala Ile Leu Leu Tyr Tyr His Asp Ile Met Asn
545                 550                 555                 560

Arg Lys Gly Asn
```

<210> SEQ ID NO 78
<211> LENGTH: 1695
<212> TYPE: DNA
<213> ORGANISM: Phaeodactylum tricornutum

<400> SEQUENCE: 78

```
atggatgaga ccgaaattac acctttgttg cgtttttcga caccttcccg agccgaacac     60

tcgtcctgga taaagcttgc ctcggaatcc tgtgcttaca gcgaaacgga cgagtttctc    120

gctgacgagg ccgctcgcgc aacccagcgt gctttgcaac atcaagaagc gctgcaaatg    180

gcccaagcca tgcctggggc aaagccagga acgctgccgc cactctactt cgcgcctacc    240

ataaagcgtt cgcgttcctt tgctaagcta caagaacatc atggagatgg gatgcctcgg    300

gtaaatatgc gtcggaccaa atcgcgagat tttaacgcgg ataagttgga tgcgcgaagt    360

accaagggct atcccccttc caagccgatg catcgtgcgg cagagccctc atacctcagc    420

gcggatgctc ccattcaaaa ctaccgagga tttctgaatt taggcgttat tattttgatt    480

gtttctaact ttcggctgat cttgggcaca atccgtagca acggatttgt cttgacgact    540

gcagtgaagc actacaagaa cctaaatcac ctcaaggaag atccctggca ggaatttcct    600

tttgtatcag gatttcttct ccagctcgtc tttgtttcga ttgcgtttgg gatcgaatgg    660

atgttgtgcc ggaaatactt caacgaaaac ttcggcatga tccttcatca cttcaatgcc    720

cactcagcct tgctgatacc tttaggtatt gtttggaatc tcatcgatag acctgcggtt    780
```

```
ggtgcaattt tgcttttaca cgctacgata acatggatga aactcatttc ttacatgttg    840

gcgaacgaag attaccggct atcatcgcgt cgcgttgggg gcaacccaca cctagctacg    900

ctcgcattag tcgaaaatct agattcagat gaggcgaaca ttaactaccc ccaaaatgtt    960

actctccgca acatttttta tttttggtgt gctccgacgt tgacttacca gattgccttc   1020

ccgaagtccc cgcgagttcg ctattggaaa atcgcggata tcctgatgcg catgacggtg   1080

tccatcgcac tattcacctt tttgctggca caaattgttc agcctgcatt ggaagagcta   1140

gtgagcgacc tggacgagac caatggatcc tacaccgcag caatatttgc cgagtactgg   1200

ctgaaacttt cgattgctaa cacatattta tggcttctta tgttctatac atatttccat   1260

ttgtatctga acctctttgc tgagcttctg cgatttggag atcgtgtgtt ctacaaagat   1320

tggtggaatt cgtcggaagt atctgcatat tggaggcttt ggaatatgcc tgttcactat   1380

tggttgatcc gacatgtgta tttcccctgc gtgcgactga agatgccgaa ggtcgctgca   1440

acctttgtcg ttttttttcct ctccgccgtt atgcacgagg tgcttgtcag cgtacccttt   1500

catattattc gtccgtggtc ttttatcggg atgatgatgc agattccttt ggttgcgttc   1560

acaaagtatc tctatcgcaa attcccgggc ggctcgattg gtaatgtcct gttctggatg   1620

acattttgcg tcattggcca gccaatggcg attctcttgt actatcatga tattatgaat   1680

cgaaaaggaa attga                                                    1695
```

<210> SEQ ID NO 79
<211> LENGTH: 503
<212> TYPE: PRT
<213> ORGANISM: Metarhizium acridum

<400> SEQUENCE: 79

```
Met Ser Thr Ala Thr Thr Thr Ser Val Ser Pro Ala Asn Gly Thr Val
1               5                   10                  15

Ser Lys Arg Asn Ala Thr Lys Arg Arg Asn Gly Asn Ala Ser Pro Gly
            20                  25                  30

Pro Val Glu Glu Glu Ser Glu Asp Ala Ala Ala Ala Glu Lys Pro Arg
        35                  40                  45

Ala Ser Val Ala Gln Lys Asn Tyr Arg His Val Ala Ala Val His Ser
    50                  55                  60

Lys Ser Arg Pro Ser Cys Leu Ser His Asp Ser Asp Ala Thr Pro Ser
65                  70                  75                  80

Phe Ile Gly Phe Arg Asn Leu Met Val Ile Val Leu Asp Val Leu Ile
                85                  90                  95

Gly Gly Leu Leu Tyr Phe Leu Ile Pro Cys His Leu Leu Val Ala Tyr
            100                 105                 110

Leu Ile Glu Leu Ala Ala Ala Lys Gln Ala Arg Gly Ser Arg Lys Arg
        115                 120                 125

Leu Lys Pro Gly Ser Thr Val Pro Ser Glu Gln Asp Asn Ser Lys Phe
    130                 135                 140

His Ser Thr Trp Val Leu Val Ala Trp Ala His Gly Ile Asn Met Thr
145                 150                 155                 160

Leu Ala Leu Ala Leu Thr Thr Phe Met Val Tyr Phe Tyr Ile His His
                165                 170                 175

Pro Leu Val Gly Thr Leu Thr Glu Met His Ala Val Ile Val Ser Leu
            180                 185                 190

Lys Thr Ala Ser Tyr Ala Phe Thr Asn Arg Asp Leu Arg His Ala Tyr
        195                 200                 205
```

```
Leu His Pro Val Lys Gly Glu Phe Ile Pro Glu Leu Tyr Ser Lys Cys
    210                 215                 220

Pro Tyr Pro Asn Asn Ile Thr Phe Gly Asn Leu Ala Tyr Phe Trp Trp
225                 230                 235                 240

Ala Pro Thr Leu Val Tyr Gln Pro Val Tyr Pro Arg Thr Asp Lys Ile
                245                 250                 255

Arg Trp Val Phe Val Phe Lys Arg Leu Gly Glu Val Cys Cys Leu Ser
            260                 265                 270

Ala Phe Ile Trp Phe Ala Ser Phe Gln Tyr Ala Ala Pro Val Leu Gln
        275                 280                 285

Asn Ser Leu Asp Lys Ile Ala Ser Leu Asp Leu Leu Met Ile Leu Glu
    290                 295                 300

Arg Leu Leu Lys Leu Ser Thr Ile Ser Leu Val Ile Trp Leu Ala Gly
305                 310                 315                 320

Phe Phe Ala Leu Phe Gln Ser Phe Leu Asn Ala Leu Ala Glu Val Leu
                325                 330                 335

Arg Phe Gly Asp Arg Ser Phe Tyr Asp Asp Trp Trp Asn Ser Glu Ser
            340                 345                 350

Leu Gly Ala Tyr Trp Arg Thr Trp Asn Arg Pro Val Tyr Thr Tyr Phe
        355                 360                 365

Lys Arg His Val Tyr Val Pro Met Ile Gly Arg Gly Trp Ser Pro Trp
    370                 375                 380

Ala Ala Ser Cys Ala Val Phe Phe Val Ser Ala Val Leu His Glu Val
385                 390                 395                 400

Leu Val Gly Val Pro Thr His Asn Ile Ile Gly Thr Leu Ser Ser Val
                405                 410                 415

Leu Ser Ile Val Leu Thr Leu Val Pro Asn Leu Tyr Ser Gly Val Ala
            420                 425                 430

Phe Leu Gly Met Phe Leu Gln Leu Pro Leu Ile Ala Ile Thr Ala Pro
        435                 440                 445

Leu Glu Lys Met Lys Trp Gly His Thr Gly Arg Val Met Gly Asn Val
    450                 455                 460

Ile Phe Trp Val Ser Phe Thr Ile Phe Gly Gln Pro Phe Ala Ala Leu
465                 470                 475                 480

Met Tyr Phe Tyr Ala Trp Gln Ala Lys Tyr Gly Ser Val Ser Lys Glu
                485                 490                 495

Pro Ile Leu Ala Leu Gln Thr
            500
```

<210> SEQ ID NO 80
<211> LENGTH: 1512
<212> TYPE: DNA
<213> ORGANISM: Metarhizium acridum

<400> SEQUENCE: 80

```
atgagcacgg ccaccaccac cagtgtcagc ccagcgaatg gcaccgtgag caagagaaat      60

gccaccaagc gtcgcaacgg caatgcatct cccggcccgg tggaagaaga atccgaagac     120

gcagccgcag ccgagaagcc cagagcctct gtcgcccaga agaactatcg ccacgtagca     180

gcagtgcatt ccaagagccg cccgtcgtgc ctaagccacg actccgatgc cacgccaagc     240

tttatcgggt ttcgaaatct catggtcatt gttttggatg tcctcatcgg cggacttctc     300

tactttctca ttccctgcca tctgttggtt gcctacttga tcgaattggc cgccgcaaaa     360

caggctcgag gatcccgaaa gcgcctcaaa ccaggctcta ctgtaccgtc ggaacaagac     420
```

aattccaagt tccattcaac atgggttctg gtggcctggg ctcatggtat caatatgacg 480
cttgctttag ccctcacaac ctttatggtt tacttttaca tccaccaccc gctcgttggg 540
accctgaccg agatgcatgc cgtcattgtg tcgttgaaga cagcctcgta cgcattcacc 600
aaccgagatc ttcgccacgc ttacctgcac cccgttaaag gagagtttat tcctgaactc 660
tactcgaaat gcccgtaccc gaataacatc acctttggca acctcgccta cttctggtgg 720
gcgccgacgc tggtctatca gcccgtatac ccgcgcaccg acaagatcag atgggtcttt 780
gtttttaaga ggctgggcga agtatgctgt ttgagcgcat tcatctggtt cgccagcttc 840
caatacgccg cgccggttct gcagaattcg ctcgacaaga ttgcttcgtt ggacttactc 900
atgatcctag agcggctgct gaagctgtca accatttctc tggttatttg gctggcagga 960
ttctttgccc tattccagtc cttcttaaac gcacttgccg aagtgctgcg gttcggcgac 1020
cgatcatttt acgacgactg gtggaacagc gagagtctcg gagcctactg gagaacgtgg 1080
aacaggcccg tatatacgta ctttaagcgc catgtgtatg tacccatgat tgggcgtgga 1140
tggagcccat gggctgcaag ttgcgccgtc tttttgtgt ctgccgtgtt acacgaggtt 1200
cttgttggtg ttcccaccca caacattatc ggtacgctat cctccgtctt atccatcgtc 1260
ttgaccctcg ttcctaacct atattcaggc gttgcttttc taggcatgtt cttgcagctt 1320
cctctcatcg ccatcacggc ccctctagag aaaatgaaat gggggcatac cggcagagta 1380
atgggaaacg taatcttttg ggtgtccttt accatcttcg gtcagccatt tgcggcattg 1440
atgtactttt acgcatggca ggccaagtac ggtagcgtca gtaaagaacc gattcttgcg 1500
ttgcagacat ga 1512

<210> SEQ ID NO 81
<211> LENGTH: 516
<212> TYPE: PRT
<213> ORGANISM: Ophiocordyceps sinensis

<400> SEQUENCE: 81

Met Ala Ala Thr Gly Thr Ser Val Glu Pro Ser Thr Gly Thr Ala Thr
1 5 10 15

Gln Arg His Ser Gly Lys Asp Gln Thr Gly Val Glu Pro Arg Thr Gly
20 25 30

Thr Val Lys Thr Ser Gln Lys Lys Tyr Arg His Val Val Val Val His
35 40 45

Ser Gln Val Arg Pro Ser Cys Leu Ser His Asp Ser Asp Ala Ala Pro
50 55 60

Ser Phe Ile Gly Phe Arg Asn Leu Met Val Ile Val Leu Val Val Gly
65 70 75 80

Asn Leu Arg Leu Met Ile Glu Asn Ile Gln Lys Ala Arg Ser Tyr Leu
85 90 95

Ser Phe Ile Pro Gly Gln Cys Ala Pro Gly Tyr Gly Val Leu Ile Cys
100 105 110

Ile Arg Cys His Ala Tyr Ser Arg Gln Asp Ile Leu Val Gly Gly Leu
115 120 125

Leu Tyr Ile Leu Ile Pro Cys His Leu Leu Ala Ala Tyr Leu Ile Glu
130 135 140

Leu Ala Ala Ala Gln Gln Ala Leu Gly Ser Arg Lys Arg Leu Lys Asp
145 150 155 160

Gly Ala Ala Ser Pro Glu Glu Glu Asp Arg Asn Ser Asn Lys Phe His
165 170 175

```
Ala Thr Trp Leu Ile Val Ala Trp Val His Ala Val Asn Ile Thr Leu
            180                 185                 190

Ala Leu Val Val Thr Ser Ala Val Val Tyr Phe Tyr Ile His His Pro
        195                 200                 205

Leu Ile Gly Thr Leu Thr Glu Met His Ala Ile Ile Val Trp Leu Lys
    210                 215                 220

Thr Ala Ser Tyr Ala Phe Thr Asn Arg Asp Leu Arg His Ala Tyr Leu
225                 230                 235                 240

His Pro Val Glu Gly Glu Leu Val Pro Asp Met Tyr Ala Lys Cys Pro
                245                 250                 255

Tyr Pro Gln Asn Ile Thr Phe Gly Asn Leu Val Tyr Phe Trp Trp Ala
            260                 265                 270

Pro Thr Leu Val Tyr Gln Pro Val Tyr Pro Arg Thr Asp Lys Ile Arg
        275                 280                 285

Trp Leu Phe Val Ala Lys Arg Leu Gly Glu Val Phe Cys Leu Ser Ala
    290                 295                 300

Phe Ile Trp Phe Ala Ser Phe Gln Tyr Ala Ala Pro Val Leu Arg Asn
305                 310                 315                 320

Ser Leu Asp Lys Ile Ala Ser Leu Asp Phe Ala Ser Ile Phe Glu Arg
                325                 330                 335

Leu Val Lys Leu Ser Thr Ile Ser Leu Val Ile Trp Leu Ala Gly Phe
            340                 345                 350

Phe Ala Leu Phe Gln Ser Phe Leu Asn Ala Leu Ala Glu Val Leu Arg
        355                 360                 365

Phe Gly Asp Arg Ala Phe Tyr Asp Asp Trp Trp Asn Ser Glu Ser Leu
    370                 375                 380

Gly Ala Tyr Trp Arg Thr Trp Asn Lys Pro Val Tyr Thr Tyr Phe Lys
385                 390                 395                 400

Arg His Val Tyr Met Pro Met Ile Gly Arg Gly Trp Ser Pro Arg Val
                405                 410                 415

Ala Ser Leu Val Val Phe Phe Ile Ser Ala Val Leu His Glu Ile Leu
            420                 425                 430

Val Gly Leu Pro Thr His Asn Val Ile Gly Val Ala Phe Leu Gly Met
        435                 440                 445

Phe Leu Gln Leu Pro Leu Ile Ala Ile Thr Ala Pro Met Glu Lys Met
    450                 455                 460

Arg Leu Gly Lys Gly Gly Lys Leu Val Gly Asn Val Ile Phe Trp Val
465                 470                 475                 480

Ser Phe Thr Ile Phe Gly Gln Pro Phe Ala Thr Leu Met Tyr Phe Tyr
                485                 490                 495

Ala Trp Gln Ala Lys Tyr Gly Ser Val Ser Arg Glu Met Gln Gln Ala
            500                 505                 510

Ala Ser Ile Lys
        515
```

<210> SEQ ID NO 82
<211> LENGTH: 1551
<212> TYPE: DNA
<213> ORGANISM: Ophiocordyceps sinensis

<400> SEQUENCE: 82

```
atggcggcta cggggaccag cgtcgagccc tcgactggta ccgcgacaca acgccactcc      60

ggcaaggatc agactggggt cgagccacgc accggcacgg tcaagacatc ccagaaaaag     120
```

-continued

```
tatcgccatg tcgttgtcgt ccactcccag gtccggccct cgtgcctcag ccacgattca    180
gatgccgccc ccagcttcat tggcttccgc aatctcatgg ttattgtcct ggtcgtcggc    240
aacttgcgat tgatgattga aaacatccaa aaggctcgtt catacctgtc gttcatacct    300
ggccaatgcg cccccggcta cggagtcttg atctgcatcc gctgccacgc ctacagccgc    360
caagacattc tcgtcggcgg gctgctgtac atcctcattc cctgccatct cctggccgcc    420
tatctcatcg agctcgccgc cgcccagcag gcactggggt cgagaaagcg cctcaaggat    480
ggcgccgcca gcccggagga ggaggaccgc aacagcaaca agtttcacgc gacatggctc    540
atcgtcgcct gggtccatgc cgtcaacatc accctggccc tggtcgtgac ctcggccgtc    600
gtctactttt acatccacca cccactcatc ggcaccctca ccgaaatgca cgccatcatc    660
gtctggctca agacggcctc gtacgccttt actaaccgcg acctgcgcca cgcgtacctg    720
caccccgtcg agggcgagct cgtcccggac atgtacgcca agtgcccgta tccgcaaaac    780
atcacctttg gcaacctcgt ctacttctgg tgggccccga cgctcgtcta ccagcccgtc    840
tatccccgga ccgacaagat caggtggctc tttgtcgcca agcggctggg agaggtcttt    900
tgcttgagcg ccttcatctg gttcgccagc ttccagtatg ccgcgcccgt cctgcgcaac    960
tctctcgaca aaattgcttc gctcgacttt gcctccatct ttgagcggct ggtgaagctg   1020
tccaccatct ccctcgtcat ctggctcgcc ggcttcttcg ccctcttcca gtcctttctc   1080
aacgccctcg ccgaggtgct tcggttcggc gaccgggctt tctacgatga ctggtggaac   1140
agcgagagcc taggcgccta ctggcggacc tggaacaagc ccgtctacac ctacttcaag   1200
cgccacgtgt acatgcccat gatcgggcgt ggctggagtc ccagggtggc cagtctggtc   1260
gtcttcttca tctcagccgt cctccacgag atccttgtcg ggctacccac tcacaacgtc   1320
atcggcgtcg cctttctcgg catgtttctc cagctgcctc tcatcgccat cacggcgccc   1380
atggagaaga tgaggctcgg caaaggcggc aagctcgtag gcaacgtcat cttctgggtg   1440
tcgtttacca tctttggcca gccctttgcg acattgatgt acttttatgc ttggcaggcc   1500
aaatacggga gcgtgagcag ggagatgcag caagcggcaa gcatcaagta a            1551
```

<210> SEQ ID NO 83
<211> LENGTH: 510
<212> TYPE: PRT
<213> ORGANISM: Trichoderma virens

<400> SEQUENCE: 83

```
Met Ala Pro Pro Ala Glu Ser Ser Thr Thr Thr Ser Val Glu Ala Ser
1               5                   10                  15

Thr Gly Ser Val Ser Arg Arg His Ala Ser Gln Ser Glu Ala Asp Leu
            20                  25                  30

Thr Ser Val Glu Pro Val Asn Gly Thr Thr Lys Asn Arg Leu Ser Lys
        35                  40                  45

Thr Pro Pro Lys Lys Tyr Arg His Val Ala Ala Val His Ser Gln Thr
    50                  55                  60

Arg Pro Ser Cys Leu Ser His Asp Ser Pro Ala Ala Pro Ser Phe Leu
65                  70                  75                  80

Gly Phe Arg Asn Leu Met Val Ile Val Leu Val Val Gly Asn Leu Arg
                85                  90                  95

Leu Met Ile Glu Asn Ile Gln Lys Tyr Gly Val Leu Ile Cys Ile Arg
            100                 105                 110

Cys His Asp Tyr Arg Arg Gln Asp Val Leu Leu Gly Leu Leu Leu Tyr
        115                 120                 125
```

```
Phe Leu Ile Pro Cys His Leu Phe Ala Ala Tyr Leu Ile Glu Leu Val
    130                 135                 140

Ala Ala Lys Gln Ala Glu Gly Ser Arg Lys Arg Ile Lys Asp Asn Asn
145                 150                 155                 160

Ser Gly Pro Ser Glu Ala Glu Arg Lys Lys Phe His Ser Ile Trp Val
                165                 170                 175

Leu Ala Ala Leu Ala His Gly Ile Asn Ile Thr Leu Ala Leu Ala Ile
            180                 185                 190

Thr Thr Val Val Val Tyr Phe Tyr Val Tyr His Pro Leu Ile Gly Thr
        195                 200                 205

Leu Thr Glu Met His Ala Ile Ile Val Trp Leu Lys Thr Ala Ser Tyr
    210                 215                 220

Ala Phe Thr Asn Arg Asp Leu Arg His Ala Tyr Leu His Pro Val Glu
225                 230                 235                 240

Gly Glu Glu Val Pro Asp Leu Tyr Lys Ser Cys Pro Tyr Pro Gln Asn
                245                 250                 255

Val Thr Met Lys Asn Leu Val Tyr Phe Trp Trp Ala Pro Thr Leu Val
            260                 265                 270

Tyr Gln Pro Val Tyr Pro Arg Thr Asp Lys Ile Arg Trp Val Phe Val
        275                 280                 285

Phe Lys Arg Leu Gly Glu Ile Phe Cys Leu Ala Val Phe Ile Trp Val
    290                 295                 300

Ala Ser Ala Gln Tyr Ala Thr Pro Val Leu Arg Asn Ser Leu Asp Lys
305                 310                 315                 320

Ile Ala Ser Leu Asp Leu Pro Asn Ile Leu Glu Arg Leu Met Lys Leu
                325                 330                 335

Ser Thr Ile Ser Leu Val Ile Trp Leu Ala Gly Phe Phe Ala Leu Phe
            340                 345                 350

Gln Ser Phe Leu Asn Ala Leu Ala Glu Ile Met Arg Phe Gly Asp Arg
        355                 360                 365

Ser Phe Tyr Asp Asp Trp Trp Asn Ser Glu Ser Leu Gly Ala Tyr Trp
    370                 375                 380

Arg Thr Trp Asn Lys Pro Val Tyr Thr Tyr Phe Lys Arg His Val Tyr
385                 390                 395                 400

Met Pro Met Ile Gly Arg Gly Trp Ser Pro Ala Ala Ala Ser Phe Ala
                405                 410                 415

Val Phe Phe Val Ser Ala Val Leu His Glu Ile Leu Val Gly Val Pro
            420                 425                 430

Thr His Asn Ile Ile Gly Val Ala Phe Phe Gly Met Phe Leu Gln Leu
        435                 440                 445

Pro Leu Ile Ala Ile Thr Thr Pro Leu Glu Lys Met Lys Leu Gly His
    450                 455                 460

Gly Gly Arg Ile Leu Gly Asn Val Ile Phe Trp Val Ser Phe Thr Ile
465                 470                 475                 480

Phe Gly Gln Pro Phe Ala Ala Leu Met Tyr Phe Tyr Ala Trp Gln Ala
                485                 490                 495

Lys Tyr Gly Ser Val Ser Arg Leu Pro Gln Met Val His His
            500                 505                 510
```

<210> SEQ ID NO 84
<211> LENGTH: 1533
<212> TYPE: DNA
<213> ORGANISM: Trichoderma virens

<400> SEQUENCE: 84

```
atggcgcctc ctgcagagtc ctccacgacg acaagcgtcg aggcctctac cggctccgtg     60
tctcgccgcc acgcctcaca aagtgaagca gatctaacgt cggtggagcc cgtcaacggc    120
acgaccaaga accggctctc caagacaccg ccgaagaaat atcgccatgt cgctgcggtg    180
cattcccaga cgcggccgtc gtgcctgagc catgattccc ctgcggctcc cagctttctc    240
ggattccgca atctcatggt cattgtgctg gttgttggca atctccgatt gatgattgag    300
aatattcaaa agtacggcgt cttaatttgc atcaggtgtc acgactacag acgtcaagat    360
gtgctcttgg gtcttttgct ttattttctt atcccctgcc atttgtttgc agcatacctg    420
atagagctgg tcgctgccaa gcaggctgag ggatccagga agcgaatcaa ggacaacaac    480
tctggcccgt cagaggcaga gcgcaagaag ttccactcaa tctgggttct tgcggctttg    540
gcccatggaa tcaacatcac tcttgccctt gcaattacca ccgttgtggt ctacttttac    600
gtctatcatc cgctgattgg cactttgacc gagatgcatg ccatcattgt gtggctcaag    660
acggcatcat atgcattcac caaccgagat cttcgtcacg cctatctgca tccagttgag    720
ggagaggaag tgcctgattt gtacaaatcc tgcccctatc cacaaaacgt gacgatgaag    780
aacttggtat acttctggtg ggctccgact ctggtgtacc aacctgttta tccgcggacc    840
gacaagattc gatgggtgtt cgtgtttaag cgactaggag agatcttttg ccttgctgtg    900
ttcatttggg ttgccagtgc ccaatatgcc acccccgttt tgcgcaactc tctcgacaag    960
attgcctctc ttgatttgcc caacatcttg gagcggctta tgaaactctc gacaatctct   1020
ttggtcatct ggctggccgg cttctttgcg ctcttccaat ctttcttaaa cgcccttgcc   1080
gagataatga ggtttggcga taggtcattc tacgacgact ggtggaacag tgagagcttg   1140
ggcgcctact ggaggacgtg gaacaagcct gtttatactt acttcaagcg ccatgtctat   1200
atgcccatga tcggacgagg ctggagcccg gccgctgcca gtttcgcagt ctttttttgtt   1260
tctgccgttc ttcatgaaat tcttgttggt gttccaacac ataacattat cggcgtcgct   1320
ttcttcggca tgttccttca gcttcctctc atcgccatta ctactccgct ggagaagatg   1380
aaactcggtc atggtggccg cattcttgga aatgtcatat tttgggtttc gtttacaatc   1440
tttggacagc cattcgcggc cctgatgtat ttctacgctt ggcaggccaa gtatggcagc   1500
gtgagtaggt tacctcagat ggtgcaccac taa                               1533
```

<210> SEQ ID NO 85
<211> LENGTH: 816
<212> TYPE: PRT
<213> ORGANISM: Yarrowia lipolytica

<400> SEQUENCE: 85

```
Met Phe Thr Ser Arg Val Ser Glu Ala Ser Thr Thr Asn Phe Ile Arg
1               5                   10                  15

Pro Thr Ala Arg Ser His Ile His Phe Phe Phe Ala Phe Ile Ala Ala
            20                  25                  30

Thr Val His Gln Leu Leu Leu Met Leu Tyr Gln Leu Leu Gly Asp Gly
        35                  40                  45

Tyr Leu Lys Ser Phe Val Asp Thr Gly Ile Thr Leu Ala Gln Gln Ser
    50                  55                  60

Gly Leu Ser Gly Ile Val Asn Ala Leu Thr Ser Glu Ala Lys Leu Arg
65                  70                  75                  80

Ile Asp Lys Arg Ser Ile Ile Lys Lys Leu Leu Glu Asp Gln Glu Asn
                85                  90                  95
```

```
Ala Glu Ser Tyr Phe Asp Trp Leu Lys Ala Ser Ser Glu Leu Asp Tyr
            100                 105                 110

Leu Leu Gly Asn Gln Glu Trp Lys Glu Arg Asp Glu Cys Pro Ala Tyr
        115                 120                 125

Asp Tyr Glu Tyr Val Arg Leu Arg Leu Asp Glu Leu Arg His Ala Arg
    130                 135                 140

Thr Asn Asn Asp Thr Thr Arg Leu Leu Tyr Leu Val Arg Thr Thr Trp
145                 150                 155                 160

Ser Arg Asn Leu Gly Asn Leu Gly Asp Val Lys Leu Tyr His Asn Ser
                165                 170                 175

Phe Thr Gly Thr Lys Arg Leu Ile Glu Asp Tyr Ile Leu Glu Cys Glu
            180                 185                 190

Leu Ala Leu Asn Ala Leu Leu Ala Ala Gly Asn Asp Lys Ile Pro Asp
        195                 200                 205

Gln Glu Leu Leu Thr Glu Leu Leu Asn Thr Arg Lys Ala Phe Gly Arg
    210                 215                 220

Thr Ala Leu Leu Leu Ser Gly Gly Gly Cys Leu Gly Leu Leu His Thr
225                 230                 235                 240

Gly Val Leu Gln Ala Leu Ser Asp Thr Ser Leu Leu Pro His Val Ile
                245                 250                 255

Ser Gly Ser Ser Ala Gly Ser Ile Met Ala Ala Gly Leu Cys Ile His
            260                 265                 270

Lys Asp Glu Glu His Glu Ala Phe Ile Thr Glu Leu Met Glu Arg Asp
        275                 280                 285

Phe Asp Ile Phe Glu Glu Ser Gly Asn Glu Asp Thr Val Leu Glu Arg
    290                 295                 300

Val Ser Arg Met Leu Lys His Gly Ser Leu Leu Asp Asn Arg Tyr Met
305                 310                 315                 320

Gln Asp Thr Met Arg Glu Leu Phe Gly Asp Met Thr Phe Leu Glu Ala
                325                 330                 335

Tyr Asn Arg Thr Arg Arg Ile Leu Asn Val Thr Val Ser Ser Ala Gly
            340                 345                 350

Ile Tyr Glu Met Pro Arg Leu Leu Asn Tyr Leu Thr Ala Pro Asn Val
        355                 360                 365

Leu Ile Trp Ser Ala Val Cys Ala Ser Cys Ser Val Pro Leu Ile Phe
    370                 375                 380

Asn Ala Tyr Thr Leu Leu Glu Lys Glu Pro Lys Thr Gly Ala Ile Gln
385                 390                 395                 400

Thr Trp Asn Ala Ser Ser Leu Arg Phe Ile Asp Gly Ser Val Tyr Ala
                405                 410                 415

Asp Val Pro Ile Ala Arg Leu Ser Glu Met Phe Asn Val Asn His Phe
            420                 425                 430

Ile Val Ser Gln Val Asn Pro His Val Ala Pro Phe Leu Lys Leu Thr
        435                 440                 445

Glu Asp Lys Ala Asn Pro Asp Ser Val Asp Glu Ile Tyr Thr Leu Lys
    450                 455                 460

Leu Trp His Asn Phe Lys Thr Leu Val Thr Asp Glu Val Met His Gln
465                 470                 475                 480

Leu Gln Val Leu Tyr Glu Phe Gly Ile Phe Lys Asn Leu Cys Ser Lys
                485                 490                 495

Met Gly Gly Val Leu Ser Gln Arg Tyr Lys Gly Asp Ile Thr Ile Leu
            500                 505                 510
```

-continued

```
Pro Gln Val His Leu Ser Glu Leu Pro Gly Ile Leu Thr Asn Pro Thr
        515                 520                 525

Ala Ala Tyr Met Lys Asp Thr Asn Arg Arg Gly Ala Gln Ala Thr Tyr
    530                 535                 540

Arg Lys Ile Ser Leu Ile Arg Asn His Cys Ala Ile Glu Leu Ala Leu
545                 550                 555                 560

Asp Arg Ala Ile His Glu Leu Lys Ala Arg Met Leu Pro Ser Lys Leu
                565                 570                 575

Gly Ser Gly Arg Thr Ser Pro Gln Gly Thr Phe Lys His Ser Gln Ser
            580                 585                 590

Ser Asn Gln Ile Ser Ala Leu Lys Pro Pro Ser Arg His Met Ser Ala
        595                 600                 605

Ser Ser Ala Thr Thr Ala His Thr Arg Leu Arg Asn Arg Lys Ser Phe
    610                 615                 620

Ser His Ala Arg Ile Lys Ser Asp Ala Ala Ala Val Phe Asp Lys Glu
625                 630                 635                 640

Pro Ile His Glu Thr Pro Lys Ser Ser Pro Gln Ser Ser Tyr Val Asn
                645                 650                 655

Leu His Arg Ser Ala Ser Glu Arg Ser Arg Arg Pro Lys Ser Ala Phe
            660                 665                 670

Asn Leu Gly Ser Leu Pro Thr Ser Pro Leu Tyr His Pro His Leu Thr
        675                 680                 685

His Ser Met Ser Met Gly Gly Ala Asn Gln Ala Pro Leu Tyr Asn Pro
    690                 695                 700

Gly Arg Gly Ser Val Ser Gln Asn Thr Ser Pro Gly Thr Lys Ile Pro
705                 710                 715                 720

Gly Asn Ala Asp Pro Ser Tyr Phe Asp Gly Pro Asn Asn Val Arg Phe
                725                 730                 735

His Trp Asp Ser Asp Asp Asp Asp Val Arg Glu Thr Glu Phe Leu Asn
            740                 745                 750

Asn Met Ser Ser Ser Ser Ser Arg Arg Val Ser Pro Val Gln Ser Arg
        755                 760                 765

Arg Ala Ser Val Asp Gly Leu Arg Asn Ser Val Val Ser Thr Ala Thr
    770                 775                 780

Ser Val Thr Asp Gly Ser Val Ser Ser Arg Pro Ser Arg Ala Trp Glu
785                 790                 795                 800

Ser Ile Ser Gln Leu Phe Glu Gly Asp Glu Asn Cys Ser Asp Ser Cys
                805                 810                 815
```

<210> SEQ ID NO 86
<211> LENGTH: 2451
<212> TYPE: DNA
<213> ORGANISM: Yarrowia lipolytica

<400> SEQUENCE: 86

```
atgttcacct ccagagtttc cgaagcaagc accaccaact ttatccggcc gacggcacgg      60

tctcacatcc actttttttt cgccttcatc gccgcaaccg tccaccaact gctgctcatg     120

ctctaccaac tgcttggaga cggctacctc aagtcgtttg tcgacacagg tatcacgctg     180

gcccaacagt cggggctttc gggtatcgtc aacgccttga cttcagaggc caaactgcgg     240

atcgataaac ggtccatcat caaaaagctg ctagaggacc aggaaaacgc cgagtcgtac     300

tttgactggc tcaaggcgtc cagcgaactc gactatctgc tcggcaacca ggaatggaag     360

gaaagagacg agtgtccagc ttacgattac gaatacgtcc gactccgatt ggacgaactg     420
```

```
agacacgccc gaaccaataa cgacaccacc cgactgcttt acctcgtgcg aacaacgtgg    480

agtagaaacc tcggcaacct cggagacgtc aagctctacc acaactcctt taccggaacc    540

aaacgactca tcgaagacta cattctggaa tgcgaactgg ctctcaacgc gctcctggca    600

gccggaaacg acaagatccc ggaccaggag ctgctcacgg agctgctcaa caccagaaag    660

gcatttggac gaactgccct tctgctgtcc ggcggaggat gtctcggtct gctccacacc    720

ggtgttctcc aggccctctc agacacatcg ctcttgcccc acgtcatatc gggttcgtcg    780

gcaggctcaa tcatggccgc gggactgtgc attcacaaag acgaagaaca cgaggctttc    840

atcaccgagc tcatggagcg agactttgac attttcgaag agtccggaaa cgaagacacg    900

gtgctcgaac gagtgtctcg aatgctcaaa catggatcgc tactcgacaa cagatatatg    960

caggacacta tgcgagaatt atttggcgac atgacctttc tggaggccta caaccggact   1020

cgccgtattc tcaacgttac ggtatcgtct gctggcatct acgaaatgcc tcgtttgctc   1080

aactacctga cggcccccaa cgtactcatt tggtcggctg tctgcgcctc ctgctcggtg   1140

cctctcattt tcaatgccta cactctgctt gaaaaggagc ccaaaaacagg agctattcag  1200

acctggaacg cttcttcgct gcggttcatt gacggatccg tctatgccga cgtgcccatt   1260

gcgcgtctct cagaaatgtt caatgtaaat catttcattg tctcgcaggt aaaccctcac   1320

gttgctcctt tcctcaagct cacagaagac aaggccaacc cggactcggt cgacgaaatc   1380

tacacgctca agctttggca caacttcaag acgctggtca ccgacgaggt catgcaccag   1440

ttgcaggtgc tgtacgagtt tggcatcttc aagaacctgt gttcgaaaat gggaggcgta   1500

ctgtcccagc gatacaaggg agacatcaca atcctgcccc aggtccatct ctcagagctc   1560

ccgggaattc ttactaaccc cactgccgca tacatgaagg acaccaaccg acgaggtgcc   1620

caggccactt atcgaaagat ctcgctcatt cgaaaccact gtgccattga gttggcgctg   1680

gatcgagcta tccacgaact caaggcccgt atgctcccct ccaagcttgg atcaggacgt   1740

acatccccgc aaggtacttt taagcattcg cagtcgtcca accagatttc tgcgctcaaa   1800

cctccttctc gtcacatgtc tgcttcatcg gcaaccacag cacatacgcg tcttcggaac   1860

cgaaagtcgt tttctcatgc acgtatcaag agtgatgcgg ccgctgtgtt cgacaaggag   1920

cctattcacg agacgcccaa gtcgtcgcct cagagctcgt atgtcaactt gcaccgatct   1980

gcaagtgagc ggtcgagacg acccaagtct gcattcaatc tgggctctct gccgacctct   2040

cctctttatc atccgcatct gacccactcc atgtctatgg ggggagccaa tcaggcgcct   2100

ctgtacaatc ctgggcgcgg ttctgtgtct cagaacacct cccctgggac caaaatcccc   2160

ggaaacgctg atccgtcgta ctttgatgga cccaacaatg tgcgtttcca ctgggacagc   2220

gacgacgacg atgtgcgaga gacggagttc ctcaacaaca tgtcttcgtc gtcttcacga   2280

agagtttctc ctgtccagag tcgtcgagcc agtgttgatg gactgcgaaa ctctgtcgta   2340

tccaccgcca ccagtgtcac cgacggttcc gtgtccagca gaccgtcccg agcgtgggag   2400

agcatttccc agctgtttga aggggacgag aactgttctg actcgtgcta a            2451
```

<210> SEQ ID NO 87
<211> LENGTH: 332
<212> TYPE: PRT
<213> ORGANISM: Ricinus communis

<400> SEQUENCE: 87

```
Met Glu Val Ser Gly Leu Gly Cys Phe Ser Ser Ala Ala Thr Pro Ser
1               5                   10                  15
```

-continued

```
Leu Cys Gly Ala Val Asp Ser Gly Gly Val Ser Ser Leu Arg Pro Arg
            20                  25                  30

Lys Ala Phe His Arg Val Ser Asp Ser Cys Leu Gly Phe Arg Asp Asn
        35                  40                  45

Gly His Leu Gln Tyr Tyr Cys Gln Gly Gly Phe Val Arg Cys Gly Gly
    50                  55                  60

Gly Asn Lys Lys Ser Ile Lys Lys Lys Leu Lys Leu Val Lys Ser Leu
65                  70                  75                  80

Ser Glu Asp Phe Ser Met Phe Pro His Asn Asn Ala Leu Leu His Gln
                85                  90                  95

Pro Gln Ser Ile Ser Leu Gln Glu Ala Ala Gln Gly Leu Met Lys Gln
            100                 105                 110

Leu Gln Glu Leu Arg Ala Lys Glu Lys Glu Leu Lys Arg Gln Lys Lys
        115                 120                 125

Gln Glu Lys Lys Ala Lys Leu Lys Ser Glu Ser Ser Ser Ser Ser Ser
    130                 135                 140

Ser Glu Ser Ser Ser Asp Ser Glu Arg Gly Glu Val Ile His Met Ser
145                 150                 155                 160

Arg Phe Arg Asp Glu Thr Ile Pro Ala Ala Leu Pro Gln Leu His Pro
                165                 170                 175

Leu Thr His His His Pro Thr Ser Thr Leu Pro Val Ser Pro Thr Gln
            180                 185                 190

Glu Cys Asn Pro Met Asp Tyr Thr Ser Thr His His Glu Lys Arg Cys
        195                 200                 205

Cys Val Gly Pro Ser Thr Gly Ala Asp Asn Ala Val Gly Asp Cys Cys
    210                 215                 220

Asn Asp Arg Asn Ser Ser Met Thr Glu Glu Leu Ser Ala Asn Arg Ile
225                 230                 235                 240

Glu Val Cys Met Gly Asn Lys Cys Lys Lys Ser Gly Gly Ala Ala Leu
                245                 250                 255

Leu Glu Glu Phe Gln Arg Val Leu Gly Val Glu Ala Ala Val Val Gly
            260                 265                 270

Cys Lys Cys Met Gly Asn Cys Arg Asp Gly Pro Asn Val Arg Val Arg
        275                 280                 285

Asn Ser Val Gln Asp Arg Asn Thr Asp Asp Ser Val Arg Thr Pro Ser
    290                 295                 300

Asn Pro Leu Cys Ile Gly Val Gly Leu Glu Asp Val Asp Val Ile Val
305                 310                 315                 320

Ala Asn Phe Phe Gly Leu Gly Leu Ala Pro Ala Ser
                325                 330
```

<210> SEQ ID NO 88
<211> LENGTH: 999
<212> TYPE: DNA
<213> ORGANISM: Ricinus communis

<400> SEQUENCE: 88

```
atggaagtct caggcctggg ctgcttctcc tcggctgcaa cgccatcttt gtgtggggcg      60

gtggattcag gcggagtatc ctctttgaga ccgaggaagg cattccatag ggtttctgat     120

tcttgtttag ggtttagaga taatggacat ctgcagtatt attgtcaagg aggatttgtc     180

aggtgcggag gagggaacaa gaaatctatc aagaaaaagt tgaaattagt gaagtccttg     240

tctgaggact tttccatgtt tcctcataac aatgctttgc tccatcaacc tcaatccatc     300

tccctccagg aagctgcaca aggattaatg aaacagctcc aagaattgcg agcaaaggag     360
```

```
aaggaattaa agaggcagaa gaaacaagag aaaaaagcca agctaaaatc tgaatcatcc    420

tcatcctcat cctctgaatc cagtagtgat agcgaacgtg gggaggttat tcacatgagc    480

cgcttcagag atgaaactat tcctgccgca ctacctcaat tgcacccact tactcatcac    540

cacccaactt ccaccctacc agtctcccca acccaagaat gcaacccgat ggattacact    600

tcaacacatc atgaaaaacg atgctgcgtt ggaccaagca ccggtgccga taacgcagtc    660

ggtgactgtt gcaatgatag gaatagctcg atgacagagg aattgtcagc aaacagaatt    720

gaggtgtgca tgggtaataa gtgcaagaag tcgggaggtg cagcgttatt ggaggaattt    780

cagagggttt tgggtgtaga ggctgcagtt gttgggtgca agtgcatggg gaactgcagg    840

gacggtccta atgtaagggt caggaattct gtccaagaca gaaacacaga tgactctgtt    900

cgaacccccct ccaatcctct ctgcattggt gttggtttgg aggatgtgga tgttattgtg   960

gccaatttct ttgggttggg tctggcccct gcatcttaa                           999


<210> SEQ ID NO 89
<211> LENGTH: 345
<212> TYPE: PRT
<213> ORGANISM: Arachis hypogaea

<400> SEQUENCE: 89

Met Glu Val Ser Gly Ala Val Leu Arg Asn Val Thr Cys Pro Ser Phe
1               5                   10                  15

Ser Val His Val Ser Ser Arg Arg Arg Gly Gly Asp Ser Cys Val Thr
            20                  25                  30

Val Pro Val Arg Met Arg Lys Lys Ala Val Val Arg Cys Cys Cys Gly
        35                  40                  45

Phe Ser Asp Ser Gly His Val Gln Tyr Tyr Gly Asp Glu Lys Lys Lys
    50                  55                  60

Glu Asn Gly Thr Ala Met Leu Ser Thr Lys Lys Lys Leu Lys Met Leu
65                  70                  75                  80

Lys Lys Arg Val Leu Phe Asp Asp Leu Gln Gly Asn Leu Thr Trp Asp
                85                  90                  95

Ala Ala Met Val Leu Met Lys Gln Leu Glu Gln Val Arg Ala Glu Glu
            100                 105                 110

Lys Glu Leu Lys Lys Lys Arg Lys Gln Glu Lys Lys Glu Ala Lys Leu
        115                 120                 125

Lys Ala Ser Lys Met Asn Thr Asn Pro Asp Cys Glu Ser Ser Ser Ser
    130                 135                 140

Ser Ser Ser Ser Glu Ser Glu Ser Glu Ser Ser Glu Ser Glu Cys Asp
145                 150                 155                 160

Asn Glu Val Val Asp Met Lys Lys Asn Ile Lys Val Gly Val Ala Val
                165                 170                 175

Ala Val Ala Asp Ser Pro Arg Lys Ala Glu Thr Met Ile Leu Tyr Thr
            180                 185                 190

Ser Leu Val Ala Arg Asp Val Ser Ala Asn His His His His Asn Ala
        195                 200                 205

Val Glu Leu Phe Ser Arg Asn Asn Asp Ile Ser Val Gly Ser Ile Asn
    210                 215                 220

Gly Gly Leu Lys Asn Glu Asn Thr Ala Val Ile Thr Thr Glu Ala Ile
225                 230                 235                 240

Pro Gln Lys Arg Ile Glu Val Cys Met Gly Asn Lys Cys Lys Lys Ser
                245                 250                 255
```

-continued

```
Gly Ser Ile Ala Leu Leu Gln Glu Phe Glu Arg Val Val Gly Ala Glu
            260                 265                 270

Gly Gly Ala Ala Ala Ala Val Val Gly Cys Lys Cys Met Gly Lys Cys
        275                 280                 285

Lys Ser Ala Pro Asn Val Arg Ile Gln Asn Ser Thr Ala Asp Lys Ile
    290                 295                 300

Ala Glu Gly Phe Asn Asp Ser Val Lys Val Pro Ala Asn Pro Leu Cys
305                 310                 315                 320

Ile Gly Val Ala Trp Arg Met Leu Lys Pro Leu Trp Leu Arg Phe Leu
                325                 330                 335

Gly Glu Asn Gln Glu Ser Thr Asn Glu
            340                 345


<210> SEQ ID NO 90
<211> LENGTH: 1038
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

atggaggttt caggcgccgt tctaaggaat gtcacgtgcc cttccttttc tgtgcacgtg     60

agttcccgtc gtcgtggtgg tgatagttgt gttacagtgc cggtgaggat gagaaaaaag    120

gcggtggtgc gttgttgctg cgggttcagt gattcggggc atgtgcagta ttacggggac    180

gagaagaaga aggagaatgg aaccgctatg ttgagcacca agaagaagct caagatgctg    240

aagaaacgtg tccttttcga tgatcttcaa ggaaacctga cttgggatgc tgctatggtt    300

ttgatgaagc agctagagca agtaagggca gaggagaagg aattgaagaa aaaaaggaag    360

caagagaaga aggaggcaaa actcaaagcc tctaagatga acaccaatcc tgattgcgaa    420

tcgtcatcgt catcgtcatc atctgaatct gaatctgaat caagtgagag tgaatgtgac    480

aatgaggtgg ttgacatgaa gaagaacatt aaggttggtg ttgccgttgc tgttgccgat    540

tccccacgaa aggcggaaac catgattcta tacacctccc ttgttgcccg agatgttagt    600

gctaatcatc atcatcataa tgccgtggaa ttattctcta gaaacaatga catatcagtt    660

ggaagcatta atggtggcct taagaatgag aatactgcgg ttattaccac tgaagctatt    720

cctcagaaga ggattgaggt atgcatggga aacaagtgca agaaatccgg atctattgca    780

ttgttgcaag aatttgagag agtggttggt gctgaaggag gtgctgctgc tgcagttgtt    840

ggatgcaagt gcatggggaa gtgcaagagt gcacctaatg tgaggattca gaactctact    900

gcagataaaa tagctgaggg gttcaatgat tcagttaagg ttccagctaa ccctctttgc    960

attggggttg catggaggat gttgaaacca ttgtggctta gattcttggg cgagaatcag   1020

gaaagtacta atgaataa                                                 1038
```